United States Patent
Protter et al.

(10) Patent No.: US 9,434,747 B2
(45) Date of Patent: Sep. 6, 2016

(54) METHODS OF TREATING DIABETES

(75) Inventors: Andrew Asher Protter, Palo Alto, CA (US); Sarvajit Chakravarty, Mountain View, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 13 days.

(21) Appl. No.: 14/000,197

(22) PCT Filed: Feb. 17, 2012

(86) PCT No.: PCT/US2012/025754
§ 371 (c)(1),
(2), (4) Date: Nov. 22, 2013

(87) PCT Pub. No.: WO2012/112965
PCT Pub. Date: Aug. 23, 2012

(65) Prior Publication Data
US 2014/0228353 A1    Aug. 14, 2014

Related U.S. Application Data

(60) Provisional application No. 61/444,616, filed on Feb. 18, 2011, provisional application No. 61/444,569, filed on Feb. 18, 2011, provisional application No. 61/444,553, filed on Feb. 18, 2011.

(51) Int. Cl.
| | | |
|---|---|---|
| *A61K 31/00* | (2006.01) | |
| *A61K 31/55* | (2006.01) | |
| *A61K 31/54* | (2006.01) | |
| *C07D 513/16* | (2006.01) | |
| *A61K 31/437* | (2006.01) | |
| *A61K 31/4375* | (2006.01) | |
| *A61K 31/46* | (2006.01) | |
| *A61K 31/4985* | (2006.01) | |
| *A61K 31/506* | (2006.01) | |
| *A61K 31/519* | (2006.01) | |
| *A61K 31/5383* | (2006.01) | |
| *A61K 31/542* | (2006.01) | |
| *A61K 31/553* | (2006.01) | |
| *C07D 451/00* | (2006.01) | |
| *C07D 471/04* | (2006.01) | |
| *C07D 471/14* | (2006.01) | |
| *C07D 471/16* | (2006.01) | |
| *C07D 471/22* | (2006.01) | |
| *C07D 487/04* | (2006.01) | |
| *C07D 487/16* | (2006.01) | |
| *C07D 498/16* | (2006.01) | |
| *C07D 498/22* | (2006.01) | |

(Continued)

(52) U.S. Cl.
CPC .......... *C07D 513/16* (2013.01); *A61K 31/437* (2013.01); *A61K 31/4375* (2013.01); *A61K 31/46* (2013.01); *A61K 31/4985* (2013.01); *A61K 31/506* (2013.01); *A61K 31/519* (2013.01); *A61K 31/5383* (2013.01); *A61K 31/542* (2013.01); *A61K 31/55* (2013.01); *A61K 31/553* (2013.01); *C07D 451/00* (2013.01); *C07D 471/04* (2013.01); *C07D 471/08* (2013.01); *C07D 471/14* (2013.01); *C07D 471/16* (2013.01); *C07D 471/22* (2013.01); *C07D 487/04* (2013.01); *C07D 487/08* (2013.01); *C07D 487/16* (2013.01); *C07D 498/16* (2013.01); *C07D 498/22* (2013.01)

(58) Field of Classification Search
CPC ...................................................... A61K 31/55
USPC ................................. 514/211.1, 215, 224.5
See application file for complete search history.

(56) References Cited

U.S. PATENT DOCUMENTS

| | | |
|---|---|---|
| 3,299,078 A | 1/1967 | Pachter |
| 5,223,625 A | 6/1993 | Van Wijngaarden et al. |

(Continued)

FOREIGN PATENT DOCUMENTS

| | | |
|---|---|---|
| EP | 0 725 068 A1 | 8/1996 |
| EP | 2 236 511 A2 | 10/2010 |

(Continued)

OTHER PUBLICATIONS

Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics.* 287(2):508-514.

Alekseyev, R. S. et al. (Jul. 2010). "γ-Carbolines and their Hydrogenated Derivatives. 2. Hydrogenated Derivatives of γ-Carbolines: Methods of Synthesis (Review)," *Chemistry of Heterocyclic Compounds* 46(7):777-821.

Bartolini, L. et al. (1996). "Aniracetam Restores Object Recognition Impaired by Age, Scopolamine, and Nucleus Basalis Lesions," *Pharmacology Biochemistry Behavior* 53(2):277-283.

(Continued)

*Primary Examiner* — Kevin E Weddington
(74) *Attorney, Agent, or Firm* — Morrison & Foerster LLP

(57) ABSTRACT

Hydrogenated pyrido[4,3-b]indoles, pyrido[3,4-b]indoles and azepino[4,5-b]indoles are described. The compounds may bind to and are antagonists of the adrenergic receptor $\alpha_{2A}$. The compounds may also bind to and are an antagonist of the adrenergic receptor $\alpha_{2B}$; or the compounds are not antagonists of the adrenergic receptor $\alpha_{2B}$ and the compounds are administered in conjunction with a second agent that reduces, or is expected to reduce, blood pressure in an individual. The compounds may find use in therapy, e.g., to regulate blood glucose level, increase insulin secretion and treat diseases or conditions that are, or are expected to be, responsive to an increase in insulin production. Use of the compounds to treat type 2 diabetes is particularly described.

9 Claims, No Drawings

(51) Int. Cl.
  *C07D 471/08* (2006.01)
  *C07D 487/08* (2006.01)

(56) References Cited

U.S. PATENT DOCUMENTS

| | | | |
|---|---|---|---|
| 5,620,973 A | 4/1997 | Goto et al. |
| 6,187,785 B1 | 2/2001 | Zefirov et al. |
| 6,548,493 B1 | 4/2003 | Robichaud et al. |
| 7,071,206 B2 | 7/2006 | Zefirov et al. |
| 8,338,408 B2 | 12/2012 | Hung et al. |
| 8,338,447 B2 | 12/2012 | Hung et al. |
| 8,362,277 B2 | 1/2013 | McKnight et al. |
| 8,541,437 B2 | 9/2013 | Ivashchenko et al. |
| 8,546,381 B2 | 10/2013 | Hung et al. |
| 8,569,287 B2 | 10/2013 | Hung et al. |
| 8,604,074 B2 | 12/2013 | McKnight et al. |
| 8,735,440 B2 | 5/2014 | McKnight et al. |
| 8,741,919 B2 | 6/2014 | Jain et al. |
| 8,791,132 B2 | 7/2014 | Protter et al. |
| 8,815,843 B2 | 8/2014 | Protter et al. |
| 8,859,561 B2 | 10/2014 | Jain et al. |
| 8,877,797 B2 | 11/2014 | McKnight et al. |
| 8,906,925 B2 | 12/2014 | Hung et al. |
| 8,907,097 B2 | 12/2014 | Hung et al. |
| 8,927,571 B2 | 1/2015 | Jain et al. |
| 8,999,977 B2 | 4/2015 | Hung et al. |
| 8,999,978 B2 | 4/2015 | Hung et al. |
| 9,006,234 B2 | 4/2015 | Jain et al. |
| 9,006,263 B2 | 4/2015 | Protter et al. |
| 9,034,865 B2 | 5/2015 | Chakravarty et al. |
| 9,034,869 B2 | 5/2015 | Hung et al. |
| 9,034,880 B2 | 5/2015 | Hung et al. |
| 9,035,056 B2 | 5/2015 | Chakravarty et al. |
| 9,040,519 B2 | 5/2015 | Chakravarty et al. |
| 9,045,482 B2 | 6/2015 | Jain et al. |
| 9,051,314 B2 | 6/2015 | Hung et al. |
| 9,079,904 B2 | 7/2015 | Jain et al. |
| 9,085,580 B2 | 7/2015 | Jain et al. |
| 9,096,591 B2 | 8/2015 | Hung et al. |
| 9,115,137 B2 | 8/2015 | Hung et al. |
| 2001/0020028 A1 | 9/2001 | Zefirov et al. |
| 2002/0115682 A1 | 8/2002 | Zefirov et al. |
| 2003/0225058 A1 | 12/2003 | Frank et al. |
| 2004/0044022 A1 | 3/2004 | Zefirov, Jr. et al. |
| 2004/0180875 A1 | 9/2004 | Lee et al. |
| 2005/0054634 A1 | 3/2005 | Busch et al. |
| 2005/0282796 A1 | 12/2005 | Acker et al. |
| 2006/0140866 A1 | 6/2006 | Zefirov et al. |
| 2006/0178362 A1 | 8/2006 | Robichaud et al. |
| 2007/0015746 A1 | 1/2007 | Martin et al. |
| 2007/0117834 A1 | 5/2007 | Hung |
| 2007/0117835 A1 | 5/2007 | Hung |
| 2007/0179174 A1 | 8/2007 | Bachurin et al. |
| 2007/0225316 A1 | 9/2007 | Bachurin et al. |
| 2008/0234310 A1 | 9/2008 | Bachurin et al. |
| 2008/0261938 A1 | 10/2008 | Ercolani et al. |
| 2009/0221627 A1 | 9/2009 | Aksinenko et al. |
| 2010/0022580 A1 | 1/2010 | Hung et al. |
| 2010/0029706 A1 | 2/2010 | Miller et al. |
| 2010/0087471 A1 | 4/2010 | Schrimpf et al. |
| 2010/0099700 A1 | 4/2010 | Hung |
| 2010/0152108 A1 | 6/2010 | Hung et al. |
| 2010/0152225 A1 | 6/2010 | Hung |
| 2010/0178277 A1 | 7/2010 | Hung et al. |
| 2010/0249105 A1 | 9/2010 | Schrimpf et al. |
| 2010/0286188 A1 | 11/2010 | Bachurin et al. |
| 2011/0046368 A1 | 2/2011 | Ivashchenko et al. |
| 2011/0112132 A1 | 5/2011 | Bachurin et al. |
| 2011/0152308 A1 | 6/2011 | Shi |
| 2011/0237582 A1 | 9/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190323 A1 | 7/2013 | Hung et al. |
| 2013/0190328 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |
| 2015/0182509 A1 | 7/2015 | Hung et al. |
| 2015/0258075 A1 | 9/2015 | Chakravarty et al. |
| 2015/0266884 A1 | 9/2015 | Protter et al. |

FOREIGN PATENT DOCUMENTS

| | | |
|---|---|---|
| JP | 05-310738 A | 11/1993 |
| WO | WO-2005/055951 A2 | 6/2005 |
| WO | WO-2005/055951 A3 | 6/2005 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/038161 A1 | 3/2009 |
| WO | WO-2009/038162 A1 | 3/2009 |
| WO | WO-2009/038163 A1 | 3/2009 |
| WO | WO-2009/038164 A1 | 3/2009 |
| WO | WO-2009/039420 A1 | 3/2009 |
| WO | WO-2009/039420 A9 | 3/2009 |
| WO | WO-2009/051503 A2 | 4/2009 |
| WO | WO-2009/051503 A3 | 4/2009 |
| WO | WO-2009/055828 A1 | 4/2009 |

(56) References Cited

FOREIGN PATENT DOCUMENTS

| WO | WO-2009/082268 A2 | 7/2009 |
|---|---|---|
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/081115 A1 | 7/2010 |
| WO | WO-2010/127177 A1 | 11/2010 |
| WO | WO-2011/008312 A2 | 1/2011 |
| WO | WO-2011/008312 A3 | 1/2011 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012/006419 A3 | 1/2012 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Bastable, J.W. et al. (Jan. 1, 1981). "Solvolytic Rearrangements of Azabicyclic Compounds," *J. Chem. Soc. Perkin.* I 1346-1351.

Berge, S.M. et al. (Jan. 1977). "Pharmaceutical Salts," *J. Pharm. Sci.* 66(1):1-19.

Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.

Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.

Brown, C.M. et al. (1990). "$\alpha_2$-Adrenoceptor Subtypes and Imidazoline-Like Binding Sites in the Rat Brain," *Br. J. Pharmacol.* 99:803-809.

Bubber, P. et al. (May 2005, e-published Apr. 25, 2005). "Mitochondrial Abnormalities in Alzheimer Brain: Mechanistic Implications," *Ann Neurol.* 57(5):695-703.

Burke, S.L. et al. (2011). "Effects of Chronic Sympatho-Inhibition on Renal Excretory Function in Renovascular Hypertension," *J. Hypertension* 29(5):945-952.

Carter, J.D. et al. (2009). "A Practical Guide to Rodent Islet Isolation and Assessment." *Biol. Proced. Online* 11(1): 3-31.

Chen, B. et al. (2011). "Sitagliptin Lowers Glucagon and Improves Glucose Tolerance in Prediabetic Obese SHROB Rats," *Exp. Biol. Med.* 236:309-414.

Cheng, Y. et al. (Sep. 15, 1973). "Relationship Between the Inhibition Constant ($K_I$) and the Concentration of Inhibitor Which Causes 50 Per Cent Inhibition ($I_{50}$) of an Enzymatic Reaction," *Biochem. Pharmacol.* 22(18):3099-3108.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Duprez, D.A. (2008). "Systolic Hypertension in the Elderly: Addressing an Unmet Need," *Am. J. Med.* 121 :179-184.

Ennaceur, A. et al. (1988). "A New One-Trial Test for Neurobiological Studies of Memory in Rats. 1: Behavioral Data," *Behav. Brain. Res.* 31:47-59.

Franklin, S. S. et al. (2011). "The Significance of Low DBP in US Adults with Isolated Systolic Hypertension," *J. Hypertension* 29(6):1101-1108.

García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.

Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTP$\gamma$S Binding Assays," *Naunyn-Schmiedeberg's Archives of Pharmacology* 361:498-504.

Grandy, D.K. et al. (Dec. 1989). "Cloning of the cDNA and Gene for a Human D$_2$ Dopamine Receptor," *Proc. Natl. Acad. Sci. USA* 86:9762-9766.

Grossman, C.J. et al. (1993). "Development of a Radioligand Binding Assay for 5-HT$_4$ Receptors in Guinea-Pig and Rat Brain," *Br. J. Pharmacol.* 109:618-624.

Hardy, J. (1996). "New Insights Into the Genetics of Alzheimer's Disease," *Annals of Medicine* 28:255-258.

Hardy, J. (1997). "Amyloid, the Presenilins and Alzheimer's Disease," *Trends Neurosci.* 20(4):154-159.

Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.

Hoyer, D. et al. (1985). "Characterization of the 5-HT$_{1B}$ Recognition Site in Rat Brain: Binding Studies with (−)[$^{125}$I]Iodocyanopindolol," *European Journal of Pharmacology* 118:1-12.

International Search Report mailed on Apr. 15, 2011 for PCT Patent Application No. PCT/US2011/025444, filed on Feb. 18, 2011, 3 pages.

International Search Report mailed on Apr. 22, 2011, for PCT Patent Application No. PCT/US2011/025475, filed on Feb. 18, 2011, 3 pages.

International Search Report mailed on Apr. 22, 2011 for PCT Patent Application No. PCT/US2011/025511, filed on Feb. 18, 2011, 3 pages.

International Search Report mailed on Jul. 28, 2011, for PCT Patent Application No. PCT/US11/25509, filed on Feb. 18, 2011, 5 pages.

International Search Report mailed on May 30, 2012, for PCT Application No. PCT/US12/25750, filed on Feb. 17, 2012, 3 pages.

International Search Report mailed on May 31, 2012, for PCT Application No. PCT/US2012/025754, filed on Feb. 17, 2012, 3 pages.

Ivashchenko, A.V. et al. (2009). "Synthesis of Substituted 1,2,3,4,5,6-Hexahydroazepine [4.3-b) Indoles," *Abstracts* 52(10):164.

Ivachtchenko, A.V. et al. (2009, e-published May 3, 2009). "Synthesis and Biological Evaluation of Novel Gamma-Caronline Analogues of Dimebon as Potent 5-HT$_6$ Receptor Antagonists," *Bioorganic & Medicinal Chemistry Letters* 19(12):3183-3187.

Ivachtchenko, A.V. et al. (2010, e-published Oct. 31, 2009). "8-Sulfonyl-Substituted Tetrahydro-1H-Pyrido[4,3-b]Indoles as 5-HT$_6$ Receptor Antagonists," *European Journal of Medicinal Chemistry* 45(2):782-789.

Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.

Jerman, J.C. et al. (2001). "Pharmacological Characterisation of Human 5-HT$_2$ Receptor Subtypes," *European Journal of Pharmacology* 414:23-30.

Jongejan, A. et al. (Jul. 2005). "Linking Agonist Binding to Histamine H$_1$ Receptor Activation," *Nat. Chem. Biol.* 1(2):98-103.

(56) References Cited

OTHER PUBLICATIONS

Kebrle, F. et al. (1959). "A New Synthesis of γ-carbolines," *Helvetica Chimica Acta* 42:907-918, Abstract only, 2 pages.
Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.
King, F.D. et al. (1993). "Substituted Benzamides With Conformationally Restricted Side Chains. 5. Azabicyclo[x.y.z] Derivatives as 5-HT4 Receptor Agonists and Gastric Motility Stimulants," *J. Med. Chem.* 36(6):683-689.
Kiseleva, B.B. et al. (1990). "New Opportunities of Search for Immunomodulators Among Compounds with Steroidal Structure," *Pharmacology and Toxicology: Moscow Medicine* 53(3): 8 pages. (with English Translation).
Kohen, R. et al. (1996). "Cloning, Characterization and Chromosomal Localization of a Human 5-$HT_6$ Serotonin Receptor," *J. Neurochem.* 66(1):47-56.
Kost, A.N. et al. (1962). "Alkaloids and Alkaloid-Like Structures," *Zhurnal Obshchei Khimii* 32:2050-2056, Abstract only, 2 pages.
Kost, A.N. et al. (1970). "9-[2-(4-Pyridyl) Ethyl]-3,6-Dimethyl-1,2,3,4-Tetrandro-γ-Carboline," *U.S.S.R Otkrytiya, Izobret., Prom. Obraztsy, Tovarnye Znaki* 47(3):33, Abstract only, 2 pages.
Krueger, K.M. et al. (Jul. 2005, e-published Apr. 8, 2005). "G Protein-Dependent Pharmacology of Histamine H3 Receptor Ligands: Evidence for Heterogeneous Active State Receptor Conformations," *J. Pharmacol. Exp. Ther.* 314(1):271-281.
Klabunde, T. et al. (2002). "Drug Design Strategies for Targeting G-Protein-Coupled Receptors," *ChemBiochem* 3(10):928-944.
Kuhn, C.M. et al. (1987). "Exaggerated Peripheral Responses to Catecholamines Contributes to Stress-Induced Hyperglycemia in the ob/ob Mouse," *Pharmacol. Biochem. Behav.* 26:491-495.
Lohr, J.B. et al. (Aug. 28, 1995). "Motor Asymmetry, a Neurobiologic Abnormality in the Major Psychoses," *Psychiatry Research* 57(3):279-282.
Makaritsis, K.P. et al. (Jan. 1999). "Role of the$\alpha_{2B}$-Adrenergic Receptor in the Development of Salt-Induced Hypertension," *Hypertension* 33:14-17.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-$HT_{1A}$ and 5-$HT_2$ Receptor Ligands in Conscious Ocular Hypertenisve Cynomolgus Monkeys," *The Journal of Pharmacology and Experimental Therapeutics* 306(1):301-309.
Meister, B. et al. (1994). Patterns of Messenger RNA Expression for Adrenergic Receptor Subtypes in the Rat Kidney, *J. Pharmacol. Exp. Therapeutics* 268(3):1606-1611.
Mewshaw, R.E. et al. (1993). "Synthesis and in Vitro Evaluation of 5,6,7,8,9,10-Hexahydro-7,10-iminocyclohept[b]indoles: High-Affinity Ligands for the N,N-Di-o-tolylguanidine-Labeled σ Binding Site," *J. Med. Chem.* 36(3):343-352.
Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.
Miller, K et al. (1992). "Membrane-Bound and Solubilized Brain 5$HT_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive $H_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Non-Final Office Action mailed on Jul. 17, 2014, for U.S. Appl. No. 13/579,911, filed Mar. 4, 2013, 10 pages.

Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Perrin, R.J. et al. (2003). Epitope Mapping and Specificity of the Anti-α-Synuclein Monoclonal Antibody Syn-1 in Mouse Brain and Cultured Cell Lines *Neurosci. Lett.* 349:133-135.
Pfaffl, M.W. (2001). "A New Mathematical Model for Relative Quantification in Real-Time RT-PCR," *Nucleic Acids Res.* 29(9):e45, 6 pages.
Piercey, M.F. et al. (1988). "Dramatic Limbic and Cortical Effects Mediated by High Affinity PCP Receptors," *Life Sciences* 43(4):379-385.
Pubchem Compound No. 10954584. (Oct. 26, 2006). Compound Summary and Structure located at <http://pubchem.ncbi.nlm.nih.gov/summary/summary.cgi?cid=10954584&loc=ec_rcs>, last visited Apr. 4, 2011, 3 pages.
Prichep, L.S. et al. (1994). "Quantitative EEG Correlates of Cognitive Deterioration in the Elderly," *Neurobiology of Aging* 15(1):85-90.
Reddy, P.H. et al. (2005, e-pub. Apr. 19, 2005). "Are Mitochondria Critical in the Pathogenesis of Alzheimer's Disease?" *Brain Res Rev.* 49(3):618-632.
Rees, S. et al. (Oct. 11, 1994). "Cloning and Characterisation of the Human 5-$HT_{5A}$ Serotonin Receptor," *FEBS Letters* 355:242-246.
Regard, J.B. et al. (Oct. 31, 2008). "Anatomical Profiling of G Protein-Coupled Receptor Expression," *Cell* 135:561-571.
Reisberg, B. et al. (Sep. 1982). "The Global Deterioration Scale for Assessment of Primary Degenerative Dementia," *Am. J. Psychiatry* 139(9):1136-1139.
Rosengren, A.H. et al. (Jan. 8, 2010). "Overexpression of Alpha2A-Adrenergic Receptors Contributes to Type 2 Diabetes," *Science* 327:217-220.
Rostom et al. (2010, e-pub. Jan. 27, 2010). "Novel Fused Pyrrole Heterocyclic Ring Systems as Structure Analogs of LE 300: Synthesis and Pharmacological Evaluation as a Serotonin 5-$HT_{2A}$, Dopamine and Histamine $H_1$ Receptor Ligands," *Arch. Pharm. Chem. Life Sci.* 343(2):73-80.
Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.
Ruat, M. et al. (Mar. 1990). "Reversible and Irreversible Labeling and Autoradiographic Localization of the Cerebral Histamine $H_2$ Receptor Using [$^{125I}$]Iodinated Probes," *Proc. Natl. Acad. Sci. USA* 87(5):1658-1662.
Saperstein, R. et al., (May 1990). "Effects of an $\alpha_2$-Adrenoceptor Antagonist on Glucose Tolerance in the Genetically Obese Mouse (C57BL/6J ob/ob)," *Metabolism* 39(5):445-451.
Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.
Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.
Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.
Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.
Swerdlow, R.H. et al. (2002). "Mitochondria in Alzheimer's Disease," *International Review of Neurobiology* 53:341-385.
Talmud, P.J. et al. (2011). "Variants of *ADRA2A* are Associated with Fasting Glucose, Blood Pressure, Body Mass Index and Type 2 Diabetes Risk: Meta-Analysis of Four Prospective Studies," *Diabetologia* 54:1710-1719.
Tanzi, R.E. et al. (1996). "The Gene Defects Responsible for Familial Alzheimer's Disease," *Neurobiology of Disease* 3:159-168.

(56) References Cited

OTHER PUBLICATIONS

Uhlén, S. et al. (1994). "The Novel Alpha-2 Adrenergic RadioLigand [$^3$H]-MK912 is Alpha-2C Selective Among Human Alpha-2A, Alpha-2B and Alpha-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vekrellis, K. et al. (2009). "Inducible Over-Expressing of α-Synuclein in Human Neuronal Cells Leads to Caspase-Dependent Non-Apoptotic Death," *J. Neurochem.* 109:1348-1362.

Velliquette, R.A. et al. (2003). "The Role of $I_1$-Imidazoline and $\alpha_2$-Adrenergic Receptors in the Modulation of Glucose Metabolism in the Spontaneously Hypertensive Obese Rat Model of Metabolic Syndrome X," *J. Pharmacol. Exp. Ther.* 306(2):646-657.

Wade, S.M. et al., (2001). "Inverse Agonist Activity at the $\alpha_{2A}$-Adrenergic Receptor," *Mol. Pharmacol.* 59(3):532-542.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

West, A.R. (1988). "Solid Solutions" Chapter 10 in *Solid State Chemistry and Its Applications*, John Wiley & Sons, New York, p. 358.

Wolf, W.A. (1997). "The Serotonin 5-HT$_{2c}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion mailed on Apr. 15, 2011 for PCT Patent Application No. PCT/US2011/025444, filed on Feb. 18, 2011, 6 pages.

Written Opinion mailed on Apr. 22, 2011, for PCT Patent Application No. PCT/US2011/025475, filed on Feb. 18, 2011, 5 pages.

Written Opinion mailed on Apr. 22, 2011, for PCT Patent Application No. PCT/US2011/025511, filed on Feb. 18, 2011, 6 pages.

Written Opinion mailed on Jul. 28, 2011, for PCT Patent Application No. PCT/US11/25509, filed on Feb. 18, 2011, 6 pages.

Written Opinion mailed on May 30, 2012, for PCT Application No. PCT/US12/25750, filed on Feb. 17, 2012, 5 pages.

Written Opinion mailed on May 31, 2012, for PCT Application No. PCT/US2012/025754, filed on Feb. 17, 2012, 4 pages.

Wu, J. et al. (Oct. 21, 2008). "Evaluation of Dimebon in Cellular Model of Huntington's Diseases," *Molecular Neurodegeneration* 3:15: 11 pages.

Yanai, K. et al. (1994). "Binding Characteristics of a Histamine H$_3$-Receptor Antagonist, [$^3$H]S-Methylthioperamide: Comparison with [$^3$H](*R*)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

U.S. Appl. No. 14/531,915, filed Nov. 3, 2014, by Hung et al.
U.S. Appl. No. 14/423,027, filed Feb. 20, 2015, by Protter et al.
U.S. Appl. No. 14/631,615, filed Feb. 25, 2015, by Hung et al.
U.S. Appl. No. 14/641,232, filed Mar. 6, 2015, by Protter et al.
U.S. Appl. No. 14/666,101, filed Mar. 23, 2015, by Chakravarty et al.
U.S. Appl. No. 14/701,244, filed Apr. 30, 2015, by Chakravarty et al.
Jain et al., U.S. Appl. No. 14/738,465, filed Jun. 12, 2015.
Mancia, et al., "Guidelines for the Management of Arterial Hypertension: The Task Force for the Management of Arterial Hypertension of the European Society of Hypertension (ESH) and of the European Society of Cardiology (ESC).", Eur. Heart J., vol. No. 28, No. 12, 2007, pp. 1462-1536.

METHODS OF TREATING DIABETES

CROSS-REFERENCE TO RELATED APPLICATIONS

This application is a national phase application under 35 U.S.C. §371 of International Application No. PCT/US2012/025754, filed Feb. 17, 2012, which claims priority to U.S. Provisional Patent Application No. 61/444,616 filed Feb. 18, 2011, U.S. Provisional Patent Application No. 61/444,553 filed Feb. 18, 2011, and U.S. Provisional Patent Application No. 61/444,569 filed Feb. 18, 2011, the disclosures of each of which are incorporated herein by reference in their entireties.

BACKGROUND OF THE INVENTION

Type 2 diabetes is a serious and prevalent disease. This form of diabetes may involve insulin resistance and impaired insulin release. Approximately 25.8 million people in the United States alone suffer from diabetes, whereby type 2 diabetes accounts for about 90-95% of all diagnosed diabetes cases. From 1980 to 2008 the number of Americans with diabetes has more than tripled. Diabetes is also increasingly prevalent elsewhere, such as in certain Asian countries whose populations have experienced a dramatic increase in the disease. For example, in India and China, where rapid lifestyle and economic changes have led to a more sedentary lifestyle and poorer diet among the overall population, diabetes is becoming a major health concern. In addition, more than a third of adults at least 20 years old have pre-diabetes, which is a significant risk factor for developing type 2 diabetes. Other diseases and indications, such as glucose intolerance and metabolic syndrome may also be associated with impaired insulin release.

There remains a need for new and improved therapies that enhance insulin secretion and/or promote insulin release into the blood stream in individuals who have a reduced or impaired ability to secrete insulin and/or release insulin into the blood stream.

BRIEF SUMMARY OF THE INVENTION

Hydrogenated pyrido[4,3-b]indoles, pyrido[3,4-b]indoles and azepino[4,5-b]indoles are described. Compositions and kits comprising the compounds are also provided, as are methods of using and making the compounds. Compounds provided herein may find use in therapy, e.g., to regulate blood glucose level, increase insulin secretion and treat diseases or conditions that are, or are expected to be, responsive to an increase in insulin production. In one aspect, compounds provided herein are $\alpha_{2A}$ antagonists that may find use in therapy, e.g., to increase insulin secretion and treat diseases or conditions that are, or are expected to be, responsive to an increase in insulin production. Use of the compounds to treat type 2 diabetes is particularly described.

In one aspect, the present invention discloses methods of regulating blood glucose levels in an individual in need thereof comprising administering to the individual an effective amount of a compound of the formulae (A1), (A2), (A3), (A4), (B1), (B2), (B3), (B4), (C1), (C2), (C3), (C4), (D1), (D2), (D3), or (D4); or a salt, solvate or N-oxide thereof; and wherein the formulae (A1) to (D4) are as described herein.

In one embodiment, the method reduces blood glucose level in the individual. In another embodiment, the method reduces blood glucose level in the individual for a period of more than 0.5 hours following administration.

In another embodiment, the method stabilizes of blood glucose level in the individual.

In another aspect, the present invention provides methods of (i) increasing insulin secretion, and/or (ii) promoting insulin release into the blood stream, in an individual in need thereof comprising administering to the individual an effective amount of a compound of the formulae (A1), (A2), (A3), (A4), (B1), (B2), (B3), (B4), (C1), (C2), (C3), (C4), (D1), (D2), (D3), or (D4); or a salt, solvate or N-oxide thereof; and wherein the formulae (A1) to (D4) are as described above.

In one embodiment, the method increases insulin secretion. In another embodiment, the method promotes insulin release into the blood stream. In one aspect a method is provided for one or more of the following: reducing blood glucose levels, increasing insulin secretion, and promoting insulin release in the blood stream.

In one embodiment, the individual has a disease or condition that involves impaired insulin secretion. In another embodiment, the individual has one or more risk factors for developing a disease or condition that involves impaired insulin secretion.

In another embodiment, the administration results in decrease of blood pressure in the individual.

In a further aspect, the invention presents methods of treating a disease or condition that is responsive to an increase in insulin secretion, comprising administering to an individual in need thereof an effective amount of a compound of the formulae (A1), (A2), (A3), (A4), (B1), (B2), (B3), (B4), (C1), (C2), (C3), (C4), (D1), (D2), (D3), or (D4); or a salt, solvate or N-oxide thereof; and wherein the formulae (A1) to (D4) are as described above.

In a further aspect, the present invention provides methods of delaying the onset of a disease or condition that is responsive to an increase in insulin secretion, comprising administering to an individual in need thereof an effective amount of a compound of the formulae (A1), (A2), (A3), (A4), (B1), (B2), (B3), (B4), (C1), (C2), (C3), (C4), (D1), (D2), (D3), or (D4); or a salt, solvate or N-oxide thereof; and wherein the formulae (A1) to (D4) are as described above.

In one embodiment, with respect to the method, the disease or condition is type 2 diabetes. In another embodiment, the disease or condition is glucose intolerance. In another embodiment, the disease or condition is metabolic syndrome.

In one embodiment, with respect to the above method, the individual is not responsive to standard treatment of type 2 diabetes.

In another embodiment, with respect to the method, the method further comprising administering to the individual in need thereof one or more anti-diabetic agents. In one embodiment, the anti-diabetic agents is an insulin sensitizer.

In another embodiment, with respect to the methods of the invention, the compound binds to and is an antagonist of the adrenergic receptor $\alpha_{2A}$ and, wherein the compound either (a) also binds to and is an antagonist of the adrenergic receptor $\alpha_{2B}$ or (b) the compound is not an antagonist of the adrenergic receptor $\alpha_{2B}$ and the compound is administered in conjunction with a second agent that reduces blood pressure in the individual. In one embodiment, the compound binds to and is an antagonist of the adrenergic receptor $\alpha_{2B}$. In another embodiment, the compound binds to and is an antagonist of the adrenergic receptor $\alpha_{1B}$. In another embodiment, the compound is not an antagonist of the adrenergic receptor $\alpha_{2B}$ and the compound is administered in conjunction with a diuretic, an angiotensin-converting enzyme (ACE) inhibitor, an angiotensin-2 receptor antagonist, a beta blocker, a calcium channel blocker, or any combination thereof.

In a further aspect, the present invention provides a kit comprising (i) a compound of formulae (A1), (A2), (A3), (A4), (B1), (B2), (B3), (B4), (C1), (C2), (C3), (C4), (D1), (D2), (D3), or (D4); or a salt, solvate or N-oxide thereof, or a pharmaceutically acceptable salt thereof, and (ii) instructions for use according to the methods of invention.

DETAILED DESCRIPTION OF THE INVENTION

Definitions

Unless clearly indicated otherwise, the terms "a," "an," and the like, refer to one or more.

It is also understood and clearly conveyed by this disclosure that reference to "the compound" or "a compound" includes and refers to any compounds (e.g., selective adrenergic receptor $\alpha_{2B}$ antagonists) or pharmaceutically acceptable salt or other form thereof as described herein.

Reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human. The invention may find use in both human medicine and in the veterinary context.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

As used herein, "treatment" or "treating" is an approach for obtaining a beneficial or desired result, including clinical results.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient, or compound which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein includes an inert or inactive substance that may be used in the production of a drug or pharmaceutical, such as a tablet containing a compound detailed herein, or a pharmaceutically acceptable salt thereof, as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

An inverse agonist is a compound that binds to a receptor and inhibits the activity of the receptor in the absence of an agonist. An inverse agonist requires that the receptor have some constitutive basal activity in the absence of an agonist. While an agonist increases activity of the receptor over basal level an inverse agonist reduces receptor activity below basal level.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —$C(O)NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$-substituted alkenyl, —$NRSO_2$-alkynyl, —$NRSO_2$-substituted alkynyl, —$NRSO_2$-cycloalkyl, —$NRSO_2$-substituted cycloalkyl, —$NRSO_2$-aryl, —$NRSO_2$-substituted aryl, —$NRSO_2$-heteroaryl, —$NRSO_2$-substituted heteroaryl, —$NRSO_2$-heterocyclic, and —$NRSO_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-aralkyl, —SO$_2$-substituted aralkyl, —SO$_2$-heteroaryl, —SO$_2$-substituted heteroaryl, —SO$_2$-heterocyclic, and —SO$_2$-substituted heterocyclic.

"Aminocarbonylalkoxy" refers to the group —NR$_a$C(O)OR$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —C(O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.
"Cyano" refers to the group —CN.
"Oxo" refers to the moiety =O.
"Nitro" refers to the group —NO$_2$.
"Thioalkyl" refers to the groups —S-alkyl.
"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

Receptor Binding Profile

In some embodiments, compounds provided herein bind to and are antagonists of the adrenergic receptor $\alpha_{2A}$. In one variation, compounds provided herein bind to and are antagonists of the adrenergic receptor $\alpha_{2A}$ and either (a) also bind to and are antagonists of the adrenergic receptor $\alpha_{2B}$ or (b) are not antagonists of the adrenergic receptor $\alpha_{2B}$ but are administered in the methods detailed herein in conjunction with a second agent that reduces, or is expected to reduce, blood pressure in an individual. By exhibiting the dual properties of binding to and being an antagonist of both the adrenergic receptor $\alpha_{2A}$ and the adrenergic receptor $\alpha_{2B}$, compounds provided herein may exert the beneficial effect of increasing insulin secretion and/or promoting insulin release in an individual while reducing or eliminating the side effect of an increase in blood pressure that may be associated with antagonizing the adrenergic receptor $\alpha_{2A}$. Alternatively, compounds provided herein that bind to and are antagonists of the adrenergic receptor $\alpha_{2A}$, but which do not bind to and are not antagonists of the adrenergic receptor $\alpha_{2B}$, may be used in therapy in conjunction with a second agent that reduces, or is expected to reduce, blood pressure in an individual, thereby allowing the adrenergic receptor $\alpha_{2A}$ antagonist to exert its therapeutic effects while reducing or eliminating the side effect of an increase in blood pressure that may be associated with antagonizing the adrenergic receptor $\alpha_{2A}$. Thus, it is understood that a second compound that reduces, or is expected to reduce, blood pressure in an individual includes a second compound that reduces or prevents an increase in an individual's blood pressure associated with antagonizing the adrenergic receptor $\alpha_{2A}$. It is further understood that any of the compounds provided herein may be administered in conjunction with a second agent that reduces, or is expected to reduce, blood pressure in an individual. For example, such a combination therapy may be utilized in an individual who has high blood pressure or has a propensity toward high blood pressure that is not associated with being administered a compound that antagonizes the adrenergic receptor $\alpha_{2A}$. Compounds that exhibit the dual properties of binding to and being an antagonist of both the adrenergic receptor $\alpha_{2A}$ and the adrenergic receptor $\alpha_{2B}$ may also be administered in conjunction with a second agent that reduces, or is expected to reduce, blood pressure in an individual.

Compounds that antagonize the adrenergic receptor $\alpha_{2A}$ and the adrenergic receptor $\alpha_{2B}$ may lower blood glucose and reduce blood pressure and be of therapeutic utility in individuals with high glucose and high blood pressure, for example individuals who have metabolic syndrome. Compounds that antagonize the adrenergic receptor $\alpha_{2A}$ and the adrenergic receptor $\alpha_{2B}$ may also block the adrenergic receptor $\alpha_{1B}$ and have utility in individuals with high blood glucose and high blood pressure.

The compounds provided herein may in some embodiments also bind to and be antagonists of the adrenergic receptor $\alpha_{1B}$, which activity may also help reduce or eliminate an increase in blood pressure in an individual in response to a compound that is an adrenergic receptor $\alpha_{2A}$ antagonist. Thus, in one variation, compounds that bind to and are antagonists of the adrenergic receptor $\alpha_{2A}$ are provided, wherein the compounds also bind to and are antagonists of the adrenergic receptors $\alpha_{2B}$ and $\alpha_{1B}$. In another variation, compounds that bind to and are antagonists of the adrenergic receptor $\alpha_{2A}$ are provided, wherein the compounds also bind to and are antagonists of the adrenergic receptor $\alpha_{1B}$ but which are not antagonists of the adrenergic receptor $\alpha_{2B}$. Such compounds, when are administered in the methods detailed herein, may be administered in conjunction with a second agent that reduces, or is expected to reduce, blood pressure in an individual.

The compounds provided herein may in some embodiments also bind to and be antagonists of the adrenergic receptor $\alpha_{1D}$, which activity may also help reduce or eliminate an increase in blood pressure in an individual in response to a compound that is an adrenergic receptor $\alpha_{2A}$ antagonist. Thus, in one variation, compounds that bind to and are antagonists of the adrenergic receptor $\alpha_{2A}$ are provided, wherein the compounds also bind to and are antagonists of the adrenergic receptors $\alpha_{2B}$, $\alpha_{1B}$ and $\alpha_{1D}$. In another variation, compounds that bind to and are antagonists of the adrenergic receptor $\alpha_{2A}$ are provided, wherein the compounds also bind to and are antagonists of the adrenergic receptor $\alpha_{1B}$ and $\alpha_{1D}$ but which are not antagonists of the adrenergic receptor $\alpha_{2B}$. In another variation, compounds that bind to and are antagonists of the adrenergic receptor $\alpha_{2A}$ are provided, wherein the compounds also bind to and are antagonists of the adrenergic receptor $\alpha_{2B}$ and $\alpha_{1D}$ but which are not antagonists of the adrenergic receptor $\alpha_{1B}$. In another variation, compounds that bind to and are antagonists of the adrenergic receptor $\alpha_{2A}$ are provided, wherein the compounds also bind to and are antagonists of the adrenergic receptors $\alpha_{1D}$, but which are not antagonists of the adrenergic receptor $\alpha_{2B}$ or $\alpha_{1B}$. Such compounds, when administered in the methods detailed herein, may be administered in conjunction with a second agent that reduces, or is expected to reduce, blood pressure in an individual.

The second agent that reduces, or is expected to reduce, blood pressure in an individual may be a diuretic, an angiotensin-converting enzyme (ACE) inhibitor, an angiotensin-2 receptor antagonist, a beta blocker, a calcium channel blocker, or any combination thereof. In one variation, the second agent that reduces, or is expected to reduce, blood pressure in an individual is a compound that binds to and is an antagonist of the adrenergic receptor $\alpha_{2B}$ but which is not an antagonist of the adrenergic receptor $\alpha_{2A}$. In one variation, the second agent is a single compound. However, it is understood that the second agent in one embodiment may be two or more compounds, such as a second agent that comprises a first compound that is a diuretic and a second compound that is an ACE-inhibitor.

In one variation, a compound provided herein exhibits equal to or greater than about 50% inhibition of $\alpha_{2A}$ ligand binding at 0.1 μM and antagonist activity to adrenergic receptor $\alpha_{2A}$. In one variation, a compound provided herein exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2A}$ ligand binding at 0.1 μM and antagonist activity to adrenergic receptor $\alpha_{2A}$. In one variation, a compound provided herein exhibits equal to or greater than about 50% inhibition of $\alpha_{2A}$ ligand binding at 0.03 μM and antagonist activity to adrenergic receptor $\alpha_{2A}$. In one variation, a compound provided herein exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2A}$ ligand binding at 0.03 μM and antagonist activity to adrenergic receptor $\alpha_{2A}$.

In another variation, a compound as provided herein (i) binds to and is an antagonist of adrenergic receptor $\alpha_{2A}$ and (ii) exhibits greater than or equal to about 50% inhibition of $\alpha_{2B}$ ligand binding at 0.1 μM and antagonist activity to adrenergic receptor $\alpha_{2B}$. In one such variation, a compound as provided herein exhibits (i) greater than or equal to about 50% inhibition of $\alpha_{2A}$ ligand binding at 0.1 μM and antagonist activity to adrenergic receptor $\alpha_{2A}$ and (ii) greater than or equal to about 50% inhibition of $\alpha_{2B}$ ligand binding at 0.1 μM and antagonist activity to adrenergic receptor $\alpha_{2B}$. When the compound exhibits greater than or equal to about 50% inhibition of $\alpha_{2B}$ ligand binding at 0.1 μM and antagonist activity to adrenergic receptor $\alpha_{2B}$, in some embodiments, it exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2B}$ ligand binding at 0.1 μM and antagonist activity to adrenergic receptor $\alpha_{2B}$. In another variation, a compound as provided herein exhibits (i) greater than or equal to about 50% inhibition of $\alpha_{2A}$ ligand binding at 0.03 μM and antagonist activity to adrenergic receptor $\alpha_{2A}$ and (ii) greater than or equal to about 50% inhibition of $\alpha_{2B}$ ligand binding at 0.03 μM and antagonist activity to adrenergic receptor $\alpha_{2B}$. In another variation, a compound as provided herein exhibits (i) greater than or equal to about 50% inhibition of $\alpha_{2A}$ ligand binding at 0.03 μM and antagonist activity to adrenergic receptor $\alpha_{2A}$ and (ii) greater than or equal to about 50% inhibition of $\alpha_{2B}$ ligand binding at 0.1 μM and antagonist activity to adrenergic receptor $\alpha_{2B}$. In another variation, a compound as provided herein exhibits (i) greater than or equal to about 50% inhibition of $\alpha_{2A}$ ligand binding at 0.1 μM and antagonist activity to adrenergic receptor $\alpha_{2A}$ and (ii) greater than or equal to about 50% inhibition of $\alpha_{2B}$ ligand binding at 0.03 μM and antagonist activity to adrenergic receptor $\alpha_{2B}$. When the compound exhibits greater than or equal to about 50% inhibition of $\alpha_{2B}$ ligand binding at 0.03 μM and antagonist activity to adrenergic receptor $\alpha_{2B}$, in some embodiments, it exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2B}$ ligand binding at 0.03 μM and antagonist activity to adrenergic receptor $\alpha_{2B}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, as if each and every combination were listed separately.

The adrenergic receptor $\alpha_{2A}$ antagonists may also be used in conjunction with other agents that antagonize the adrenergic receptor $\alpha_{2B}$. Administration in conjunction with another compound includes administration in the same or different composition, either sequentially, simultaneously, or continuously.

In one variation, compounds provided herein that bind to and are antagonists of the adrenergic receptor $\alpha_{2A}$ will also bind to and antagonize the adrenergic receptor $\alpha_{1B}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, will also bind to and antagonize the adrenergic receptor $\alpha_{1B}$. In some embodiments, compounds provided herein may exhibit greater than or equal to about 50% inhibition of $\alpha_{1B}$ ligand binding at 0.1 μM and antagonist activity to adrenergic receptor $\alpha_{1B}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.1 μM and antagonist activity to adrenergic receptor $\alpha_{1B}$. In some embodiments, compounds provided herein may exhibit greater than or equal to about 50% inhibition of $\alpha_{1B}$ ligand binding at 0.03 μM and antagonist activity to adrenergic receptor $\alpha_{1B}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.03 μM and antagonist activity to adrenergic receptor $\alpha_{1B}$. For example, in one variation, a compound provided herein exhibits equal to or greater than about 50% inhibition of $\alpha_{2A}$ ligand binding at 0.1 μM and antagonist activity to adrenergic receptor $\alpha_{2A}$ and greater than or equal to about 50% inhibition of $\alpha_{1B}$ ligand binding at 0.1 μM and antagonist activity to adrenergic receptor $\alpha_{1B}$. In another variation, a compound provided herein exhibits equal to or greater than about 50% inhibition of $\alpha_{2A}$ ligand binding at 0.1 μM and antagonist activity to adrenergic receptor $\alpha_{2A}$, greater than or equal to about 50% inhibition of $\alpha_{2B}$ ligand binding at 0.1 μM and antagonist activity to adrenergic receptor $\alpha_{2B}$ and greater than or equal to about 50% inhibition of $\alpha_{1B}$ ligand binding at 0.1 μM and antagonist activity to adrenergic receptor $\alpha_{1B}$. In one variation, a compound provided herein exhibits equal to or greater than about 50% inhibition of $\alpha_{2A}$ ligand binding at 0.1 μM and antagonist activity to adrenergic receptor $\alpha_{2A}$, greater than or equal to about 50% inhibition of $\alpha_{2B}$ ligand binding at 0.1 μM and antagonist activity to adrenergic receptor $\alpha_{2B}$ and greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.1 μM and antagonist activity to adrenergic receptor $\alpha_{1B}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, and/or any of the adrenergic receptor $\alpha_{1B}$ binding profiles described herein as if each and every combination were listed separately.

The adrenergic receptor $\alpha_{2A}$ antagonists may also be used in conjunction with other agents that antagonize the adrenergic receptor $\alpha_{1B}$. Administration in conjunction with another compound includes administration in the same or different composition, either sequentially, simultaneously, or continuously.

In one variation, compounds provided herein that bind to and are antagonists of the adrenergic receptor $\alpha_{2A}$ will also bind to and antagonize the adrenergic receptor $\alpha_{1D}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, will also bind to and antagonize the adrenergic receptor $\alpha_{1D}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, and bind to and are antagonists of the adrenergic receptor $\alpha_{1B}$ will also bind to and antagonize the adrenergic receptor $\alpha_{1D}$. In some embodiments, compounds provided herein may exhibit greater than or equal to about 50% inhibition of $\alpha_{1D}$ ligand binding at 0.1 μM and antagonist activity to adrenergic receptor $\alpha_{1D}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.1 μM and antagonist activity to adrenergic receptor $\alpha_{1D}$. In some embodiments, compounds provided herein may exhibit greater than or equal to about 50% inhibition of $\alpha_{1D}$ ligand binding at 0.03 μM and antagonist activity to adrenergic receptor $\alpha_{1D}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.03 μM and antagonist activity to adrenergic receptor $\alpha_{1D}$. For example, in one variation, a compound provided herein exhibits equal to or greater than about 50% inhibition of $\alpha_{2A}$ ligand binding at 0.1 μM and antagonist activity to adrenergic receptor $\alpha_{2A}$ and greater than or equal to about 50% inhibition of $\alpha_{1D}$ ligand binding at 0.1 μM and antagonist activity to adrenergic receptor $\alpha_{1D}$. In another variation, a compound provided herein exhibits equal to or greater than about 50% inhibition of $\alpha_{2A}$ ligand binding at 0.1 μM and antagonist activity to adrenergic receptor $\alpha_{2A}$, greater than or equal to about 50% inhibition of $\alpha_{2B}$ ligand binding at 0.1 μM and antagonist activity to adrenergic receptor $\alpha_{2B}$ and greater than or equal to about 50% inhibition of $\alpha_{1D}$ ligand binding at 0.1 μM and antagonist activity to adrenergic receptor $\alpha_{1D}$. In another variation, a compound provided herein exhibits equal to or greater than about 50% inhibition of $\alpha_{2A}$ ligand binding at 0.1 μM and antagonist activity to adrenergic receptor $\alpha_{2A}$, greater than or equal to about 50% inhibition of $\alpha_{2B}$ ligand binding at 0.1 μM and antagonist activity to adrenergic receptor $\alpha_{2B}$, greater than or equal to about 50% inhibition of $\alpha_{1B}$ ligand binding at 0.1 μM and antagonist activity to adrenergic receptor $\alpha_{1B}$, and greater than or equal to about 50% inhibition of $\alpha_{1D}$ ligand binding at 0.1 μM and antagonist activity to adrenergic receptor $\alpha_{1D}$. In one variation, a compound provided herein exhibits equal to or greater than about 50% inhibition of $\alpha_{2A}$ ligand binding at 0.1 μM and antagonist activity to adrenergic receptor $\alpha_{2A}$, greater than or equal to about 50% inhibition of $\alpha_{2B}$ ligand binding at 0.1 μM and antagonist activity to adrenergic receptor $\alpha_{2B}$, greater than or equal to about 50% inhibition of $\alpha_{1B}$ ligand binding at 0.1 μM and antagonist activity to adrenergic receptor $\alpha_{1B}$ and greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.1 μM and antagonist activity to adrenergic receptor $\alpha_{1D}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, and/or any of the adrenergic receptor $\alpha_{1B}$ binding profiles described herein and/or any of the adrenergic receptor $\alpha_{1D}$ binding profiles described herein as if each and every combination were listed separately.

The adrenergic receptor $\alpha_{2A}$ antagonists may also be used in conjunction with other agents that antagonize the adrenergic receptor $\alpha_{1D}$. Administration in conjunction with another compound includes administration in the same or different composition, either sequentially, simultaneously, or continuously.

The binding properties to adrenergic receptors of compounds disclosed herein may be assessed by methods known in the art, such as competitive binding assays. In one variation, compounds are assessed by the binding assays detailed herein. In one variation, inhibition of binding of a ligand to a receptor is measured by the assays described herein. In another variation, inhibition of binding of a ligand is measured in an assay known in the art.

Functional Assay Profile

Antagonist activity to the adrenergic receptor $\alpha_{2A}$, $\alpha_{2B}$, $\alpha_{1B}$ and $\alpha_{1D}$ may be assessed by methods known in the art, such as standard $\alpha_{2A}$, $\alpha_{2B}$, $\alpha_{1B}$ and $\alpha_{1D}$ receptor cell membrane-based or intact cell-based activity assays. For example, the Aequorin-based assay may be used to assess antagonist activity to the adrenergic receptor $\alpha_{2A}$, $\alpha_{2B}$, $\alpha_{1B}$ or $\alpha_{1D}$ and the cell membrane-based GTPγS binding assay may be used to assess antagonist activity to the adrenergic receptor $\alpha_{2B}$.

In one variation, adrenergic receptor $\alpha_{2A}$ antagonists as provided herein exhibit an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay.

In another variation, a compound provided herein binds to and is an antagonist of the adrenergic receptor $\alpha_{2A}$, wherein the compound is also an antagonist of the adrenergic receptor $\alpha_{2B}$ and exhibits an $IC_{50}$ value that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an adrenergic receptor $\alpha_{2B}$ antagonist assay. In some embodiments, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay), and (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay). In another variation, a compound provided herein binds to and is an antagonist of the adrenergic receptor $\alpha_{2A}$, wherein the compound is also an antagonist of the adrenergic receptor $\alpha_{1B}$ and exhibits an $IC_{50}$ value that is equal to or less than about any one of 100 nM, 30 nM or 10 nM at a given concentration of agonist (e.g. concentration corresponding to $EC_{80}$ of cirazoline (for Aequorin assay) in an adrenergic receptor $\alpha_{1B}$ antagonist assay. In some embodiments, adrenergic receptor $\alpha_{2A}$ antagonists as provided herein exhibit: (i) an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay, and (ii) an $IC_{50}$ value equal or less than about any one of 100 nM or 30 nM or 10 nM at a given concentration of agonist (e.g. concentration corresponding to $EC_{80}$ of cirazoline) in an adrenergic receptor $\alpha_{1B}$ antagonist assay. In yet another variation, a compound provided herein binds to and is an antagonist of the adrenergic receptor $\alpha_{2A}$, wherein the compound is also an antagonist of the adrenergic receptor $\alpha_{1D}$ and exhibits an $IC_{50}$ value that is equal to or less than about any one of 100 nM, 30 nM or 10 nM at a given concentration of agonist (e.g. concentration corresponding to $EC_{80}$ of cirazoline (for Aequorin assay) in an adrenergic receptor $\alpha_{1D}$ antagonist assay. In some embodiments, adrenergic receptor $\alpha_{2A}$ antagonists as provided herein exhibit: (i) an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay, and (ii) an $IC_{50}$ value equal or less than about any one of 100 nM or 30 nM or 10 nM at a given concentration of agonist (e.g. concentration corresponding to $EC_{80}$ of cirazoline) in an adrenergic receptor $\alpha_{1D}$ antagonist assay.

In yet another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay. In another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay. In another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay; and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay.

In yet another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay; and (iv) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay.

In one variation, adrenergic receptor $\alpha_{2A}$ antagonists as provided herein exhibit an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay. In one variation, adrenergic receptor $\alpha_{2A}$ antagonists as provided herein exhibit an $IC_{50}$ value equal to or less than about 10 nM at a given concentration of agonist (e.g. concentration corresponding to $EC_{80}$ of UK14304 (for Aequorin assay) in an adrenergic receptor $\alpha_{2A}$ antagonist assay. In one variation, adrenergic receptor $\alpha_{2A}$ antagonists as provided herein exhibit an $IC_{50}$ value in an adrenergic receptor $\alpha_{2A}$ antagonist assay equal to or less than about any one of 100 nM, 30 nM or 10 nM at a concentration of UK14304 (for Aequorin assay) corresponding to its $EC_{80}$ concentration obtained by assay protocols described herein. In one variation, adrenergic receptor $\alpha_{2A}$ antagonists as provided herein exhibit an $IC_{50}$ value equal to or less than about any one of 100 nM, 30 nM or 10 nM at a concentration of UK14304 between about 0.4 and about 40 nM in an adrenergic receptor $\alpha_{2A}$ (Aequorin) antagonist assay. In one variation, adrenergic receptor $\alpha_{2A}$ antagonists as provided herein exhibit an $IC_{50}$ value equal to or less than about any one of 100 nM, 30 nM or 10 nM at a concentration of about 4.57 nM UK14304 in an adrenergic receptor $\alpha_{2A}$ (Aequorin) antagonist assay.

In one variation adrenergic receptor $\alpha_{2A}$ antagonists as provided herein exhibit an $IC_{50}$ value equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay. In some embodiments, adrenergic receptor $\alpha_{2A}$ antagonists as provided herein exhibit an $IC_{50}$ value equal to or less than about 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay. In some embodiments, a compound described herein exhibits an $IC_{50}$ value in an $\alpha_{2B}$ antagonist assay equal to or less than about any one of 100 nM, 30 nM or 10 nM at a concentration of oxymetazoline corresponding to its $EC_{80}$ concentration as obtained by assay protocols described herein. In some embodiments, a compound described herein exhibits an $IC_{50}$ value in an $\alpha_{2B}$ antagonist (Aequorin) assay equal to or less than about any one of 100 nM, 30 nM or 10 nM at a concentration of oxymetazoline between about 50 nM to about 5000 nM. In some embodiments, a compound described herein exhibits an $IC_{50}$ value in an $\alpha_{2B}$ antagonist (Aequorin) assay equal to or less than about any one of 100 nM, 30 nM or 10 nM at a concentration of about 480 nM oxymetazoline. In some embodiments, a compound described herein exhibits an $IC_{50}$ value in an $\alpha_{2B}$ antagonist (GTPγS) assay equal to or less than about any one of 100 nM, 30 nM or 10 nM at a concentration of guanfacine between about 50 nM to about 5000 nM. In some embodiments, a compound described herein exhibits an $IC_{50}$ value in an $\alpha_{2B}$ antagonist assay equal to or less than about any one of 100 nM, 30 nM or 10 nM at a concentration of about 500 nM guanfacine, which is a particular variation, is 504 nM guanfacine.

In one variation, a compound described herein exhibits an $IC_{50}$ value in an am antagonist assay equal to or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay. In some embodiments, a compound described herein exhibits an $IC_{50}$ value in an $\alpha_{1B}$ antagonist assay equal to or less than about 10 nM at a given concentration of agonist (e.g. concentration corresponding to $EC_{80}$ of cirazoline) in an adrenergic receptor $\alpha_{1B}$ antagonist assay. In some embodiments, a compound described herein exhibits an $IC_{50}$ value in an $\alpha_{1B}$ antagonist assay equal to or less than about any one of 100 nM, 30 nM or 10 nM at a concentration of cirazoline corresponding to its $EC_{80}$ concentration as obtained by assay protocols described herein. In some embodiments, a compound described herein exhibits an $IC_{50}$ value in an $\alpha_{1B}$ antagonist (Aequorin) assay equal to or less than about any one of 100 nM, 30 nM or 10 nM at a concentration of cirazoline between about 2.3 nM and about 230 nM. In some embodiments, a compound described herein exhibits an $IC_{50}$ value in an $\alpha_{1B}$ antagonist (Aequorin) assay equal to or less than about any one of 100 nM, 30 nM or 10 nM at a concentration of about 25 nM cirazoline, which in a particular variation is 23.56 nM cirazoline.

In one variation, a compound described herein exhibits an $IC_{50}$ value in an am antagonist assay equal to or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay. In some embodiments, a compound described herein exhibits an $IC_{50}$ value in an $\alpha_{1D}$ antagonist assay equal to or less than about 10 nM at a given concentration of agonist (e.g. concentration corresponding to $EC_{80}$ of cirazoline) in an adrenergic receptor $\alpha_{1D}$ antagonist assay. In some embodiments, a compound described herein exhibits an $IC_{50}$ value in an $\alpha_{1D}$ antagonist assay equal to or less than about any one of 100 nM, 30 nM or 10 nM at a concentration of cirazoline corresponding to its $EC_{80}$ concentration as obtained by assay protocols described herein. In some embodiments, a compound described herein exhibits an $IC_{50}$ value in an $\alpha_{1D}$ antagonist assay equal to or less than about any one of 100 nM, 30 nM or 10 nM at a concentration of cirazoline between about 2.3 nM and about 230 nM. In some embodiments, a compound described herein exhibits an $IC_{50}$ value in an $\alpha_{1D}$ antagonist assay equal to or less than about any one of 100 nM, 30 nM or 10 nM at a concentration of about 25 nM cirazoline, which in a particular variation is 23.56 nM cirazoline.

In some embodiments, compounds provided herein exhibit inverse agonist activity for the adrenergic receptor $\alpha_{2A}$. In some embodiments, the compound binds to and is an inverse agonist of the adrenergic receptor $\alpha_{2A}$ and binds to and is antagonist of one or more of the adrenergic receptors $\alpha_{2B}$, $\alpha_{1B}$ and $\alpha_{1D}$. In one variation, the compound binds to and is an inverse agonist of the adrenergic receptor $\alpha_{2A}$ and binds to and is antagonist of any one of the adrenergic receptors $\alpha_{2B}$, $\alpha_{1B}$ and $\alpha_{1D}$. In another variation, the compound binds to and is an inverse agonist of the adrenergic receptor $\alpha_{2A}$ and binds to and is antagonist of any two of the adrenergic receptors $\alpha_{2B}$, $\alpha_{1B}$ and $\alpha_{1D}$. In yet another variation, the compound binds to and is an inverse agonist of the adrenergic receptor $\alpha_{2A}$ and binds to and is antagonist of adrenergic receptors $\alpha_{2B}$, $\alpha_{1B}$ and $\alpha_{1D}$. Inverse agonist activity to the adrenergic receptor $\alpha_{2A}$ may be assessed by methods known in the art, such as those described in Wade, S. M. et al., *Mol. Pharmacol.* 59:532-542 (2001).

It is understood and clearly conveyed herein that any of the binding profiles detailed herein can be combined with any of the antagonist profiles detailed herein, as if each and every combination were listed separately. For example, in one variation, a compound provided herein exhibits (i) greater than or equal to about any one of 50%, 55%, 60%, 65%, 70%, 80%, 85%, 90%, 95%, or between about 50% and 90%, between about 60% and about 90%, between about 70% and about 90%, or about 80% and about 100% inhibition of $\alpha_{2A}$ ligand binding at 0.1 µM to adrenergic receptor $\alpha_{2A}$ and an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay; and (ii) greater than or equal to about any one of 50%, 55%, 60%, 65%, 70%, 80%, 85%, 90%, 95%, or between about 50% and 90%, between about 60% and about 90%, between about 70% and about 90%, or about 80% and about 100% inhibition of $\alpha_{2B}$ ligand binding at 0.1 µM to adrenergic receptor $\alpha_{2B}$ and $IC_{50}$ value equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay.

Medical Use

Without being bound by theory, it is believed that compounds that bind to and are antagonists of the adrenergic receptor $\alpha_{2A}$ affect an increase in insulin secretion and/or promote insulin release into the blood stream in an individual, which aids in glucose uptake. However, such compounds may also increase an individual's blood pressure. When the adrenergic receptor $\alpha_{2A}$ antagonists as provided herein also bind to and are antagonists of the adrenergic receptor $\alpha_{2B}$ and/or the adrenergic receptor $\alpha_{1B}$, and/or the adrenergic receptor $\alpha_{1D}$, it is believed that the increases in an individual's blood pressure due to antagonizing the adrenergic receptor $\alpha_{2A}$ may be reduced or eliminated. If an adrenergic receptor $\alpha_{2A}$ antagonist as provided herein is not also an antagonist of the adrenergic receptor $\alpha_{2B}$ and/or the adrenergic receptor $\alpha_{1B}$ and/or the adrenergic receptor $\alpha_{1D}$, then the increase in an individual's blood pressure as a result of the adrenergic receptor $\alpha_{2A}$ antagonist may be reduced or eliminated by administering the compound in conjunction with a second agent that reduces, or is expected to reduce, blood pressure in an individual.

Compounds provided herein, such as the adrenergic receptor $\alpha_{2A}$ antagonists provided herein, are expected to find use in therapy, particularly in indications in which an increase in an individual's insulin secretion and/or an increase in insulin release into the blood stream would be, or would be expected to be, beneficial. Thus, individuals who have a disease or condition that involves reduced or impaired insulin secretion and/or release may benefit from the compounds detailed herein, or pharmaceutically acceptable salts thereof. Such indications include, but are not limited to type 2 diabetes, glucose intolerance and metabolic syndrome. An individual who has a disease or condition that involves reduced or impaired insulin secretion and/or release may experience one or more beneficial or desirable results upon administration of an adrenergic receptor $\alpha_{2A}$ antagonist provided herein, or pharmaceutically acceptable salt thereof. In one aspect, the beneficial or desirable result is a reduction in the individual's blood glucose level for a period of time (e.g., about any one of 6, 12, 24 or 48 hours or more) following administration of the compound or pharmaceutically acceptable salt thereof. In another aspect, the beneficial or desirable result is an increase in glucose metabolism for a period of time (e.g., about any one of 6, 12, 24 or 48 hours or more) following administration of the compound or pharmaceutically acceptable salt thereof.

Compounds that are inverse agonists of the adrenergic receptor $\alpha_{2A}$ may stimulate islet cell release of insulin even in the absence of sympathetic stimulation of the adrenergic receptor $\alpha_{2A}$ with epinephrine and/or norepinephrine. Inverse agonists of the adrenergic receptor $\alpha_{2A}$ provided herein are thus expected to find use in therapy, particularly in indications in which stimulation of islet cell release of insulin would be, or would be expected to be, beneficial. Individuals who have a disease or condition responsive to inhibition of the adrenergic receptor $\alpha_{2A}$ may benefit from the compounds detailed herein, or pharmaceutically acceptable salts thereof. Such indications include, but are not limited to type 2 diabetes, metabolic syndrome, and glucose intolerance.

In one aspect, compounds are provided that do not bind appreciably any one or more of the histamine, dopamine and serotonin receptors. In any of the methods detailed herein, in one variation the individual does not have a cognitive disorder, psychotic disorder, neurotransmitter-mediated disorder and/or neuronal disorder. As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI). As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression. As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

The adrenergic receptor $\alpha_{2A}$ antagonists provided herein may also be administered in combination with an insulin sensitizer, and as such find use in therapy for treating indications in which increasing in an individual's insulin secretion and/or insulin release into the blood stream would be, or would be expected to be, beneficial, provided that the therapy also promotes insulin responsiveness to glucose. In one aspect, where the adrenergic receptor $\alpha_{2A}$ antagonists provided herein may be administered in combination with another anti-diabetic drug, such as an insulin sensitizer, the beneficial or desirable result of which is a reduction in the individual's blood glucose levels for a period of time (e.g., about any one of 6, 12, 24 or 48 hours or more) following administration of the compound or pharmaceutically acceptable salt thereof. In a particular variation, such a therapy may include an adrenergic receptor $\alpha_{2A}$ antagonist provided herein and a second agent that reduces, or is expected to reduce, blood pressure and an insulin sensitizer. In a further variation, such a therapy may include an adrenergic receptor $\alpha_{2A}$ antagonist provided herein and a second agent that (i) is an agent that reduces, or is expected to reduce, blood pressure; (ii) is an agent that is an insulin sensitizer or (iii) is an agent that induces no or reduced (in number and/or severity) hypoglycemic episodes.

Methods

Methods of using the compounds detailed herein, or pharmaceutical salts thereof, to increase an individual's ability to secrete insulin and/or to release insulin into the blood stream are provided. In any of the methods detailed herein, the method may comprise the step of administering an adrenergic receptor $\alpha_{2A}$ antagonist, or pharmaceutically acceptable salt thereof, to an individual in need thereof. In one aspect, the adrenergic receptor $\alpha_{2A}$ antagonists of the methods also bind to and are antagonists of one or more of the adrenergic receptors $\alpha_{2B}$, $\alpha_{1B}$ and $\alpha_{1D}$. In one variation, a method of increasing insulin secretion and/or release into the blood stream in an individual in need thereof is provided, wherein the method comprises administering to an individual in need thereof a compound that binds to and is an antagonists of the adrenergic receptor $\alpha_{2A}$. In another variation, a method of increasing insulin secretion and/or release into the blood stream in an individual in need thereof is provided, wherein the method comprises administering to an individual in need thereof a compound that binds to and is an antagonists of the adrenergic receptor $\alpha_{2A}$, wherein the compound either (a) also binds to and is an antagonist of the adrenergic receptor $\alpha_{2B}$ or (b) is administered in conjunction with a second agent that reduces, or is expected to reduce, blood pressure in the individual. In some variations, methods of using the compounds detailed herein to increase an individual's ability to secrete insulin and/or release insulin into the blood stream while reducing or eliminating an increase in the individual's blood pressure due to antagonizing the adrenergic receptor $\alpha_{2A}$ are thus provided. Methods of using the compounds detailed herein to promote an individual's ability to metabolize glucose while reducing or eliminating an increase in the individual's blood pressure due to antagonizing the adrenergic receptor $\alpha_{2A}$ are also provided. It is understood that in methods of promoting an individual's ability to metabolize glucose, the method in one variation may employ administration of both an adrenergic receptor $\alpha_{2A}$ antagonist and an insulin sensitizer. The compounds or pharmaceutical salts thereof may also find use in treating a disease or condition that is, or is expected to be, responsive to an increase in an individual's ability to secrete insulin and/or release of insulin into the blood stream. Individuals to be treated in such methods in one variation have a reduced or impaired ability to secrete insulin and/or release insulin into the blood stream. The compounds as provided herein may also be used in a method of delaying the onset and/or development of a disease or condition associated with reduced or impaired ability to secrete insulin and/or release insulin into the blood stream, comprising administering a compound as provided herein, or a pharmaceutical salt thereof, to an individual who is at risk of developing a disease or condition associated with reduced or impaired ability to secrete insulin and/or release insulin into the blood stream. The compounds as provided herein may also be used in a method of delaying the onset and/or development of a disease or condition associated with reduced or impaired ability to metabolize glucose, comprising administering an adrenergic receptor $\alpha_{2A}$ antagonist as provided herein, or a pharmaceutical salt thereof, to an individual who is at risk of developing a disease or condition associated with reduced or impaired ability to metabolize glucose. The individual may be an adult, child or teen who has or is at risk of developing type 2 diabetes, glucose intolerance or metabolic syndrome.

Non-limiting examples of a second agent that lowers blood pressure include diuretics, angiotensin-converting enzyme (ACE) inhibitors, angiotensin-2 receptor antagonists, beta blockers, calcium channel blockers, or any combination thereof.

Also provided herein are methods of using an adrenergic receptor $\alpha_{2A}$ antagonist, or a pharmaceutically acceptable salt thereof, in combination with one or more of other anti-diabetic agents, such as insulin sensitizers and secretagogue agents. Non-limiting examples of anti-diabetic agents include insulin therapies (e.g., insulin glargine and insulin lispro), secretagogue agents that increase insulin secretion and/or release (e.g., sulfonylureas such as glimepiride, glipizide and glyburide; meglitinides such as repaglinide and nateglinide), agents that increase insulin sensitivity (e.g., thiazolidinediones, such as pioglitazone and rosiglitazone), agents that decrease glucose absorption (e.g., alpha-glucosidase inhibitors such as miglitol and acarbose); and agents that reduce gluconeogenesis (biguanide such as metformin); amylinomimetics such as pramlintide, and agents that sequester bile acids.

Further provided herein are methods of using an adrenergic receptor $\alpha_{2A}$ antagonist, or a pharmaceutically acceptable salt thereof, in combination with an insulin sensitizer to promote insulin responsiveness and increase an individual's ability to secrete insulin and/or to release insulin into the blood stream. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In one variation, a method of promoting insulin responsiveness and increasing insulin secretion and/or release into the blood stream in an individual in need thereof is provided, wherein the method comprises administering to an individual in need thereof an insulin sensitizer and an adrenergic receptor $\alpha_{2A}$ antagonist. In another variation, a method of promoting insulin responsiveness and increasing insulin secretion and/or release into the blood stream in an individual in need thereof is provided, wherein the method comprises administering to an individual in need thereof an insulin sensitizer and a compound that binds to and is an antagonists of the adrenergic receptor $\alpha_{2A}$, wherein the compound either (a) also binds to and is an antagonist of the adrenergic receptor $\alpha_{2B}$ or (b) is administered in conjunction with a second agent that reduces, or is expected to reduce, blood pressure in the individual. In a particular variation, a method of promoting insulin responsiveness and increasing insulin secretion and/or release into the blood stream in an individual in need thereof is provided, wherein the method comprises administering to an individual in need thereof an insulin sensitizer and an adrenergic receptor $\alpha_{2A}$ antagonist that also binds to and is an antagonist of one or more of the adrenergic receptors $\alpha_{2B}$, $\alpha_{1B}$ and $\alpha_{1D}$. In some embodiments, the method comprises administering any of the compounds detailed herein in combination with an insulin sensitizer.

In one aspect, a method of treating type 2 diabetes is provided, where the method comprises administering to an individual in need thereof a compound detailed herein, such as an adrenergic receptor $\alpha_{2A}$ antagonist detailed herein. In one aspect, the compound binds to and is an adrenergic receptor $\alpha_{2A}$ antagonist. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating type 2 diabetes is provided, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in an individual. Individuals to be treated in such methods in one variation have type 2 diabetes. The compounds as provided herein may also be used in a method of delaying the onset and/or development of type 2 diabetes, comprising administering an adrenergic receptor $\alpha_{2A}$ antagonist, or pharmaceutically acceptable salt thereof, to an individual who has one or more risk factors associated with developing type 2 diabetes. In one variation, the compounds as provided herein are used in a method of delaying the onset and/or development of type 2 diabetes; and inducing extra-pancreatic effects such as reducing hepatic glucose production via glycogenolysis or gluconeogenesis or both, comprising administering an adrenergic receptor $\alpha_{2A}$ antagonist, or pharmaceutically acceptable salt thereof, to an individual such as an individual who has one or more risk factors associated with developing type 2 diabetes. In one variation, compounds provided herein may (i) have an extra-pancreatic effect and/or (ii) prevent or lower hepatic glucose production.

Risk factors may include gender, race, ethnicity, age, family history, weight and/or lifestyle. For example, certain races and ethnicities (e.g., Blacks, Hispanics, Native Americans and Asians (which as used herein includes individuals of the continent of Asia, such as Indians and Chinese) and individuals of such descent) are more likely to develop type 2 diabetes. Being overweight (e.g., having a body mass index >25) is also a risk factor for type 2 diabetes, with higher amount of fatty tissue also correlating with higher resistance of cells to insulin. Inactivity, which can lead to weight gain, is also a risk factor for type 2 diabetes (physical activity helps not only to control an individual's weight, but also utilizes glucose as energy and makes cells more sensitive to insulin). Family history is often a risk factor for many diseases, including type 2 diabetes, where the risk of developing type 2 diabetes increases if a parent or sibling has type 2 diabetes. The risk of developing type 2 diabetes also increases with age, especially after age 45, which may also correlate with a tendency to exercise less, lose muscle mass and gain weight with age. However, as obesity rates rise in children and young adults, type 2 diabetes is increasing common in these individuals and children and young adults who are overweight and/or sedentary are also at risk of developing type 2 diabetes. Being pre-diabetic, in which an individual's blood sugar level is higher than normal, but not high enough to be classified as type 2 diabetes, if left untreated, often progresses to type 2 diabetes. Other risk factors associated with type 2 diabetes include: a woman who has had gestational diabetes, gave birth to a baby weighing more than 9 pounds or has a history of polycystic ovary disease (PCOS); an individual who has metabolic syndrome; an individual who has hypertension; an individual who has a high-density lipoprotein (HDL) value under 35 mg/dL (milligrams per deciliter) and/or a triglyceride level over 250 mg/dL; and an individual with a history of vascular disease, such as stroke. Individuals who have more than one risk factor are particularly susceptible to developing type 2 diabetes.

In one aspect, a method of treating glucose intolerance is provided, where the method comprises administering to an individual in need thereof an adrenergic receptor $\alpha_{2A}$ antagonist, or pharmaceutically acceptable salt thereof. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating glucose intolerance is provided, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in the individual. The compounds as provided herein may also be used in a method of delaying the onset and/or development of glucose intolerance, comprising administering a compound as provided herein to an individual who has one or more risk factors associated with developing glucose intolerance. A method of reducing blood glucose levels in an individual in need thereof is also provided, the method comprising administering an adrenergic receptor $\alpha_{2A}$ antagonist, or pharmaceutically acceptable salt thereof, to the individual. A method of enhancing glucose metabolism in an individual in need thereof is also provided, the method comprising administering an adrenergic receptor $\alpha_{2A}$ antagonist, or pharmaceutically acceptable salt thereof, to the individual.

Further provided are methods of using the compounds detailed herein, or pharmaceutical salts thereof, to regulate blood glucose levels in an individual, for example, an individual experiencing hyperglycemia and/or undesirable fluctuation in blood glucose levels. In some embodiments, provided is a method of regulating blood glucose levels in an individual in need thereof, where the method comprises administering to an individual in need thereof an adrenergic receptor $\alpha_{2A}$ antagonist. In some embodiments, administration of an adrenergic receptor $\alpha_{2A}$ antagonist reduces the blood glucose levels in an individual (e.g., a hyperglycemic individual). In some embodiments, administration of an adrenergic receptor $\alpha_{2A}$ antagonist stabilizes the blood glucose levels in an individual (e.g., an individual experiencing undesirable fluctuations in blood glucose levels). In some embodiments, administration of an adrenergic receptor $\alpha_{2A}$ antagonist reduces and stabilizes the blood glucose levels in an individual. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, provided is a method of regulating (e.g., reducing and/or stabilizing) blood glucose levels in an individual in need thereof, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in an individual. In some embodiments, the adrenergic receptor $\alpha_{2A}$ antagonist described herein may also be an inverse agonist of the adrenergic receptor $\alpha_{2A}$.

In some embodiments, provided is a method of reducing blood glucose level in an individual in need thereof, comprises administering to an individual in need thereof an adrenergic receptor $\alpha_{2A}$ antagonist, wherein the blood glucose level is reduced to a desirable level. The adrenergic receptor $\alpha_{2A}$ antagonist may be administered alone or in combination with other agents such as an agent that reduces blood pressure in the individual. In some embodiments, the blood glucose level is reduced by about 10%, about 20%, about 30%, about 40%, about 50%, about 60%, or about 70%, provided that the reduction in glucose level does not result in hypoglycemia. In some embodiments, the blood glucose level is reduced by at least about 10%, at least about 20%, at least about 30%, at least about 40%, at least about 50%, or at least about 60%, provided that the reduction in glucose level does not result in hypoglycemia. In some embodiments, the blood glucose level is reduced by less than about 10%, between about 10% and about 30%, between about 30% and about 50%, between about 10% and about 50%, between about 50% and about 70%, between about 30% and about 70%, between about 20% and about 40%, between about 40% and about 60%, or between about 20% and about 60%, provided that the reduction in glucose level does not result in hypoglycemia. The reduction of blood glucose level occurs over a period of time after administration of the adrenergic receptor $\alpha_{2A}$ antagonist. In some embodiments, the reduction of blood glucose occurs within about 15 minutes after administration of the compound or pharmaceutically acceptable salt thereof. In some embodiments, the reduction of blood glucose occurs within about 30 minutes, within about 1 hour, or within about 2 hours after administration of the adrenergic receptor $\alpha_{2A}$ antagonist. In some embodiments, the reduction of blood glucose occurs at about 15 minutes or more, at about 30 minutes or more, at about 1 hour or more, or at about 2 hours or more after administration of the adrenergic receptor $\alpha_{2A}$ antagonist. In some embodiments, the method results in a reduction in the individual's blood glucose level by any of the amount described herein for a period of time (e.g., about any one of 0.5, 1, 2, 3, 6, 12, 24 or 48 hours or more) following administration of the compound or pharmaceutically acceptable salt thereof. In some embodiments, the method results in a reduction in the individual's blood glucose level by any of the amount described herein for a period of about 1 hour, about 2 hours, about 3 hours, about 6 hours, about 12 hours, or about 24 hours or more following administration of the compound or pharmaceutically acceptable salt thereof.

The blood glucose levels in an individual can be measured by methods known in the art, such as by a calorimetric method or by using a device (e.g., a glucose meter). A blood glucose level in the range of about 80 to 120 mg/dL pre-meal and about 100 to 140 mg/dL post-meal is considered desirable in healthy human beings. A blood glucose level at above the desirable level is considered hyperglycemic, such as that in diabetic patients. The blood glucose level in a mildly diabetic human is about 100 to 200 mg/dL. The blood glucose level in a moderately diabetic human is about 200 to 350 mg/dL. The blood glucose level in a severely diabetic human is above 400 mg/dL. A blood glucose level at below the desirable level is considered hypoglycemic, e.g., at below 60 to 80 mg/dL. The blood glucose levels may be measured at a single time point. However, a more accurate measurement requires an average over multiple time points or an area under the curve (AUC) over a period of time (e.g., 2 to 3 hours). The blood glucose level over a past period of about 2~3 months may be established by measuring the glycosylated hemoglobin (HbA1c) level in the blood. HbA1c is a useful way to monitor a patient's overall response to diabetes treatment over time. The HbA1c in a healthy human being is about 5%. It is desirable for a diabetic patient to keep the HbA1c level below about 7%. Provided is a method of reducing blood glucose level in an individual having an Hb1Ac level of above about 7%, comprises administering to the individual an adrenergic receptor $\alpha_{2A}$ antagonist, wherein the Hb1Ac level is reduced to below about 7% following administration of the compound or pharmaceutically acceptable salt thereof. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$.

In one aspect, a method of treating metabolic syndrome is provided, where the method comprises administering to an individual in need thereof a compound detailed herein, such as an adrenergic receptor $\alpha_{2A}$ antagonist detailed herein. In one aspect, the compound binds to and is an adrenergic receptor $\alpha_{2A}$ antagonist. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating metabolic syndrome is provided, where the method comprises administering to an individual in need thereof a compound as provided herein, wherein the compound binds to and is an antagonist of the adrenergic receptor $\alpha_{2A}$, and wherein the compound either (a) also binds to and is an antagonist of the adrenergic receptor $\alpha_{2B}$ or (b) is administered in conjunction with a second agent that reduces, or is expected to reduce, blood pressure in an individual. The compounds as provided herein may also be used in a method of delaying the onset and/or development of metabolic syndrome, comprising administering a compound as provided herein to an individual who has one or more risk factors associated with developing metabolic syndrome. In a particular variation of the methods relating to metabolic syndrome, the adrenergic receptor $\alpha_{2A}$ antagonist is administered to an individual in conjunction with an insulin sensitizer.

As is understood by those of skill in the art, metabolic syndrome is a cluster of conditions, which may include increased blood pressure, excess body fat around the waist, abnormal cholesterol levels and elevated insulin levels due to insulin resistance whereby cells have a diminished ability to respond to insulin and the pancreas compensates by secreting more insulin leading to high insulin levels in blood. According to the American Heart Association and the National Heart, Lung, and Blood Institute, metabolic syndrome is present if an individual has three or more of the following signs: blood pressure equal to or higher than 130/85 mm Hg; fasting blood sugar (glucose) equal to or higher than 100 mg/dL; large waist circumference, which for men is 40 inches or more and for women is 35 inches or more; low HDL cholesterol, which for men is under 40 mg/dL and for women is under 50 mg/dL; and triglycerides equal to or higher than 150 mg/dL.

Treatment of metabolic syndrome requires a careful and well-balanced approach to account for both treatment of elevated insulin levels and high blood pressure. Thus, it is desirable in the context of treating metabolic syndrome that a compound that is an antagonist of the adrenergic receptor $\alpha_{2A}$ is also an antagonist of the adrenergic receptor $\alpha_{2B}$ and/or $\alpha_{1B}$ and/or $\alpha_{1D}$ to reduce blood pressure. Alternatively, an adrenergic receptor $\alpha_{2A}$ antagonist that does not also antagonize the adrenergic receptor $\alpha_{2B}$ and/or $\alpha_{1B}$ may be administered in conjunction with a second agent that reduces, or is expected to reduce blood pressure in an individual. In one aspect, provided is a method of regulating (e.g., reducing and/or stabilizing) blood glucose levels and reducing the blood pressure in an individual in need thereof (e.g., an individual experiencing metabolic syndrome, or an individual with hypertension who is also suffering from obesity and/or type 2 diabetes), where the method comprises administering to an individual in need thereof an adrenergic receptor $\alpha_{2A}$ antagonist. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, provided a method of regulating (e.g., reducing and/or stabilizing) blood glucose levels and reducing the blood pressure in an individual in need thereof, where the method comprises administering to an individual in need thereof a compound as provided herein, wherein the compound binds to and is an antagonist of the adrenergic receptor $\alpha_{2A}$, and wherein the compound either (a) also binds to and is an antagonist of the adrenergic receptor $\alpha_{2B}$ or (b) is administered in conjunction with a second agent that reduces, or is expected to reduce, blood pressure in an individual. In some embodiments, the compound is an antagonist and an inverse agonist of the adrenergic receptor $\alpha_{2A}$.

Risk factors associated with developing metabolic syndrome include: more than one parent or sibling who has type 2 diabetes, individuals with high blood pressure and/or cardiovascular disease; individuals who are obese or overweight (e.g., individual's having a body mass index above 25); individuals who have more fat around their waist than around their hips (an apple shape); age greater than 40 years (although it is understood that children and young adults, particularly those who are overweight and/or sedentary, may also be at risk for developing metabolic syndrome); a woman who had gestational diabetes when pregnant or who has a history of polycystic ovary syndrome (PCOS); individuals who are pre-diabetic and individuals of Latino, Black, Asian or Native American ethnicity.

Further provided herein are methods of determining if an individual suffering from glucose intolerance (e.g., an individual testing negative in a glucose tolerance test) has (i) reduced or impaired insulin secretion or (ii) has reduced or impaired responsiveness to insulin, the method comprising administering a compound provided herein to the individual and testing the individual in a glucose tolerance test, wherein an increase in insulin levels after glucose challenge (the glucose tolerance test) indicates that the individual has reduced or impaired insulin secretion; or wherein insufficient increases in insulin levels indicates that the individual has reduced or impaired responsiveness to insulin.

Provided herein are methods of assessing whether an individual is likely to be responsive to a compound that promotes an increase in insulin secretion and/or release (e.g., an adrenergic receptor $\alpha_{2A}$ antagonist, or pharmaceutically acceptable salt thereof), administered either alone or in conjunction with an insulin sensitizer. In one aspect of such a method, an individual who has failed a glucose tolerance test (e.g., an individual whose glucose levels do not return to normal levels following glucose challenge and/or whose insulin levels are not sufficiently elevated in response to administration of glucose, as measured by methods and as assessed by standards known in the art), is administered glucose following administration of an adrenergic receptor $\alpha_{2A}$ antagonist, or pharmaceutically acceptable salt thereof, and their insulin levels are then assessed. In one embodiment of such methods, the adrenergic receptor $\alpha_{2A}$ antagonist is administered to the individual about any one of 5, 10, 15, 30 and 60 minutes or more or between about 5 and about 15 or between about 5 and about 30 or between about 5 and about 60 or between about 15 and about 30 or between about 30 and about 60 minutes prior to administration of glucose. If such an individual, after administration of glucose and an adrenergic receptor $\alpha_{2A}$ antagonist, or pharmaceutically acceptable salt thereof, exhibits an increase in insulin levels, the individual may be an individual who is responsive to a compound that promotes an increase in insulin secretion and/or release (e.g., an adrenergic receptor $\alpha_{2A}$ antagonist, or pharmaceutically acceptable salt thereof). If such an individual exhibits an increase in insulin levels, but the individual's glucose levels do not decrease, then the individual may be an individual who is responsive to a compound that can increase insulin secretion and/or release (including but not limited to an adrenergic receptor $\alpha_{2A}$ antagonist, or pharmaceutically acceptable salt thereof), used in conjunction with an insulin sensitizer. Sufficient levels of insulin increase and/or glucose decrease are known by those of skill in the art. Thus, a method of assessing whether an individual suffering from glucose intolerance (e.g., an individual who has failed (e.g., within the last 6 months, 3 months, 1 month, 2 weeks or 1 week) a glucose tolerance test administered in the absence of an adrenergic receptor $\alpha_{2A}$ antagonist) is more likely to be responsive or less likely to be responsive to a therapy that can increase insulin secretion and/or release (including but not limited to an adrenergic receptor $\alpha_{2A}$ antagonist, or pharmaceutically acceptable salt thereof), is provided, the method comprising administering an adrenergic receptor $\alpha_{2A}$ antagonist, or pharmaceutically acceptable salt thereof, to the individual and testing the individual in a glucose tolerance test, wherein an increase in insulin levels after glucose challenge (the glucose tolerance test) indicates that the individual is more likely to be responsive to said therapy, and wherein a reduced or insignificant or no increase in insulin levels indicates that the individual is less likely to be responsive to said therapy.

Also provided herein are methods of selecting an individual suffering from glucose intolerance (e.g., an individual who has failed a glucose tolerance test) for a therapy comprising a compound which increases insulin secretion and/or release (e.g. an adrenergic receptor $\alpha_{2A}$ antagonist) based on the levels of insulin and/or glucose of the individual following a glucose tolerance test in which the individual is administered an adrenergic receptor $\alpha_{2A}$ antagonist prior to glucose challenge, wherein an increase in insulin levels after glucose challenge and/or failure of the individual's glucose levels to return to normal selects the individual for said therapy. Thus, a method of selecting an individual for therapy comprising a compound that increases insulin secretion and/or release is provided (e.g., an adrenergic receptor $\alpha_{2A}$ antagonist), the method comprising the steps of (i) administering an adrenergic receptor $\alpha_{2A}$ antagonist to an individual who has failed (e.g., within the last 6 months, 3 months, 1 month, 2 weeks or 1 week) a glucose tolerance test administered in the absence of an adrenergic receptor $\alpha_{2A}$ antagonist; (2) administering a glucose tolerance test in which glucose is administered after the administration of the adrenergic receptor $\alpha_{2A}$ antagonist; and (3) correlating the results of the glucose tolerance test administered in conjunction with the administration of the adrenergic receptor $\alpha_{2A}$ antagonist to the individual (e.g., where glucose is administered about any one of 5, 15, 30, 60 or more minutes following administration of the adrenergic receptor $\alpha_{2A}$ antagonist) with whether the individual is more or less likely to be responsive to an adrenergic receptor $\alpha_{2A}$ antagonist, either alone, or in conjunction with an insulin sensitizer; and (4) selecting an individual who is more likely to be responsive to a compound that increases insulin secretion and/or release (e.g., an adrenergic receptor $\alpha_{2A}$ antagonist for adrenergic receptor $\alpha_{2A}$ antagonist therapy). An individual so selected may then be administered a compound that increases insulin secretion and/or release (e.g., an adrenergic receptor $\alpha_{2A}$ antagonist for adrenergic receptor $\alpha_{2A}$ antagonist therapy). In one aspect, the individual is selected for therapy if their insulin levels increase in response to the glucose tolerance test administered in conjunction with the administration of the adrenergic receptor $\alpha_{2A}$ antagonist. If such an individual also exhibits a normal reduction in glucose levels, the individual may be selected for monotherapy with a compound that increases insulin secretion and/or release (e.g., an adrenergic receptor $\alpha_{2A}$ antagonist). However, if such an individual does not exhibit a normal reduction in glucose levels, the individual may be selected for therapy with a compound that increases insulin secretion and/or release (e.g., an adrenergic receptor $\alpha_{2A}$ antagonist) in conjunction with an insulin sensitizer. Individuals so selected may then be administered a compound that increases insulin secretion and/or release (e.g., an adrenergic receptor $\alpha_{2A}$ antagonist), either alone or in conjunction with an insulin sensitizer. Methods of monitoring the treatment of an individual for glucose intolerance are also provided.

Also provided herein are methods of treating an individual suffering from a disease or condition which is, or is expected to be, responsive to an increase in insulin secretion and/or release, the method comprising (i) determining insulin levels of an individual in a glucose tolerance test after administration of an adrenergic receptor $\alpha_{2A}$ antagonist and (ii) administering a compound that increases insulin secretion and/or release (e.g., an adrenergic receptor $\alpha_{2A}$ antagonist) to an individual having an increase in insulin levels after the glucose tolerance test. In one aspect of such a method, the individual has failed (e.g., recently failed) a glucose tolerance test administered in the absence of an adrenergic receptor $\alpha_{2A}$ antagonist and the individual's insulin levels increase in response to a glucose tolerance test which employed administration of glucose and an adrenergic receptor $\alpha_{2A}$ antagonist.

In any of the methods employing a glucose tolerance test in conjunction with an adrenergic receptor $\alpha_{2A}$ antagonist, in one variation, if the individual's insulin does not increase in response to a glucose challenge in conjunction with an adrenergic receptor $\alpha_{2A}$ antagonist, the individual may have type 2 diabetes with a defect in insulin secretion. Therefore, also provided are methods of identifying individuals who may have type 2 diabetes with a defect in insulin secretion.

Some genetic polymorphisms of the adrenergic receptor $\alpha_{2A}$ gene associate with high blood glucose and can be used to screen for patients who respond to an adrenergic receptor $\alpha_{2A}$ antagonist with an increase in insulin secretion and a decrease in blood glucose. For example the DNA polymorphism Rs553668 located in the 3' UTR region of adrenergic receptor $\alpha_{2A}$ associates with overexpression of the adrenergic receptor $\alpha_{2A}$, reduced insulin secretion, and increased type 2 diabetes risk (Rosengren et al., *Science* 327:217 (2010) and Talmud et al., *Diabetologia* 54:1710 (2011)). Human pancreatic islets from Rs553668 allele carriers exhibited reduced granule docking and secreted less insulin in response to glucose. Individuals with elevated blood glucose would be screened for the polymorphism. Individuals heterozygous or homozygous for this polymorphism would be anticipated to respond to treatment with an adrenergic receptor $\alpha_{2A}$ antagonist. Other DNA polymorphisms may also be used to identify individuals with elevated blood sugar that would respond to an adrenergic receptor $\alpha_{2A}$ antagonist; for example Rs7911129, Rs1971596, Rs602618, and Rs2203616. Thus provided herein is a method of selecting an individual for therapy comprising a compound that (i) increases insulin secretion and/or release, and/or (ii) regulates blood glucose (e.g., an adrenergic receptor $\alpha_{2A}$ antagonist), the method comprising screening the individual for polymorphisms of the adrenergic receptor $\alpha_{2A}$ gene associate with high blood glucose, such as one or more of the DNA polymorphisms Rs553668, Rs7911129, Rs1971596, Rs602618 and Rs2203616.

Also provided is a method of regulating (e.g., reducing and/or stabilizing) blood glucose levels in an individual, the method comprises the steps of (i) screening the individual for genetic polymorphisms of the adrenergic receptor $\alpha_{2A}$ gene associate with high blood glucose; and (ii) administering to the individual carrying one or more genetic polymorphisms of the adrenergic receptor $\alpha_{2A}$ gene associated with high blood glucose an adrenergic receptor $\alpha_{2A}$ antagonist. In one variation, provided is a method of increasing insulin seretion and/or release into the blood stream in an individual, the method comprises the steps of (i) screening the individual for genetic polymorphisms of the adrenergic receptor $\alpha_{2A}$ gene associate with high blood glucose; and (ii)

administering to the individual carrying one or more genetic polymorphisms of the adrenergic receptor $\alpha_{2A}$ gene associated with high blood glucose an adrenergic receptor $\alpha_{2A}$ antagonist. Further provided are methods of treating type 2 diabetes, glucose intolerance and/or metabolic syndrome, where the method comprises administering to an individual in need thereof an adrenergic receptor $\alpha_{2A}$ antagonist, wherein the individual carries one or more genetic polymorphisms of the adrenergic receptor $\alpha_{2A}$ gene associated with high blood glucose, such as one or more of the DNA polymorphisms Rs553668, Rs7911129, Rs1971596, Rs602618 and Rs2203616. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In some embodiments, the adrenergic receptor $\alpha_{2A}$ antagonist also binds to and is an antagonist of the adrenergic receptors $\alpha_{2B}$. In some embodiments, the method of regulating blood glucose levels, increasing insulin seretion and/or release into the blood stream, or treating type 2 diabetes, glucose intolerance and/or metabolic syndrome, further comprises administering to the individual a second agent that reduces, or is expected to reduce, blood pressure in an individual.

Compounds described herein showing adrenergic receptors $\alpha_{2A}$ and adrenergic receptor $\alpha_{2B}$ antagonist activity may find particular use in patients with fatty liver or/and obesity or/and hypertension with type-2 diabetes associated with glucose intolerance; and super-added with polymorphisms in the adrenergic receptor $\alpha_{2A}$ gene.

Cell Viability and Mitochondrial Health

Methods of promoting cellular viability by promoting mitochondrial health are provided, the methods comprising contacting the cell with a compound detailed herein. The methods are applicable to various cells, such as neuronal and non-neuronal cells. In one variation, the cell is a non-neuronal cell, such as a renal or cardiac cell (e.g., myocardial muscle cell). In one aspect, methods of promoting cellular viability are provided wherein the cell is one whose viability would be, or would be expected to be, promoted by nutrient influx and/or oxygenation. Methods of promoting cellular viability in a cell experiencing, or exhibiting symptoms of, mitochondrial stress are also provided.

Methods of treating a disease or condition that is, or is expected to be, responsive to promoting mitochondrial health and cell viability are also described, the methods comprising administering to an individual in need thereof an effective amount of a compound provided herein. In one variation, the disease or condition is one which is associated with dysfunction of mitochondria in a non-neuronal cell. In a particular variation, the disease or condition is one which is associated with dysfunction of mitochondria in a renal or cardiac cell (e.g., myocardial muscle cell). In another variation, the disease or condition is one which would benefit from cellular (e.g., renal or cardiac) nutrient influx and/or oxygenation.

Thus, individuals who have a disease or condition that is associated with, or believed to be associated with, mitochondrial dysfunction may benefit from the compounds detailed herein, or pharmaceutically acceptable salts thereof. An individual who has a disease or condition that is associated with mitochondrial dysfunction should experience one or more beneficial or desirable results upon administration of an effective amount of a compound provided herein, or pharmaceutically acceptable salt thereof. In one aspect, the beneficial or desirable result is an increase in nutrient influx and/or oxygenation of a cell. In another aspect, the beneficial or desirable result is a reduction in the number and/or severity of symptoms associated with a disease or condition that is associated with mitochondrial dysfunction.

In one variation, a method of treating a renal or cardiac condition is provided, comprising administering to an individual in need thereof a compound as detailed herein. Such conditions include, but are not limited to, renal failure, such as acute renal failure and chronic renal failure, coronary (e.g., myocardial) ischemia, heart failure, such as acute and chronic congestive heart failure (including the muscle fatigue associated with these conditions), and coronary artery disease. Methods of treating other diseases and conditions are also described, such as methods of treating sleep apnea, acute respiratory distress syndrome (adult and infant) and peripheral vascular disease. The compounds as provided herein may also be used in a method of delaying the onset and/or development of a disease or condition associated with mitochondrial dysfunction, comprising administering a compound as provided herein, or a pharmaceutical salt thereof, to an individual who is at risk of developing a disease or condition associated with mitochondrial dysfunction.

Compounds that do not bind appreciably to neurotransmitter receptors but nevertheless enhance mitochondrial function, e.g., when administered to cells in the setting of mitochondrial stress (e.g., excess intracellular calcium), may be used in the methods herein to promote cell survival. In one aspect, the compounds exhibit the ability to enhance mitochondrial function by protecting against cell death mediated by mitochondrial dysfunction in an assay detailed herein. Thus, it is understood and clearly conveyed that enhancing mitochondrial function includes protecting a cell against cell death mediated by mitochondrial dysfunction. The compounds may also be assessed in assays known in the art.

It is understood and clearly conveyed that the binding and activity profiles detailed herein (e.g., in the disclosure above) in one variation apply to the formulae provided herein (e.g., the formulae for use in the methods). In one aspect, selective adrenergic receptor $\alpha_{2B}$ antagonists are of the formula (I) or any variations detailed herein.

Compounds of the Invention

Compounds according to the invention are detailed herein, including in the Brief Summary of the Invention and elsewhere. The invention includes the use of all of the compounds described herein, including any and all stereoisomers, including geometric isomers (cis/trans or E/Z isomers), salts and solvates of the compounds described herein, as well as methods of making such compounds.

In one aspect, compounds of formulae (A1)-(A2) are provided:

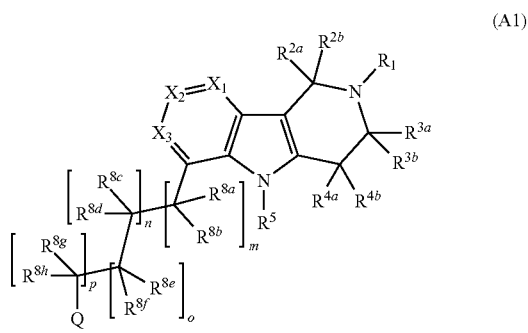

(A1)

-continued (A2)

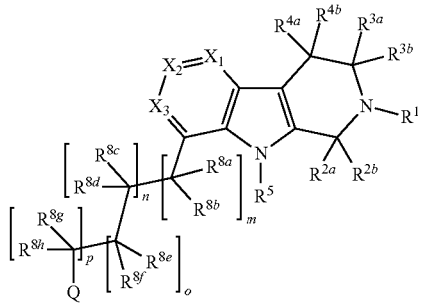

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^{2b}$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

$R^5$ is H or unsubstituted $C_1$-$C_8$ alkyl;

each $X^1$, $X^2$ and $X^3$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In some variations, compounds of the formula (A1), and salts and solvates thereof, are embraced, provided that:

(1) when each m, n, o and p is 0 and $R^5$ is H, then Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, acyloxy, cyano, alkynyl, acylamino, a group of the formula —CR$^9$=CR$^{10a}$R$^{10b}$, or amino substituted with one or two substituted or unsubstituted C$_1$-C$_8$ alkyl; and (2) when each m, n, o and p is 0 and R$^5$ is methyl, then Q is substituted or unsubstituted aryl other than unsubstituted phenyl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, aminoacyl, acyloxy, carboxyl, carbonylalkoxy, alkynyl, aminocarbonylalkoxy, a group of the formula —CR$^9$=CR$^{10a}$R$^{10b}$, or amino substituted with one or two substituted or unsubstituted C$_1$-C$_8$ alkyl;

(3) wherein at least one of m, n, o and p is 1 and R$^5$ is H, then Q substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$; and (4) wherein at least one of m, n, o and p is 1 and R$^5$ is methyl, then Q substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl other than a substituted piperazinyl, aminoacyl, acyloxy, carboxyl, cyano, alkynyl, aminocarbonylalkoxy, acylamino, or is a group of the formula —CR$^9$=CR$^{10a}$R$^{10b}$, or amino substituted with one or two substituted or unsubstituted C$_1$-C$_8$ alkyl.

In one variation, compounds of the formula (A1), and salts and solvates thereof, are embraced, provided that when none of R$^1$, R$^{2a}$, R$^{2b}$, R$^{3a}$, R$^{3b}$, R$^{4a}$ and R$^{4b}$ are taken together to form a ring, at least one of m, n, o and p is 1 and each R$^{8a}$, R$^{8b}$, R$^{8c}$, R$^{8d}$, R$^{8e}$, R$^{8f}$, R$^{8g}$ and R$^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, or is taken together with a geminal R$^{8(a-h)}$ to form a substituted or unsubstituted methylene moiety or is taken together with a geminal R$^{8(a-h)}$ and the carbon to which they are attached to form a carbonyl moiety, then:

(i) when Q is a carbonylalkoxy of the formula —COOCH$_3$ and R$^5$ is an unsubstituted C$_1$-C$_8$ alkyl where the unsubstituted C$_1$-C$_8$ alkyl is methyl, then one or more of provisions (a)-(d) apply: (a) at least one of X$^1$, X$^2$ and X$^3$ is N or CR$^6$; (b) R$^{2a}$ and R$^{2b}$ are both H; (c) R$^1$ is H or an unsubstituted C$_1$-C$_8$ alkyl; and (d) R$^5$ is H;

(ii) when either (1) Q is carbonylalkoxy of the formula —COOCH$_3$ or —COOCH$_2$CH$_3$ or (2) Q is an alkoxy of formula —OCH$_3$ or —OCH$_2$CH$_3$ and is bound to a carbonyl group to form a moiety of the formula —COOCH$_3$ or —COOCH$_2$CH$_3$, then one or more of provisions (a)-(c) apply: (a) at least one of X$^1$, X$^2$ and X$^3$ is N or CR$^6$, provided that if X$^2$ is CR$^6$ where R$^6$ is methyl, then R$^5$ is an unsubstituted C$_1$-C$_8$ alkyl; (b) R$^5$ is an unsubstituted C$_1$-C$_8$ alkyl; and (c) at least one of n, m, o and p is 1;

(iii) when either (1) Q is an acylamino of the formula —CONH$_2$ or (2) Q is an unsubstituted amino bound to a carbonyl group to form a moiety of the formula —CONH$_2$, then one or more of provisions (a)-(e) apply: (a) at least one of X$^1$, X$^2$ and X$^3$ is N or CR$^6$, provided that if X$^2$ is CR$^6$ where R$^6$ is methyl, then R$^5$ is an unsubstituted C$_1$-C$_8$ alkyl; (b) R$^5$ is an unsubstituted C$_2$-C$_8$ alkyl; (c) R$^5$ and R$^1$ are independently an unsubstituted C$_1$-C$_8$ alkyl; (d) at least one of n, m, o and p is 1; and (e) when R$^5$ is an unsubstituted C$_1$-C$_8$ alkyl, then R$^{2a}$ and R$^{2b}$ are both H;

(iv) when Q is cyano, then one or more of provisions (a)-(d) apply: (a) at least one of X$^1$, X$^2$ and X$^3$ is N or CR$^6$; (b) R$^{2a}$ and R$^{2b}$ are both H; (c) R$^1$ is an unsubstituted C$_1$-C$_8$ alkyl; and (d) at least one of n, m, o and p is 1;

(v) when Q is an acyloxy of the formula —COOH, then one or more of provisions (a)-(c) apply: (a) at least one of X$^1$, X$^2$ and X$^3$ is N or CR$^6$; (b) R$^5$ is an unsubstituted C$_1$-C$_8$ alkyl; and (c) at least one of n, m, o and p is 1;

(vi) when Q is an acyloxy of the formula —COO-substituted alkyl, then one or more of provisions (a)-(c) apply: (a) at least one of X$^1$, X$^2$ and X$^3$ is N or CR$^6$; (b) R$^5$ is an unsubstituted C$_1$-C$_8$ alkyl; and (c) R$^1$ is other than H.

In some variations, compounds of the formula (A2), and salts and solvates thereof, are embraced, provided that:

(1) when each m, n, o and p is 0 and R$^5$ is H, then Q is substituted or unsubstituted aryl other than unsubstituted phenyl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, cyano, alkynyl, aminocarbonylalkoxy, acylamino, a group of the formula —CR$^9$=CR$^{10a}$R$^{10b}$, or amino substituted with one or two substituted or unsubstituted C$_1$-C$_8$ alkyl;

(2) when each m, n, o and p is 0 and R$^5$ is unsubstituted C$_1$-C$_8$ alkyl, then Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, aminoacyl, acyloxy, carbonylalkoxy, cyano, alkynyl, aminocarbonylalkoxy, acylamino, or is a group of the formula —CR$^9$=CR$^{10a}$R$^{10b}$; and (3) when at least one of m, n, o and p is 1 and R$^5$ is H, then Q is substituted or unsubstituted aryl other than unsubstituted phenyl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted amino, aminoacyl, acyloxy, cyano, alkynyl, aminocarbonylalkoxy, or is a group of the formula —CR$^9$=CR$^{10a}$R$^{10b}$.

In one variation, compounds of the formula (A2), and salts and solvates thereof, are embraced, provided that:

(i) when m, n, o and p are each 0 and Q is a substituted aryl wherein the substituted aryl is a carboline moiety, then one or more of provisions (a)-(c) apply: (a) X$^1$, X$^2$ and X$^3$ are independently N or CH; (b) R$^5$ is an unsubstituted C$_1$-C$_8$ alkyl; and (c) R$^1$ is an unsubstituted C$_1$-C$_8$ alkyl;

(ii) when none of R$^1$, R$^{2a}$, R$^{2b}$, R$^{3a}$, R$^{3b}$, R$^{4a}$ and R$^{4b}$ are taken together to form a ring, at least one of m, n, o and p is 1 and each R$^{8a}$, R$^{8b}$, R$^{8c}$, R$^{8d}$, R$^{8e}$, R$^{8f}$, R$^{8g}$ and R$^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, or is taken together with a geminal R$^{8(a-h)}$ to form a substituted or unsubstituted methylene moiety or is taken together with a geminal R$^{8(a-h)}$ and the carbon to which they are attached to form a carbonyl moiety, then:

(A) when Q is a carboxyl moiety, then one or more of provisions (a)-(e) apply: (a) at least one of X$^1$, X$^2$ and X$^3$ is independently N or CR$^6$; (b) two or more of m, n, o and p are 1; (c) at least one of R$^{8a}$, R$^{8b}$, R$^{8c}$, R$^{8d}$, R$^{8e}$, R$^{8g}$ and R$^{8h}$ is other than H; (d) when R$^5$ is an unsubstituted C$_1$-C$_8$ alkyl then at least one of m, n, o and p is 1; and (e) when R$^5$ is H then R$^{2a}$ and R$^{2b}$ are each H;

(B) when one of R$^{2a}$ and R$^{2b}$ is methyl or when R$^{2a}$ and R$^{2b}$ are taken together to form a carbonyl, then one or more of provisions (a)-(c) apply: (a) R$^5$ is an unsubstituted C$_1$-C$_8$ alkyl; (b) R$^1$ is an unsubstituted C$_1$-C$_8$ alkyl; and (c) Q is a substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, aminoacyl, cyano, alkynyl, aminocarbonylalkoxy; and (C) when R$^1$ and R$^{2a}$ are taken together to form a butylene (—CH$_2$CH$_2$CH$_2$CH$_2$—), then one or more of provisions (a)-(d) apply: (a) R$^5$ is an unsubstituted C$_1$-C$_8$ alkyl; (b) the 6-membered ring formed when R$^1$ and R$^{2a}$ are taken together to form a butylene (—CH$_2$CH$_2$CH$_2$CH$_2$—) moiety is not further substituted with a cyclic structure and is not substituted with an alkenyl or cyano-containing moiety; (c) X$^3$ is CH and X$^1$ and X$^2$ are independently N or CR$^6$; and (d) Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, aminoacyl, acyloxy, carbonylalkoxy, cyano, alkynyl, aminocarbonylalkoxy or acylamino moiety.

In specific variations, compounds of formula (A1) have the structure:

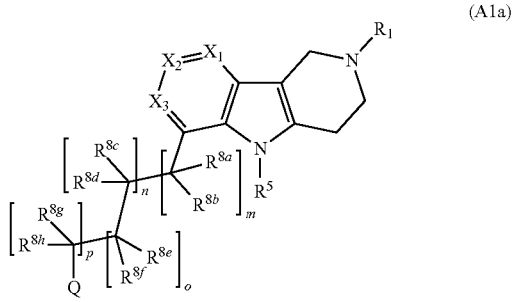

(A1a)

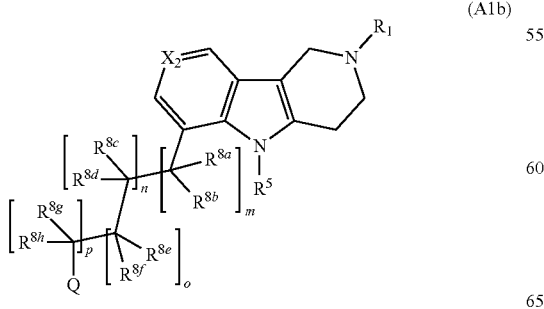

(A1b)

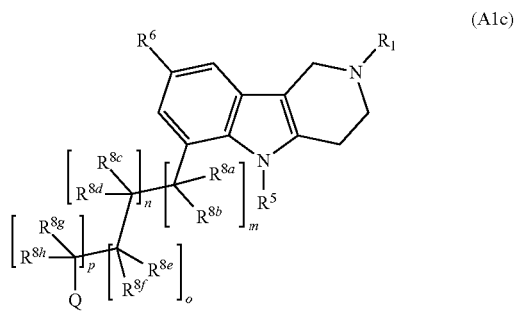

(A1c)

or a salt or solvate thereof; wherein R$^1$, R$^5$, R$^6$, X$^1$, X$^2$, X$^3$, R$^{8(a-h)}$, m, n, o, p and Q, where present, are defined as for formula (A1) and, where applicable, any variation thereof detailed herein. That is, variations of formula (A1) detailed throughout, where applicable, apply equally to any of formulae (A1a)-(A1c) the same as if each and every variation were specifically and individually listed for formulae (A1a)-(A1c). Pharmaceutically acceptable salts of compounds of formulae (A1a)-(A1c) are also provided.

In specific variations, compounds of formula (A1) have the structure:

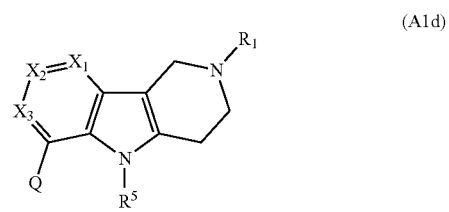

(A1d)

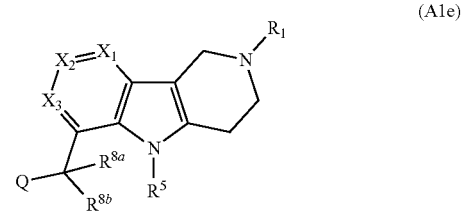

(A1e)

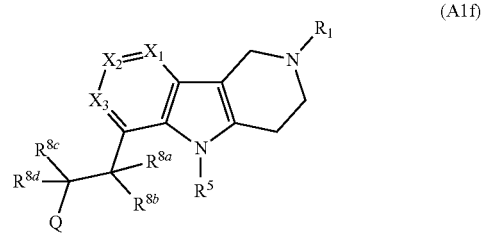

(A1f)

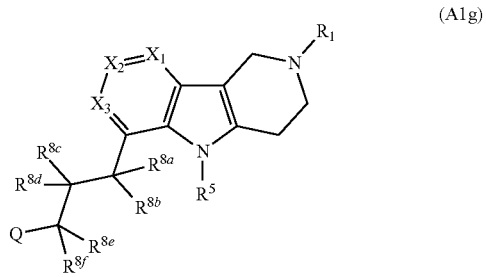

(A1g)

(A1h)

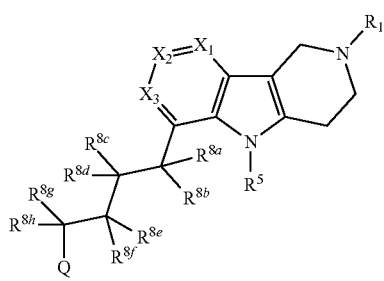

or a salt or solvate thereof; wherein $R^1$, $R^5$, $X^1$, $X^2$, $X^3$, $R^{8(a-h)}$ and Q, where present, are defined herein and, where applicable, any variation thereof detailed herein. That is, variations of the formula (A1) detailed throughout, where applicable, apply equally to any of formulae (A1d)-(A1h) the same as if each and every variation were specifically and individually listed for formulae (A1d)-(A1h). Pharmaceutically acceptable salts of compounds of formulae (A1d)-(A1h) are also provided.

In another variation, compounds of formula (A1) have the structure:

(A1i)

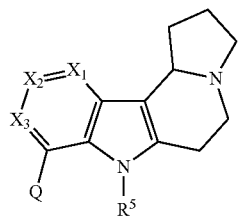

(A1j)

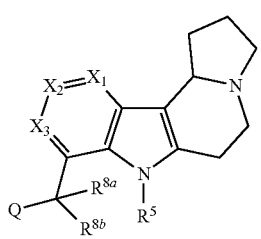

(A1k)

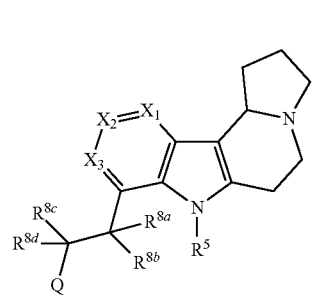

(A1l)

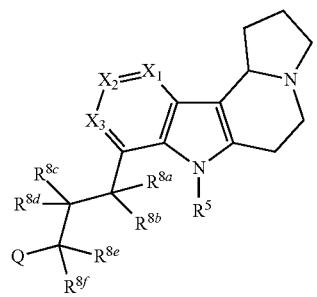

(A1m)

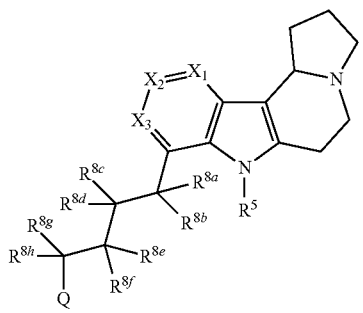

(A1n)

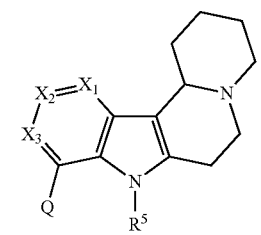

(A1o)

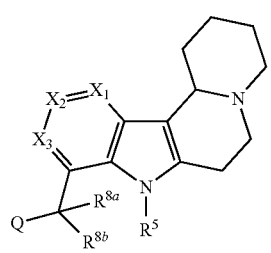

(A1p)

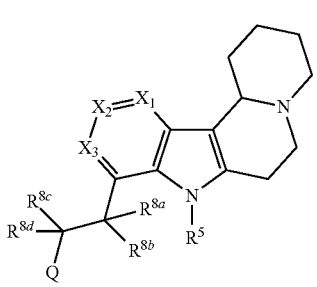

-continued

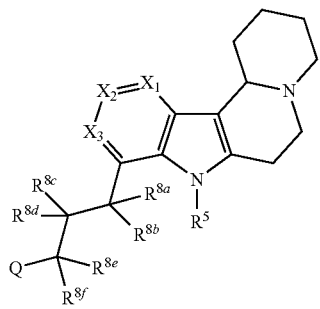
(A1q)

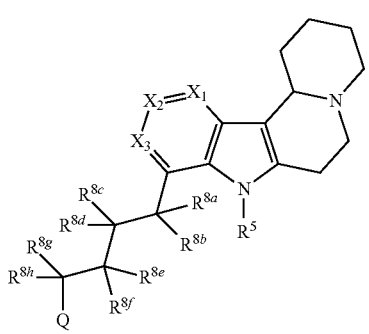
(A1r)

or a salt or solvate thereof; wherein $R^5$, $R^{8(a-h)}$, $X^1$, $X^2$, $X^3$ and Q, where present, are defined herein and, where applicable, any variation thereof detailed herein. That is, variations of the formula (A1) detailed throughout, where applicable, apply equally to any of formulae (A1i)-(A1r) the same as if each and every variation were specifically and individually listed for formulae (A1i)-(A1r). In one embodiment, compounds of the formula (A1) are provided wherein the compounds are of the formula (A1i)-(A1r) except that, instead of $R^1$ of formula (A1) being taken together with $R^{2a}$ of formula (A1) to provide compounds of the formula (A1i)-(A1r), $R^1$ is taken together with $R^{3a}$ to form a propylene moiety or a butylene moiety. In another embodiment, compounds of the formula (A1) are provided wherein the compounds are of the formula (A1i)-(A1r) except that, instead of $R^1$ of formula (A1) being taken together with $R^{2a}$ of formula (A1) to provide compounds of the formula (A1i)-(A1r), $R^1$ is taken together with $R^{4a}$ to form an ethylene moiety or a propylene moiety. In a further embodiment, compounds of the formula (A1) are provided wherein the compounds are of the formula (A1i)-(A1r) except that, instead of $R^1$ of formula (A1) being taken together with $R^{2a}$ of formula (A1) to provide compounds of the formula (A1i)-(A1r), $R^{2a}$ and $R^{3a}$ are taken together to form an ethylene moiety or a propylene moiety. In still a further embodiment, compounds of the formula (A1) are provided wherein the compounds are of the formula (A1i)-(A1r) except that, instead of $R^1$ of formula (A1) being taken together with $R^{2a}$ of formula (A1) to provide compounds of the formula (A1i)-(A1r), $R^{2a}$ and $R^{4a}$ are taken together to form a methylene moiety or an ethylene moiety. In yet another embodiment, compounds of the formula (A1) are provided wherein the compounds are of the formula (A1i)-(A1r) except that, instead of $R^1$ of formula (A1) being taken together with $R^{2a}$ of formula (A1) to provide compounds of the formula (B1)-(B10), $R^{3a}$ and $R^{4a}$ are taken together to form a propylene moiety or a butylene moiety. Variations detailed throughout, where applicable, apply to such formulae the same as if each and every variation were specifically and individually listed. Pharmaceutically acceptable salts of such formulae are also provided. Pharmaceutically acceptable salts of compounds of formulae (A1i)-(A1r) are also provided.

All variations referring to the formulae herein, such as formulae (A1a)-(A1r), where applicable, may apply to formula (A2), the same as if each and every variation were specifically and individually listed.

In some embodiments, compounds of the formula (A1a) have the structures (F1)-(F5):

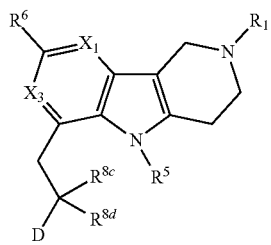
(F1)

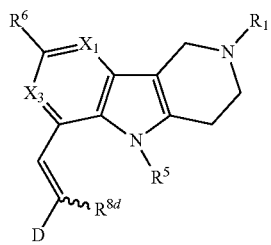
(F2)

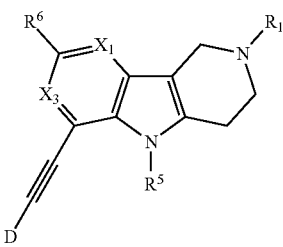
(F3)

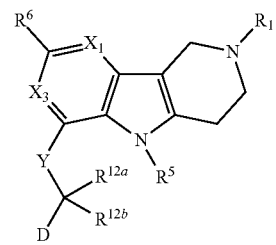
(F4)

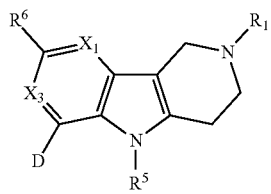
(F5)

wherein:
$R^1$ is H or substituted or unsubstituted $C_1$-$C_8$ alkyl;
$R^5$ is H or unsubstituted $C_1$-$C_8$ alkyl;
$R^6$ is H, halo, or substituted or unsubstituted $C_1$-$C_8$ alkyl;
$R^{8c}$, where present, is H, OH or substituted or unsubstituted $C_1$-$C_8$ alkyl;

$R^{8d}$, where present, is H or substituted or unsubstituted $C_1$-$C_8$ alkyl, and the ⁓ bond indicates the presence of either an E or Z double bond configuration;

Y, where present, is O or $NR^{11}$;

each $R^{11}$, $R^{12a}$ and $R^{12b}$ is independently H or substituted or unsubstituted $C_1$-$C_8$ alkyl;

each $X^1$ and $X^3$ is independently CH or N; and

D is substituted or unsubstituted aryl, or substituted or unsubstituted heteroaryl;

provided that when the compound is of the formula (F5), D is other than unsubstituted phenyl.

In some embodiments, the compound is of the formula (F1). In some embodiments, wherein the compound is of the formula (F2). In some embodiments, the compound is of the formula (F3). In some embodiments, the compound is of the formula (F4). In some embodiments, the compound is of the formula (F5).

In another aspect, compounds of formulae (A3)-(A4) are provided:

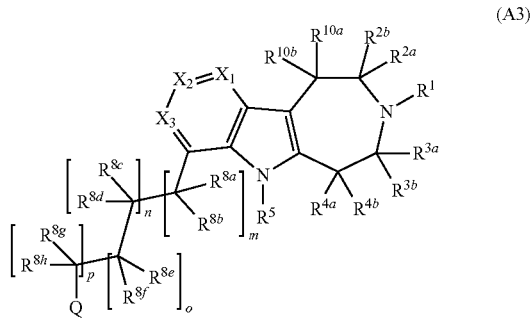

(A3)

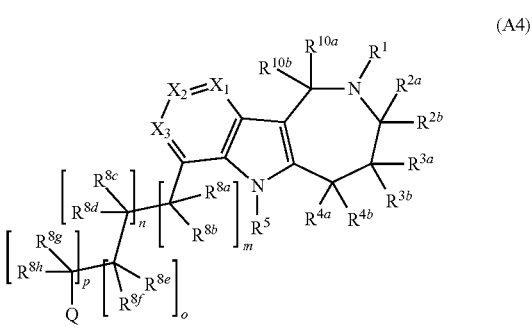

(A4)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$. $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

$R^5$ is H or unsubstituted $C_1$-$C_8$ alkyl;

each $X^1$, $X^2$ and $X^3$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —$CR^9$=$CR^{10a}R^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In a particular variation, compounds of formula (A3) have the structure:

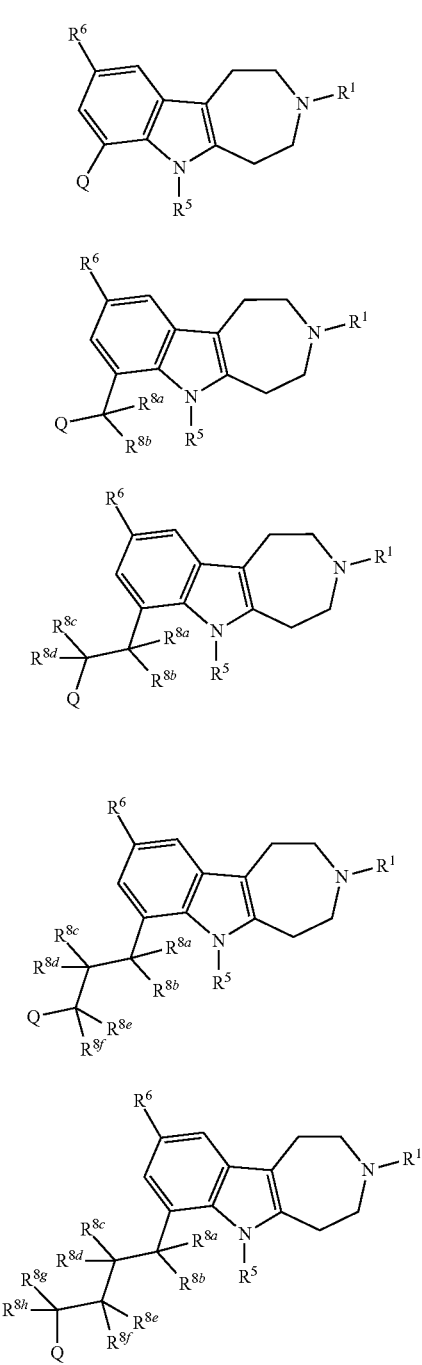

(A3a)
(A3b)
(A3c)
(A3d)
(A3e)

or a salt or solvate thereof; wherein $R^1$, $R^5$, $R^6$ and $R^{8(a-h)}$, where present, and Q are defined as for formula (A3) and, where applicable, any variation thereof detailed herein. That is, variations of formula (A3) detailed throughout, where applicable, apply to formulae (A3a)-(A3e) the same as if each and every variation were specifically and individually listed for formulae (A3a)-(A3e). Pharmaceutically acceptable salts of compounds of formulae (A3a)-(A3e) are also provided.

In particular variation, compounds of formula (A3) have the structure:

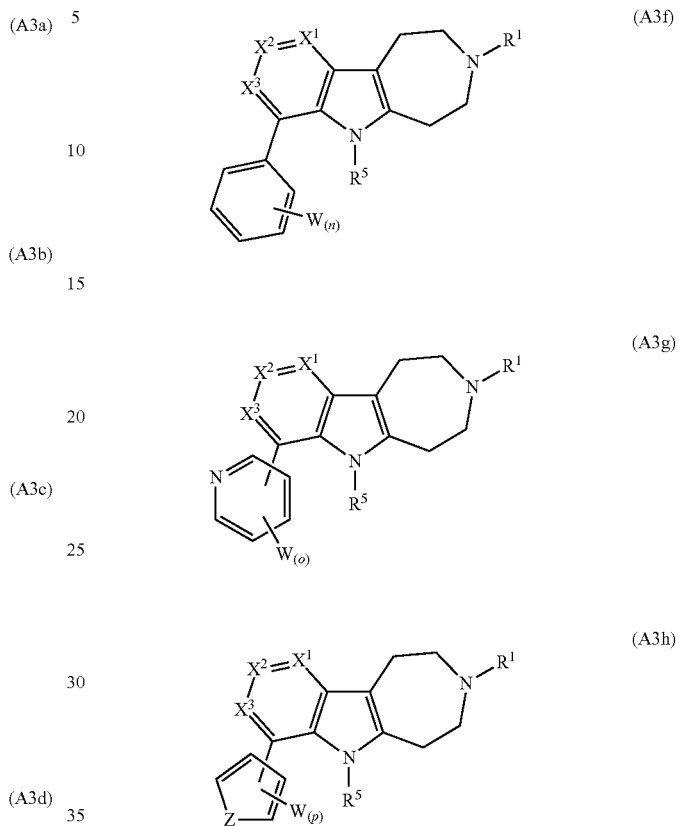

(A3f)
(A3g)
(A3h)

or a salt or solvate thereof; wherein $R^1$, $R^5$, $X^1$, $X^2$ and $X^3$ are defined as for formula (A3) and, where applicable, any variation thereof detailed herein, n is 0-5, o is 0-4, p is 0-3, Z is NH, N—$CH_3$, O or S, and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino. In one particular aspect of this variation, W is H, substituted or unsubstituted aryl, or substituted or unsubstituted heteroaryl. In one particular aspect of this variation, Z is S. In another particular aspect of this variation, one of $X^1$, $X^2$ or $X^3$ is N. Variations of formula (A3) detailed throughout, where applicable, apply equally to any of formulae (A3f)-(A3h), the same as if each and every variation were specifically and individually listed for formula (A3f)-(A3h). Pharmaceutically acceptable salts of compounds of formulae (A3f)-(A3h) are also provided.

All variations referring to the formulae herein, such as formulae (A3a)-(A3h), where applicable, may apply to formula (A4), the same as if each and every variation were specifically and individually listed.

In another aspect, compounds of formulae (B1)-(B2) are provided:

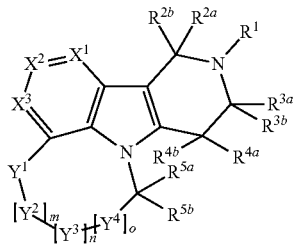

(B1)

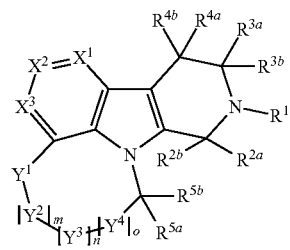

(B2)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$ and $X^3$ is independently N, CH or $CR^6$;

$Y^1$ is $CR^{7a}R^{7b}$, $NR^8$, O, S, S(O) or SO$_2$, provided that when $Y^1$ is $NR^8$, O, S, S(O) or SO$_2$, then $Y^2$, where present, is $CR^{7c}R^{7d}$;

$Y^2$, where present, is $CR^{7c}R^{7d}$, $NR^8$, O, S, S(O) or SO$_2$, provided that when $Y^2$ is $NR^8$, O, S, S(O) or SO$_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or SO$_2$, provided that when $Y^3$ is $NR^8$, O, S, S(O) or SO$_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or SO$_2$, provided that when $Y^4$ is $NR^8$, O, S, S(O) or SO$_2$, then $Y^3$ is $CR^{7e}R^{7f}$;

$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, compounds of the formula (B1) where m-o are each 0, and salts and solvates thereof, are embraced, provided that when $Y^1$ is $CR^{7a}R^{7b}$ where $R^{7a}$ and $R^{7b}$ are both H and none of $R^1$, $R^{2a}$, $R^{2b}$, $R^{3a}$, $R^{3b}$, $R^{4a}$ and $R^{4b}$ are taken together to form a ring, then (i) at least one of $R^{5a}$ and $R^{5b}$ is other than H, and (ii) when at least one of $R^{5a}$ and $R^{5b}$ is other than H, then one or more of provisions (a)-(c) apply: (a) at least one of $X^1$, $X^2$ and $X^3$ is N or $CR^6$; (b) $R^{5a}$ and $R^{5b}$ are both other than H; and (c) $R^{5a}$ is H and $R^{5b}$ is an unsubstituted aryl other than phenyl.

In another variation, compounds of the formula (B1) where m-o are each 0, and salts and solvates thereof, are embraced, provided that when $Y^1$ is $CR^{7a}R^{7b}$ where $R^{7a}$ and $R^{7b}$ are both H and none of $R^1$, $R^{2a}$, $R^{2b}$, $R^{3a}$, $R^{3b}$, $R^{4a}$ and $R^{4b}$ are taken together to form a ring, then (i) when each $R^{5a}$ and $R^{5b}$ is H, at least one of $X^1$, $X^2$ and $X^3$ is N or $CR^6$ where $R^6$ is other than unsubstituted and substituted phenyl; and (ii) when at least one of $R^{5a}$ and $R^{5b}$ is other than H, then one or more of provisions (a)-(c) apply: (a) at least one of $X^1$, $X^2$ and $X^3$ is N or $CR^6$; (b) $R^{5a}$ and $R^{5b}$ are both other than H; and (c) $R^{5a}$ is H and $R^{5b}$ is an unsubstituted aryl other than phenyl.

In one variation, compounds of the formula (B2) where m-o are each 0, and salts and solvates thereof, are embraced, provided that when $Y^1$ is $CR^{7a}R^{7b}$ where $R^{7a}$ and $R^{7b}$ are both H and none of $R^1$, $R^{2a}$, $R^{2b}$, $R^{3a}$, $R^{3b}$, $R^{4a}$ and $R^{4b}$ are taken together to form a ring, then at least one of $R^{5a}$ and $R^{5b}$ is other than H.

In one variation, compounds of the formula (B1) where m is 1 and n-o are each 0, and salts and solvates thereof, are embraced, provided that:

(1) when $Y^2$ is $CR^{7c}R^{7d}$ where $R^{7c}$ and $R^{7d}$ are each H and $Y^1$ is O or $CR^{7a}R^{7b}$ where $R^{7a}$ and $R^{7b}$ are each H and none of $R^1$, $R^{2a}$, $R^{2b}$, $R^{3a}$, $R^{3b}$, $R^{4a}$ and $R^{4b}$ are taken together to form a ring, then (i) at least one of $R^{5a}$ and $R^{5b}$ is other than H, and (ii) when at least one of $R^{5a}$ and $R^{5b}$ is other than H, then one or more of provisions (a)-(c) apply: (a) at least one of $X^1$, $X^2$ and $X^3$ is N or $CR^6$; $R^{5a}$ and $R^{5b}$ are each other than H; and (c) at least one of $R^{5a}$ and $R^{5b}$ is a substituted or unsubstituted heteroaryl, a substituted aryl or an unsubstituted aryl other than phenyl;

(2) when $Y^2$ is $CR^{7c}R^{7d}$ where $R^{7c}$ and $R^{7d}$ are each H and $Y^1$ is S and none of $R^1$, $R^{2a}$, $R^{2b}$, $R^{3a}$, $R^{3b}$, $R^{4a}$ and $R^{4b}$ are taken together to form a ring, then (i) at least one of $R^{5a}$ and $R^{5b}$ is other than H, and (ii) when at least one of $R^{5a}$ and $R^{5b}$ is other than H, then one or more of provisions (a)-(c) apply: (a) at least one of $X^1$, $X^2$ and $X^3$ is N or $CR^6$; $R^{5a}$ and $R^{5b}$ are each other than H; and (c) at least one of $R^{5a}$ and $R^{5b}$ is a substituted or unsubstituted heteroaryl or aryl moiety;

(3) when $Y^1$ is NH, none of $R^1$, $R^{2a}$, $R^{2b}$, $R^{3a}$, $R^{3b}$, $R^{4a}$ and $R^{4b}$ are taken together to form a ring, and $R^{7c}$, if present, is not taken together with $R^{5a}$ to form a bond, then one or more of provisions (a)-(c) apply: (a) at least one of $X^1$, $X^2$ and $X^3$ is N or $CR^6$; (b) $Y^2$ is other than C(O); and (c) at least one of $R^{5a}$ and $R^{5b}$ is other than H; and (4) when $Y^1$ is $NR^8$ where $R^8$ is methyl, none of $R^1$, $R^{2a}$, $R^{2b}$, $R^{3a}$, $R^{3b}$, $R^{4a}$ and $R^{4b}$ are taken together to form a ring, and $R^{7c}$, if present, is not taken together with $R^{5a}$ to form a bond, then one or both of provisions (a) and (b) apply: (a) at least one of $X^1$, $X^2$ and $X^3$ is N or $CR^6$ and (b) at least one of $R^{5a}$ and $R^{5b}$ is other than H and methyl.

In another variation, compounds of the formula (B1) where m is 1 and n-o are each 0, and salts and solvates thereof, are embraced, provided that:

(1) when $Y^1$ is $CR^{7a}R^{7b}$ where $R^{7a}$ and $R^{7b}$ are each H, $Y^2$ is $CR^{7c}R^{7d}$ where $R^{7c}$ and $R^{7d}$ are each H, and none of $R^1$, $R^{2a}$, $R^{2b}$, $R^{3a}$, $R^{3b}$, $R^{4a}$ and $R^{4b}$ are taken together to form a ring, then one or more of provisions (i)-(iii) apply: (i) at least one of $R^{5a}$ and $R^{5b}$ is other than H and at least one of $X^1$, $X^2$ and $X^3$ is N or $CR^6$; (ii) when each of $R^{5a}$ and $R^{5b}$ is H, at least one of $X^1$, $X^2$ and $X^3$ is N or $CR^6$ where $R^6$ is chloro or substituted or unsubstituted alkyl (e.g., methyl); and (iii) when each of $X^1$, $X^2$ and $X^3$ is CH, at least one of $R^{5a}$ and $R^{5b}$ is other than H, phenyl and $CH_2CH_2NMe_2$;

(2) when $Y^1$ is O or S and none of $R^1$, $R^{2a}$, $R^{2b}$, $R^{3a}$, $R^{3b}$, $R^{4a}$ and $R^{4b}$ are taken together to form a ring, then (i) when $Y^2$ is $CR^{7c}R^{7d}$ where $R^{7c}$ and $R^{7d}$ are each H, at least one of $R^{5a}$ and $R^{5b}$ is other than H; or (ii) when $Y^2$ is $CR^{7c}R^{7d}$ where one of $R^{7c}$ and $R^{7d}$ is H and the other is phenyl, at least one of $R^{5a}$ and $R^{5b}$ is other than H or at least one of $X^1$, $X^2$ and $X^3$ is N or $CR^6$;

(3) when $Y^1$ is $NR^8$ where $R^8$ is H, none of $R^1$, $R^{2a}$, $R^{2b}$, $R^{3a}$, $R^{3b}$, $R^{4a}$ and $R^{4b}$ are taken together to form a ring, and $R^{7c}$ is not taken together with $R^{5a}$ to form a bond, then one or both of provisions (i) and (ii) apply: (i) at least one of $X^1$, $X^2$ and $X^3$ is N or $CR^6$; and (ii) $Y^2$ is $CR^{7c}R^{7d}$ where $R^{7c}$ and $R^{7d}$ are not taken together with the carbon to which they are attached to form a carbonyl moiety;

(4) when $Y^1$ is $NR^8$ where $R^8$ is methyl, none of $R^1$, $R^{2a}$, $R^{2b}$, $R^{3a}$, $R^{3b}$, $R^{4a}$ and $R^{4b}$ are taken together to form a ring, and $R^{7c}$ is not taken together with $R^{5a}$ to form a bond, then at least one of $X^1$, $X^2$ and $X^3$ is N or $CR^6$; and (5) when $Y^2$ is $CR^{7c}R^{7d}$ where $R^{7c}$ and $R^{7d}$ are taken together with the carbon to which they are attached to form a carbonyl moiety, none of $R^1$, $R^{2a}$, $R^{2b}$, $R^{3a}$, $R^{3b}$, $R^{4a}$ and $R^{4b}$ are taken together to form a ring, and each of $X^1$, $X^2$ and $X^3$ is CH, then $Y^1$ is not $NR^8$ where $R^8$ is an alkyl substituted with a substituted amino group (e.g., $(CH_2)_3NMe_2$).

In one variation, compounds of the formula (B2) where m is 1 and n-o are each 0, and salts and solvates thereof, are embraced, provided that:

(1) when $Y^1$ is $CR^{7a}R^{7b}$ and $Y^2$ is $CR^{7c}R^{7d}$ where each of $R^{7a}$, $R^{7b}$, $R^{7c}$ and $R^{7d}$ is H, $R^{2a}$ and $R^{2b}$ are taken together with the carbon to which they are attached to form a cycloalkyl moiety, and none of $R^1$, $R^{2a}$, $R^{2b}$, $R^{3a}$, $R^{3b}$, $R^{4a}$ and $R^{4b}$ are taken together to form a ring, then one or more of provisions (a)-(d) apply: (a) at least one of $X^1$, $X^2$ and $X^3$ is N or $CR^6$; (b) $R^{5a}$ is H and $R^{5b}$ is other than H; (c) at least one of $R^{5a}$ and $R^{5b}$ is a unsubstituted or unsubstituted heteroaryl or aryl moiety; and (d) $R^1$ is a substituted or unsubstituted $C_1$-$C_8$ alkyl;

(2) when $Y^1$ is NH, $Y^2$ is $CR^{7c}R^{7d}$ where $R^{7c}$ and $R^{7d}$ are each H, none of $R^1$, $R^{2a}$, $R^{2b}$, $R^{3a}$, $R^{3b}$, $R^{4a}$ and $R^{4b}$ are taken together to form a ring, and $R^{7c}$, if present, is not taken together with $R^{5a}$ to form a bond, then (i) at least one of $R^{5a}$ and $R^{5b}$ is other than H, and (ii) when at least one of $R^{5a}$ and $R^{5b}$ is other than H, then one or both of provisions (a) and (b) apply: (a) at least one of $R^{5a}$ and $R^{5b}$ is other than an unsubstituted $C_1$-$C_8$alkyl; (b) $R^1$ is a substituted or unsubstituted $C_1$-$C_8$ alkyl and at least one of $X^1$, $X^2$ and $X^3$ is N or $CR^6$; and (3) when $Y^1$ is O, $Y^2$ is $CR^{7c}R^{7d}$ where $R^{7c}$ and $R^{7d}$ are each H, none of $R^1$, $R^{2a}$, $R^{2b}$, $R^{3a}$, $R^{3b}$, $R^{4a}$ and $R^{4b}$ are taken together to form a ring, and $R^{7c}$, if present, is not taken together with $R^{5a}$ to form a bond, then one or more of provisions (a)-(d) apply: (a) when $R^{5a}$ is H then $R^{5b}$ is other than an unsubstituted $C_1$-$C_8$alkyl; (b) only one or more than two of $X^1$, $X^2$ and $X^3$ is $CR^6$; (c) $R^1$ is other than H; and (d) at least one of $R^{2a}$ and $R^{2b}$ is H.

In another variation, compounds of the formula (B2) where m is 1 and n-o are each 0, and salts and solvates thereof, are embraced, provided that:

(1) when $Y^1$ is $CR^{7a}R^{7b}$ and $Y^2$ is $CR^{7c}R^{7d}$ where each of $R^{7a}$, $R^{7b}$, $R^{7c}$ and $R^{7d}$ is H, and none of $R^1$, $R^{2a}$, $R^{2b}$, $R^{3a}$, $R^{3b}$, $R^{4a}$ and $R^{4b}$ are taken together to form a ring except that $R^{2a}$ and $R^{2b}$ may be taken together with the carbon to which they are attached to form a cycloalkyl moiety, then (i) at least one of $R^{5a}$ and $R^{5b}$ is other than H, and (ii) when one of $R^{5a}$ and $R^{5b}$ is an unsubstituted $C_1$-$C_8$alkyl, at least one of $X^1$, $X^2$ and $X^3$ is N or $CR^6$;

(2) when $Y^1$ is $CR^{7a}R^{7b}$ where both of $R^{7a}$ and $R^{7b}$ are unsubstituted $C_1$-$C_8$alkyl, $Y^2$ is $CR^{7c}R^{7d}$ where each $R^{7c}$ and $R^{7d}$ is H, and none of $R^1$, $R^{2a}$, $R^{2b}$, $R^{3a}$, $R^{3b}$, $R^{4a}$ and $R^{4b}$ are taken together to form a ring, then (i) at least one of $R^{5a}$ and $R^{5b}$ is other than H, or (ii) $R^1$ is a other than H; and (3) when $Y^1$ is O, $Y^2$ is $CR^{7c}R^{7d}$ where $R^{7c}$ and $R^{7d}$ are each H, and none of $R^1$, $R^{2a}$, $R^{2b}$ $R^{3a}$, $R^{3b}$, $R^{4a}$ and $R^{4b}$ are taken together to form a ring, then one or more of provisions (a)-(d) apply: (a) when $R^{5a}$ is H then $R^{5b}$ is other than an unsubstituted $C_1$-$C_8$alkyl; (b) only one or more than two of $X^1$, $X^2$ and $X^3$ is $CR^6$; (c) $R^1$ is other than H; and (d) at least one of $R^{2a}$ and $R^{2b}$ is H.

In one variation, compounds of the formula (B1) where m-n are each 1 and o is 0, and salts and solvates thereof, are embraced, provided that:

(1) when $Y^1$ is $CR^{7a}R^{7b}$, $Y^2$ is $CR^{7c}R^{7d}$ and $Y^3$ is $CR^{7e}R^{7f}$ where each of $R^{7a}$, $R^{7b}$, $R^{7c}$, $R^{7d}$, $R^{7e}$ and $R^{7f}$ are H and none of $R^1$, $R^{2a}$, $R^{2b}$, $R^{3a}$, $R^{3b}$, $R^{4a}$ and $R^{4b}$ are taken together to form a ring, then one or both of provisions (a) and (b) apply: (a) at least one of $R^{5a}$ and $R^{5b}$ is other than H; and (b) $R^1$ is an unsubstituted $C_1$-$C_8$ alkyl;

(2) when $Y^1$ is S or $CR^{7a}R^{7b}$, $Y^2$ is S, S(O) or $CR^{7c}R^{7d}$ and $Y^3$ is $CR^{7e}R^{7f}$ where each of $R^{7a}$, $R^{7b}$, $R^{7c}$, $R^{7d}$, $R^{7e}$ and $R^{7f}$, if present, is H and none of $R^1$, $R^{2a}$, $R^{2b}$, $R^{3a}$, $R^{3b}$, $R^{4a}$ and $R^{4b}$ are taken together to form a ring and where either $Y^1$ is S and $Y^2$ is $CR^{7c}R^{7d}$ or $Y^2$ is S or S(O) and $Y^1$ is $CR^{7a}R^{7b}$, then (i) at least one of $R^{5a}$ and $R^{5b}$ is other than H, and (ii) when at least one of $R^{5a}$ and $R^{5b}$ is other than H, then one or both of provisions (a) and (b) apply: (a) at least one of $X^1$, $X^2$ and $X^3$ is N or $CR^6$; and (b) $R^1$ is methyl and at least one of $R^{5a}$ and $R^{5b}$ is a substituted or unsubstituted heteroaryl or aryl moiety;

(3) when $Y^1$ is O or $CR^{7a}R^{7b}$, $Y^2$ is O or $CR^{7c}R^{7d}$ and $Y^3$ is $CR^{7e}R^{7f}$ where each of $R^{7a}$, $R^{7b}$, $R^{7c}$, $R^{7d}$, $R^{7e}$ and $R^{7f}$, if present, is H and none of $R^1$, $R^{2a}$, $R^{2b}$, $R^{3a}$, $R^{3b}$, $R^{4a}$ and $R^{4b}$ are taken together to form a ring and where either $Y^1$ is O and $Y^2$ is $CR^{7c}R^{7d}$ or $Y^2$ is O and $Y^1$ is $CR^{7a}R^{7b}$, then (i) at least one of $R^{5a}$ and $R^{5b}$ is other than H, and (ii) when at least one of $R^{5a}$ and $R^{5b}$ is other than H, then one or both of provisions (a) and (b) apply: (a) at least one of $X^1$, $X^2$ and $X^3$ is N or $CR^6$; and (b) $R^1$ is other than H; and (4) when $Y^1$ is NH and $Y^3$ is $CR^{7e}R^{7f}$, where $R^{7e}$ and $R^{7f}$ are both H, and where none of $R^1$, $R^{2a}$, $R^{2b}$, $R^{3a}$, $R^{3b}$, $R^{4a}$ and $R^{4b}$ are taken together to form a ring then (i) at least one of $R^{5a}$ and $R^{5b}$ is other than H and (ii) when $Y^2$ is $CR^{7c}R^{7d}$, $R^{7c}$ and $R^{7d}$ are not taken together to form a carbonyl moiety.

In another variation, compounds of the formula (B1) where m-n are each 1 and o is 0, and salts and solvates thereof, are embraced, provided that when $R^{5a}$ and $R^{5b}$ is H and none of $R^1$, $R^{2a}$, $R^{2b}$, $R^{3a}$, $R^{3b}R^{4a}$ and $R^{4b}$ are taken together to form a ring, then one or more of provisions (1) to (5) apply:

(1) when $Y^3$ is $CR^{7e}R^{7f}$ where one of $R^{7e}$ and $R^{7f}$ is an unsubstituted $C_1$-$C_8$alkyl, then one or more of provisions (i) to (iv) apply: (i) at least one of $X^1$, $X^2$ and $X^3$ is N or $CR^6$; (ii) $Y^2$ is other than $CR^{7c}R^{7d}$ where each of $R^{7c}$ and $R^{7d}$ is H; (iii) $Y^1$ is other than S; and (iv) $R^1$ is other than H;

(2) when $Y^2$ is $CR^{7c}R^{7d}$ and $Y^3$ is $CR^{7e}R^{7f}$ where each of $R^{7c}$, $R^{7d}$, $R^{7e}$ and $R^{7f}$ is H, then (i) $Y^1$ is other than $CR^{7a}R^{7b}$ where each of $R^{7a}$ and $R^{7b}$ is H and $NR^8$ where $R^8$ is H; and (ii) when $Y^1$ is O, S or S(O), $X^2$ is N or $CR^6$;

(3) when $Y^3$ is $CR^{7e}R^{7f}$ where each of $R^{7e}$ and $R^{7f}$ is H and $Y^2$ is $CR^{7c}R^{7d}$ where at least one of $R^{7c}$ and $R^{7d}$ is other than H, then one or both provisions (i) and (ii) apply: (i) at least one of $X^1$, $X^2$ and $X^3$ is N or $CR^6$; and (ii) $Y^1$ is other than S and NH;

(4) when $Y^2$ is S and $Y^3$ is $CR^{7e}R^{7f}$ where each $R^{7e}$ and $R^{7f}$ is H, then one or more of provisions (i) to (iii) apply: (i) at least one of $X^1$, $X^2$ and $X^3$ is N or $CR^6$; (ii) $Y^1$ is $CR^{7a}R^{7b}$ where at least one of $R^{7a}$ and $R^{7b}$ is other than H; and (iii) $R^1$ is other than H; and (5) when $Y^2$ is O and $Y^3$ is $CR^{7e}R^{7f}$ where each $R^{7e}$ and $R^{7f}$ is H, then (i) $Y^1$ is $CR^{7a}R^{7b}$ where at least one of $R^{7a}$ and $R^{7b}$ is other than H; and (ii) when $Y^1$ is $CR^{7a}R^{7b}$ where one of $R^{7a}$ and $R^{7b}$ is methyl or phenyl, then one or both of provisions (a) and (b) apply: (a) at least one of $X^1$, $X^2$ and $X^3$ is N or $CR^6$; and (b) $R^1$ is other than H.

In one variation, compounds of the formula (B2) where m-n are each 1 and o is 0, and salts and solvates thereof, are embraced, provided that:

(1) when $Y^1$ is $CR^{7a}R^{7b}$, $Y^2$ is $CR^{7c}R^{7d}$ and $Y^3$ is $CR^{7e}R^{7f}$ where each of $R^{7a}$, $R^{7b}$, $R^{7e}$ and $R^{7f}$ are H and none of $R^1$, $R^{2a}$, $R^{2b}$, $R^{3a}$, $R^{3b}$, $R^{4a}$ and $R^{4b}$ are taken together to form a ring, then (i) when $R^{7c}$ and $R^{7d}$ are both H, at least one of $R^{5a}$ and $R^{5b}$ is other than H, and (ii) when $R^{7c}$ and $R^{7d}$ are both methyl, then one or both of provisions (a) and (b) apply: (a) $R^{2a}$ and $R^{2b}$ are both H and (b) at least one of $X^1$, $X^2$ and $X^3$ is N or $CR^6$;

(2) when $Y^1$ is S or O, $Y^2$ is $CR^{7c}R^{7d}$ and $Y^3$ is $CR^{7e}R^{7f}$ where each of $R^{7c}$, $R^{7d}$, $R^{7e}$ and $R^{7f}$ is H, and none of $R^1$, $R^{2a}$, $R^{2b}$, $R^{3a}$, $R^{3b}R^{4a}$ and $R^{4b}$ are taken together to form a ring, then one or both of provisions (a) and (b) apply: (a) at least one of $X^1$, $X^2$ and $X^3$ is N or $CR^6$; and (b) at least one of $R^{5a}$ and $R^{5b}$ is other than H.

In one variation, compounds of the formula (B1) where m-o are each 1, and salts and solvates thereof, are embraced, provided that:

when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ where each of $R^{7a}$, $R^{7b}$, $R^{7c}$, $R^{7d}$, $R^{7e}$, $R^{7f}$, $R^{7g}$ and $R^{7h}$ are H, and none of $R^1$, $R^{2a}$, $R^{2b}$, $R^{3a}$, $R^{3b}$, $R^{4a}$ and $R^{4b}$ are taken together to form a ring, then one or more of provisions (a)-(c) apply: (a) at least one of $R^{5a}$ and $R^{5b}$ is other than H; (b) at least one of $X^1$, $X^2$ and $X^3$ is N or $CR^6$; and (c) $R^1$ is other than H.

In another variation, compounds of the formula (B1) where m-o are each 1, and salts and solvates thereof, are embraced, provided that when $Y^1$ is $CR^{7a}R^{7b}$ where each $R^{7a}$ and $R^{7b}$ is H, $Y^2$ is S, $Y^3$ is $CR^{7e}R^{7f}$ where each $R^{7e}$ and $R^{7f}$ is H, $Y^4$ is $CR^{7g}R^{7h}$ where each $R^{7g}$ and $R^{7h}$ is H, and none of $R^1$, $R^{2a}$, $R^{2b}$, $R^{3a}$, $R^{3b}$, $R^{4a}$ and $R^{4b}$ are taken together to form a ring, then one or more of provisions (i)-(iii) apply: (i) at least one of $R^{5a}$ and $R^{5b}$ is other than H; (ii) at least one of $X^1$, $X^2$ and $X^3$ is N or $CR^6$; and (iii) $R^1$ is other than H.

In one variation, compounds of the formula (B2) where m-o are each 1, and salts and solvates thereof, are embraced, provided that:

when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ where each of $R^{7a}$, $R^{7b}$, $R^{7c}$, $R^{7d}$, $R^{7e}$, $R^{7f}$, $R^{7g}$ and $R^{7h}$ are H, and none of $R^1$, $R^{2a}$, $R^{2b}$, $R^{3a}$, $R^{3b}$, $R^{4a}$ and $R^{4b}$ are taken together to form a ring, then one or more of provisions (a)-(c) apply: (a) at least one of $R^{5a}$ and $R^{5b}$ is other than H; (b) at least one of $X^1$, $X^2$ and $X^3$ is N or $CR^6$; and (c) $R^1$ is other than H.

In specific variations, compounds of the formula (B1) have the structure:

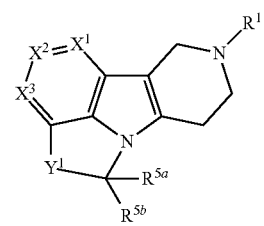

(B1a)

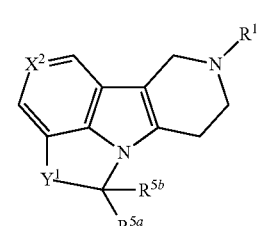

(B1b)

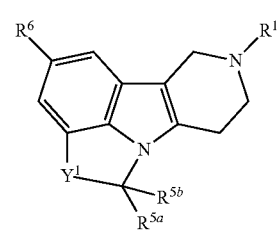

(B1c)

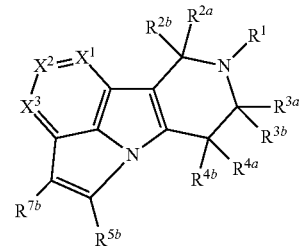

(B1d)

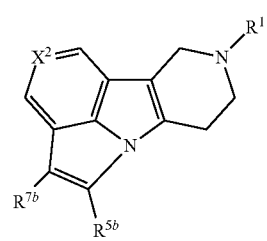

(B1e)

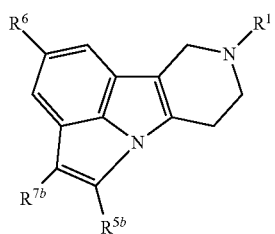
(B1f)
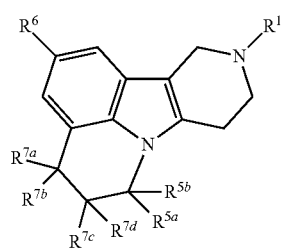
(B1l)
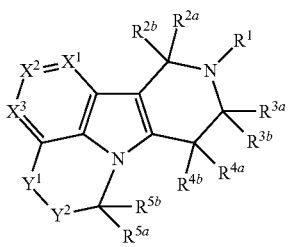
(B1g)
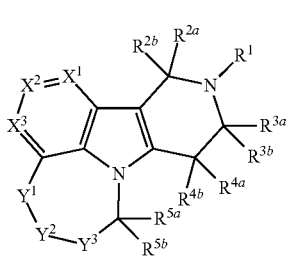
(B1m)
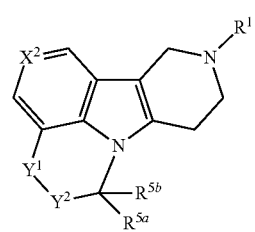
(B1h)
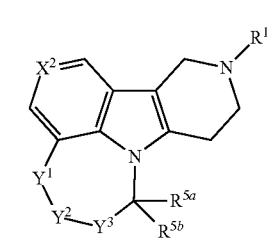
(B1n)
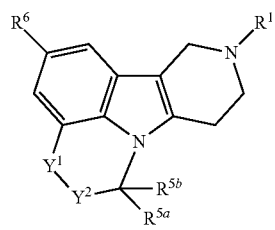
(B1i)
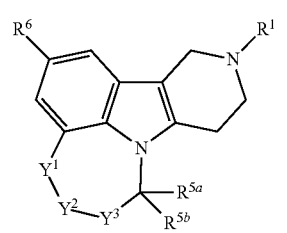
(B1o)
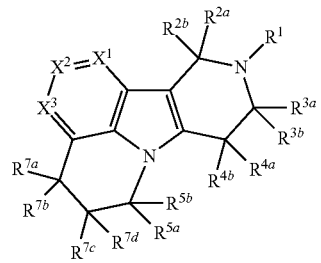
(B1j)
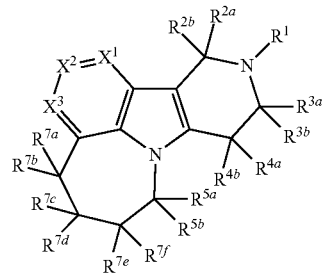
(B1p)
(B1k)
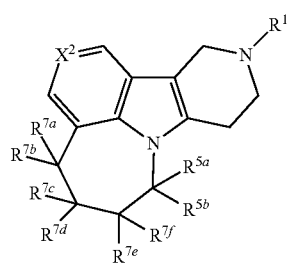
(B1q)

-continued
(B1r) 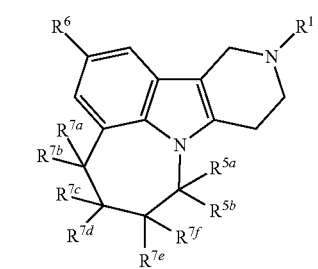
(B1s) 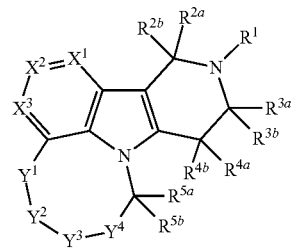
(B1t) 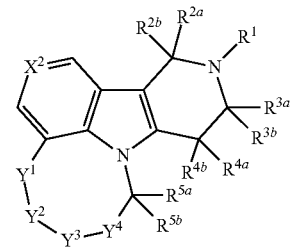
(B1u) 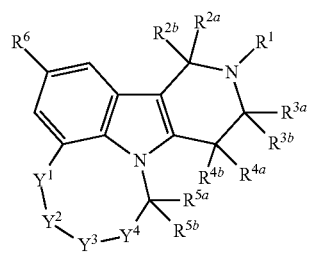
(B1v) 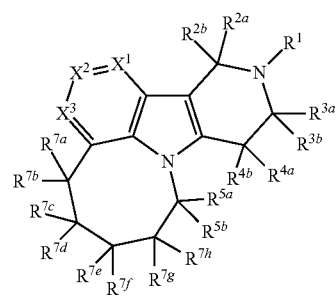
(B1w) 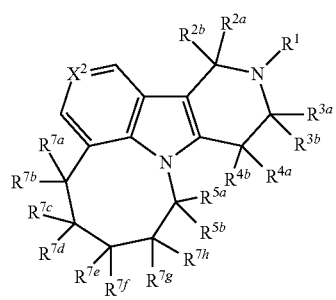
-continued
(B1x) 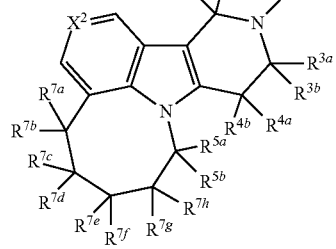
(B1y) 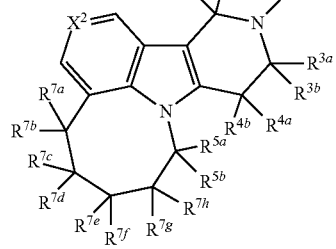
(B1z) 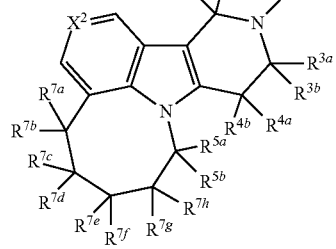
(B1aa) 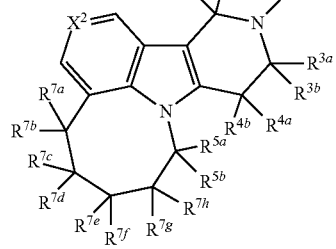
(B1ab) 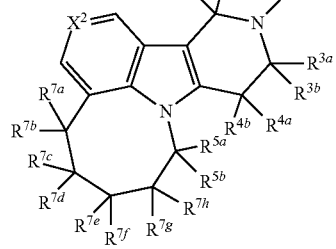
(B1ac) 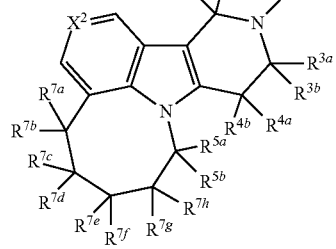

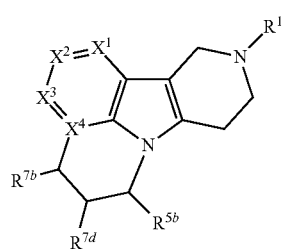 (B1ad)
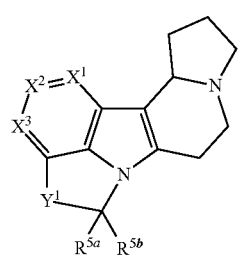 (B1ae)
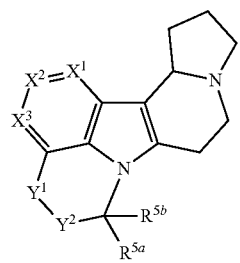 (B1af)
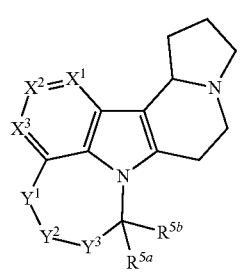 (B1ag)
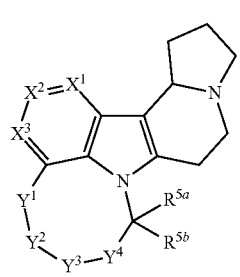 (B1ah)
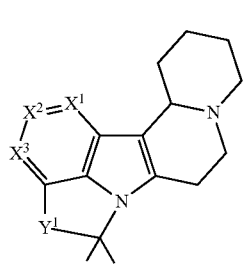 (B1ai)
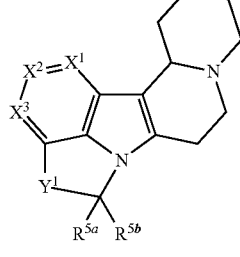 (B1aj)
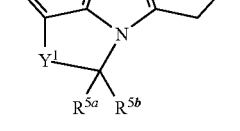 (B1ak)
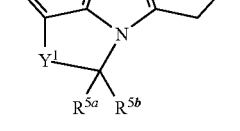 (B1al)
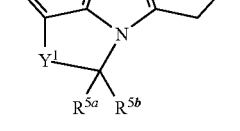 (B1am)
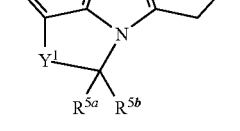 (B1an)
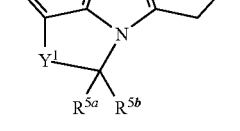 (B1ao)

(B1ap)
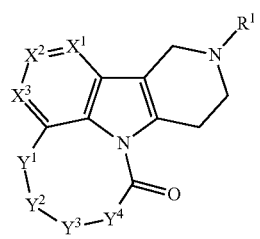
(B1aq)
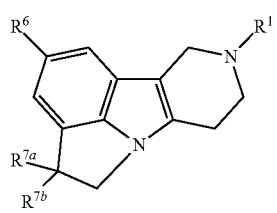
(B1ar)
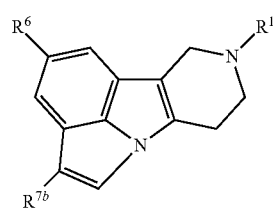
(B1as)
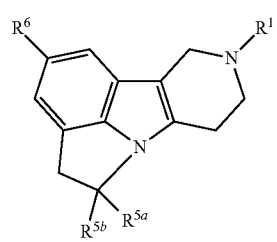
(B1at)
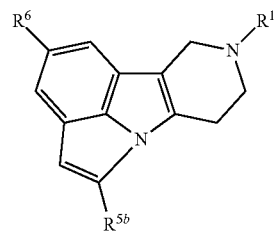
(B1au)
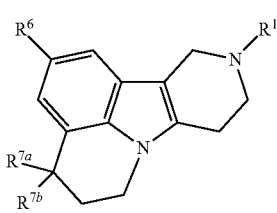
(B1av)
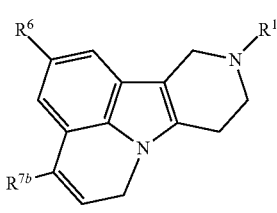
(B1aw)
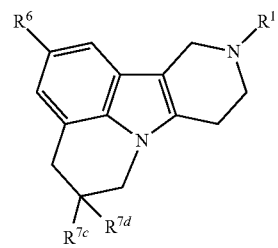
(B1ax)
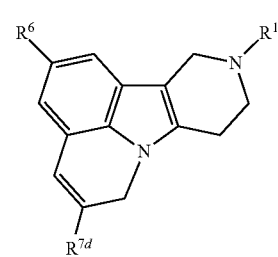
(B1ay)
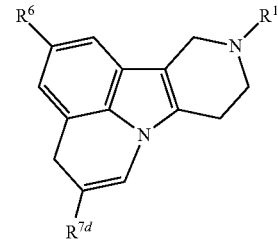
(B1az)
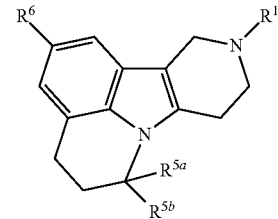
(B1ba)
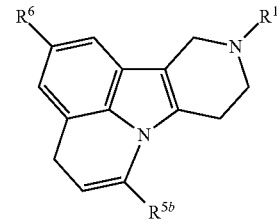
(B1bb)
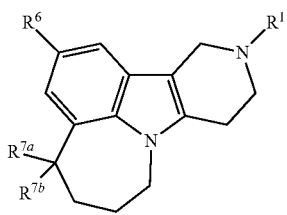

(B1bc) 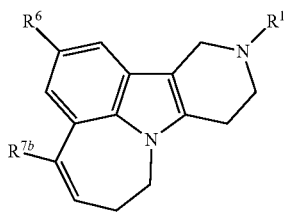

(B1bd) 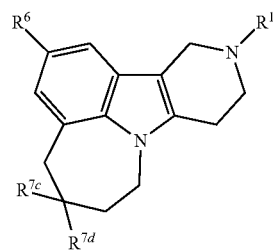

(B1be) 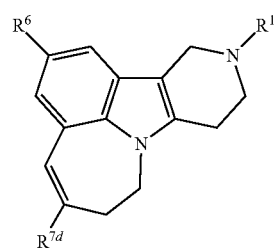

(B1bf) 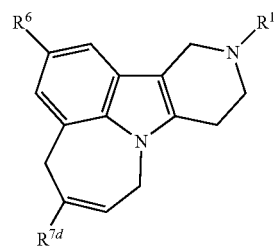

(B1bg) 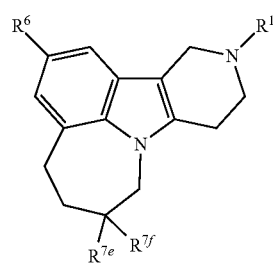

(B1bh) 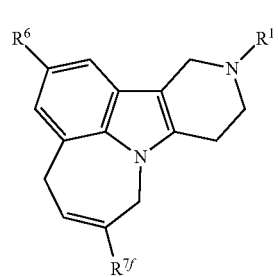

(B1bi) 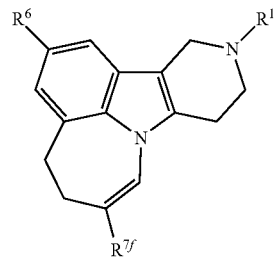

(B1bj) 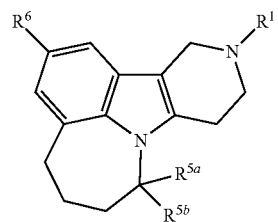

(B1bk) 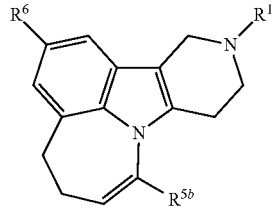

(B1bl) 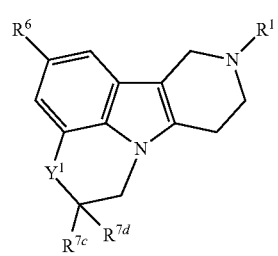

(B1bm) 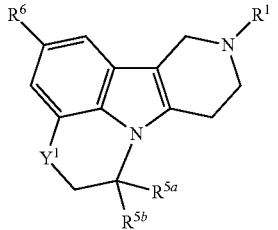

or a salt or solvate thereof; wherein $R^1$, $R^{2a}$, $R^{2b}$, $R^{3a}$, $R^{3b}$, $R^{4a}$, $R^{4b}$, $R^{5a}$, $R^{5b}$, $R^6$, $R^{7(a-h)}$, $X^1$, $X^2$, $X^3$, $Y^1$, $Y^2$, $Y^3$ and $Y^4$, where present, are defined as for formula (B1) and, where applicable, any variation thereof detailed herein. That is, variations of formula (B1) detailed throughout, where applicable, apply to formulae (B1a)-(B1bm), the same as if each and every variation were specifically and individually listed for formulae (B1a)-(B1bm). Pharmaceutically acceptable salts of compounds of formulae (B1a)-(B1bm) are also provided.

In some variations, compounds of formula (B1) where m is 1 and n-o are each 0 have the structure (B1bl), provided that:

(1) when $Y^1$ is $CR^{7a}R^{7b}$ where each $R^{7a}$ and $R^{7b}$ is H, then one or both of provisions (i) and (ii) apply: (i) $R^6$ is other than H, fluoro, methoxy, unsubstituted phenyl and substituted phenyl; and (ii) at least one of $R^{7c}$ and $R^{7d}$ is other than H; and (2) when $Y^1$ is $NR^8$, O, S, S(O) or $SO_2$, then (iii) $R^{7c}$ and $R^{7d}$ are not taken together with the carbon to which they are attached to form a carbonyl; and (iv) at least one of $R^{7c}$ and $R^{7d}$ is other than H, methyl and unsubstituted phenyl.

In some variations, compounds of formula (B1) where m is 1 and n-o are each 0 have the structure (B1bm), provided that:

(1) when $Y^1$ is $CR^{7a}R^{7b}$ where each $R^{7a}$ and $R^{7b}$ is H, then $R^6$ is other than H, fluoro, methoxy, unsubstituted phenyl and substituted phenyl; and (2) when $Y^1$ is $NR^8$, O, S, S(O) or $SO_2$, then at least one of $R^{5a}$ and $R^{5b}$ is other than H. In some variations of formulae (B1), (B1a), (B1d), (B1g), (B1j), (B1m), (B1s), (B1v) and (B1y)-(B1ap), at least one of $X^1$, $X^2$ and $X^3$ is N. In another variation, one of $X^1$, $X^2$ and $X^3$ is N. In one variation, $X^1$ is N and each $X^2$ and $X^3$ is independently CH or $CR^6$. In another variation, $X^2$ is N and each $X^1$ and $X^3$ is independently CH or $CR^6$. In yet another variation, $X^3$ is N and each $X^1$ and $X^2$ is independently CH or $CR^6$. In another variation, two of $X^1$, $X^2$ and $X^3$ is N. In one variation, each $X^1$ and $X^3$ is N and $X^2$ is CH or $CR^6$.

All variations referring to the formulae herein, such as formulae (B1a)-(B1bm), where applicable, may apply to formula (B2), the same as if each and every variation were specifically and individually listed.

In another aspect, compounds of formulae (B3)-(B4) are provided:

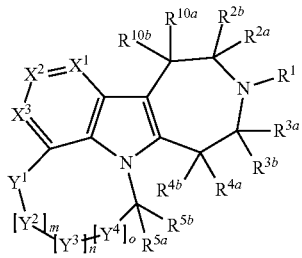
(B3)

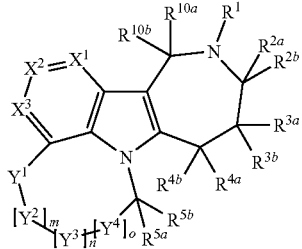
(B4)

or a salt or solvate thereof, wherein:

$R^1$ is H, hydroxyl, substituted or unsubstituted $C_1$-$C_8$alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$ and $X^3$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;

each $R^{7c}$ and $R^{7d}$, where present, is independently H, hydroxyl, halo, nitro, cyano, substituted or unsubstituted $C_1$-$C_8$alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In a particular variation, compounds of formula (B3) have the structure:

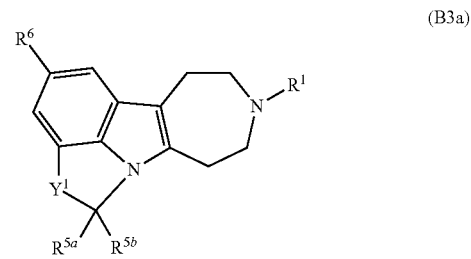

(B3a)

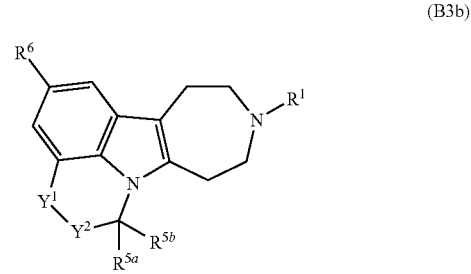

(B3b)

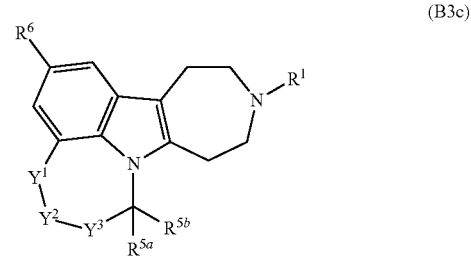

(B3c)

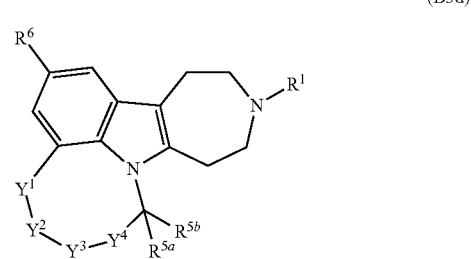

(B3d)

or a salt or solvate thereof; wherein $R^1$, $R^{5a}$, $R^{5b}$, $R^6$, $Y^1$, $Y^2$, $Y^3$ and $Y^4$, where present, are defined as for formulae (B3) and, where applicable, any variation thereof detailed herein. That is, variations of formulae (B3) detailed throughout, where applicable, apply to formulae (B3a)-(B3d) the same as if each and every variation were specifically and individually listed for formulae (B3a)-(B3d). Pharmaceutically acceptable salts of compounds of formulae (B3a)-(B3d) are also provided.

All variations referring to the formulae herein, such as formulae (B3a)-(B3d), where applicable, may apply to formula (B4), the same as if each and every variation were specifically and individually listed.

In some embodiments, compounds of the formula (B5) are provided:

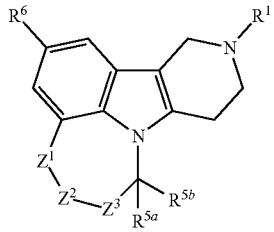

(B5)

or a salt or solvate thereof; wherein:
$R^1$ is H or substituted or unsubstituted $C_1$-$C_8$ alkyl;
each $R^{5a}$ and $R^{5b}$ is independently H, substituted or unsubstituted aryl, substituted or unsubstituted heteroaryl, substituted or unsubstituted cycloalkyl, substituted or unsubstituted heterocyclyl, or substituted or unsubstituted aralkyl, or $R^{5a}$ is taken together with a vicinal $R^{7(a\text{-}f)}$ to form a bond;
$Z^1$ is O or $CR^{7a}R^{7b}$;
$Z^2$ is a bond or $CR^{7c}R^{7d}$;
$Z^3$ is a bond or $CR^{7e}R^{7f}$;
$R^6$ is H, chloro, or substituted or unsubstituted $C_1$-$C_8$ alkyl; and
each $R^{7a}$, $R^{7b}$, $R^{7c}$, $R^{7d}$, $R^{7e}$ and $R^{7f}$, when present, is independently H, substituted or unsubstituted aryl, substituted or unsubstituted heteroaryl, substituted or unsubstituted cycloalkyl, substituted or unsubstituted heterocyclyl, or substituted or unsubstituted aralkyl, or is taken together with a vicinal $R^{7(a\text{-}f)}$ or $R^{5a}$ to form a bond.

In one variation, compounds of the formula (B5), and salts and solvates thereof, are embraced, provided that:
(1) when $Z^1$ is $CR^{7a}R^{7b}$ and at least one of $Z^2$ and $Z^3$ is a bond, then one or both of provisions (i) and (ii) apply: (i) $R^6$ is chloro or substituted or unsubstituted $C_1$-$C_8$ alkyl; and (ii) at least one of $R^{5a}$, $R^{5b}$, $R^{7a}$, $R^{7b}$, $R^{7c}$, $R^{7d}$, $R^{7e}$ and $R^{7f}$, when present, is other than H and unsubstituted phenyl;
(2) when $Z^1$ is O and at least one of $Z^2$ and $Z^3$ is a bond, then (iii) at least one of $R^{5a}$, $R^{5b}$, $R^{7c}$, $R^{7d}$, $R^{7e}$ and $R^{7f}$, when present, is other than H; and (iv) when one of $R^{7c}$, $R^{7d}$, $R^{7e}$ and $R^{7f}$, when present, is unsubstituted phenyl, $R^6$ is chloro or substituted or unsubstituted $C_1$-$C_8$ alkyl; and
(3) when $Z^2$ is $CR^{7c}R^{7d}$ and $Z^3$ is $CR^{7e}R^{7f}$, then one or both of provisions (v) and (vi) apply: (v) $R^6$ is chloro or substituted or unsubstituted $C_1$-$C_8$ alkyl; and (vi) at least one of $R^{5a}$, $R^{5b}$, $R^{7a}$, $R^{7b}$, $R^{7c}$, $R^{7d}$, $R^{7e}$ and $R^{7f}$, when present, is other than H.

In another aspect, compounds of formulae (C1)-(C2) are provided:

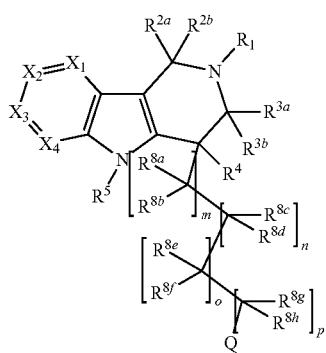

(C1)

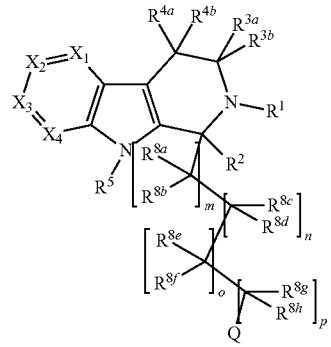

(C2)

or a salt or solvate thereof; wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—$CH_2CH_2CH_2$—) moiety or a butylene (—$CH_2CH_2CH_2CH_2$—) moiety, or $R^1$ and $R^{2a}$, where present, are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$, where present, are taken together to form an ethylene (—$CH_2CH_2$—) moiety or a propylene (—$CH_2CH_2CH_2$—) moiety or $R^1$ and $R^{4a}$, where present, are taken together to form an ethylene (—$CH_2CH_2$—) moiety or a propylene (—$CH_2CH_2CH_2$—) moiety;
each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—$CH_2CH_2CH_2$—) moiety or a butylene (—$CH_2CH_2CH_2CH_2$—) moiety, or $R^{2a}$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^2$ and $R^4$ are taken together to form a methylene (—$CH_2$—) moiety or an ethylene (—$CH_2CH_2$—) moiety or $R^{2a}$ and $R^4$ are taken together to form a methylene (—$CH_2$—) moiety or an ethylene (—$CH_2CH_2$—) moiety, or $R^2$ and a vicinal $R^{8(a\text{-}h)}$ are taken together to form a bond;
each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^2$ are taken together to form an ethylene (—CH$_2$CH$_2$—) moiety or a propylene (—CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^4$ are taken together to form a propylene (—CH$_2$CH$_2$CH$_2$—) moiety or a butylene (—CH$_2$CH$_2$CH$_2$CH$_2$—) moiety or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^4$ or $R^{4a}$, where present, is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—CH$_2$CH$_2$—) moiety or a propylene (—CH$_2$CH$_2$CH$_2$—) moiety, or $R^{4a}$ and $R^1$ are taken together to form an ethylene (—CH$_2$CH$_2$—) moiety or a propylene (—CH$_2$CH$_2$CH$_2$—) moiety, or $R^4$ and $R^{2a}$ are taken together to form a methylene (—CH$_2$—) moiety or an ethylene (—CH$_2$CH$_2$—) moiety, or $R^4$a and $R^{2a}$ are taken together to form a methylene (—CH$_2$—) moiety or an ethylene (—CH$_2$CH$_2$—) moiety, or $R^4$ and $R^{3a}$ are taken together to form a propylene (—CH$_2$CH$_2$CH$_2$—) moiety or a butylene (—CH$_2$CH$_2$CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety, or $R^4$ and a vicinal $R^{8(a-h)}$ are taken together to form a bond;

$R^5$ is H or unsubstituted C$_1$-C$_8$ alkyl;

each $X^1$, $X^2$, $X^3$ and $X^4$ is independently N, CH or CR$^6$;

each m, n, o and p is independently 0 or 1;

$R^6$ is hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol, or is taken together with vicinal $R^2$, where present, to form a bond, or is taken together with vicinal $R^4$, where present, to form a bond; and Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety.

In some variations, the compound is of the formula (C1), wherein $R^1$, $R^{2a}$, $R^{2b}$, $R^{3a}$, $R^{3b}$, $R^4$, $R^5$, m, n, o, p, $R^{8a}$, $R^{8b}$, $R^{8c}$, $R^{8d}$, $R^{8e}$, $R^{8f}$, $R^{8g}$, $R^{8h}$, $X^1$, $X^2$, $X^3$, $X^4$ and Q are as defined for formula (C1), provided that one or more of (i)-(iii) applies: (i) when none of $R^1$, $R^{2a}$, $R^{2b}$, $R^{3a}$, $R^{3b}$ and $R^4$ are taken together to form a ring, at least one of m, n, o and p is 1, none of $R^{8a}$, $R^{8b}$, $R^{8c}$, $R^{8d}$, $R^{8e}$, $R^{8f}$, $R^{8g}$ and $R^{8h}$ is taken together with a vicinal $R^{8(a-h)}$ and the carbon atoms to which they are attached to form a ring and $R^5$ is H, Q is other than carboxyl, carbonylalkoxy and unsubstituted phenyl; (ii) at least two of $R^1$, $R^{2a}$, $R^{2b}$, $R^{3a}$, $R^{3b}$ and $R^4$ are taken together to form a ring; and (iii) at least one of m, n, o and p is 1 and at least one of $R^{8a}$, $R^{8b}$, $R^{8c}$, $R^{8d}$, $R^{8e}$, $R^{8f}$, $R^{8g}$ and $R^{8h}$ is taken together with a vicinal $R^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety.

In some variations, the compound is of the formula (C2), wherein $R^1$, $R^2$, $R^{3a}$, $R^{3b}$, $R^{4a}$, $R^{4b}$, $R^5$, m, n, o, p, $R^{8a}$, $R^{8b}$, $R^{8c}$, $R^{8d}$, $R^{8e}$, $R^{8f}$, $R^{8g}$, $R^{8h}$, $X^1$, $X^2$, $X^3$, $X^4$ and Q are as defined for formula (C2), provided that at least one of m, n, o and p is 1 and one or more of (i)-(v) applies: (i) when none of $R^1$, $R^2$, $R^{3a}$, $R^{3b}$, $R^{4a}$ and $R^{4b}$ are taken together to form a ring and each $X^1$, $X^2$, $X^3$, and $X^4$ is CH, $R^5$ is an unsubstituted C$_2$-C$_8$ alkyl and Q is other than cyano, aminocarbonyl, dimethylamino and 4-methyl-1-piperazinyl; (ii) when none of $R^1$, $R^2$, $R^{3a}$, $R^{3b}$, $R^{4a}$ and $R^{4b}$ are taken together to form a ring, each $X^1$, $X^3$, and $X^4$ is CH and $X^2$ is CR$^6$ where R$^6$ is chloro or methoxy, $R^5$ is an unsubstituted C$_2$-C$_8$ alkyl and Q is other than carbonylalkoxy and cyclobutyl; (iii) when $R^1$ and $R^2$ are taken together to form a propylene (—CH$_2$CH$_2$CH$_2$—) moiety or a butylene (—CH$_2$CH$_2$CH$_2$CH$_2$—) moiety and both of $R^{3a}$ and $R^{3b}$ are H, Q is other than carboxyl or carbonylalkoxy; (iv) when $R^1$ and $R^{4a}$ are taken together to form an ethylene (—CH$_2$CH$_2$—) moiety or a propylene (—CH$_2$CH$_2$CH$_2$—) moiety, $X^2$ is CH or CR$^6$ where R$^6$ is methoxy, benzyloxy or methylthio and both of $R^{3a}$ and $R^{3b}$ are H, Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, or substituted or unsubstituted heterocyclyl, substituted or unsubstituted C$_3$-C$_8$ cycloalkylidene, a substituted or unsubstituted C$_3$-C$_8$ cycloalkenylidene, or a substituted or unsubstituted heterocyclylidene, substituted amino, aminoacyl, acyloxy, cyano, alkynyl or aminocarbonylalkoxy; and (v) when $R^{3a}$ and $R^{4a}$ are taken together to form a propylene (—$CH_2CH_2CH_2$—) moiety or a butylene (—$CH_2CH_2CH_2CH_2$—) moiety, both of $R^{3b}$ and $R^{4b}$ are H and only one of m, n, o, p is 1, Q is other than carboxyl, 1-naphthyl and 3,4-dimethoxyphenyl.

In specific variations, compounds of formula (C1) have the structure:

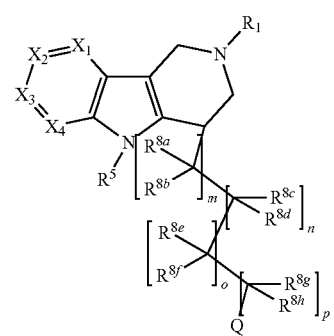

(C1a)

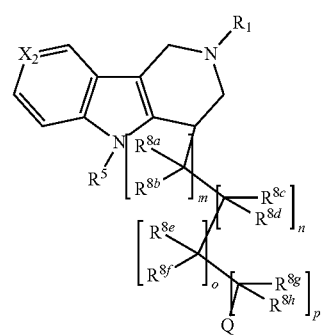

(C1b)

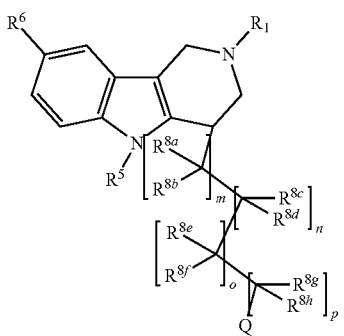

(C1c)

or a salt or solvate thereof; wherein $R^1$, $R^5$, $R^6$, $X^1$, $X^2$, $X^3$, $X^4$, $R^{8(a-h)}$, m, n, o, p and Q are defined as for formula (C1) and, where applicable, any variation thereof detailed herein. That is, variations of formula (C1) detailed throughout, where applicable, apply equally to any of formulae (C1a)-(C1c) the same as if each and every variation were specifically and individually listed for formulae (C1a)-(C1c). Pharmaceutically acceptable salts of compounds of formulae (C1a)-(C1c) are also provided.

In specific variations, compounds of formula (C1) have the structure:

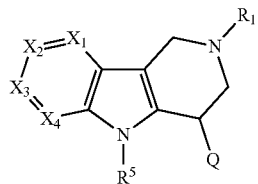

(C1d)

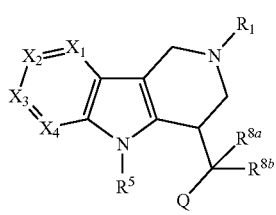

(C1e)

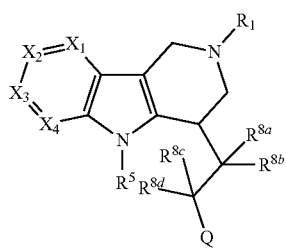

(C1f)

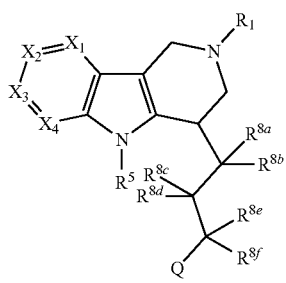

(C1g)

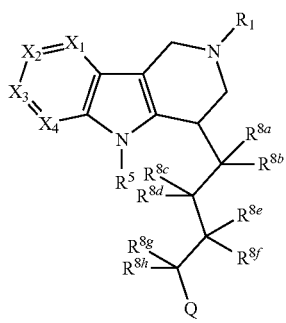

(C1h)

or a salt or solvate thereof; wherein $R^1$, $R^5$, $X^1$, $X^2$, $X^3$, $X^4$, $R^{8(a-h)}$ and Q, where present, are defined herein and, where applicable, any variation thereof detailed herein. That is, variations of the formula (C1) detailed throughout, where applicable, apply equally to any of formulae (C1d)-(C1h) the same as if each and every variation were specifically and individually listed for formulae (C1d)-(C1h). Pharmaceutically acceptable salts of compounds of formulae (C1d)-(C1h) are also provided.

In another variation, compounds of formula (C1) have the structure:

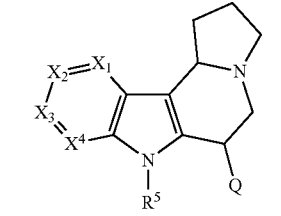
(C1i)

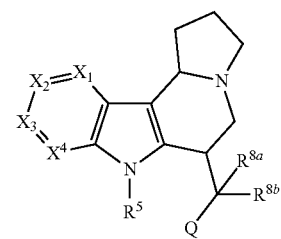
(C1j)

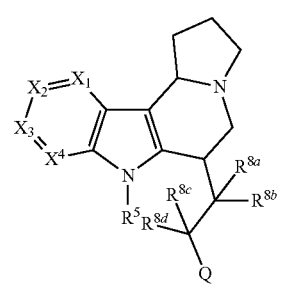
(C1k)

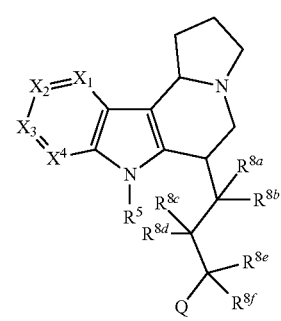
(C1l)

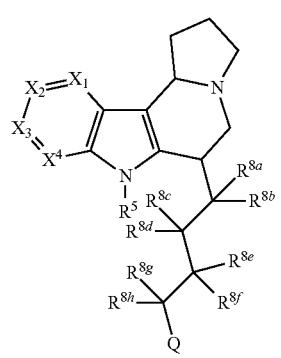
(C1m)

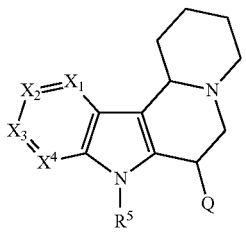
(C1n)

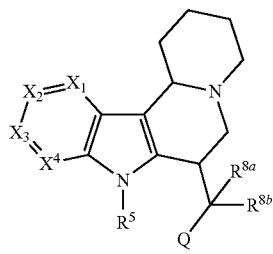
(C1o)

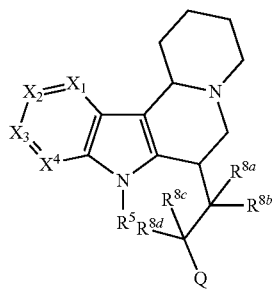
(C1p)

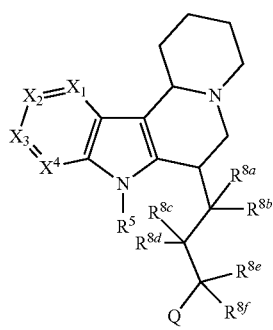
(C1q)

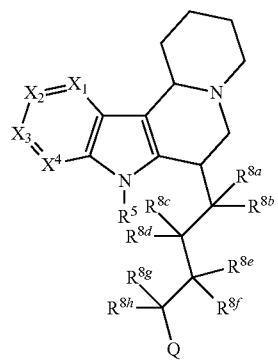
(C1r)

or a salt or solvate thereof; wherein $R^5$, $R^{8(a-h)}$, $X^1$, $X^2$, $X^3$, $X^4$ and Q, where present, are defined herein and, where applicable, any variation thereof detailed herein. That is, variations of the formula (C1) detailed throughout, where applicable, apply equally to any of formulae (C1i)-(C1r) the same as if each and every variation were specifically and individually listed for formulae (C1i)-(C1r). In one embodiment, compounds of the formula (C1) are provided wherein the compounds are of the formula (C1i)-(C1r) except that, instead of $R^1$ of formula (C1) being taken together with $R^{2a}$ of formula (IA) to provide compounds of the formula (C1i)-(C1r), $R^1$ is taken together with $R^{3a}$ to form a propylene moiety or a butylene moiety. In another embodiment, compounds of the formula (C1) are provided wherein the compounds are of the formula (C1i)-(C1r) except that, instead of $R^1$ of formula (C1) being taken together with $R^{2a}$ of formula (C1) to provide compounds of the formula (C1i)-(C1r), $R^1$ is taken together with $R^4$ to form an ethylene moiety or a propylene moiety. In a further embodiment, compounds of the formula (C1) are provided wherein the compounds are of the formula (C1i)-(C1r) except that, instead of $R^1$ of formula (C1) being taken together with $R^{2a}$ of formula (C1) to provide compounds of the formula (C1i)-(C1r), $R^{2a}$ and $R^{3a}$ are taken together to form an ethylene moiety or a propylene moiety. In still a further embodiment, compounds of the formula (C1) are provided wherein the compounds are of the formula (C1i)-(C1r) except that, instead of $R^1$ of formula (C1) being taken together with $R^{2a}$ of formula (C1) to provide compounds of the formula (C1i)-(C1r), $R^{2a}$ and $R^4$ are taken together to form a methylene moiety or an ethylene moiety. In yet another embodiment, compounds of the formula (C1) are provided wherein the compounds are of the formula (C1i)-(C1r) except that, instead of $R^1$ of formula (C1) being taken together with $R^{2a}$ of formula (C1) to provide compounds of the formula (C1i)-(C1r), $R^{3a}$ and $R^4$ are taken together to form a propylene moiety or a butylene moiety. Variations detailed throughout, where applicable, apply to such formulae the same as if each and every variation were specifically and individually listed. Pharmaceutically acceptable salts of such formulae are also provided. Pharmaceutically acceptable salts of compounds of formulae (C1i)-(C1r) are also provided.

All variations referring to the formulae herein, such as formulae (C1a)-(C1r), where applicable, may apply to formula (C2), the same as if each and every variation were specifically and individually listed.

In some embodiments, compounds of the formula (CIA) have structures of formulae (G1)-(G5):

(G1)
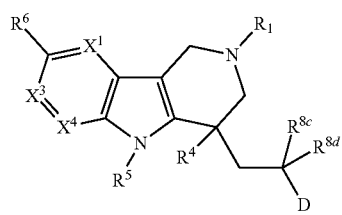

(G2)
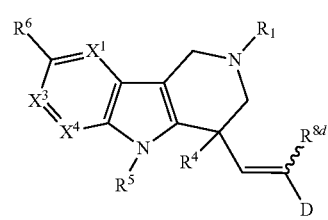

(G3)
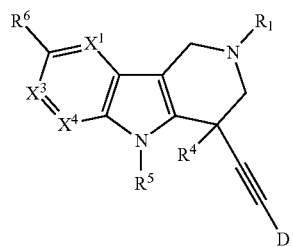

(G4)
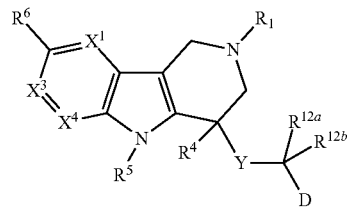

(G5)
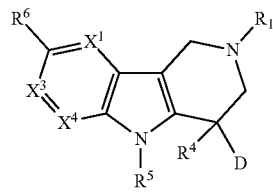

wherein:

$R^1$ is H or substituted or unsubstituted $C_1$-$C_8$ alkyl;

each $R^4$ and $R^5$ is independently H or unsubstituted $C_1$-$C_8$ alkyl;

$R^6$ is H, halo, or substituted or unsubstituted $C_1$-$C_8$ alkyl;

$R^{8c}$ is H, OH or substituted or unsubstituted $C_1$-$C_8$ alkyl;

$R^{8d}$ is H or substituted or unsubstituted $C_1$-$C_8$ alkyl, and the ⁓ bond indicates the presence of either an E or Z double bond configuration;

Y is O or $NR^{11}$;

each $R^{11}$, $R^{12a}$ and $R^{12b}$ is independently H or substituted or unsubstituted $C_1$-$C_8$ alkyl;

each $X^1$, $X^3$ and $X^4$ is independently CH or N; and

D is substituted or unsubstituted aryl or substituted or unsubstituted heteroaryl;

provided that when the compound is of the formula (G5), D is other than unsubstituted phenyl.

In some embodiments, the compound is of the formula (G1). In some embodiments, wherein the compound is of the formula (G2). In some embodiments, the compound is of the formula (G3). In some embodiments, the compound is of the formula (G4). In some embodiments, the compound is of the formula (G5).

In another aspect, compounds of formulae (C3)-(C4) are provided:

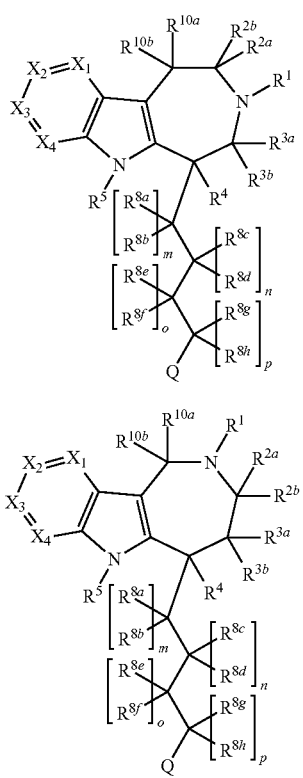

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and a vicinal $R^{8a}$, where present, are taken together to form a bond;

$R^5$ is H or unsubstituted $C_1$-$C_8$ alkyl;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$alkyl, substituted or unsubstituted $C_3$-$C_8$cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol, or is taken together with vicinal $R^4$ to form a bond; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In a particular variation, compounds of formulae (C3) have the structure:

(C3a)
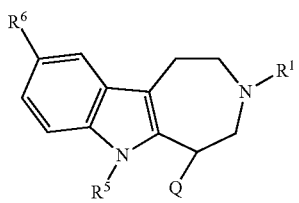

(C3b)
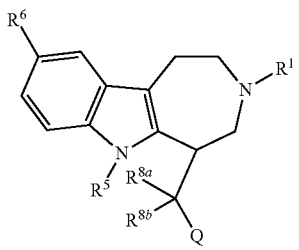

(C3c)
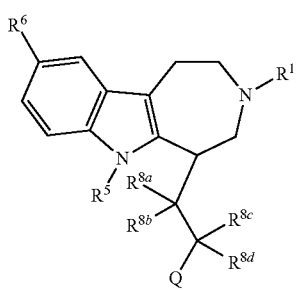

(C3d)
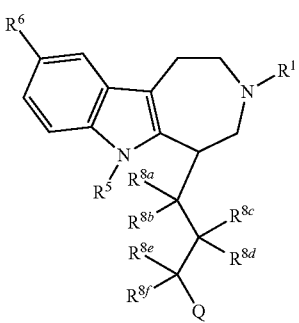

(C3e)
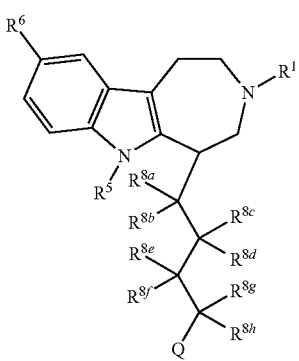

or a salt or solvate thereof; wherein $R^1$, $R^5$, $R^6$ and $R^{8(a-h)}$, where present, and Q are defined as for formula (C3) and, where applicable, any variation thereof detailed herein. That is, variations of formula (C3) detailed throughout, where applicable, apply to formulae (C3a)-(C3e) the same as if each and every variation were specifically and individually listed for formulae (C3a)-(C3e). Pharmaceutically acceptable salts of compounds of formulae (C3a)-(C3e) are also provided.

In particular variation, compounds of formula (C3) have the structure:

(C3f)
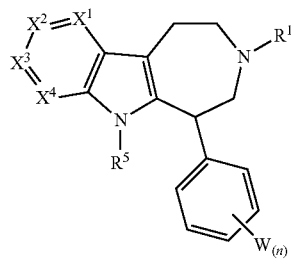

(C3g)
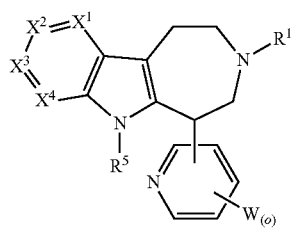

(C3h)
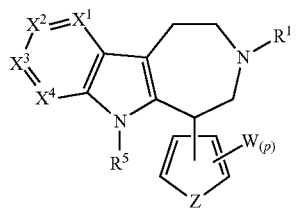

or a salt or solvate thereof; wherein $R^1$, $R^5$, $X^1$, $X^2$, $X^3$ and $X^4$ are defined as for formula (C3) and, where applicable, any variation thereof detailed herein, n is 0-5, o is 0-4, p is 0-3, Z is NH, N—$CH_3$, O or S, and W is H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino. In one particular aspect of this variation, W is H, substituted or unsubstituted aryl, or substituted or unsubstituted heteroaryl. In one particular aspect of this variation, Z is S. Variations of formula (C3) detailed throughout, where applicable, apply equally to any of formulae (C3f)-(C3h), the same as if each and every variation were specifically and individually listed for formula (C3f)-(C3h). Pharmaceutically acceptable salts of compounds of formulae (C3f)-(C3h) are also provided.

All variations referring to the formulae herein, such as formulae (C3a)-(C3h), where applicable, may apply to formula (C4), the same as if each and every variation were specifically and individually listed.

In another aspect, compounds of formulae (D1)-(D2) are provided:

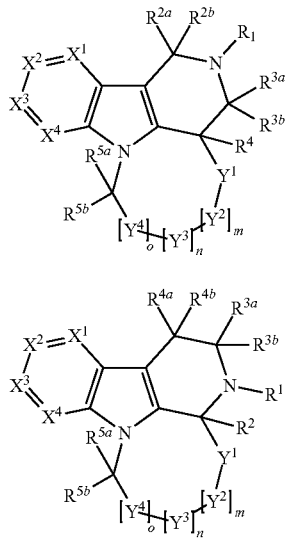

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—CH$_2$CH$_2$CH$_2$—) moiety or a butylene (—CH$_2$CH$_2$CH$_2$CH$_2$—) moiety, or $R^1$ and $R^{2a}$, where present, are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^4$, where present, are taken together to form an ethylene (—CH$_2$CH$_2$—) moiety or a propylene (—CH$_2$CH$_2$CH$_2$—) moiety or $R^1$ and $R^{4a}$, where present, are taken together to form an ethylene (—CH$_2$CH$_2$—) moiety or a propylene (—CH$_2$CH$_2$CH$_2$—) moiety;

each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ a and $R^1$ are taken together to form a propylene (—CH$_2$CH$_2$CH$_2$—) moiety or a butylene (—CH$_2$CH$_2$CH$_2$CH$_2$—) moiety, or $R^2$ and $R^{3a}$ are taken together to form an ethylene (—CH$_2$CH$_2$—) moiety or a propylene (—CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^2$ and $R^4$ are taken together to form a methylene (—CH$_2$—) moiety or an ethylene (—CH$_2$CH$_2$—) moiety or $R^{2a}$ and $R^4$ are taken together to form a methylene (—CH$_2$—) moiety or an ethylene (—CH$_2$CH$_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^2$ are taken together to form an ethylene (—CH$_2$CH$_2$—) moiety or a propylene (—CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^4$ are taken together to form a propylene (—CH$_2$CH$_2$CH$_2$—) moiety or a butylene (—CH$_2$CH$_2$CH$_2$CH$_2$—) moiety or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^4$ or $R^{4a}$, where present, is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—CH$_2$CH$_2$—) moiety or a propylene (—CH$_2$CH$_2$CH$_2$—) moiety, or $R^{4a}$ and $R^1$ are taken together to form an ethylene (—CH$_2$CH$_2$—) moiety or a propylene (—CH$_2$CH$_2$CH$_2$—) moiety, or $R^4$ and $R^{2a}$ are taken together to form a methylene (—CH$_2$—) moiety or an ethylene (—CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^4$ and $R^{3a}$ are taken together to form a propylene (—CH$_2$CH$_2$CH$_2$—) moiety or a butylene (—CH$_2$CH$_2$CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^2$ are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (D2) where m-o are each 0, provided that the compound is other than cis-4-ethyl-2,3,3a,4-tetrahydro-3-(phenylmethyl)benzo[b]pyrido[2,3,4-gh]pyrrolizin-5(1H)-one and 1,2,3,3a,4,5-hexahydro-8-methoxy-4,4-dimethylbenzo[b]pyrido[2,3,4-gh]pyrrolizine.

In another variation, the compound is of the formula (D2) where m-o are each 0, provided that (i) when each $X^1$, $X^2$, $X^3$ and $X^4$ is CH, each $R^2$, $R^{3a}$, $R^{3b}$, $R^{4a}$ and $R^{4b}$ is H, $R^{5a}$ and $R^{5b}$ are taken together with the carbon to which they are attached to form a carbonyl moiety, and $Y^1$ is $CR^{7a}R^{7b}$ where one of $R^{7a}$ and $R^{7b}$ is ethyl and the other is hydrogen, $R^1$ is other than benzyl, and (ii) when each $X^1$, $X^2$ and $X^4$ is CH, $X^3$ is $CR^6$ where $R^6$ is methoxy, CH, each $R^2$, $R^{3a}$, $R^{3b}$, $R^{4a}$, $R^{4b}$, $R^{5a}$ and $R^{5b}$ is H, and $R^{5b}$ is H, and $Y^1$ is $CR^{7a}R^{7b}$ where each $R^{7a}$ and $R^{7b}$ is methyl, $R^1$ is other than hydrogen.

In one variation, the compound is of the formula (D1) where m is 1 and n-o are each 0, provided that the compound is other than 1,2,3,3a,5,6-hexahydro-4H-indolo[3,2,1-ij][1,6]naphthyridin-4-one.

In one variation, the compound is of the formula (D1) where m is 1 and n-o are each 0, provided that when each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is carbonyl and $Y^2$ is $CH_2$, $R^1$ is other than hydrogen.

In one variation, the compound is of the formula (D2) where m is 1 and n-o are each 0, wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$ and $R^2$ are as defined for formula (D2), provided that at least one of $X^1$, $X^2$, $X^3$ and $X^4$ is N or CR6.

In another variation, the compound is of the formula (D2) where m is 1 and n-o are each 0, wherein $R^1$, $R^2$, $R^{3a}$, $R^{3b}$ $R^{4a}$ $R^{4b}$, $R^{5a}$, $R^{5b}$, $X^1$, $X^2$, $X^3$, $X^4$, $Y^1$ and $Y^2$ are as defined for formula (D2), provided that at least one of $X^1$, $X^2$, $X^3$ and $X^4$ is N or $CR^6$, and when $Y^1$ is $CR^{7a}R^{7b}$ and $Y^2$ is $CR^{7c}R^{7d}$, at least one of $R^{5a}$, $R^{5b}$, $R^{7a}$, $R^{7b}$, $R^{7c}$ and $R^{7d}$ is a group containing a cyclic moiety. In one such variation, at least one of $R^{5a}$, $R^{5b}$, $R^{7a}$, $R^{7b}$, $R^{7c}$ and $R^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In one variation, the compound is of the formula (D2) where m-n are each 1 and n is 0, wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$ and $Y^3$ are as defined for formula (D2), provided that at least one of $X^1$, $X^2$, $X^3$ and $X^4$ is N or $CR^6$.

In another variation, the compound is of the formula (D2) where m-n are each 1 and n is 0, wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$ and $Y^3$ are as defined for formula (D2), provided that at least one of $X^1$, $X^2$, $X^3$ and $X^4$ is N or $CR^6$, and when $Y^1$ is $CR^{7a}R^{7b}$ and $Y^2$ is $CR^{7c}R^{7d}$, at least one of $R^{5a}$, $R^{5b}$, $R^{7a}$, $R^{7b}$, $R^{7c}$ and $R^{7d}$ is a group containing a cyclic moiety. In one such variation, at least one of $R^{5a}$, $R^{5b}$, $R^{7a}$, $R^{7b}$, $R^{7c}$ and $R^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (D2) where m-n are each 1 and n is 0, wherein $R^1$, $R^2$, $R^{3a}$, $R^{3b}$, $R^{4a}R^{4b}$, $R^{5a}R^{5b}$, $X^1$, $X^2$, $X^3$, $X^4$, $Y^1$, $Y^2$ and $Y^3$ are as defined for formula (D2), provided that at least one of $X^1$, $X^2$, $X^3$ and $X^4$ is N or $CR^6$, and when $Y^1$ is $CR^{7a}R^{7b}$, $Y^2$ is $CR^{7c}R^{7d}$ and $Y^3$ is $CR^{7e}R^{7f}$ at least one of $R^{5a}$, $R^{5b}$, $R^{7a}$, $R^{7b}$, $R^{7c}$, $R^{7d}$, $R^{7e}$ and $R^{7f}$ is a group containing a cyclic moiety. In one such variation, at least one of $R^{5a}$, $R^{5b}$, $R^{7a}$, $R^{7b}$, $R^{7c}$, $R^{7d}$, $R^{7e}$ and $R^{7f}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$, $R^{7d}$ $R^{7e}$ and $R^{7f}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^5$, $R^{5b}$, $R^{7a}$, $R^{7b}$, $R^{7c}$, $R^{7d}$, $R^{7e}$ and $R^{7f}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In one variation, the compound is of the formula (D2) where m-o are each 1, wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$, $Y^3$ and $Y^4$ are as defined for formula (D2), provided when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ at least one of $R^{5a}$, $R^{5b}$ $R^{7a}$, $R^{7b}$, $R^{7c}$, $R^{7d}$, $R^{7e}$, $R^{7f}$, $R^{7g}$ and $R^{7h}$ is a group containing a cyclic moiety. In one such variation, at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ $R^{7d}$, $R^{7e}$, $R^{7f}$, $R^{7g}$ and $R^{7h}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (D2) where m-o are each 1, wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$, $Y^3$ and $Y^4$ are as defined for formula (D2), provided when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ at least one of $X^1$, $X^2$, $X^3$ and $X^4$ is N or $CR^6$ and $R^{5a}$ and $R^{5b}$ are not taken together with the carbon to which they are attached to form a carbonyl moiety.

In specific variations, compounds of the formula (D1) have the structure:

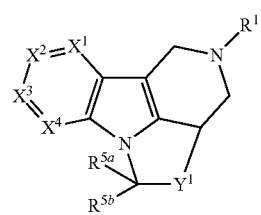

(D1a)

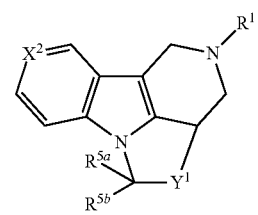

(D1b)

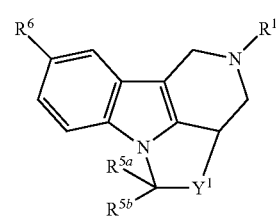

(D1c)

-continued
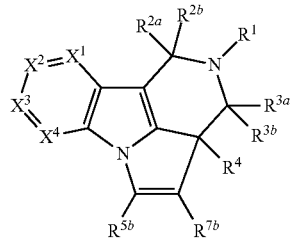
(D1d)
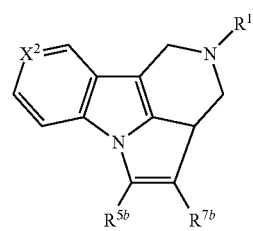
(D1e)
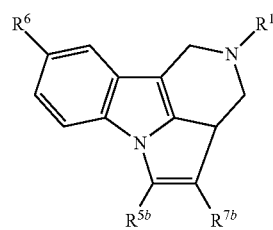
(D1f)
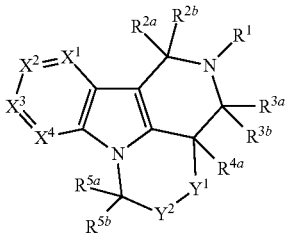
(D1g)
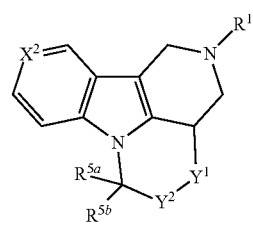
(D1h)
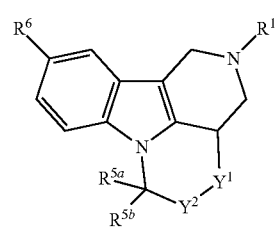
(D1i)
-continued
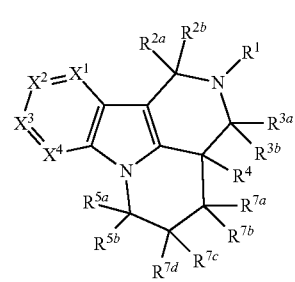
(D1j)
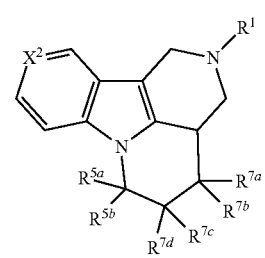
(D1k)
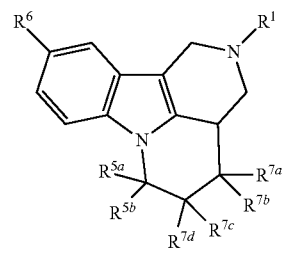
(D1l)
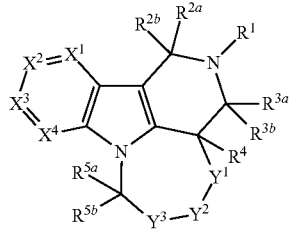
(D1m)
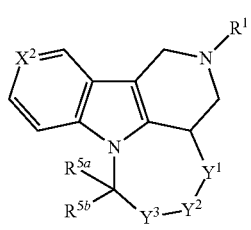
(D1n)
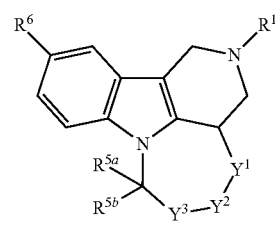
(D1o)

(D1p)
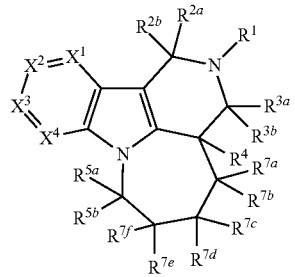
(D1q)
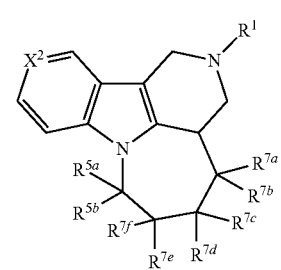
(D1r)
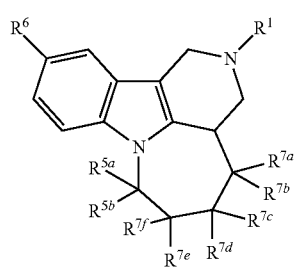
(D1s)
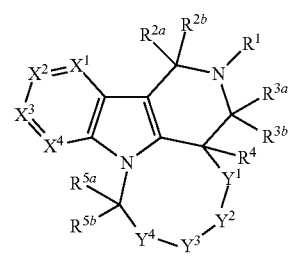
(D1t)
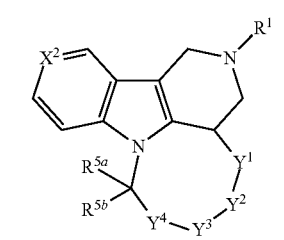
(D1u)
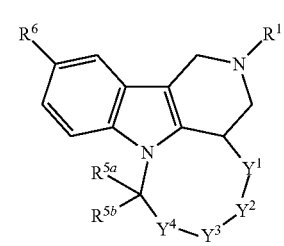
(D1v)
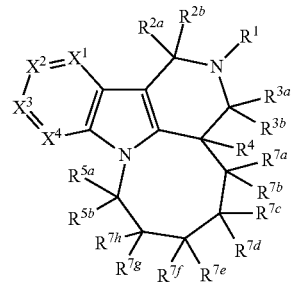
(D1w)
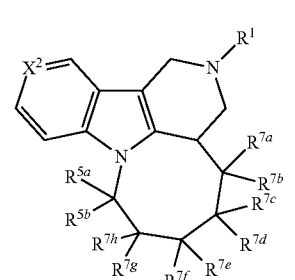
(D1x)
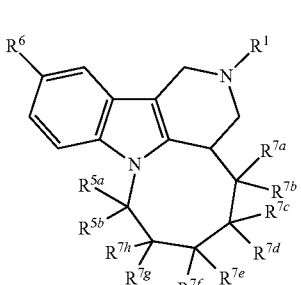
(D1y)
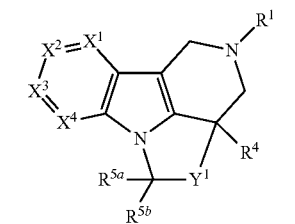
(D1z)
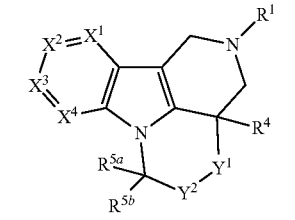
(D1aa)
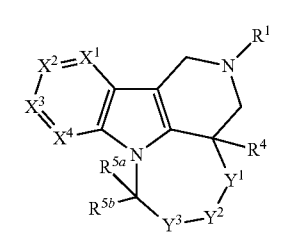

-continued
(D1ab)
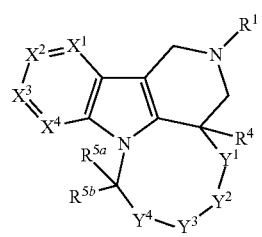
(D1ac)
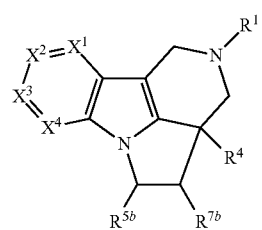
(D1ad)
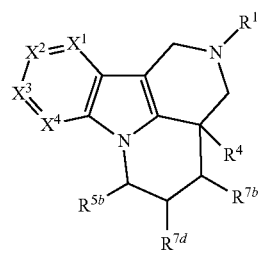
(D1ae)
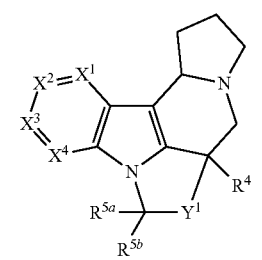
(D1af)
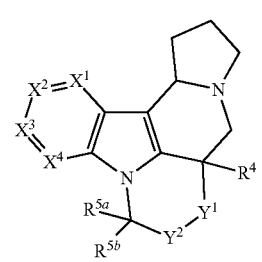
(D1ag)
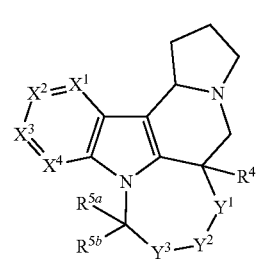
-continued
(D1ah)
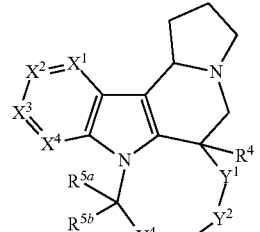
(D1ai)
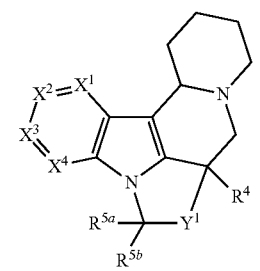
(D1aj)
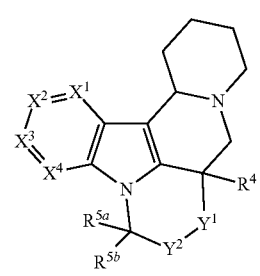
(D1ak)
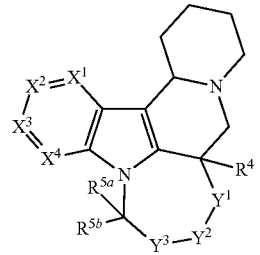
(D1al)
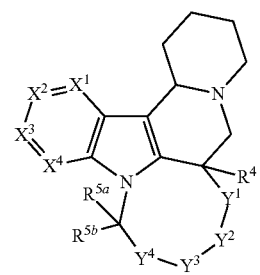
(D1am)
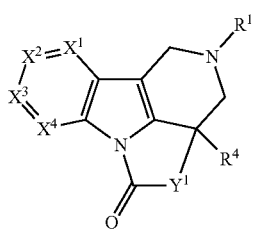

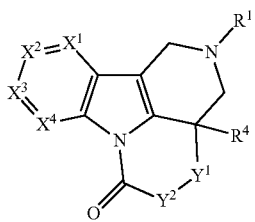 (D1an)
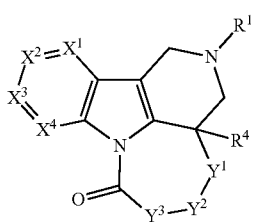 (D1ao)
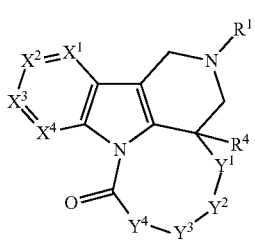 (D1ap)
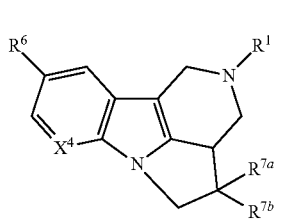 (D1aq)
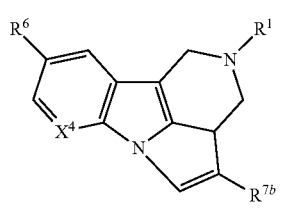 (D1ar)
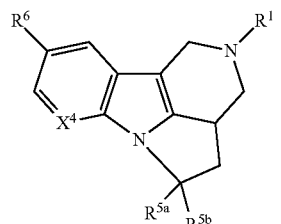 (D1as)
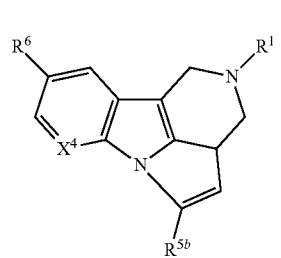 (D1at)
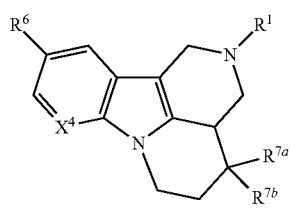 (D1au)
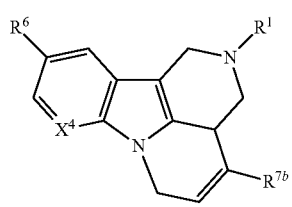 (D1av)
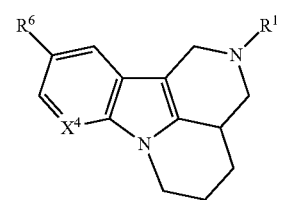 (D1aw)
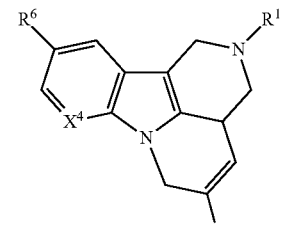 (D1ax)
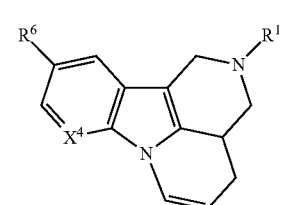 (D1ay)
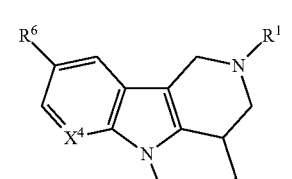 (D1az)
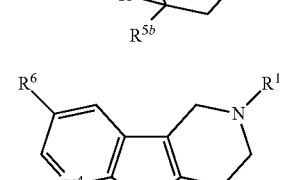 (D1ba)
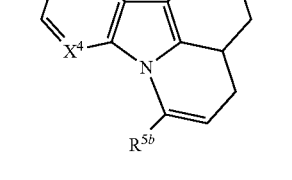

(D1bb) 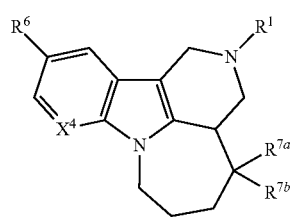

(D1bc) 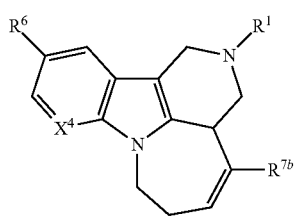

(D1bd) 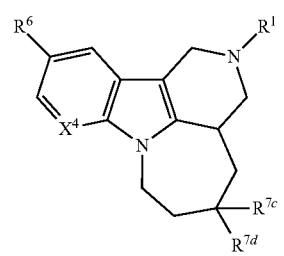

(D1be) 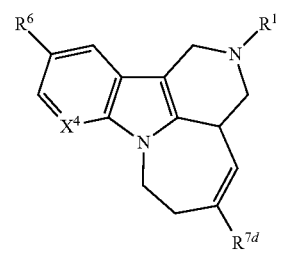

(D1bf) 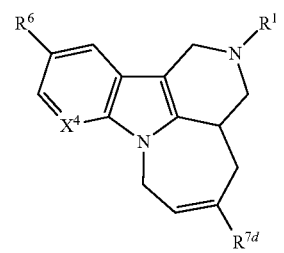

(D1bg) 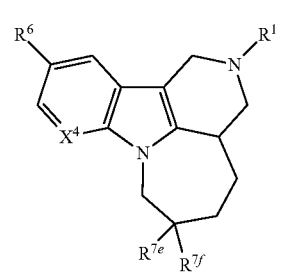

(D1bh) 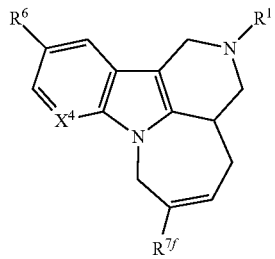

(D1bi) 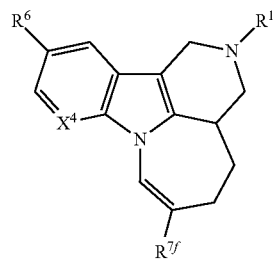

(D1bj) 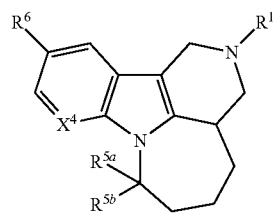

(D1bk) 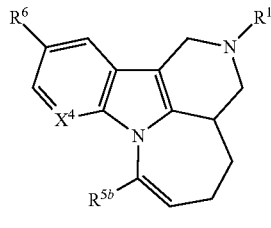

(D1bl) 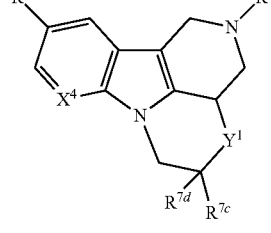

(D1bm) 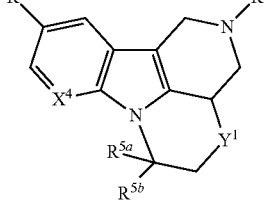

or a salt or solvate thereof; wherein $R^1$, $R^{2a}$, $R^{2b}$, $R^{3a}$, $R^{3b}$, $R^{4a}$, $R^{4b}$, $R^{5a}$, $R^{5b}$, $R^6$, $R^{7(a\text{-}h)}$, $X^1$, $X^2$, $X^3$, $X^4$, $Y^1$, $Y^2$, $Y^3$ and $Y^4$, where present, are defined as for formula (D1) and, where applicable, any variation thereof detailed herein. That is, variations of formula (D1) detailed throughout, where applicable, apply to formulae (D1a)-(D1bm) the same as if each and every variation were specifically and individually listed for formulae (D1a)-(D1bm). Pharmaceutically acceptable salts of compounds of formulae (D1a)-(D1bm) are also provided.

All variations referring to the formulae herein, such as formulae (D1a)-(D1bm), where applicable, may apply to formula (D2), the same as if each and every variation were specifically and individually listed.

In another aspect, compounds of formulae (D3)-(D4) are provided:

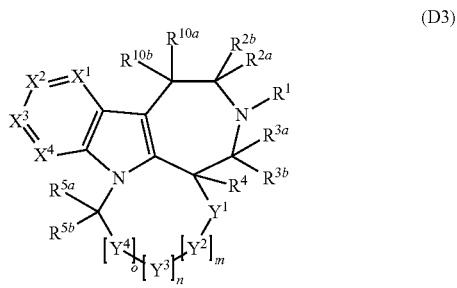

(D3)

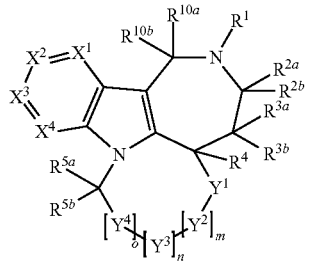

(D4)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7c}R^{7f}$;

$Y^3$, where present, is $CR^{7e}CR^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

$R^6$ is hydroxyl, nitro, cyano, halo, $C_1$-$C_8$perhaloalkyl, substituted or unsubstituted $C_1$-$C_8$ alkyl, substituted or unsubstituted $C_2$-$C_8$alkenyl, substituted or unsubstituted $C_2$-$C_8$ alkynyl, substituted or unsubstituted aryl, substituted or unsubstituted heteroaryl, $C_1$-$C_8$perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In particular variation, compounds of formulae (D3) have the structure:

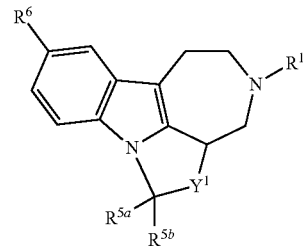

(D3a)

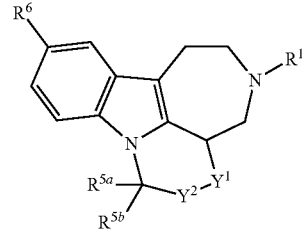

(D3b)

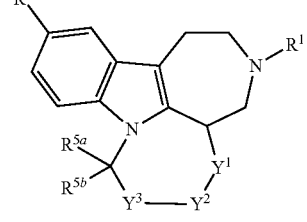

(D3c)

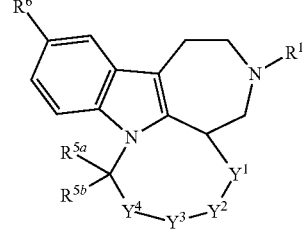

(D3d)

or a salt or solvate thereof; wherein $R^1$, $R^{5a}$, $R^{5b}$, $R^6$, $Y^1$, $Y^2$, $Y^3$ and $Y^4$, where present, are defined as for formulae (D3) and, where applicable, any variation thereof detailed herein. That is, variations of formulae (D3) detailed throughout, where applicable, apply to formulae (D3a)-(D3d) the same as if each and every variation were specifically and individually listed for formulae (D3a)-(D3d). Pharmaceutically acceptable salts of compounds of formulae (D3a)-(D3d) are also provided.

All variations referring to the formulae herein, such as formulae (D3a)-(D3d), where applicable, may apply to formula (D4), the same as if each and every variation were specifically and individually listed.

In one variation of formulae (A1)-(A4) or (B1)-(B2), or any variation therefrom, at least one of $X^1$, $X^2$ and $X^3$ is N. In another variation, one of $X^1$, $X^2$ and $X^3$ is N. In one variation, $X^1$ is N and each $X^2$ and $X^3$ is independently CH or $CR^6$. In another variation, $X^2$ is N and each $X^1$ and $X^3$ is independently CH or $CR^6$. In yet another variation, $X^3$ is N and each $X^1$ and $X^2$ is independently CH or $CR^6$. In another variation, two of $X^1$, $X^2$ and $X^3$ is N. In one variation, each $X^1$ and $X^3$ is N and $X^2$ is CH or $CR^6$.

In another variation of formulae (C1)-(C4) or (D1)-(D4), or any variation therefrom, at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

In one variation of formulae (A1)-(A4) or (C1)-(C4), the chain comprising $R^{8a}$, $R^{8b}$, $R^{8c}$, $R^{8d}$, $R^{8e}$, $R^{8f}$, $R^{8g}$, $R^{8h}$ and Q is selected from the following structures:

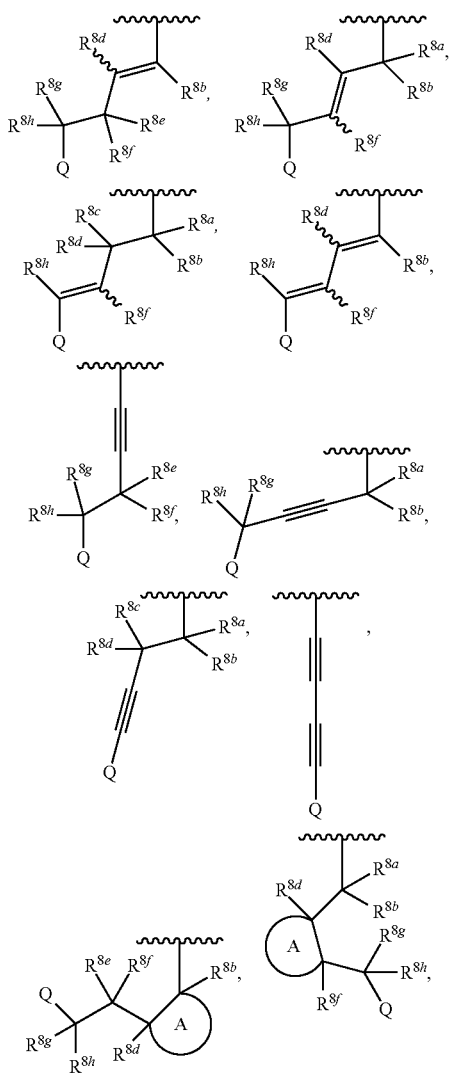

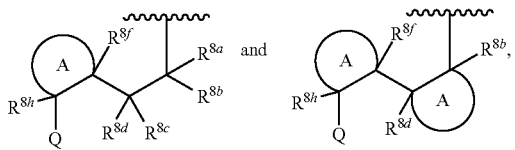

or a salt or solvate thereof, wherein $R^{8a}$, $R^{8b}$, $R^{8c}$, $R^{8d}$, $R^{8e}$, $R^{8f}$, $R^{8g}$, $R^{8h}$ and Q are as defined herein and ring A comprises a substituted or unsubstituted $C_3$-$C_8$ cycloalkyl, substituted or unsubstituted $C_3$-$C_8$ cycloalkenyl, or substituted or unsubstituted heterocyclyl group.

In another variation of formulae (A1)-(A4) or (C1)-(C4), the chain comprising $R^{8a}$, $R^{8b}$, $R^{8c}$, $R^{8d}$, $R^{8e}$, $R^{8f}$, $R^{8g}$, $R^{8h}$ and Q is selected from the following structures:

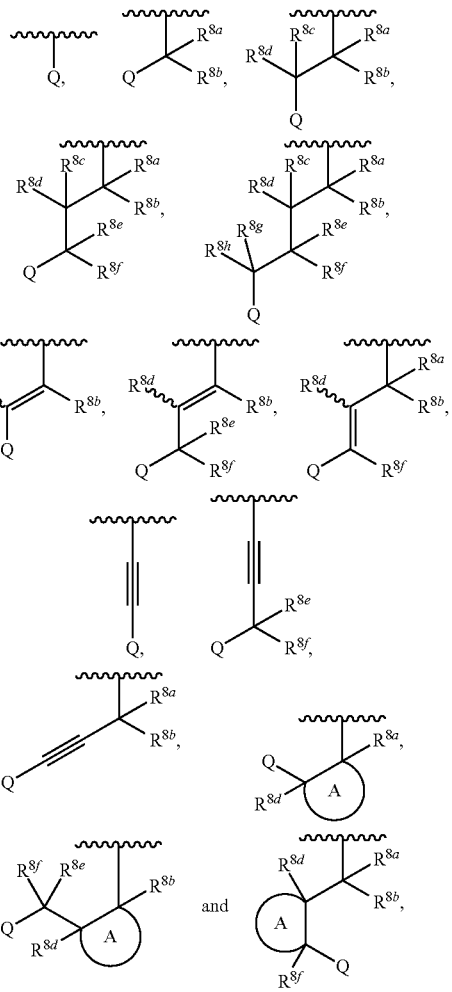

or a salt or solvate thereof, wherein $R^{8a}$, $R^{8b}$, $R^{8c}$, $R^{8d}$, $R^{8e}$, $R^{8f}$, $R^{8g}$, $R^{8h}$ and Q are as defined herein and ring A comprises a substituted or unsubstituted $C_3$-$C_8$ cycloalkyl, substituted or unsubstituted $C_3$-$C_8$ cycloalkenyl, or substituted or unsubstituted heterocyclyl group. In a particular variation, when o and p are each 0, the chain comprising $R^{8a}$, $R^{8b}$, $R^{8c}$, $R^{8d}$ and Q is selected from the following structures:

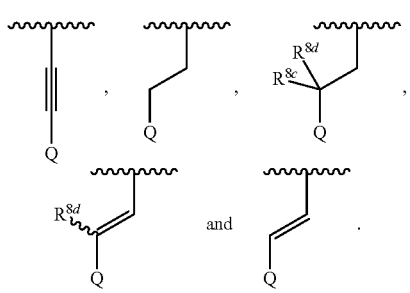

In a particular variation, where ring A depicted above comprises a substituted or unsubstituted $C_3$-$C_8$cycloalkenyl, the double-bond of the cycloalkenyl ring is at a position other than in the linear chain. For example, if the carbon atoms bearing $R^{8a}$ and $R^{8c}$ are part of a substituted or unsubstituted $C_3$-$C_8$cycloalkenyl ring, e.g., ring A depicted above, then the carbon atoms bearing $R^{8a}$ and $R^{8c}$ are connected by a single bond.

In certain embodiments, compounds are provided wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy. In specific embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl. In more specific embodiments, $R^1$ is an unsubstituted $C_1$-$C_8$ alkyl such as methyl and cyclopropyl.

In certain embodiments, compounds are provided where $R^1$ is selected from the following moieties:

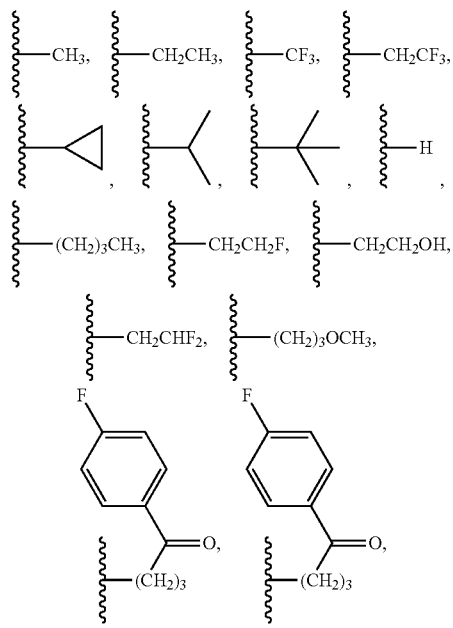

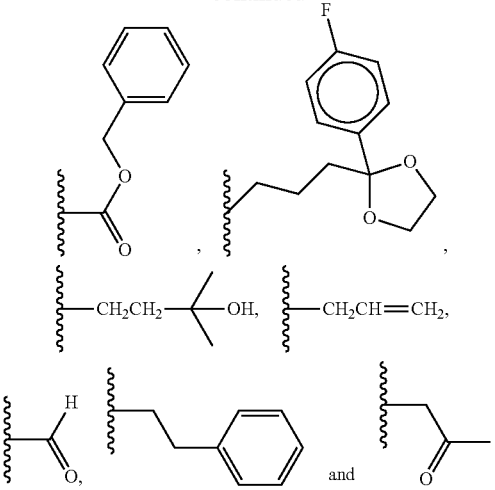

In certain compounds described herein, each $R^2$, $R^{2a}$ and $R^{2b}$, where present, is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{2a}$ and $R^{2b}$ is independently H or fluoro. In another specific embodiment, $R^{2a}$ and $R^{2b}$ are both H. In a further specific embodiment, $R^{2a}$ and $R^{2b}$ are both H and $R^{3a}$ and $R^{3b}$ are both H.

In certain compounds described herein, each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety. In specific embodiments, each $R^{3a}$ and $R^{3b}$ is independently H, methyl, fluoro or $R^{3a}$ and $R^{3b}$ are taken together to form a carbonyl moiety. In a specific embodiment, $R^{3a}$ and $R^{3b}$ are both H.

In certain compounds, each $R^4$, $R^{4a}$ and $R^{4b}$, where present, is independently H, substituted or unsubstituted $C_1$-$C_8$alkyl, halo, cyano, hydroxyl, alkoxy, nitro or $R^{4a}$ and $R^{4b}$ are taken together to form a carbonyl moiety. In specific embodiments, each $R^{4a}$ and $R^{4b}$ is independently H, halo, hydroxyl or methyl or $R^{4a}$ and $R^{4b}$ are taken together to form a carbonyl moiety. In another specific embodiment, $R^{4a}$ and $R^{4b}$ are both H. In a further specific embodiment, $R^{4a}$ and $R^{4b}$ are both H and $R^{2a}$, $R^{2b}$, $R^{3a}$ and $R^{3b}$ are each H.

In certain compounds described herein, each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together to form a carbonyl moiety. In specific embodiments, each $R^{10a}$ and $R^{10b}$ is independently H, methyl, fluoro or $R^{10a}$ and $R^{10b}$ are taken together to form a carbonyl moiety. In a specific embodiment, $R^{10a}$ and $R^{10b}$ are both H.

In certain compounds, each $X^1$, $X^2$, $X^3$ and $X^4$, where present, is independently N, CH or $CR^6$. In certain embodiments, each $X^1$, $X^2$, $X^3$ and $X^4$, where present, is CH or $CR^6$, such that the ring comprising $X^1$, $X^2$, $X^3$ and $X^4$, where present, is an optionally substituted phenyl ring. In specific embodiments, $X^2$ is $CR^6$ where $R^6$ is halo or alkyl and $X^1$ and $X^3$ are each CH. In other embodiments, one of $X^1$, $X^2$, $X^3$ and $X^4$ is N, and the others are CH or $CR^6$, such that the ring comprising $X^1$, $X^2$, $X^3$ and $X^4$ is an optionally substituted pyridine ring. In further embodiments, two of $X^1$, $X^2$, $X^3$ and $X^4$ are N, and the other is CH or $CR^6$, such that the ring comprising $X^1$, $X^2$, $X^3$ and $X^4$ is an optionally substituted pyrimidine or pyrazine ring.

In certain compounds, each $R^6$, where present, is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In one variation, at least one of $X^1$-$X^3$ is $CR^6$ where $R^6$ is halo. In a particular variation, one of $X^1$-$X^3$ is $CR^6$ where $R^6$ is chloro and the others are CH. In a specific variation, $X^1$ and $X^3$ are each CH and $X^2$ is $CR^6$ where $R^6$ is chloro.

In certain embodiments, each $R^6$, where present, is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, —S(O)-alkyl, —S(O)-aryl, —S(O)-aralkyl, substituted or unsubstituted amino, alkylsulfonylamino or acyl. In further embodiments, each $R^6$, where present, is independently hydroxyl, halo, $C_1$-$C_4$ perhaloalkyl, substituted or unsubstituted $C_1$-$C_4$ alkyl, substituted or unsubstituted aryl, substituted or unsubstituted heteroaryl, or $C_1$-$C_4$ alkoxy; or in still a further variation, each $R^6$, where present, is independently halo, unsubstituted $C_1$-$C_4$ alkyl or $C_1$-$C_4$ perhaloalkyl.

In specific embodiments, the ring comprising $X^1$, $X^2$, $X^3$ and $X^4$, where present, is a phenyl, pyridyl, pyrimidinyl or pyrazinyl ring, optionally substituted with 0-3 $R^6$ groups (i.e., $(R^6)_n$ where n is 0, 1, 2 or 3). In some such embodiments, n is 1, 2 or 3 and each $R^6$ is independently halo, methyl or $CF_3$.

In compounds of formulae (B1-B4) and (D1-D4), and variations thereof, at least one of $R^{5a}$, $R^{5b}$, $R^{7(a\text{-}h)}$ or Q, where present, is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino. In one variation, compounds are provided where at least one of $R^{5a}$, $R^{5b}$, $R^{7(a\text{-}h)}$ or Q, where present, is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In certain embodiments, at least one of $R^{5a}$, $R^{5b}$, $R^{7(a\text{-}h)}$ or Q, where present, is a substituted or unsubstituted 5- or 6-membered aryl or heteroaryl. In some such embodiments, at least one of $R^{5a}$, $R^{5b}$, $R^{7(a\text{-}h)}$ or Q, where present, is a substituted or unsubstituted phenyl, pyridyl or pyrimidinyl ring. When at least one of $R^{5a}$, $R^{5b}$, $R^{7(a\text{-}h)}$ or Q, where present, is substituted, it is frequently substituted with from 1-3 substituents selected from group consisting of halo, $C_1$-$C_4$ alkyl, $C_1$-$C_4$ perhaloalkyl, and $C_1$-$C_4$ alkoxy.

In a particular variation, compounds of formulae (B1-B4) and (D1-D4), and variations thereof, have at least one of $R^{5a}$, $R^{5b}$, $R^{7(a\text{-}h)}$ or Q, where present, is a substituted heteroaryl, a monosubstituted aryl group substituted with a chloro or alkyl group or a di- or tri-substituted aryl moiety. For instance, at least one of $R^{5a}$, $R^{5b}$, $R^{7(a\text{-}h)}$ or Q, where present, in one variation is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In one aspect, at least one of $R^{5a}$, $R^{5b}$, $R^{7(a\text{-}h)}$ or Q, where present, is a substituted pyridyl such as 6-methyl-3-pyridyl, 6-trifluoromethyl-3-pyridyl and 5-trifluoromethyl-3-pyridyl.

In some embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{3a}$ and $R^{3b}$ are taken together to form a carbonyl moiety; each $R^{4a}$ and $R^{4b}$ is independently H or fluoro; and each $R^{3a}$ and $R^{3b}$ is independently H, halo, hydroxyl or methyl or $R^{2a}$ and $R^{2b}$ are taken together to form a carbonyl moiety. In particular variations, $R^1$ is an unsubstituted $C_1$-$C_8$ alkyl and $R^{2a}$, $R^{2b}$, $R^{3a}$, $R^{3b}$, $R^{4a}$ and $R^{4b}$ are each H. In still a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H and at least one of $R^{5a}$, $R^{5b}$, $R^{7(a\text{-}h)}$ or Q, where present, is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In still a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H and $X^2$ is $CR^6$ where $R^6$ is chloro. In yet a further variation, $R^1$ is an unsubstituted $C_1$-$C_8$ alkyl, $R^{2a}$, $R^{2b}$, $R^{3a}$, $R^{3b}$, $R^{4a}$ and $R^{4b}$ are each H, $X^2$ is $CR^6$ where $R^6$ is chloro and at least one of $R^{5a}$, $R^{5b}$, $R^{7(a\text{-}h)}$ or Q, where present, is a substituted or unsubstituted aryl or a substituted or substituted heteroaryl. In one such variation, at least one of $R^{5a}$, $R^{5b}$, $R^{7(a\text{-}h)}$ or Q, where present, is a substituted phenyl.

In certain embodiments, compounds of formulae (A1)-(A4) or (C1)-(C4), and variations thereof, are provided where Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino. In one variation, compounds are provided where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In certain embodiments, Q is a substituted or unsubstituted 5- or 6-membered aryl or heteroaryl. In some such embodiments, Q is a substituted or unsubstituted phenyl, pyridyl or pyrimidinyl ring. When Q is substituted, it is frequently substituted with from 1-3 substituents selected from group consisting of halo, $C_1$-$C_4$ alkyl, $C_1$-$C_4$ perhaloalkyl, and $C_1$-$C_4$ alkoxy.

In a particular variation of compounds of formulae (A1)-(A4) or (C1)-(C4), and variations thereof, Q is a substituted heteroaryl, a mono-substituted aryl group substituted with a chloro or alkyl group or a di- or tri-substituted aryl moiety. For instance, each Q in one variation is independently selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In one aspect, Q is a substituted pyridyl such as 6-methyl-3-pyridyl, 6-trifluoromethyl-3-pyridyl and 5-trifluoromethyl-3-pyridyl.

In particular embodiments, each $X^1$, $X^2$, $X^3$ and $X^4$, where present, is CH or $CR^6$. In other embodiments, at least one of $X^1$, $X^2$, $X^3$ and $X^4$, where present, is N. Another variation provides a compound where at least two of $X^1$, $X^2$, $X^3$ and $X^4$, where present, are N. A further variation provides a compound where two of $X^1$, $X^2$, $X^3$ and $X^4$, where present, are N and one of $X^1$, $X^2$, $X^3$ and $X^4$, where present, is CH or $CR^6$. Compounds where one of $X^1$, $X^2$, $X^3$ and $X^4$, where present, is N and two of $X^1$, $X^2$, $X^3$ and $X^4$, where present, are CH or $CR^6$ are also embraced by this invention.

In one variation, compounds of formulae (A1)-(A4) and (B1)-(B4), and variations thereof, are provided wherein the ring comprising $X^1$, $X^2$ and $X^3$ is an aromatic moiety selected from the following structures:

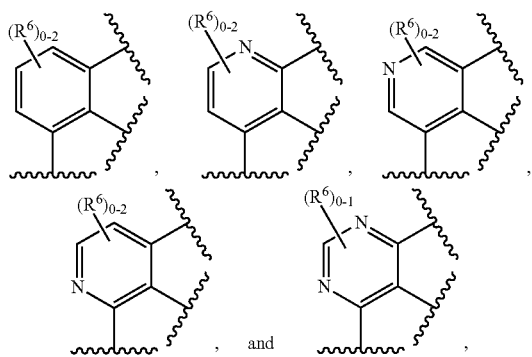

where each $R^6$ is as defined. In a particular variation, each $R^6$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^6$ is independently halo, unsubstituted $C_1$-$C_4$ alkyl, $C_1$-$C_4$ perhaloalkyl, or $C_1$-$C_4$alkoxy.

In a further variation, compounds of formulae (A1)-(A4) and (B1)-(B4), and variations thereof, are provided, wherein the ring comprising $X^1$, $X^2$ and $X^3$ is an aromatic moiety selected from the following structures:

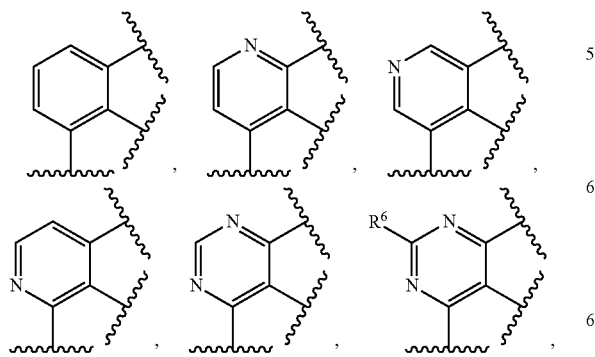

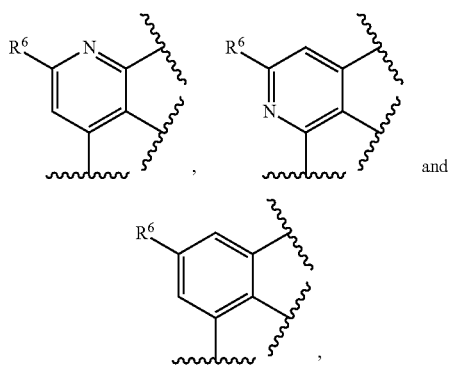

wherein $R^6$ is as defined herein; or in a particular variation, where $R^6$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^6$ is independently halo, unsubstituted $C_1$-$C_4$ alkyl, $C_1$-$C_4$ perhaloalkyl, or $C_1$-$C_4$ alkoxy.

In a further variation, compounds of formulae (A1)-(A4) and (B1)-(B4), and variations thereof, are provided wherein the ring comprising $X^1$, $X^2$ and $X^3$ is an aromatic moiety selected from the following structures:

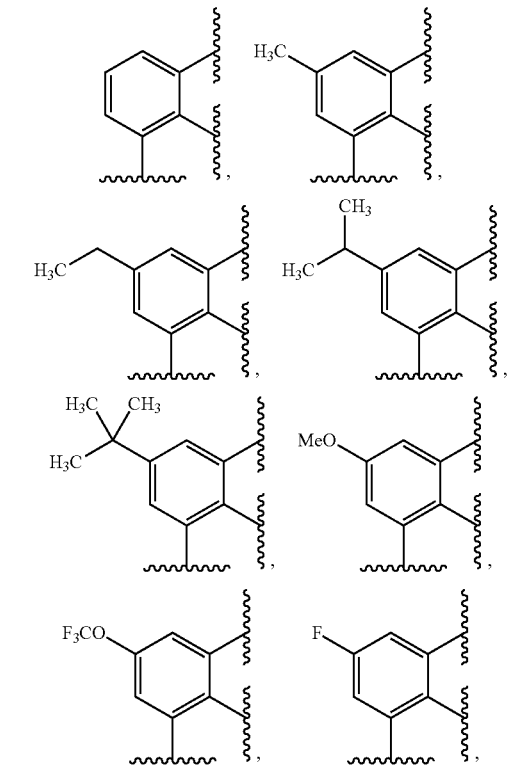

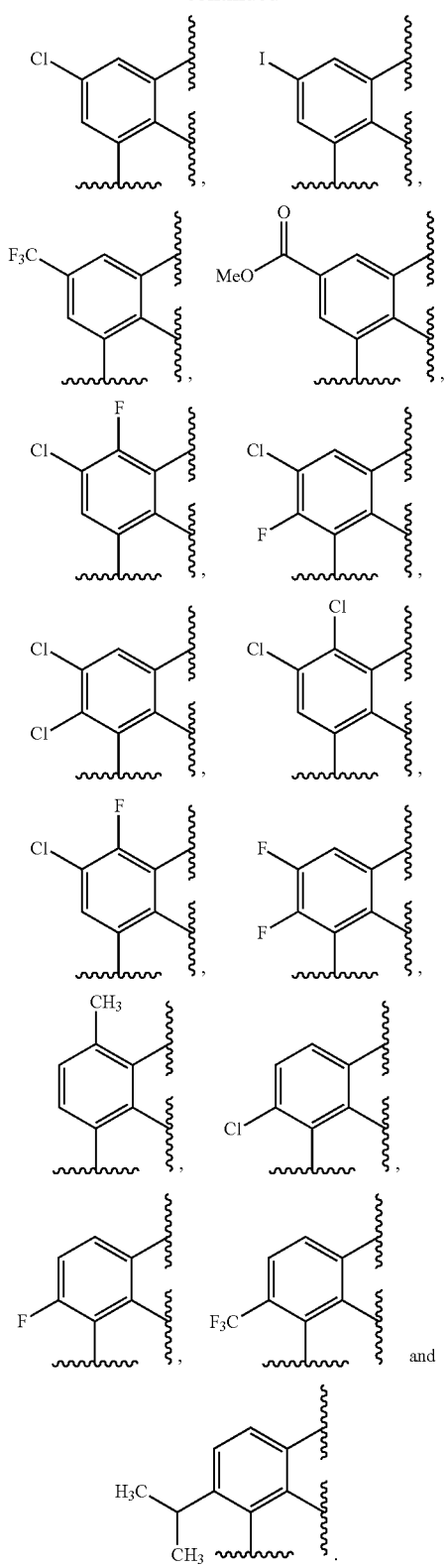

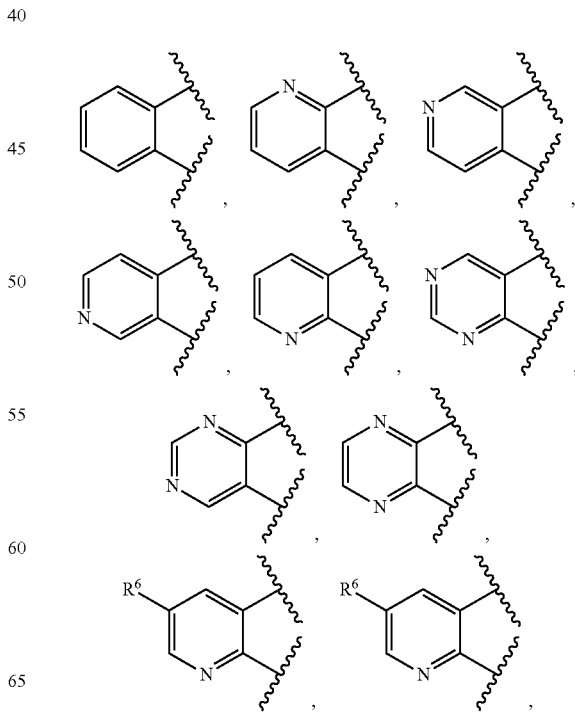

where each $R^6$ is as defined. In a particular variation, each $R^6$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^6$ is independently halo, unsubstituted $C_1$-$C_4$ alkyl, $C_1$-$C_4$ perhaloalkyl, or $C_1$-$C_4$ alkoxy.

In a further variation, of formulae (C1)-(C4) and (D1)-(D4), and variations thereof, are provided, wherein the ring comprising $X_1$, $X^2$, $X^3$ and $X^4$ is an aromatic moiety selected from the following structures:

In another variation, compounds of formulae (C1)-(C4) and (D1)-(D4), and variations thereof, are provided wherein the ring comprising $X^1$, $X^2$, $X^3$, and $X^4$ is an aromatic moiety selected from the following structures:

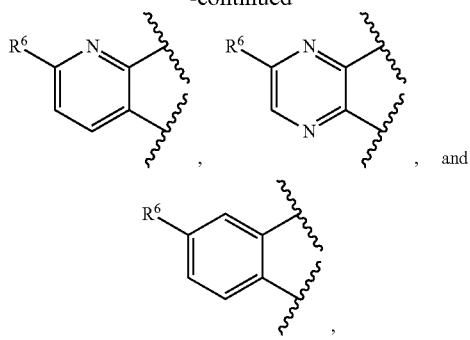

wherein R⁶ is as defined herein; or in a particular variation, where $R^6$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^6$ is independently halo, unsubstituted $C_1$-$C_4$ alkyl, $C_1$-$C_4$ perhaloalkyl, or $C_1$-$C_4$ alkoxy.

In a further variation, compounds of formulae (C1)-(C4) and (D1)-(D4), and variations thereof, are provided wherein the ring comprising $X_1$, $X^2$, $X^3$ and $X^4$ is an aromatic moiety selected from the following structures:

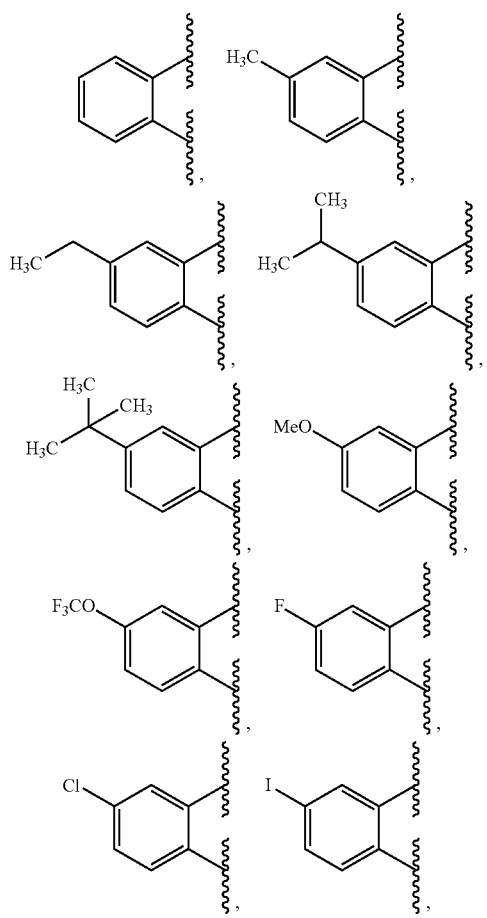

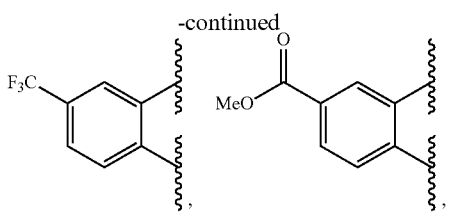

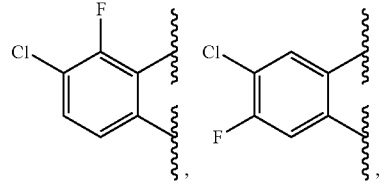

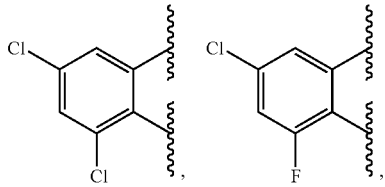

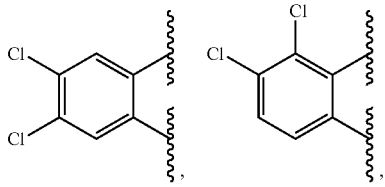

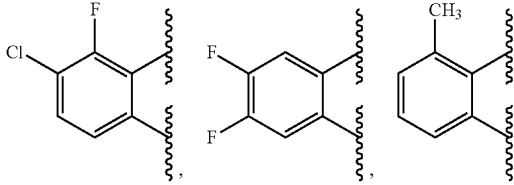

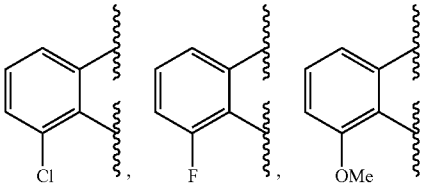

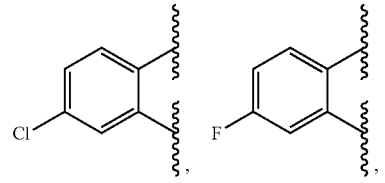

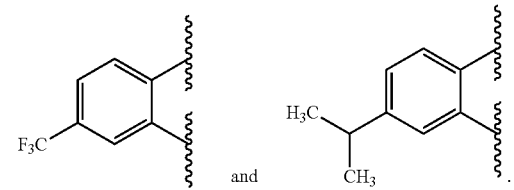

Any formula detailed herein, where applicable, may in one variation have $X^1$, $X^2$, $X^3$ and $X^4$, where present, taken together to provide an aromatic moiety detailed herein above. It is understood that by "where applicable" it is intended that in one variation such $X_1$, $X^2$, $X^3$ and $X^4$ groups are taken together to provide a moiety hereinabove if the formula encompasses such a structure. For example, if a given formula does not encompass structures wherein $X^1$, $X^2$, $X^3$ and $X^4$ groups are taken together provide a pyridyl moiety, then a pyridyl moiety as detailed hereinabove is not applicable to that particular formula, but remains applicable to formulae that do encompass structures where $X^1$, $X^2$, $X^3$ and $X^4$ groups are taken together provide a pyridyl moiety.

In another embodiment, a compound of the invention is provided, wherein $X^1$-$X^4$, where present, are as defined or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is provided, wherein $X^1$-$X^4$ are as defined or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is provided, wherein $X^1$-$X^4$ are as defined or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

When any carbon of the preceding formulae bearing $R^{2a}$ and $R^{2b}$, or $R^{3a}$ and $R^{3b}$, or $R^{4a}$ and $R^{4b}$, or $R^{10a}$ and $R^{10b}$ is optically active, it may be in the (R)- or (S)-configuration and compositions comprising substantially pure (R) or (S) compound or mixtures thereof in any amount are embraced by this invention.

In one variation, compounds of formulae (A1) and (B1), and variations thereof, are provided wherein the ring comprising N, $R^{2a}$, $R^{2b}$, $R^{3a}$, $R^{3b}$, $R^{4a}$ and $R^{4b}$ is a moiety selected from the following structures:

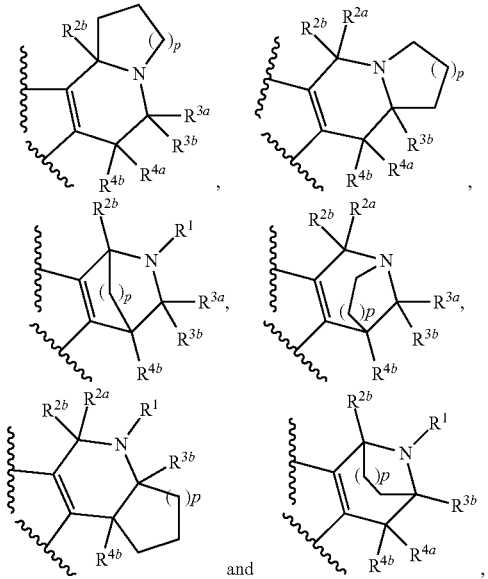

wherein $R^1$, $R^{2a}$, $R^{2b}$, $R^{3a}$, $R^{3b}$, $R^{4a}$ and $R^{4b}$ are as defined, and p is 1 or 2.

In another variation, compounds of formulae (A2) and (B2), and variations thereof, are provided wherein the ring comprising N, $R^{2a}$, $R^{2b}$, $R^{3a}$, $R^{3b}$, $R^{4a}$ and $R^{4b}$ is a moiety selected from the following structures:

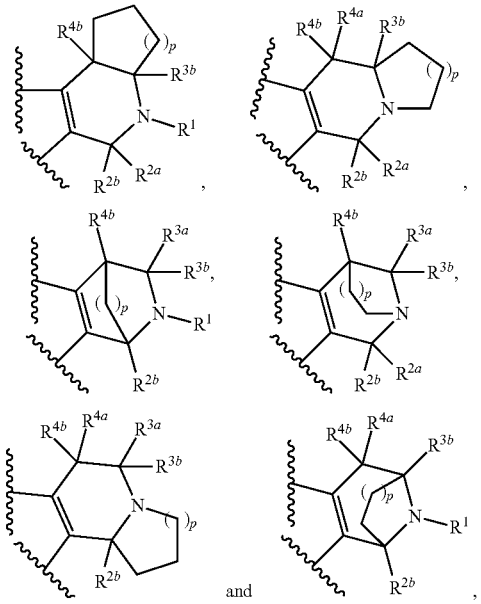

wherein R1, $R^{2a}$, $R^{2b}$, $R^{3a}$, $R^{3b}$, $R^{4a}$ and $R^{4b}$ are as defined, and p is 1 or 2.

In another variation, compounds of formulae (A1) and (B1), and variations thereof, are provided wherein the ring comprising N, $R^{2a}$, $R^{2b}$, $R^{3a}$, $R^{3b}$, $R^{4a}$ and $R^{4b}$ is a moiety selected from the following structures:

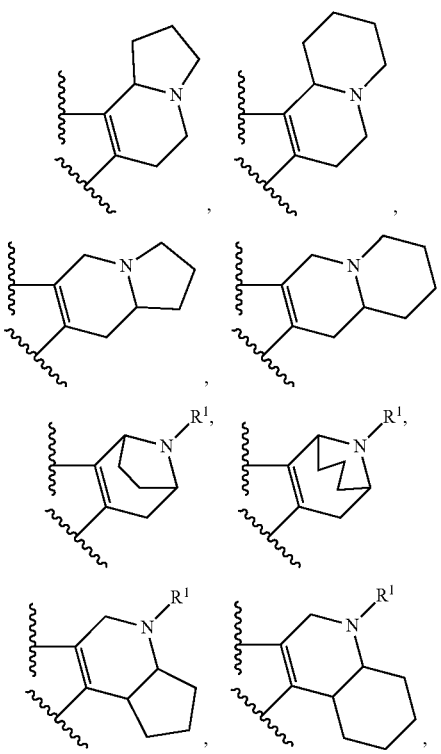

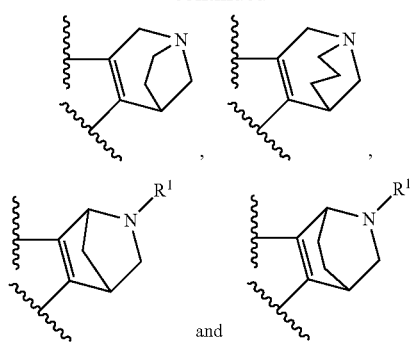

In another variation, compounds of formulae (A2) and (B2), and variations thereof, are provided wherein the ring comprising N, $R^{2a}$, $R^{2b}$, $R^{3a}$, $R^{3b}$, $R^{4a}$ and $R^{4b}$ is a moiety selected from the following structures:

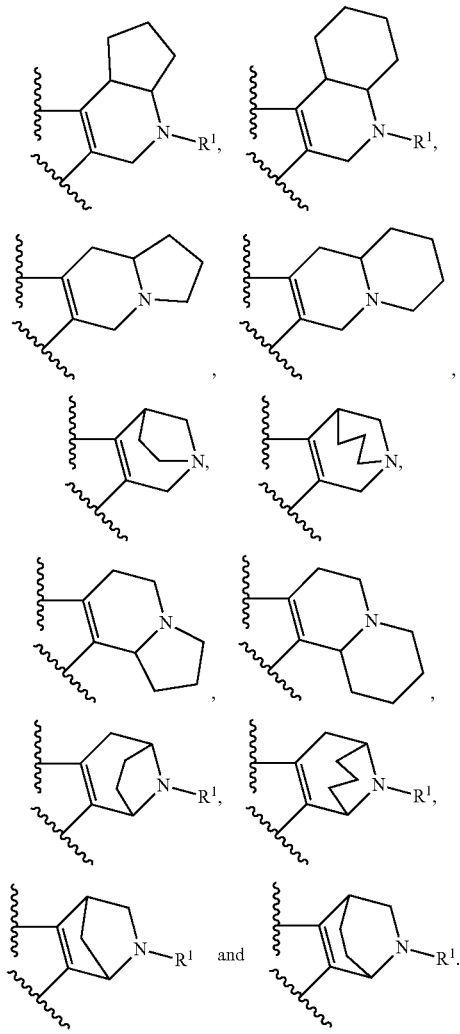

In any one of the variations of compounds of the formulae described herein, all stereoisomers are intended. For example, the ring can be either or .

Where more than one stereocenter is present, it is understood that all such stereoisomers are intended. For example, a compound having two stereocenters may be present in the (S), (S); (S), (R); (R), (R); and (R), (S) forms. Compositions comprising a single stereoisomer or mixtures of more than one stereoisomer are also intended. Compositions comprising a mixture of stereoisomers in any ratio are embraced, including mixtures of two or more stereochemical forms of a compound of the invention in any ratio, such that racemic, non-racemic, enantioenriched and scalemic mixtures of a compound are embraced.

In some embodiments of formulae (A1) and (B1), and variations thereof, are provided, the ring comprising N, $R^{2a}$, $R^{2b}$, $R^{3a}$, $R^{3b}$, $R^{4a}$ and $R^{4b}$ is a moiety selected from the following structures:

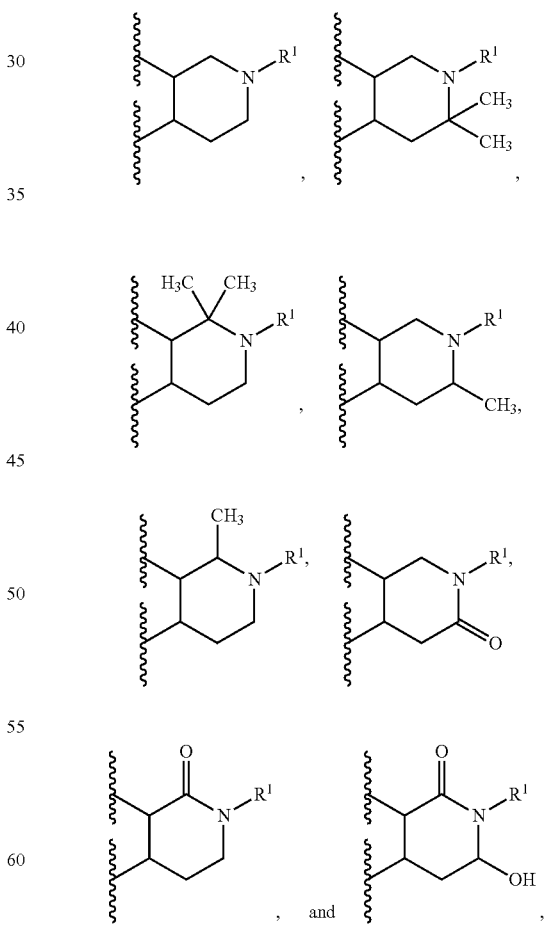

where $R^1$ in the structures above is as defined or as detailed in any particular variation detailed herein. In some embodiments, the ring is of the formula:

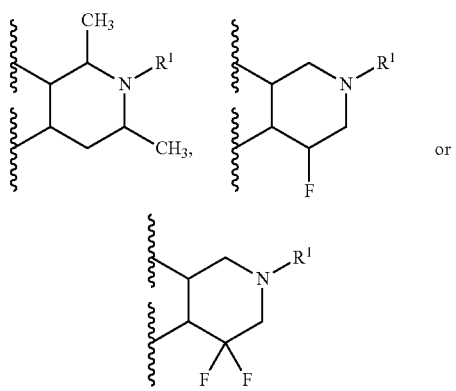

where R¹ is as detailed in any particular variation detailed herein. Any formula detailed herein, where applicable, may in one variation have a ring according to the structures above.

Compounds according to formulae (A1)-(A4) or (C1)-(C4), or any variation thereof, in one variation are provided where m, n, o, p, and $R^{8(a-h)}$, if present and where applicable, are taken together to form a moiety selected from the group consisting of the structures:

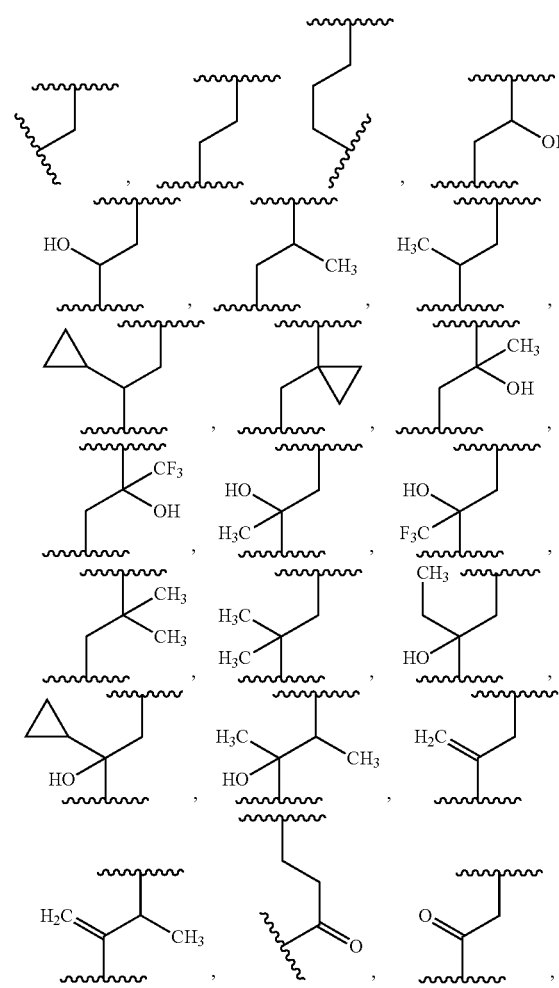

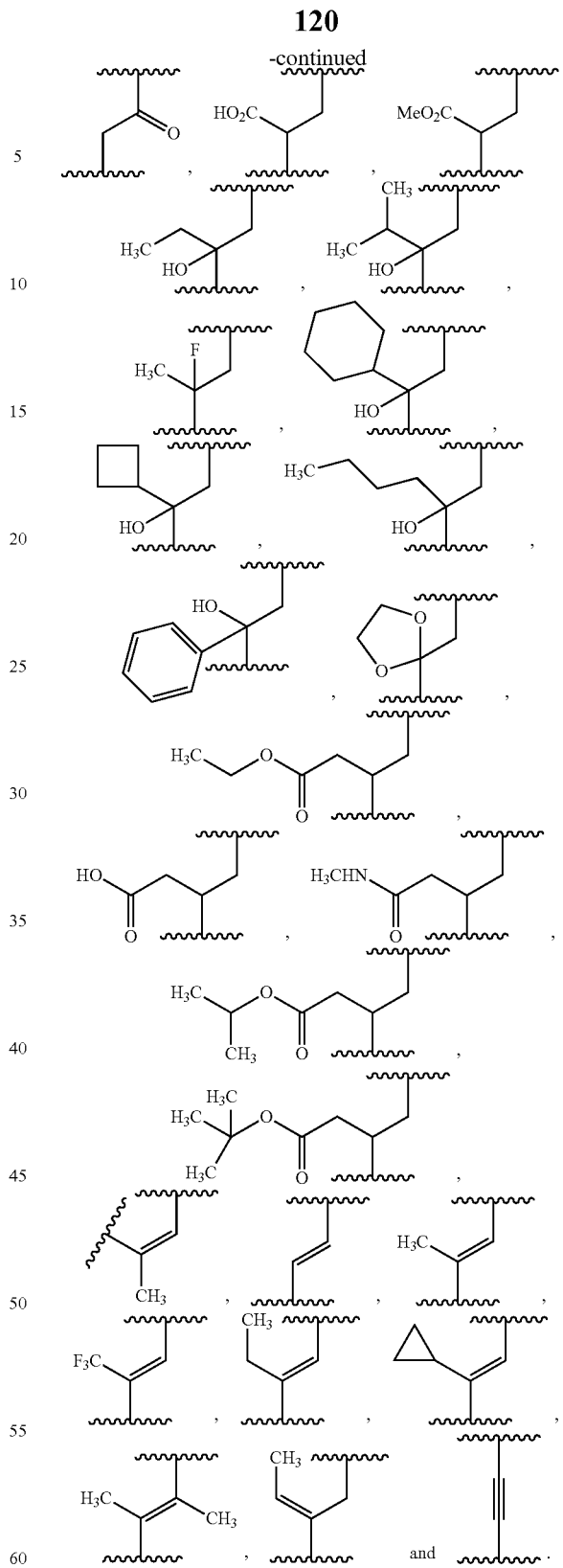

When the above structures are applied to formulae (A1)-(A4) or (C1)-(C4), or any variation thereof, herein, it is understood that m, n, o, p and $R^{8(a-h)}$, where applicable, are taken together to form the foregoing moieties, including but not limited to, the structures of this paragraph. Likewise, any formula detailed herein, where applicable, may in one variation have m, n, o, p and $R^{8(a-h)}$, if present, taken together to form a moiety as detailed herein above, including but not limited to, the structures of this paragraph. It is understood that by "where applicable" it is intended that in one variation such m, n, o, p and $R^{8(a-h)}$ groups, if present, are taken together to provide a moiety hereinabove if the formula encompasses such a structure. For example, if a given formula does not encompass structures wherein m, n, o, p and $R^{8(a-h)}$ groups, if present, are taken together to provide a —$CH_2CH_2$— moiety, then a —$CH_2CH_2$— moiety as detailed hereinabove is not applicable to that particular formula, but remains applicable to formulae that do encompass structures where m, n, o, p and $R^{8(a-h)}$ groups, if present, are taken together to provide a —$CH_2CH_2$— moiety.

In one aspect, at least one of $R^{8(a-h)}$ is a $C_1$-$C_8$ alkyl substituted with a carbonylalkoxy, carboxyl or acylamino moiety.

Compounds according to formulae (A1)-(A4) or (C1)-(C4), or any variation thereof, where applicable, in one variation are provided where one or more of $R^{8(a-h)}$ and the carbon to which it is attached, together with a vicinal $R^8$ and the carbon to which it is attached, form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

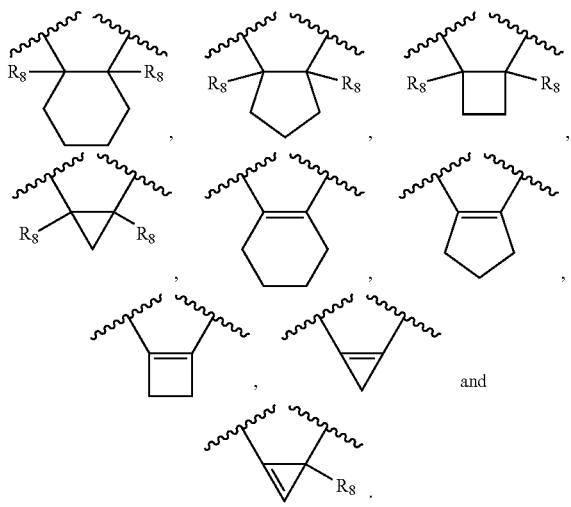

In another variation, any double bond, if present in the cycloalkenyl ring, may also be present at any location in the ring, where chemically feasible, as exemplified above for the cyclopropenyl moiety.

In certain compounds where applicable in one variation, at least one of $R^{5a}$, $R^{5b}$, $R^{7(a-h)}$ or Q, where present, is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is provided, where at least one of $R^{5a}$, $R^{5b}$, $R^{7(a-h)}$ or Q, where present, is a substituted or unsubstituted phenyl or pyridyl group. In a particular variation, at least one of $R^{5a}$, $R^{5b}$, $R^{7(a-h)}$ or Q, where present, is a phenyl or pyridyl group substituted with at least one methyl, trifluoromethyl, methoxy or halo substituent. In another variation, a compound of the invention is provided, where at least one of $R^{5a}$, $R^{5b}$, $R^{7(a-h)}$ or Q, where present, is a pyridyl, phenyl, pyrimidinyl, pyrazinyl, imidazolyl, furanyl, pyrrolyl or thiophenyl group substituted with at least one substituted or unsubstituted $C_1$-$C_4$ alkyl, $C_1$-$C_4$ alkoxy, halo or $C_1$-$C_4$ perhaloalkyl moiety.

In still another variation, compounds are provided, where at least one of $R^{5a}$, $R^{5b}$, $R^{7(a-h)}$ or Q, where present, is a substituted or unsubstituted $C_3$-$C_8$ cycloalkyl or a substituted or unsubstituted heterocyclyl. In another variation, at least one of $R^{5a}$, $R^{5b}$, $R^{7(a-h)}$ or Q, where present, is a substituted or unsubstituted $C_3$-$C_8$ cycloalkyl or a substituted or unsubstituted heterocyclyl. In yet another variation, a compound of the invention is provided where at least one of $R^{5a}$, $R^{5b}$, $R^{7(a-h)}$ or Q, where present, is a substituted or unsubstituted pyridyl, phenyl, pyrazinyl, piperazinyl, pyrrolidinyl or thiomorpholinyl group. In a particular variation, at least one of $R^{5a}$, $R^{5b}$, $R^{7(a-h)}$ or Q, where present, is a pyridyl, phenyl, pyrazinyl, piperazinyl, pyrrolidinyl or thiomorpholinyl group substituted with at least one methyl, $CF_3$, methoxy or halo group.

In one variation, compounds are provided where at least one of $R^{5a}$, $R^{5b}$, $R^{7(a-h)}$ or Q, where present, is an unsubstituted cycloalkyl or an unsubstituted heterocyclyl. In another variation, at least one of $R^{5a}$, $R^{5b}$, $R^{7(a-h)}$ or Q, where present, is an unsubstituted $C_3$-$C_8$ cycloalkyl or an unsubstituted heterocyclyl. In another variation, a compound of the invention is provided where at least one of $R^{5a}$, $R^{5b}$, $R^{7(a-h)}$ or Q, where present, is a substituted or unsubstituted cyclohexyl, morpholinyl, piperazinyl, thiomorpholinyl, cyclopentyl or pyrrolidinyl moiety. In yet another variation, a compound of the invention is provided where at least one of $R^{5a}$, $R^{5b}$, $R^{7(a-h)}$ or Q, where present, is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group. $R^{5a}$, $R^{5b}$, $R^{7(a-h)}$ or Q, where present, groups may be attached to the parent structure at any available position on the $R^{5a}$, $R^{5b}$, $R^{7(a-h)}$ or Q moiety. Thus, although specific attachment points for certain $R^{5a}$, $R^{5b}$, $R^{7(a-h)}$ or Q moieties are depicted herein, it is understood that such $R^{5a}$, $R^{5b}$, $R^{7(a-h)}$ or Q moieties, may also be connected to the parent structure at any available position. For example, if a mono-fluoro-phenyl is depicted herein, it is understood that each of the available mono-fluoro-phenyl moieties are intended, e.g., 2-fluoro-phenyl, 3-fluoro-phenyl and 4-fluoro-phenyl. It is also understood that any formula detailed herein, where applicable, may in one variation have a $R^{5a}$, $R^{5b}$, $R^{7(a-h)}$ or Q, where present, moiety as detailed herein and below.

In still another variation, a compound of the invention is provided where at least one of $R^{5a}$, $R^{5b}$, $R^{7(a-h)}$ or Q, where present, is a moiety selected from the structures:

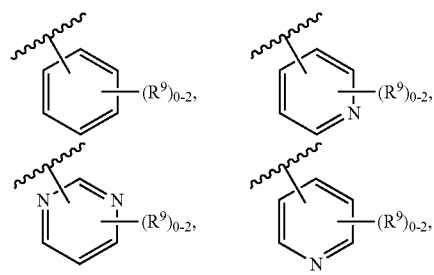

-continued

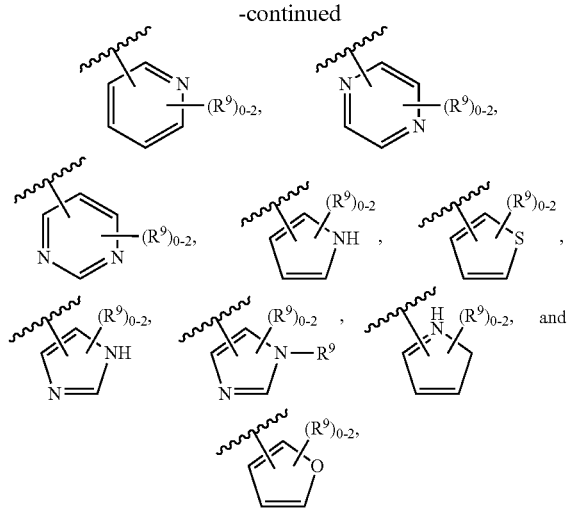

wherein each $R^9$ is independently a halo, cyano, nitro, perhaloalkyl ($C_1$-$C_8$), perhaloalkoxy ($C_1$-$C_8$), substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, the $R^{5a}$, $R^{5b}$, $R^{7(a-h)}$ or Q, where present, is substituted with no more than one $R^9$ group. In another variation, the $R^{5a}$, $R^{5b}$, $R^{(a-h)}$ or Q, where present, is substituted with only one $R^9$ group. In one variation, the $R^{5a}$, $R^{5b}$, $R^{7(a-h)}$ or Q, where present, is substituted with two $R^9$ groups. In a further variation, at least one of $R^{5a}$, $R^{5b}$, $R^{7(a-h)}$ or Q, where present, is selected from the aromatic structures detailed where the residue has the moiety $(R^9)_0$ such that the $R^{5a}$, $R^{5b}$, $R^{7(a-h)}$ or Q either contains no $R^9$ functionality or a moiety of the formula N—$R^9$. In one variation, at least one of $R^{5a}$, $R^{5b}$, $R^{7(a-h)}$ or Q, where present, is selected from the aromatic structures detailed where the $R^{5a}$, $R^{5b}$, $R^{7(a-h)}$ or Q, where present, is substituted with no more than one $R^9$ group. In another variation, the $R^{5a}$, $R^{5b}$, $R^{7(a-h)}$ or Q, where present, is substituted with only one $R^9$ group. In one variation, the $R^{5a}$, $R^{5b}$, $R^{7(a-h)}$ or Q, where present, is substituted with two $R^9$ groups. In a further variation, at least one of $R^{5a}$, $R^{5b}$, $R^{7(a-h)}$ or Q, where present, is selected from the aromatic structures detailed where the residue has the moiety $(R^9)_0$ such that the $R^{5a}$, $R^{5b}$, $R^{7(a-h)}$, or Q, where present, either contains no $R^9$ functionality or a moiety of the formula N—$R^9$.

In another variation, a compound of the invention is provided where at least one of $R^{5a}$, $R^{5b}$, $R^{7(a-h)}$ or Q, where present, is a moiety selected from the structures:

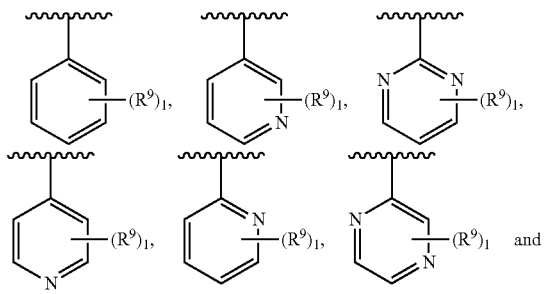

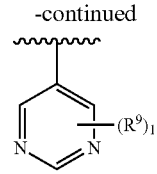

wherein $R^9$ is connected to the $R^{5a}$, $R^{5b}$, $R^{7(a-h)}$ or Q, where present, ortho or para to the position at which $R^{5a}$, $R^{5b}$, $R^{7(a-h)}$ or Q, where present, is connected to the carbon bearing the $R^{5a}$, $R^{5b}$, $R^{7(a-h)}$ or Q, where present. In a particular variation, at least one of $R^{5a}$, $R^{5b}$, $R^{7(a-h)}$ or Q, where present, is a structure of the formula

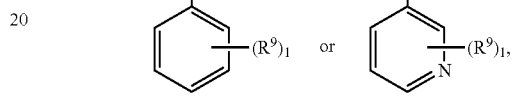

and $R^9$ is connected to the $R^{5a}$, $R^{5b}$, $R^{7(a-h)}$ or Q, where present, para to the position at which the $R^{5a}$, $R^{5b}$, $R^{7(a-h)}$ or Q, where present, is connected to the carbon bearing the $R^{5a}$, $R^{5b}$, $R^{7(a-h)}$ or Q, where present. In another particular variation, at least one of $R^{5a}$, $R^{5b}$, $R^{(a-h)}$ or Q, where present, is a structure of the formula

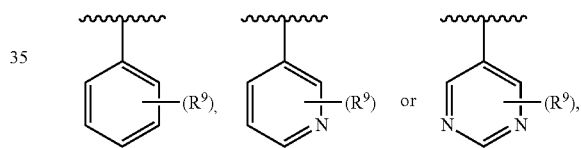

where each $R^9$ is independently alkyl, perhaloalkyl or halo.

In another variation, a compound of the invention is provided where at least one of $R^{5a}$, $R^{5b}$, $R^{(a-h)}$ or Q, where present, is a moiety selected from the structures:

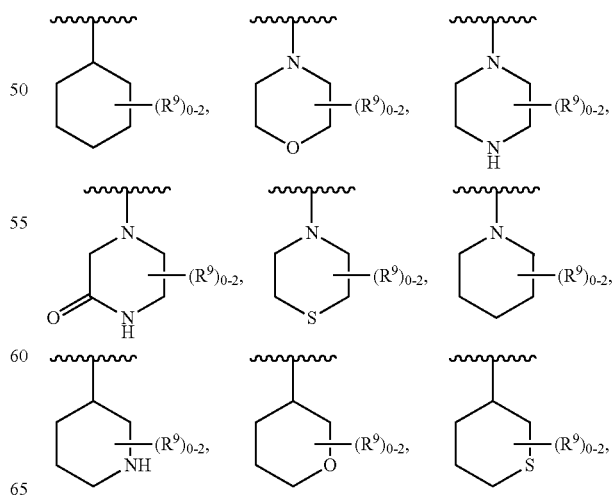

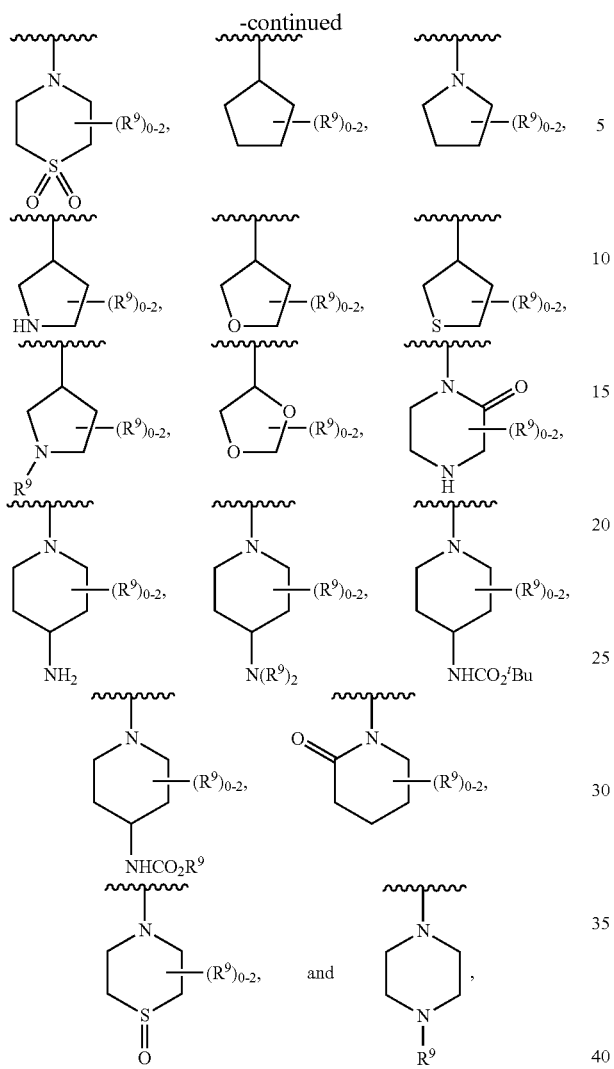

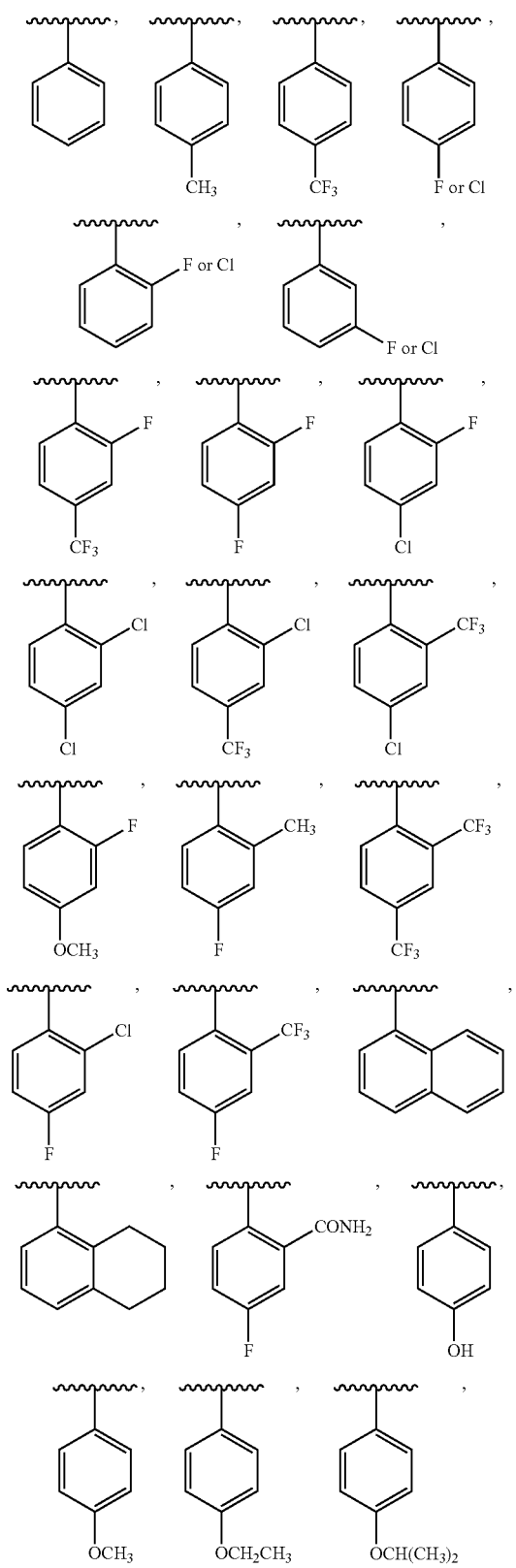

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, the $R^{5a}$, $R^{5b}$, $R^{7(a-h)}$ or Q, where present, is substituted with no more than one $R^9$ group. In another variation, at least one of $R^{5a}$, $R^{5b}$, $R^{7(a-h)}$ or Q, where present, is substituted with only one $R^9$ group. In yet another variation, at least one of $R^{5a}$, $R^{5b}$, $R^{7(a-h)}$ or Q, where present, is substituted with two $R^9$ groups. In a particular variation, at least one of $R^{5a}$, $R^{5b}$, $R^{7(a-h)}$ or Q, where present, is selected from the carbocyclic and heterocyclic structures detailed where the residue has the moiety $(R^9)_0$ such that at least one of $R^{5a}$, $R^{5b}$, $R^{7(a-h)}$ or Q, where present, either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is provided where at least one of $R^{5a}$, $R^{5b}$, $R^{7(a-h)}$ or Q, where present, is a moiety selected from the structures:

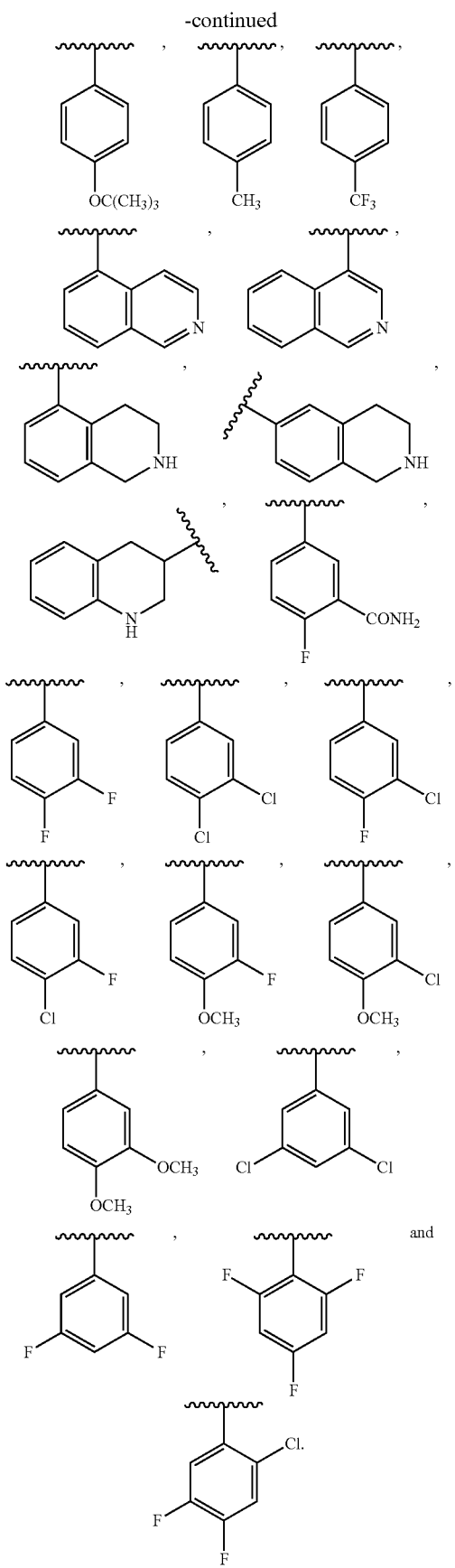
In another variation, a compound of the invention is provided where at least one of $R^{5a}$, $R^{5b}$, $R^{7(a-h)}$ or Q, where present, is a moiety selected from the structures:
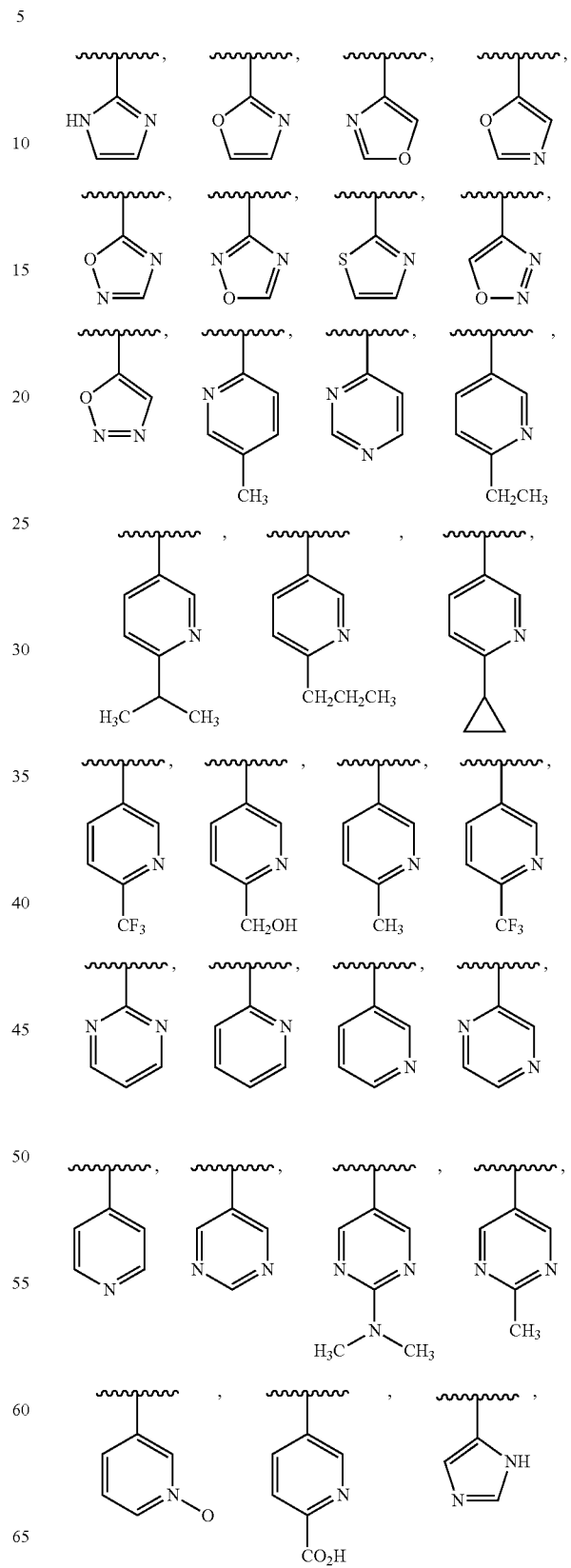

-continued
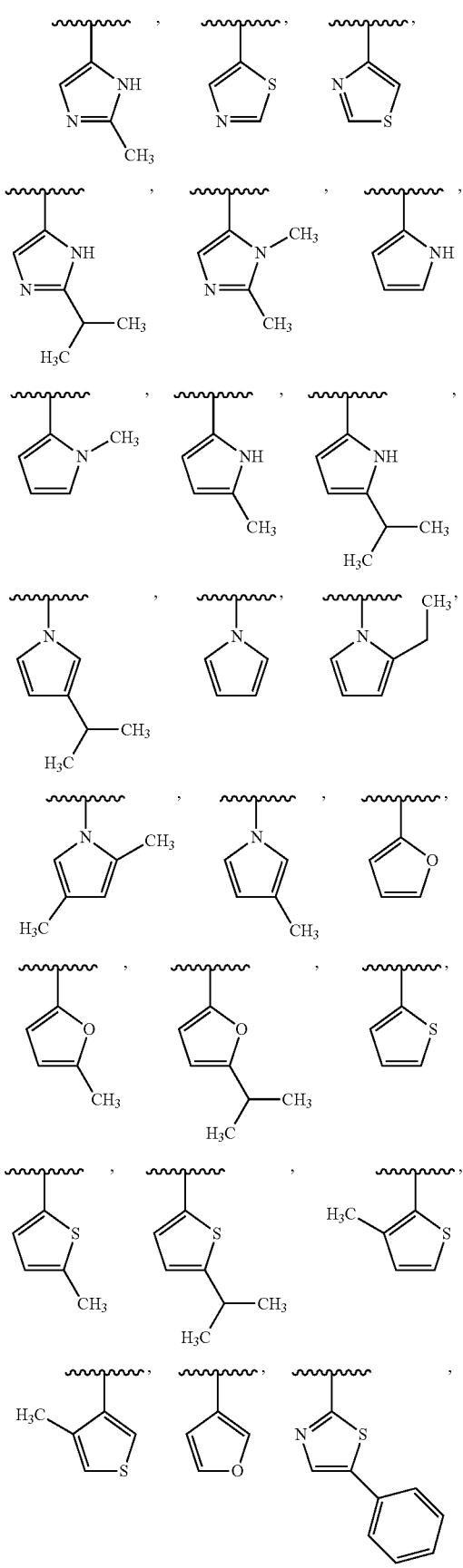
-continued
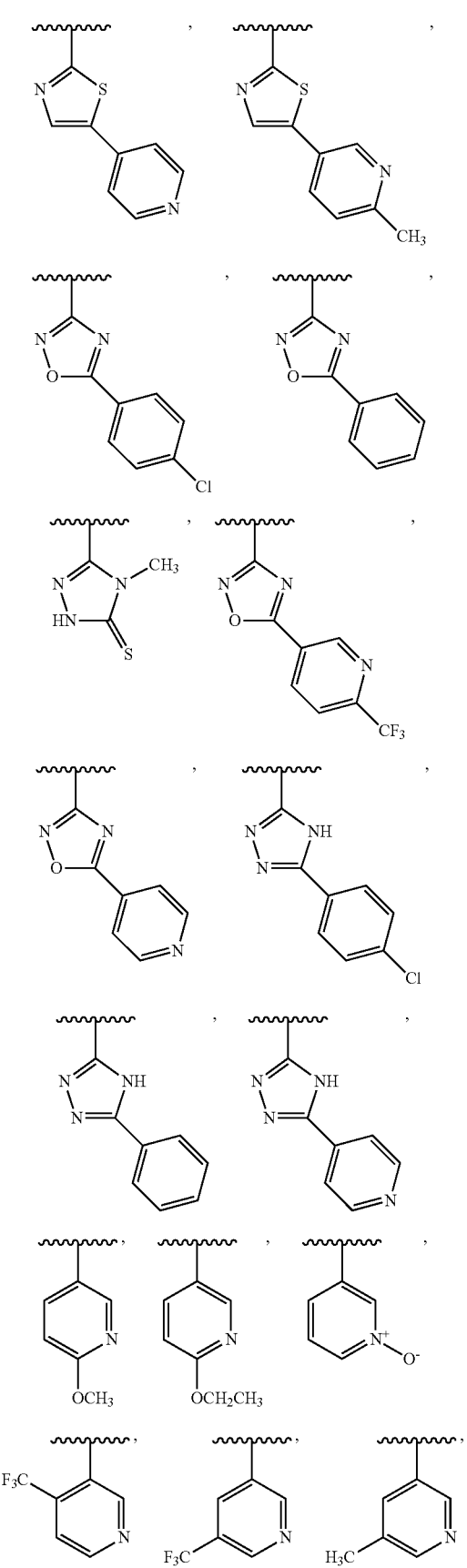

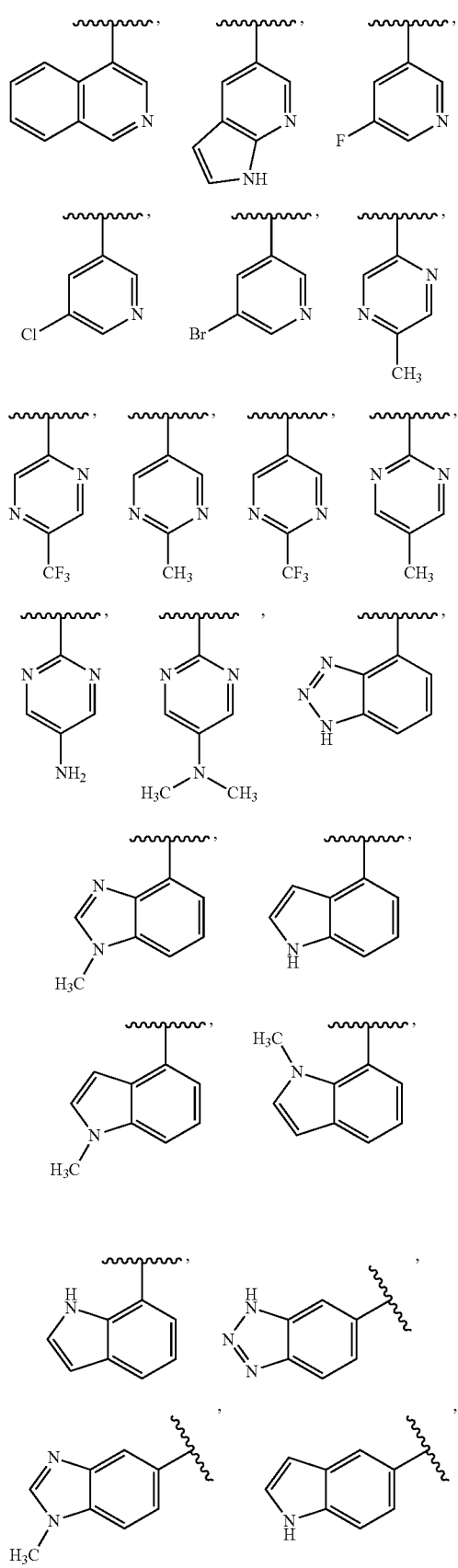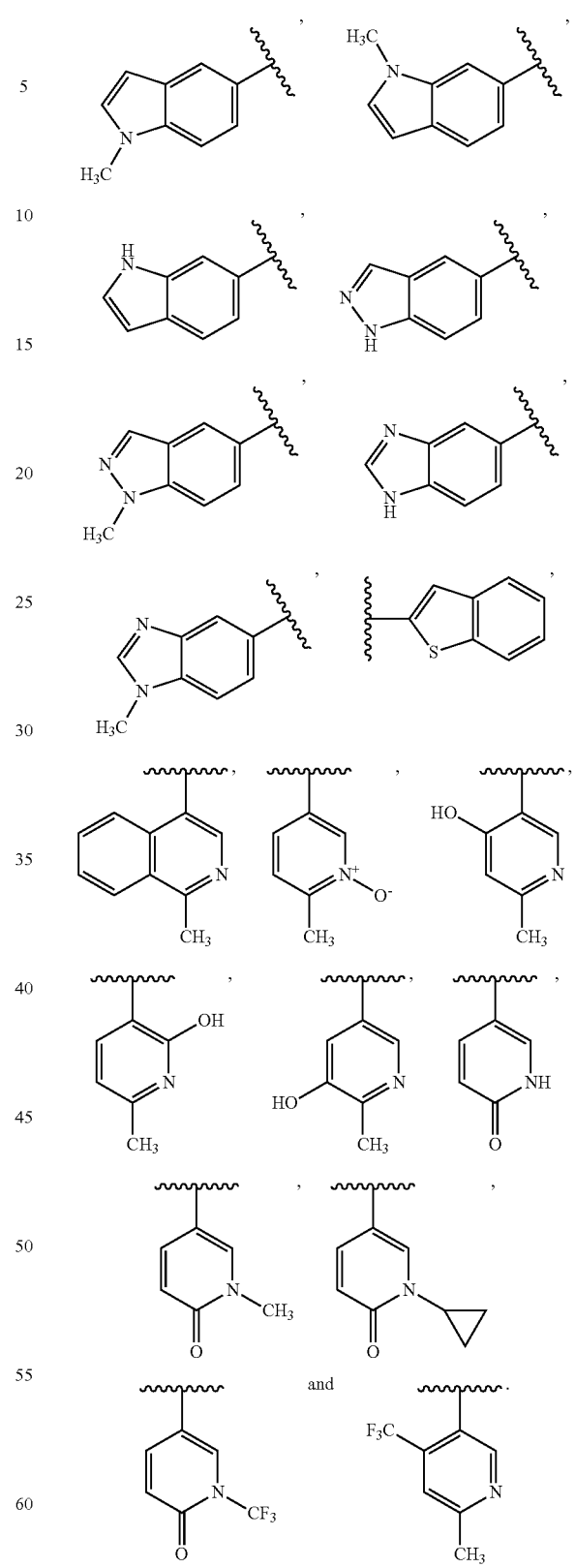
In another variation, a compound of the invention is provided where at least one of $R^{5a}$, $R^{5b}$, $R^{7(a-h)}$ or Q, where present, is a moiety selected from the structures:

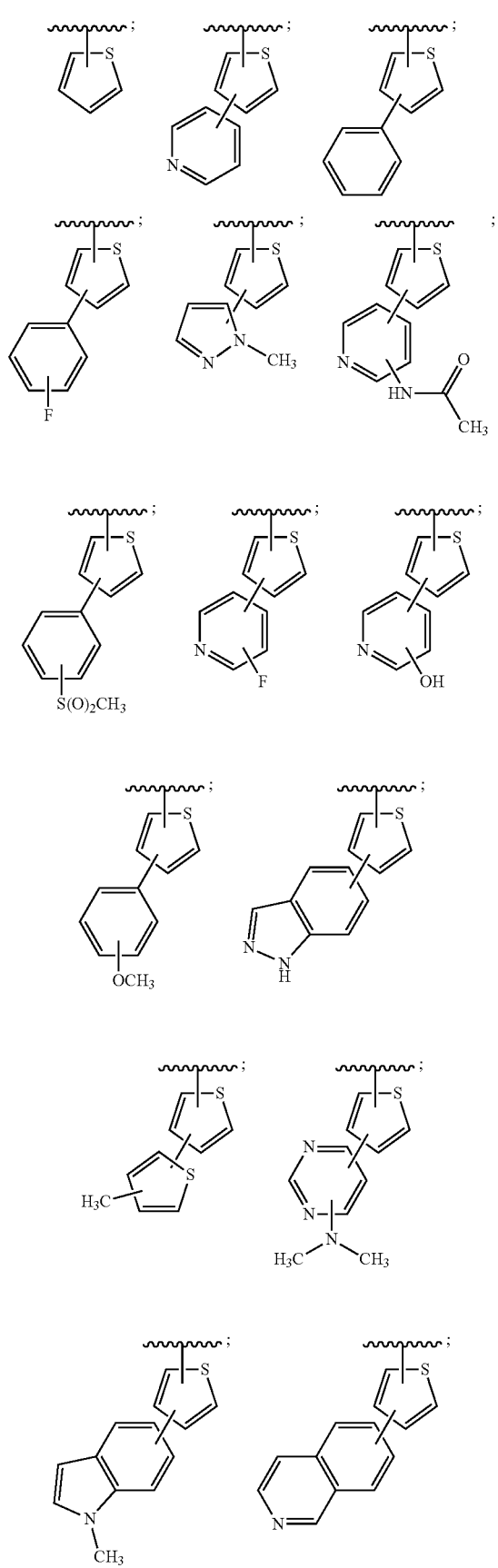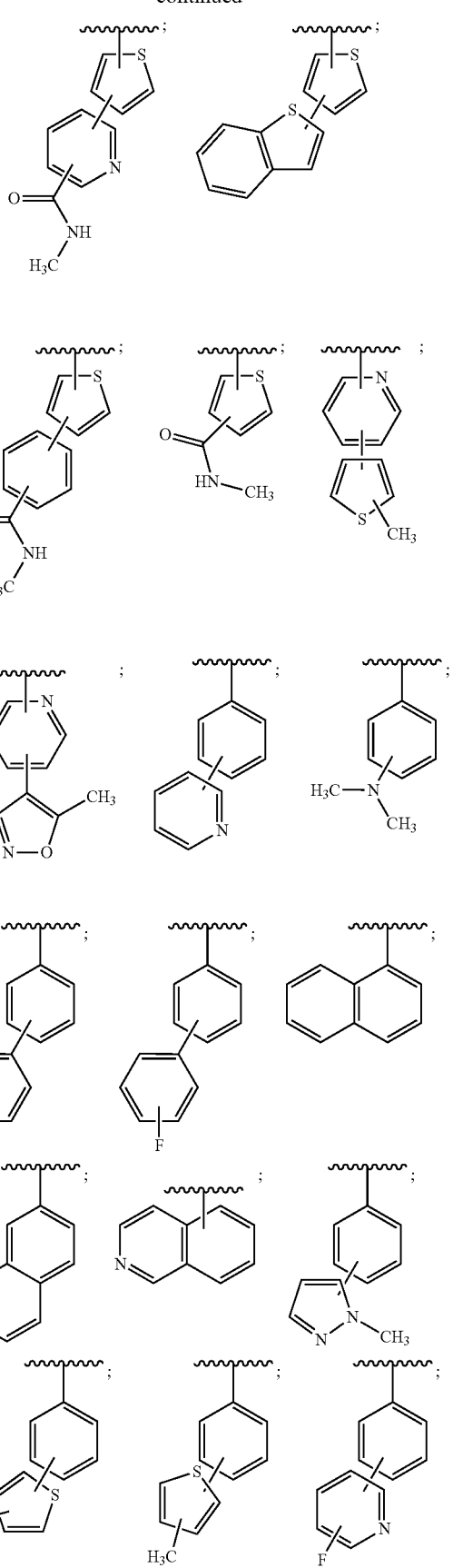

-continued
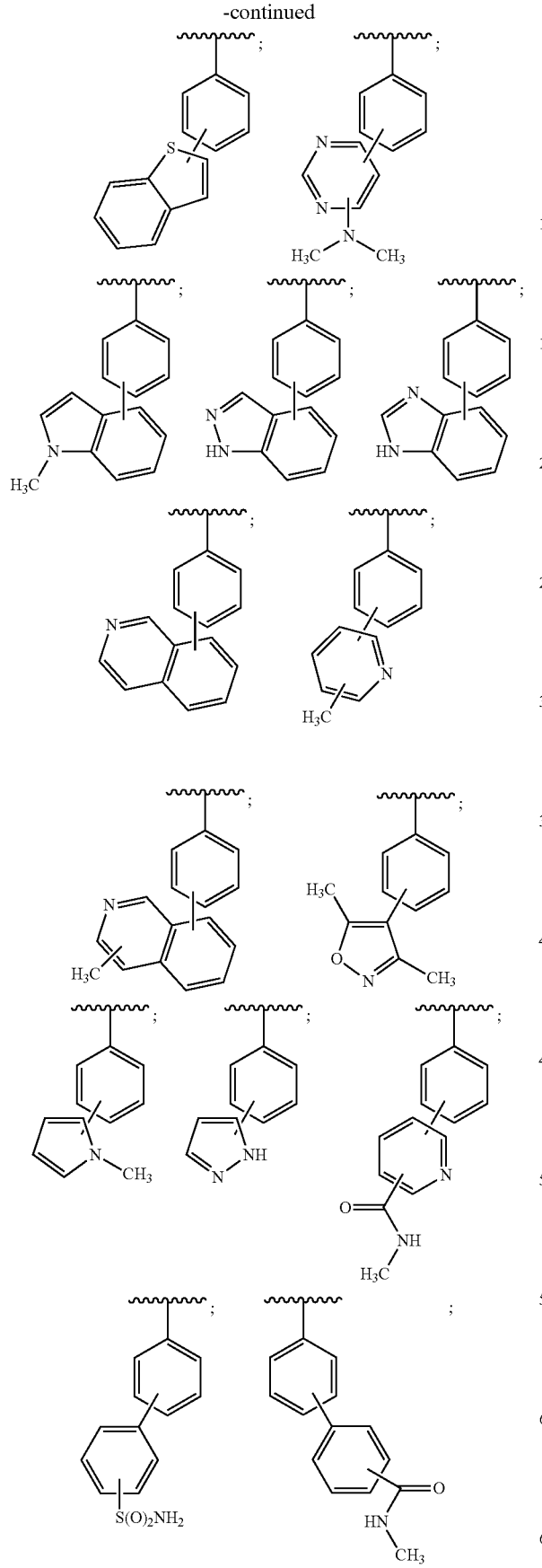
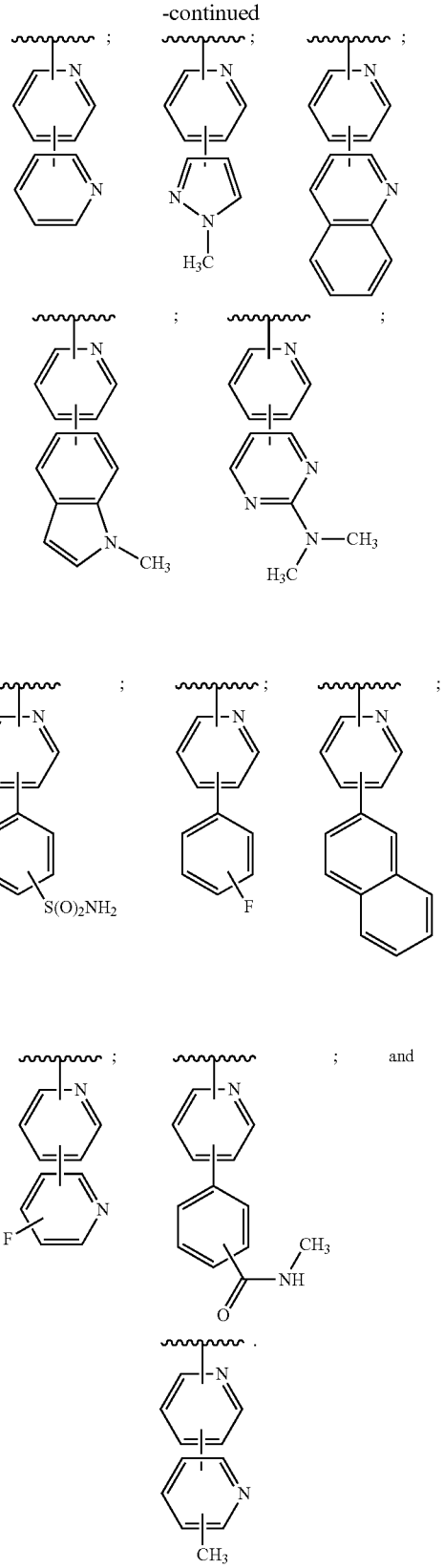
In yet another variation, a compound of the invention is provided where at least one of $R^{5a}$, $R^{5b}$, $R^{7(a\text{-}h)}$ or Q, where present, is a moiety selected from the structures:

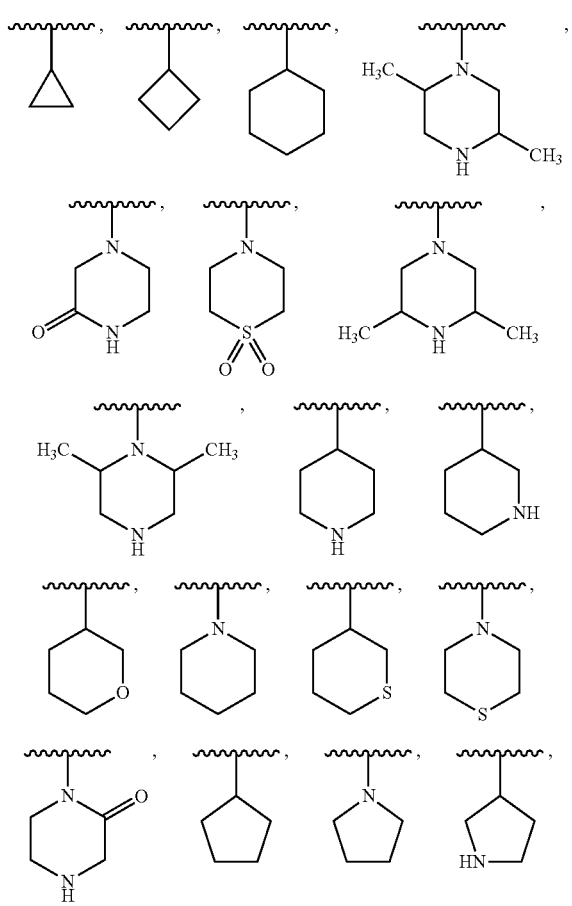

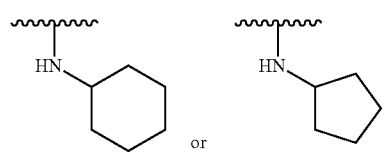

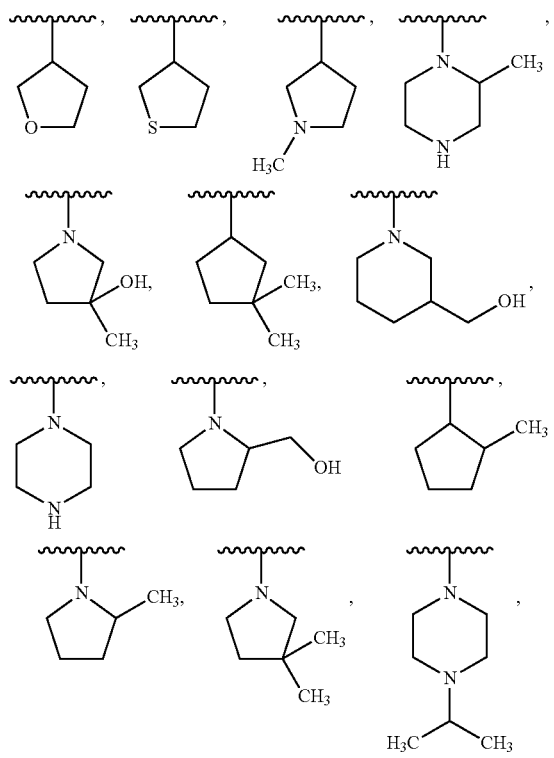

In any of the variations described herein for $R^{5a}$, $R^{5b}$, $R^{7(a-h)}$, or Q, where present, only one point of attachment of each moiety to the parent structure may be depicted, however it is understood that the moiety may be attached to the parent structure at any position, where chemically feasible.

In another variation, a compound of the invention is provided where at least one of $R^{5a}$, $R^{5b}$, $R^{7(a-h)}$ or Q, where present, is a substituted or unsubstituted amino, alkoxy, aminoacyl, acyloxy, carbonylalkoxy, aminocarbonylalkoxy or acylamino moiety. In a particular variation, at least one of $R^{5a}$, $R^{5b}$, $R^{7(a-h)}$ or Q, where present, is an unsubstituted amino. In another variation, at least one of $R^{5a}$, $R^{5b}$, $R^{7(a-h)}$ or Q, where present, is a substituted amino of the formula —N(C$_1$-C$_8$ alkyl)$_2$ such as the moiety —N(Me)$_2$ or —N(CH$_3$)(CH$_2$CH$_3$). In another variation, at least one of $R^{5a}$, $R^{5b}$, $R^{7(a-h)}$ or Q, where present, is a substituted amino of the formula —N(H)(cycloalkyl or substituted cycloalkyl), such as a moiety of the formula:

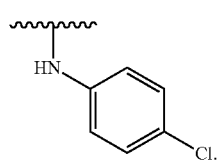 [SMILES: *Nc1ccc(Cl)cc1]

In another variation, at least one of $R^{5a}$, $R^{5b}$, $R^{7(a-h)}$ or Q, where present, is independently a substituted amino of the formula —N(H)(aryl or substituted aryl), such as a moiety of the formula:

The invention also embraces compounds where at least one of $R^{5a}$, $R^{5b}$, $R^{7(a-h)}$ or Q, where present, is an aminoacyl moiety. In one variation, at least one of $R^{5a}$, $R^{5b}$, $R^{7(a-h)}$ or Q, where present, is an aminoacyl group where at least one of $R_a$ and $R_b$ is H, such as when at least one of $R^{5a}$, $R^{5b}$, $R^{7(a-h)}$ or Q, where present, is of the formula —NHC(O)R$_b$. In one variation, at least one of $R^{5a}$, $R^{5b}$, $R^{7(a-h)}$ or Q, where present, is an aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-aralkyl and —NHC(O)-substituted aryl. In another variation, at least one of $R^{5a}$, $R^{5b}$, $R^{7(a-h)}$ or Q, where present, is an aminoacyl moiety selected from the group consisting of: —NHC(O)—$C_5$-$C_7$ heterocyclyl, —NHC(O)—$C_1$-$C_6$ alkyl, —NHC(O)—$C_3$-$C_7$ cycloalkyl, —NHC(O)—$C_1$-$C_3$ aralkyl and —NHC(O)-substituted phenyl. In a particular variation, at least one of $R^{5a}$, $R^{5b}$, $R^{7(a-h)}$ or Q, where present, is a moiety of the formula:

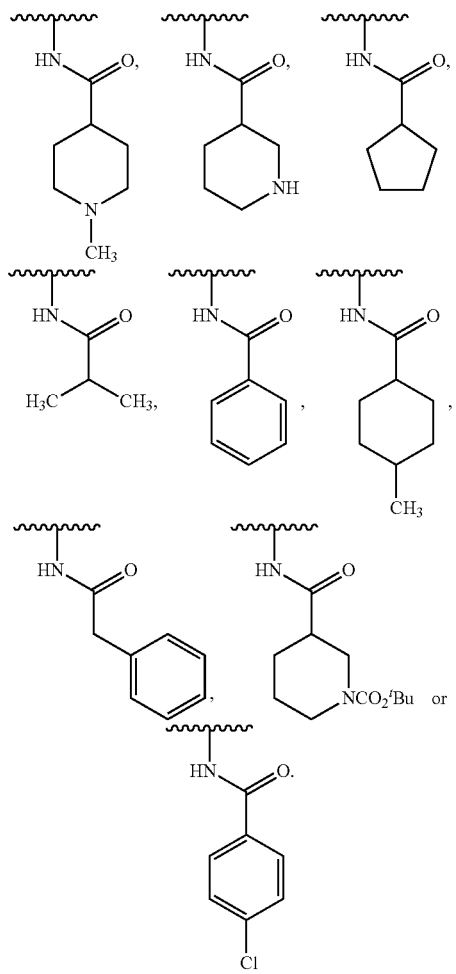

In one variation, a compound of the invention is provided where at least one of $R^{5a}$, $R^{5b}$, $R^{7(a-h)}$ or Q, where present, is acyloxy.

In one variation, a compound of the invention is provided where at least one of $R^{5a}$, $R^{5b}$, $R^{7(a-h)}$ or Q, where present, is a carbonylalkoxy moiety. In one variation, at least one of $R^{5a}$, $R^{5b}$, $R^{7(a-h)}$ or Q, where present, is a carbonylalkoxy moiety of the formula —C(O)—O—R where R is H, alkyl, substituted alkyl or alkaryl. In one variation, at least one of $R^{5a}$, $R^{5b}$, $R^{7(a-h)}$ or Q, where present, is a carbonylalkoxy moiety of the formula —C(O)—O—$C_1$-$C_6$ alkyl. In a particular variation, at least one of $R^{5a}$, $R^{5b}$, $R^{7(a-h)}$ or Q, where present, is a carbonylalkoxy moiety of the formula —C(O)—O—$C_2H_5$. In one variation, at least one of $R^{5a}$, $R^{5b}$, $R^{7(a-h)}$ or Q, where present, is a carbonylalkoxy moiety selected from the group consisting of: —C(O)—O—$C_1$-$C_{10}$alkyl, —C(O)-β-$C_1$-$C_3$alkaryl, —C(O)—O—$C_1$-$C_3$ substituted alkyl and —C(O)—OH. In another variation, $R^{5a}$, $R^{5b}$, $R^{7(a-h)}$ or Q, where present, is —C(O)—O—$C_1$-$C_6$alkyl. In a particular variation, at least one of $R^{5a}$, $R^{5b}$, $R^{7(a-h)}$ or Q, where present, is a moiety of the formula:

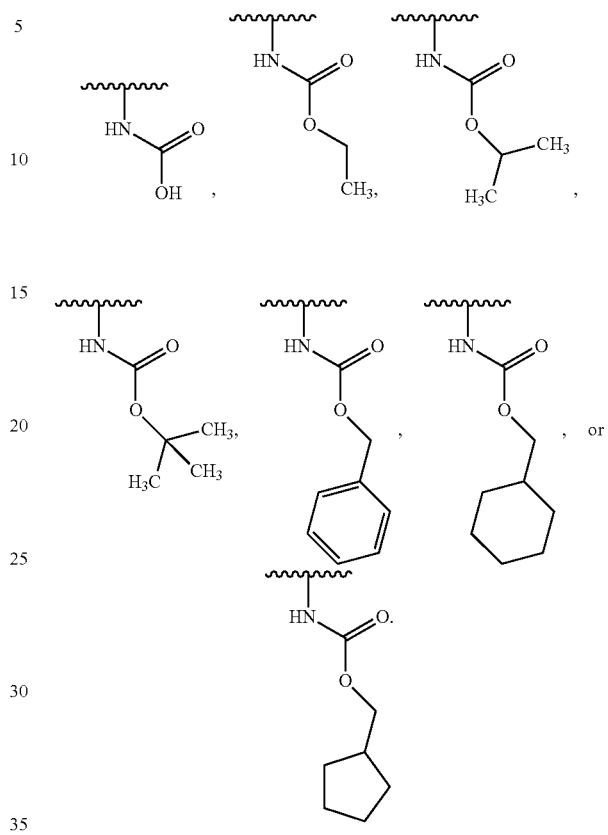

In another variation, a compound of the invention is provided where at least one of $R^{5a}$, $R^{5b}$, $R^{7(a-h)}$ or Q, where present, is an aminocarbonylalkoxy moiety. In one variation, at least one of $R^{5a}$, $R^{5b}$, $R^{7(a-h)}$ or Q, where present, is an aminocarbonylalkoxy moiety of the formula —NHC(O)—O—$R_b$. In another variation, at least one of $R^{5a}$, $R^{5b}$, $R^{7(a-h)}$ or Q, where present, is an aminocarbonylalkoxy moiety of the formula —NHC(O)—O—$R_b$ where $R_b$ is a substituted alkyl group. In a particular variation, at least one of $R^{5a}$, $R^{5b}$, $R^{7(a-h)}$ or Q, where present, is a moiety of the formula —NH—C(O)—O—$CH_2$—$CCl_3$.

The invention also embraces compounds where at least one of $R^{5a}$, $R^{5b}$, $R^{7(a-h)}$ or Q, where present, is an acylamino moiety. In one variation, at least one of $R^{5a}$, $R^{5b}$, $R^{7(a-h)}$ or Q, where present, is an acylamino group where at least one of $R_a$ and $R_b$ is H, such as when $R^{5a}$, $R^{5b}$, $R^{7(a-h)}$ or Q, where present, is of the formula —C(O)N(H)($R_b$). In another variation, at least one of $R^{5a}$, $R^{5b}$, $R^{7(a-h)}$ or Q, where present, is an acylamino group where both $R_a$ and $R_b$ are alkyl. In one variation, at least one of $R^{5a}$, $R^{5b}$, $R^{7(a-h)}$ or Q, where present, is an acylamino moiety selected from the group consisting of: —C(O)—N(H)(alkyl), —C(O)—N(alkyl)$_2$, —C(O)—N(H)(aralkyl) and —C(O)—N(H)(aryl). In another variation, at least one of $R^{5a}$, $R^{5b}$, $R^{7(a-h)}$ or Q, where present, is an acylamino moiety selected from the group consisting of: —C(O)—N(H)$_2$, —C(O)—N(H)($C_1$-$C_8$alkyl), —C(O)—N($C_1$-$C_6$ alkyl)$_2$ and —C(O)—N(H)($C_1$-$C_3$ aralkyl). In a particular variation, at least one of $R^{5a}$, $R^{5b}$, $R^{7(a-h)}$ or Q, where present, is a moiety of the formula:

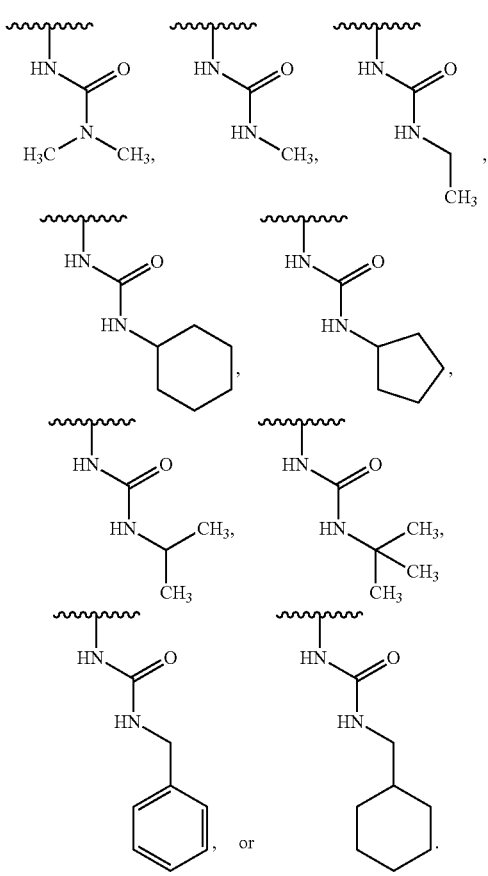

In a further variation, a compound of the invention is provided where $R^1$ is an unsubstituted alkyl, $R^{2a}$, $R^{2b}$, $R^{3a}$, $R^{3b}$, $R^{4a}$ and $R^{4b}$ are each H, each $X^1$, $X^2$ and $X^3$ and $X^4$, where present, is independently N or CH, and at least one of $R^{5a}$, $R^{5b}$, $R^{7(a-h)}$ or Q, where present, is a substituted or unsubstituted aryl, substituted or unsubstituted heteroaryl, including but not limited to a substituted or unsubstituted phenyl or pyridyl group. Where at least one of $R^{5a}$, $R^{5b}$, $R^{7(a-h)}$ or Q, where present, is a substituted phenyl or pyridyl group, in one variation it is substituted with at least one methyl or halo group.

In yet a further variation, a compound of the invention is provided where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^1$, $X^2$ and $X^3$ and $X^4$, where present, is CH or $CR^6$, where $R^6$ is as defined or as detailed in a particular variation, $R^6$ is halo, pyridyl, methyl or trifluoromethyl; $R^{4a}$ and $R^{4b}$ are both H, and at least one of $R^{5a}$, $R^{5b}$, $R^{7(a-h)}$ or Q, where present, is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, at least one of $R^{5a}$, $R^{5b}$, $R^{7(a-h)}$ or Q, where present, is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is provided where $R^1$ is a substituted or unsubstituted $C_1$-$C_8$ alkyl; each $R^{2a}$, $R^{2b}$, $R^{3a}$ and $R^{3b}$ is independently H or halo; each $R^6$ is independently halo, $C_1$-$C_8$ perhaloalkyl, substituted or a unsubstituted $C_1$-$C_8$ alkyl; and at least one of $R^{5a}$, $R^{5b}$, $R^{7(a-h)}$ or Q, where present, is a substituted or unsubstituted cyclohexyl, morpholinyl, piperazinyl, thiomorpholinyl, cyclopentyl or pyrrolidinyl moiety. The invention also embraces a compound where $R^1$ is a methyl; at least one of $X^1$, $X^2$ and $X^3$ and $X^4$, where present, is $CR^6$, and each $R^6$ is independently halo, methyl or trifluoromethyl. The invention embraces compounds where at least one of $R^{5a}$, $R^{5b}$, $R^{7(a-h)}$ or Q, where present, in any variation detailed is substituted with at least one carbonyl, hydroxymethyl, methyl or hydroxyl group, to the extent such substituent makes chemical sense.

In a particular variation, a compound is provided where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; each $R^{4a}$ and $R^{4b}$ is independently H, halo, a substituted or unsubstituted $C_1$-$C_8$ alkyl, hydroxyl, alkoxy or $R^{4a}$ and $R^{4b}$ are taken together to form a carbonyl moiety, provided that at least one of $R^{4a}$ and $R^{4b}$ is other than H. In one aspect of this variation, at least one of $R^{5a}$, $R^{5b}$, $R^{7(a-h)}$ or Q, where present, may be a substituted or unsubstituted pyridyl, phenyl, pyrazinyl, piperazinyl, pyrrolidinyl or thiomorpholinyl group. In another aspect of this variation, at least one of $R^{5a}$, $R^{5b}$, $R^{7(a-h)}$ or Q, where present, is a pyridyl, phenyl, pyrazinyl, piperazinyl, pyrrolidinyl or thiomorpholinyl group substituted with at least one methyl or halo group. In yet another aspect of this variation, each $X^1$, $X^2$ and $X^3$ and $X^4$, where present, is independently CH or $CR^6$ and each $R^6$ is independently halo or methyl.

In a particular variation, a compound is provided wherein $R^1$, $R^{2a}$, $R^{2b}$, $R^{3a}$, $R^{3b}$, $R^{10a}$, $R^{10b}$, $R^{11a}$ and $R^{11b}$ are taken together to form a ring selected from the structures:

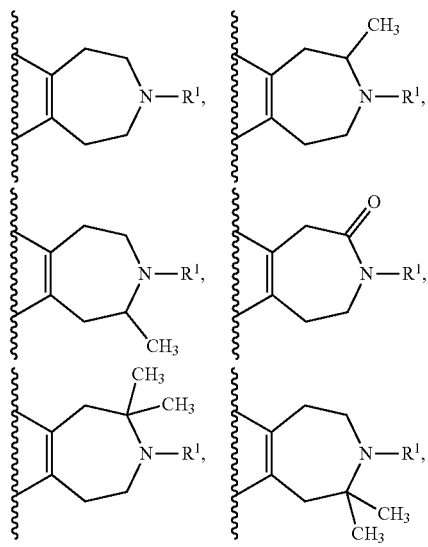

-continued

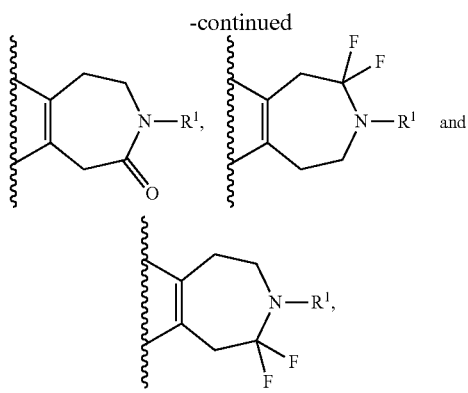

where R¹ in the structures above is as defined herein.

In one embodiment, the invention embraces compounds detailed herein provided that the compound is other than dimebon and metabolites of dimebon. In another embodiment, the invention embraces dimebon or a salt thereof for uses detailed herein. In another embodiment, the invention embraces a dimebon metabolite or salt thereof for uses detailed herein, such as use in therapy, e.g., to increase insulin secretion and treat diseases or conditions that are, or are expected to be, responsive to an increase in insulin production, or to treat type 2 diabetes.

The embodiments and variations described herein are suitable for compounds of any formulae detailed herein, where applicable.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of "substantially pure" compound contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a cognitive disorder, psychotic disorder, neurotransmitter-mediated disorder or a neuronal disorder.

Articles of manufacture comprising a compound of the invention, or a salt or solvate thereof, in a suitable container are provided. The container may be a vial, jar, ampoule, preloaded syringe, i.v. bag, and the like.

In one aspect, an adrenergic receptor $\alpha_{2A}$ antagonist as provided herein exhibits the ability to cross the blood-brain barrier. In another aspect, an adrenergic receptor $\alpha_{2A}$ antagonist as provided herein is not able to cross the blood-brain barrier. In one aspect, an adrenergic receptor $\alpha_{2A}$ antagonist as provided herein exerts its therapeutic effect in the brain only. In one aspect, an adrenergic receptor $\alpha_{2A}$ antagonist as provided herein exerts its therapeutic effect in the periphery only. In one aspect, an adrenergic receptor $\alpha_{2A}$ antagonist as provided herein exerts its therapeutic effect both in the brain and peripherally. In some embodiments, the adrenergic receptor $\alpha_{2A}$ antagonist also exhibits adrenergic receptor $\alpha_{2A}$ inverse agonist activity.

Blood brain barrier permeability can be measured in rodents or dog by administering the compound orally or intravenously, recovering a blood and brain tissue sample at different time points and comparing how much compound is in each sample. Blood fraction is typically processed to plasma for determination of compound content. Brain exposure can be described from the ratio of brain to plasma levels of drug. In one variation, a compound that poorly crosses the blood brain barrier has a brain to plasma ratio of compound of about 0.1 or less. In another variation, the compound has a brain to plasma ratio of about 0.2 or less, about 0.3 or less, about 0.4 or less, about 0.5 or less, about 0.8 or less, or about 1.0 or less.

Preferably, the compounds provided herein are orally bioavailable. However, the compounds may also be formulated for parenteral (e.g., intravenous) administration. In some settings, parenteral administration may be desired.

One or several compounds described herein can be used in the preparation of a medicament by combining the compound or compounds as an active ingredient with a pharmaceutically acceptable carrier, which are known in the art. Depending on the therapeutic form of the medication, the carrier may be in various forms. In one variation, the manufacture of a medicament is for use in any of the methods disclosed herein, e.g., increasing insulin secretion of an individual or treating or delaying the onset and/or development of type 2 diabetes, glucose intolerance or metabolic syndrome.

Methods as provided herein may comprise administering to an individual a pharmacological composition that contains an effective amount of a compound and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Compositions comprising a compound provided herein are also described. In one variation, the composition comprises a compound and a pharmaceutically acceptable carrier or excipient. In another variation, a composition of substantially pure compound is provided.

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for any one or more of the following uses: treating, preventing, and/or delaying the onset and/or development of diabetes type 2 and/or a disease or condition which is responsive, or expected to be responsive, to an increase in insulin secretion.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., type 2 diabetes) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention also provides compositions (including pharmacological compositions) as described herein for the use in treating, preventing, and/or delaying the onset and/or development of diabetes type 2 and/or a disease or condition which is responsive, or expected to be responsive, to an increase in insulin secretion and other methods described herein. In certain embodiments, the composition comprises a pharmaceutical formulation which is present in a unit dosage form. As used herein, the term "unit dosage form" refers to a formulation that contains a predetermined dose of a compound as disclosed herein and optionally a second pharmaceutically active compound useful for treatment of a disease or condition detailed herein (e.g., type 2 diabetes).

Representative compounds of the invention are shown in Tables 1-4.

TABLE 1

Representative Compounds of the Invention

| Compound No. | Structure |
|---|---|
| A1 | 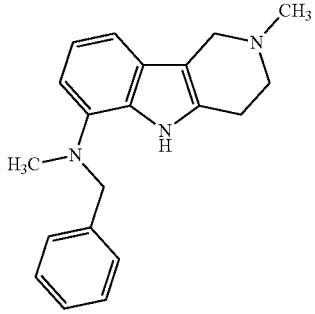 |
| A2 | 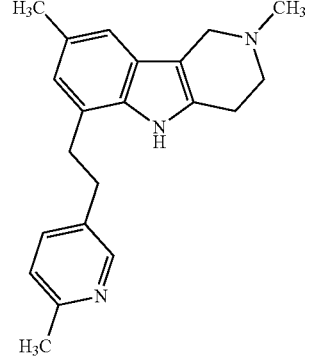 [SMILES: Cc1cc(CCc2ccc(C)nc2)c2[nH]c3c(c2c1)CN(C)CC3] |

TABLE 1-continued

Representative Compounds of the Invention

| Compound No. | Structure |
|---|---|
| A3 | 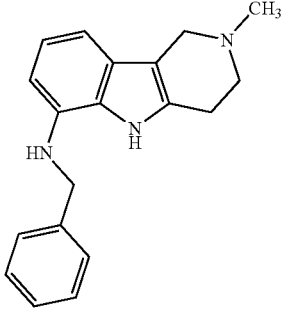 [SMILES: CN1CCc2[nH]c3c(NCc4ccccc4)cccc3c2C1] |
| A4 | 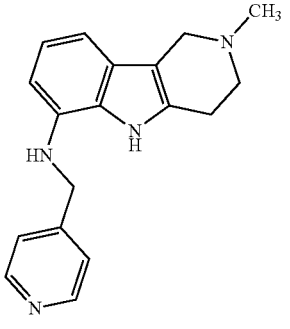 [SMILES: CN1CCc2[nH]c3c(NCc4ccncc4)cccc3c2C1] |
| A5 | 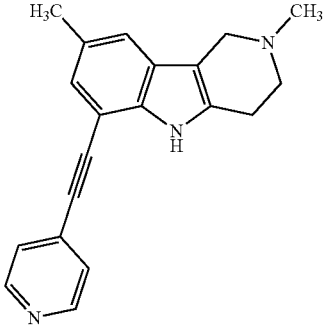 [SMILES: Cc1cc(C#Cc2ccncc2)c2[nH]c3c(c2c1)CN(C)CC3] |
| A6 | 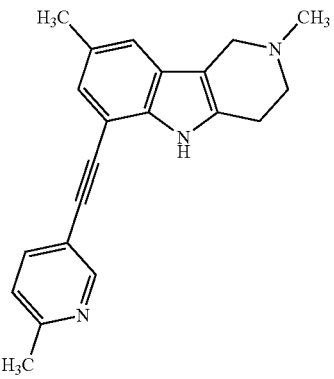 [SMILES: Cc1cc(C#Cc2ccc(C)nc2)c2[nH]c3c(c2c1)CN(C)CC3] |

TABLE 1-continued
Representative Compounds of the Invention
| Compound No. | Structure |
|---|---|
| A7 | 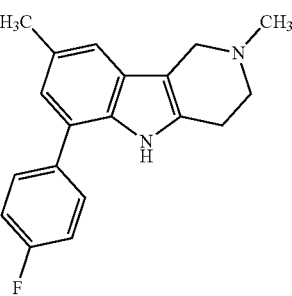 [SMILES: Cc1cc(-c2ccc(F)cc2)c2[nH]c3c(c2c1)CN(C)CC3] |
| A8 | 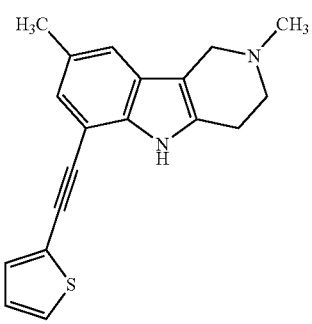 [SMILES: Cc1cc(C#Cc2cccs2)c2[nH]c3c(c2c1)CN(C)CC3] |
| A9 | 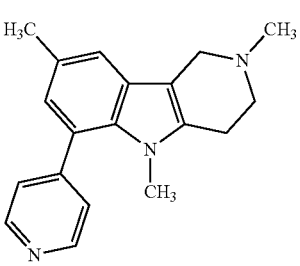 [SMILES: Cc1cc(-c2ccncc2)c2c(c1)c1c(n2C)CCN(C)C1] |
| A10 | 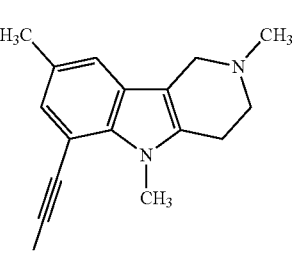 |
| A11 | 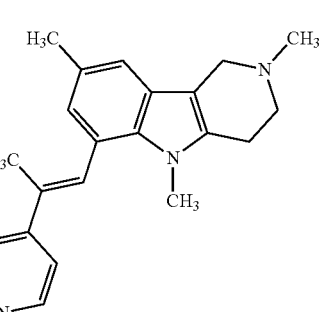 |
| A12 | 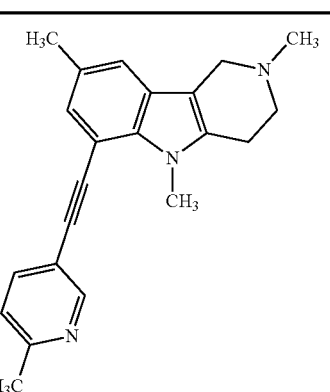 |
| A13 | 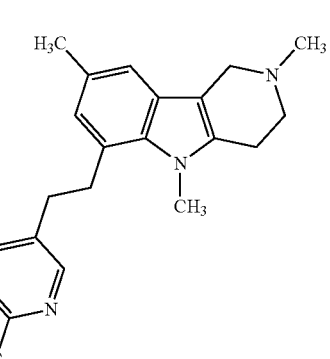 |
| A14 | 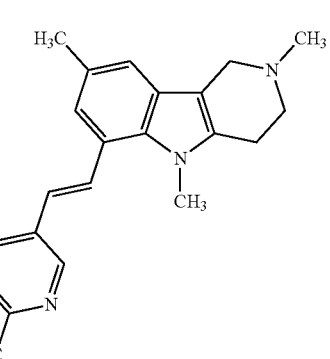 |
| A15 | 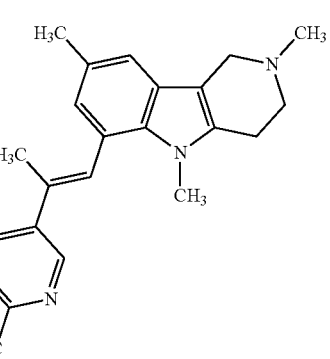 |

TABLE 1-continued
Representative Compounds of the Invention
| Compound No. | Structure |
|---|---|
| A16 | 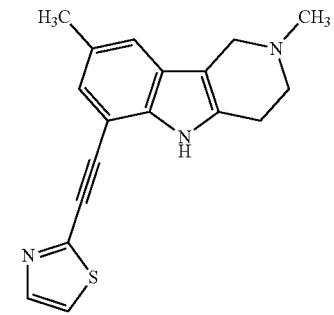 [SMILES: Cc1cc(C#Cc2nccs2)c2[nH]c3c(c2c1)CN(C)CC3] |
| A17 | 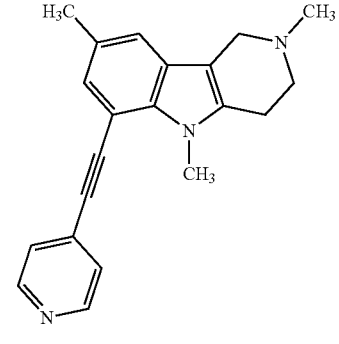 [SMILES: Cc1cc(C#Cc2ccncc2)c2c(c1)c1c(n2C)CCN(C)C1] |
| A18 | 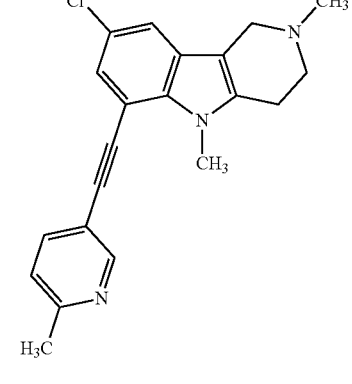 |
| A19 | 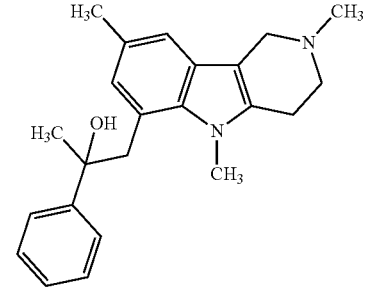 [SMILES: Cc1cc(CC(C)(O)c2ccccc2)c2c(c1)c1c(n2C)CCN(C)C1] |
| A20 | 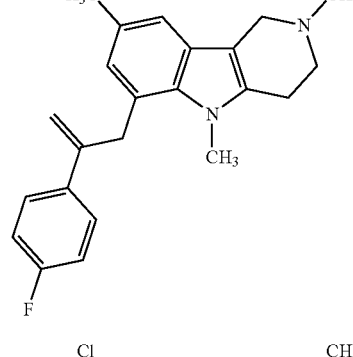 |
| A21 | 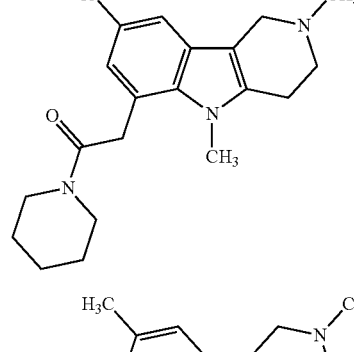 |
| A22 | 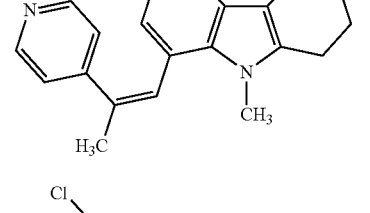 |
| A23 | 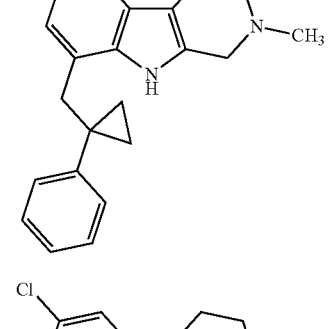 |
| A24 | 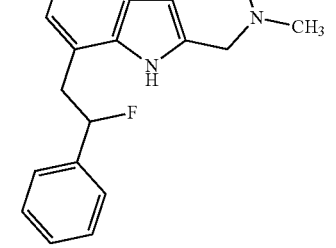 |

TABLE 1-continued
Representative Compounds of the Invention
| Compound No. | Structure |
|---|---|
| A25 | 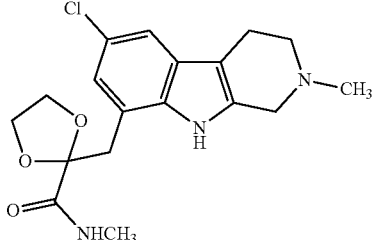 |
| A26 | 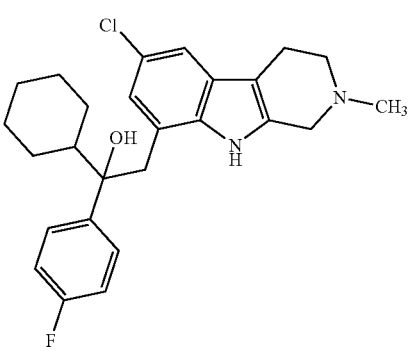 [SMILES: CN1CCc2c([nH]c3c(CC(O)(c4ccc(F)cc4)C4CCCCC4)cc(Cl)cc23)C1] |
| A27 | 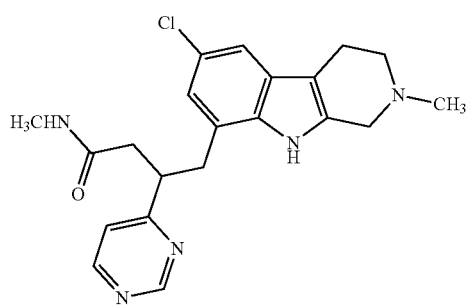 [SMILES: CNC(=O)CC(Cc1cc(Cl)cc2c3c([nH]c12)CN(C)CC3)c1ccncn1] |
| A28 | 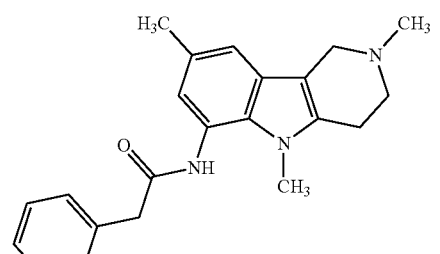 |
| A29 | 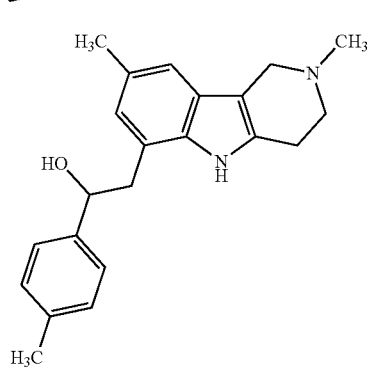 |
| A30 | 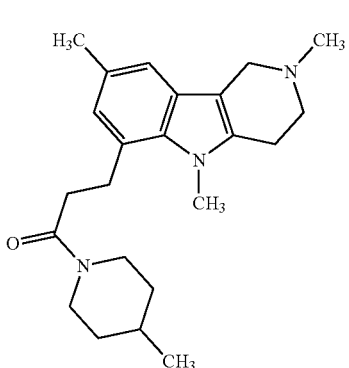 |
| A31 | 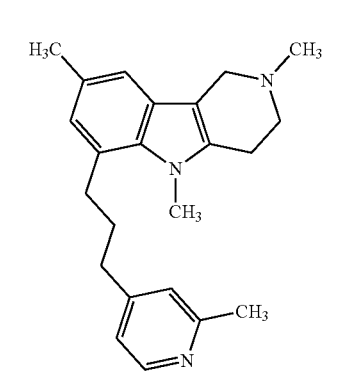 |
| A32 | 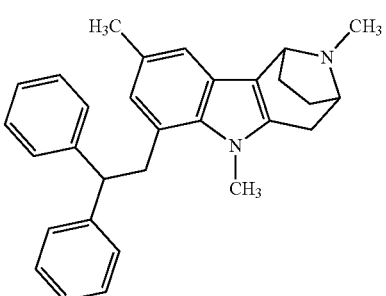 |
| A33 | 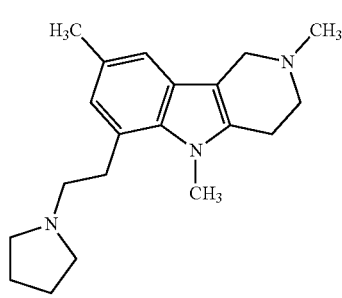 [SMILES: Cc1cc(CCN2CCCC2)c2c(c1)c1c(n2C)CCN(C)C1] |

TABLE 1-continued

Representative Compounds of the Invention

| Compound No. | Structure |
|---|---|
| A34 | (structure) |
| A35 | (structure) |
| A36 | (structure) |
| A37 | (structure) |
| A38 | (structure) |
| A39 | (structure) |
| A40 | (structure) |
| A41 | (structure) |
| A42 | (structure) |
| A43 | (structure) |

TABLE 1-continued

Representative Compounds of the Invention

| Compound No. | Structure |
|---|---|
| A44 | (structure) |
| A45 | (structure) |
| A46 | (structure) |
| A47 | (structure) |
| A48 | (structure) |
| A49 | (structure) |
| A50 | (structure) |
| A51 | (structure) |
| A52 | (structure) |
| A53 | (structure) |

TABLE 1-continued

Representative Compounds of the Invention

| Compound No. | Structure |
|---|---|
| A54 | (structure) |
| A55 | (structure) |
| A56 | (structure) |
| A57 | (structure) |
| A58 | (structure) |
| A59 | (structure) |
| A60 | (structure) |
| A61 | (structure) |
| A62 | (structure) |

TABLE 1-continued

Representative Compounds of the Invention

| Compound No. | Structure |
|---|---|
| A63 | (structure) |
| A64 | (structure) |
| A65 | (structure) |
| A66 | (structure) |
| A67 | (structure) |
| A68 | (structure) |
| A69 | (structure) |
| A70 | (structure) |

TABLE 1-continued
Representative Compounds of the Invention
| Compound No. | Structure |
|---|---|
| A71 | 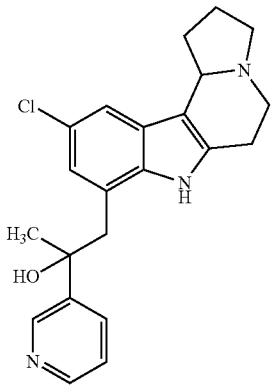 [SMILES: CC(O)(Cc1cc(Cl)cc2c3c([nH]c12)CCN1CCCC31)c1cccnc1] |
| A72 | 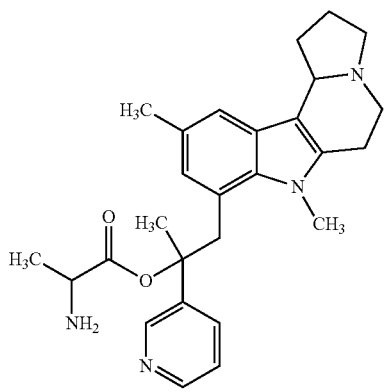 [SMILES: Cc1cc(CC(C)(OC(=O)C(C)N)c2cccnc2)c2c(c1)c1c(n2C)CCN2CCCC12] |
| A73 | 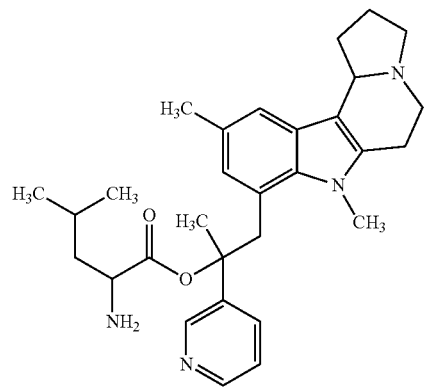 [SMILES: Cc1cc(CC(C)(OC(=O)C(N)CC(C)C)c2cccnc2)c2c(c1)c1c(n2C)CCN2CCCC12] |
| A74 | 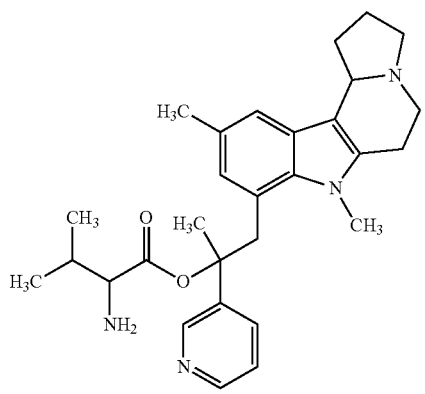 [SMILES: Cc1cc(CC(C)(OC(=O)C(N)C(C)C)c2cccnc2)c2c(c1)c1c(n2C)CCN2CCCC12] |
| A75 | 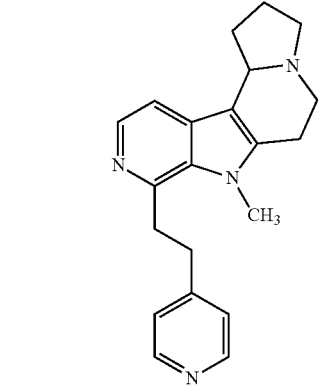 [SMILES: Cn1c2c(c3ccnc(CCc4ccncc4)c31)C1CCCN1CC2] |
| A76 |  |

TABLE 1-continued
Representative Compounds of the Invention
| Compound No. | Structure |
|---|---|
| A77 | 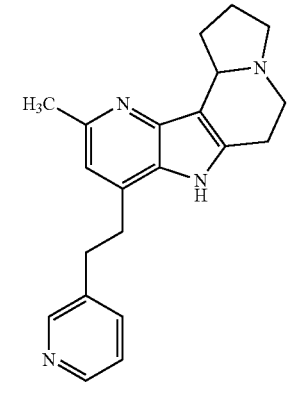 [SMILES: Cc1cc(CCc2cccnc2)c2[nH]c3c(c2n1)C1CCCN1CC3] |
| A78 | 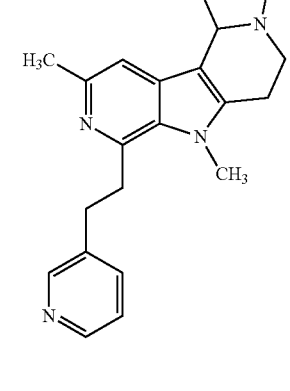 |
| A79 | 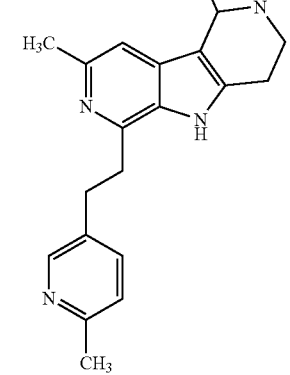 |
| A80 | 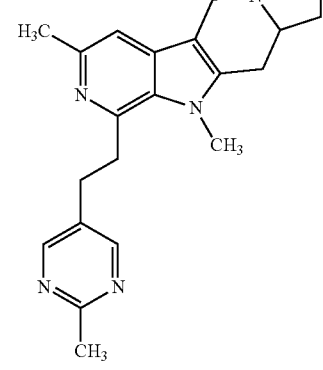 |
| A81 | 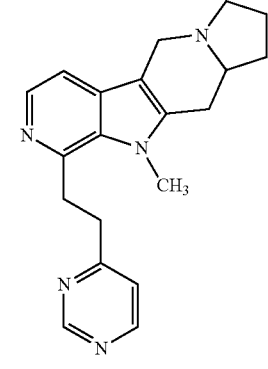 [SMILES: Cn1c2c(c3ccnc(CCc4ccncn4)c31)CN1CCCC1C2] |
| A82 | 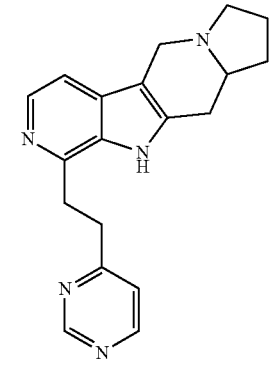 [SMILES: c1cc(CCc2nccc3c4c([nH]c23)CC2CCCN2C4)ncn1] |
| A83 | 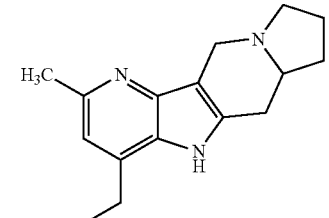 |

TABLE 1-continued
Representative Compounds of the Invention
| Compound No. | Structure |
|---|---|
| A84 | 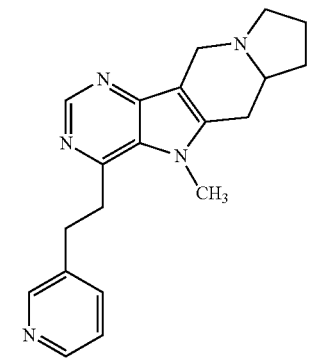 [SMILES: Cn1c2c(c3ncnc(CCc4cccnc4)c31)CN1CCCC1C2] |
| A85 | 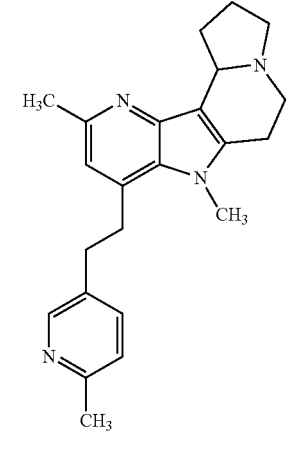 [SMILES: Cc1ccc(CCc2cc(C)nc3c4c(n(C)c23)CCN2CCCC42)cn1] |
| A86 | 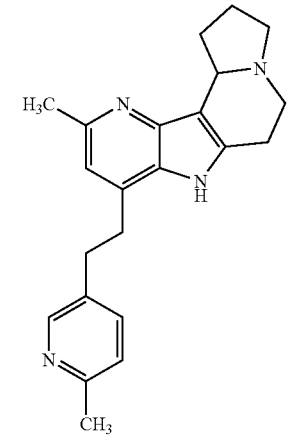 [SMILES: Cc1ccc(CCc2cc(C)nc3c4c([nH]c23)CCN2CCCC42)cn1] |
| A87 | 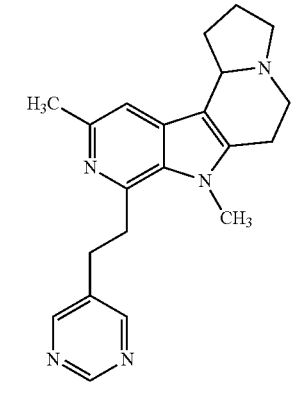 |
| A88 | 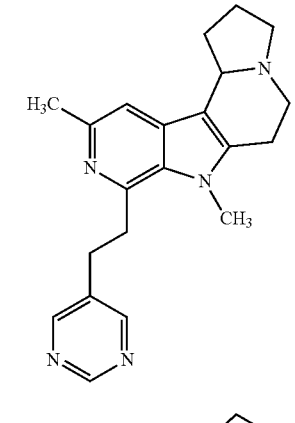 |
| A89 | 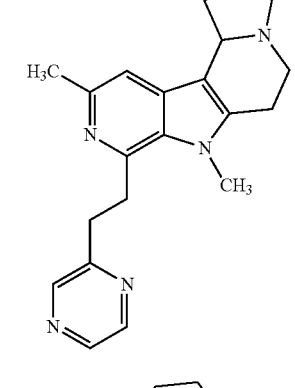 |
| A90 | 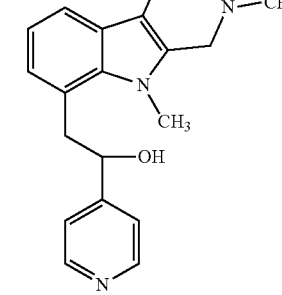 |

TABLE 1-continued

Representative Compounds of the Invention

| Compound No. | Structure |
|---|---|
| A91 | 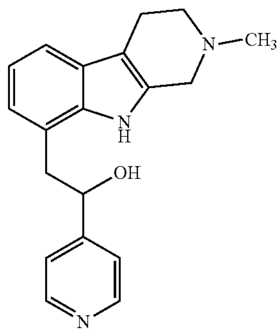 [SMILES: CN1CCc2c([nH]c3c(CC(O)c4ccncc4)cccc23)C1] |
| A92 | 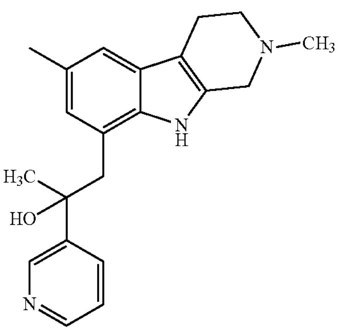 |
| A93 | 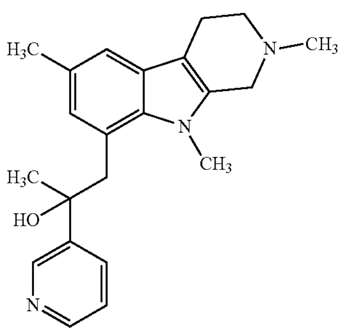 |
| A94 | 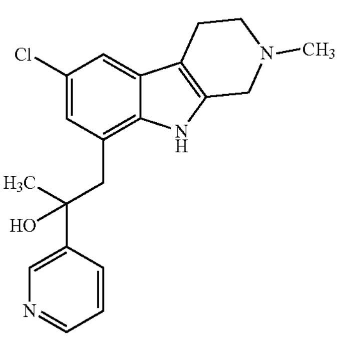 [SMILES: CN1CCc2c([nH]c3c(CC(C)(O)c4cccnc4)cc(Cl)cc23)C1] |
| A95 | |
| A96 | |
| A97 | |
| A98 | |

TABLE 1-continued

Representative Compounds of the Invention

| Compound No. | Structure |
|---|---|
| A99 | 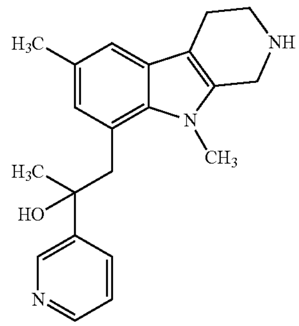 [SMILES: Cc1cc(CC(C)(O)c2cccnc2)c2c(c1)c1c(n2C)CNCC1] |
| A100 | 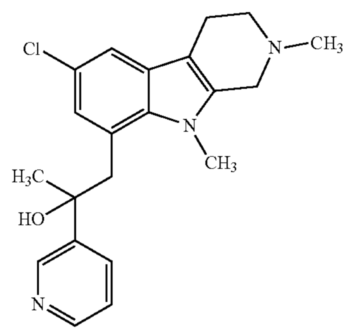 [SMILES: CN1CCc2c(n(C)c3c(CC(C)(O)c4cccnc4)cc(Cl)cc23)C1] |
| A101 | 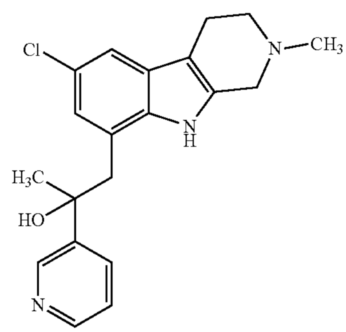 [SMILES: CN1CCc2c([nH]c3c(CC(C)(O)c4cccnc4)cc(Cl)cc23)C1] |
| A102 | 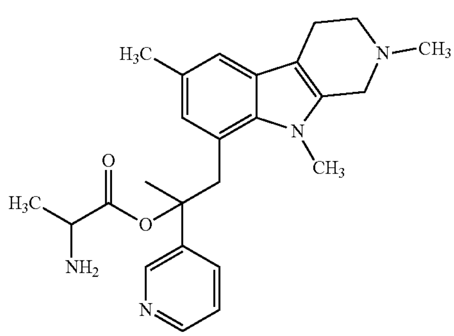 [SMILES: Cc1cc(CC(C)(OC(=O)C(C)N)c2cccnc2)c2c(c1)c1c(n2C)CN(C)CC1] |
| A103 | |
| A104 | |
| A105 | |
| A106 | |

TABLE 1-continued

Representative Compounds of the Invention

| Compound No. | Structure |
|---|---|
| A107 | 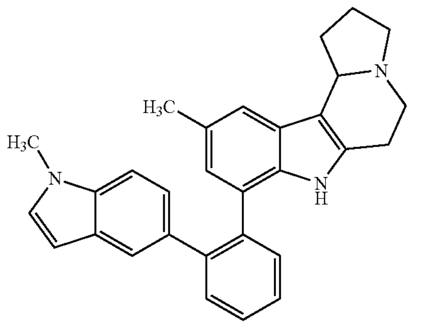 [SMILES: Cc1cc(-c2ccccc2-c2ccc3c(ccn3C)c2)c2[nH]c3c(c2c1)C1CCCN1CC3] |
| A108 | 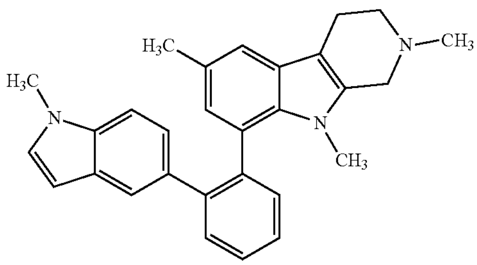 [SMILES: Cc1cc(-c2ccccc2-c2ccc3c(ccn3C)c2)c2c(c1)c1c(n2C)CN(C)CC1] |
| A109 | 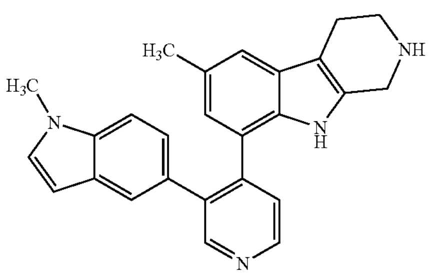 [SMILES: Cc1cc(-c2ccncc2-c2ccc3c(ccn3C)c2)c2[nH]c3c(c2c1)CCNC3] |
| A110 | 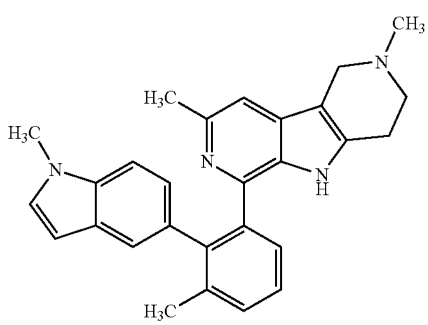 [SMILES: Cc1cc2c3c([nH]c2c(-c2cccc(C)c2-c2ccc4c(ccn4C)c2)n1)CCN(C)C3] |
| A111 | 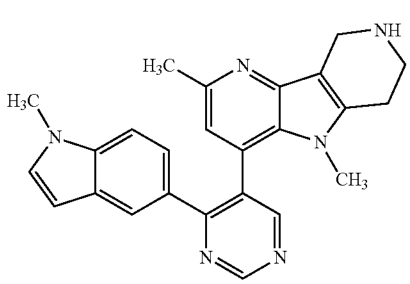 [SMILES: Cc1cc(-c2cncnc2-c2ccc3c(ccn3C)c2)c2c(n1)c1c(n2C)CCNC1] |
| A112 | |
| A113 | |
| A114 | |
| A115 | |
| A116 | |

TABLE 1-continued

Representative Compounds of the Invention

| Compound No. | Structure |
|---|---|
| A117 | (structure) |
| A118 | (structure) |
| A119 | (structure) |
| A120 | (structure) |
| A121 | (structure) |
| A122 | (structure) |
| A123 | (structure) |
| A124 | (structure) |
| A125 | (structure) |

TABLE 1-continued
Representative Compounds of the Invention
| Compound No. | Structure |
|---|---|
| A126 | 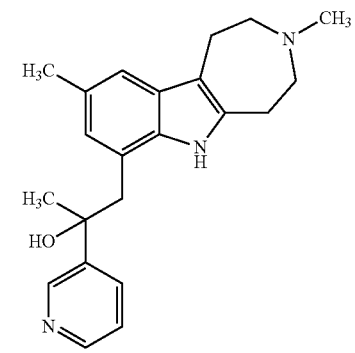 [SMILES: Cc1cc(CC(C)(O)c2cccnc2)c2[nH]c3c(c2c1)CCN(C)CC3] |
| A127 | 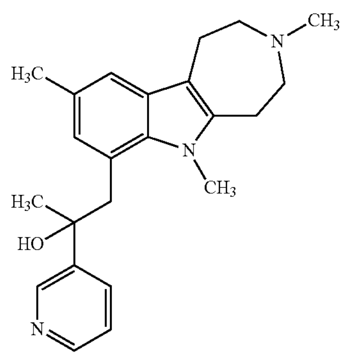 [SMILES: Cc1cc(CC(C)(O)c2cccnc2)c2c(c1)c1c(n2C)CCN(C)CC1] |
| A128 | 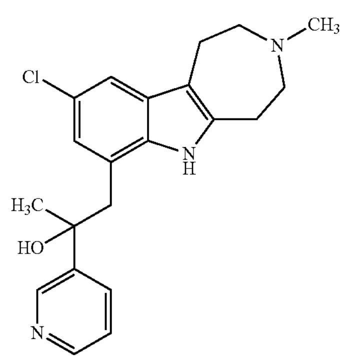 [SMILES: CN1CCc2[nH]c3c(CC(C)(O)c4cccnc4)cc(Cl)cc3c2CC1] |
| A129 | 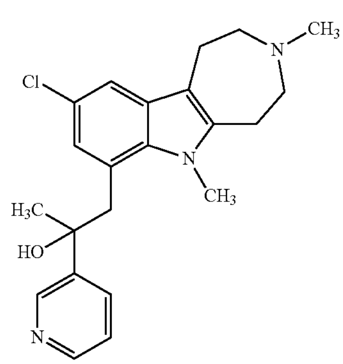 [SMILES: CN1CCc2c(n(C)c3c(CC(C)(O)c4cccnc4)cc(Cl)cc23)CC1] |
| A130 | 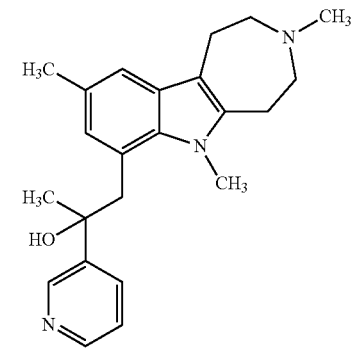 |
| A131 | |
| A132 | |
| A133 | |

TABLE 1-continued

Representative Compounds of the Invention

| Compound No. | Structure |
|---|---|
| A134 | 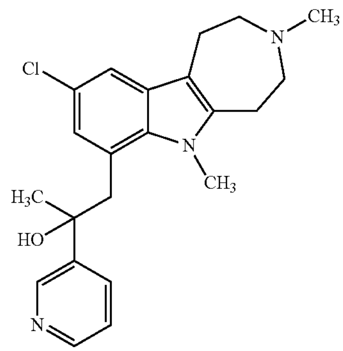 [SMILES: CN1CCc2c(n(C)c3c(CC(C)(O)c4cccnc4)cc(Cl)cc23)CC1] |
| A135 | 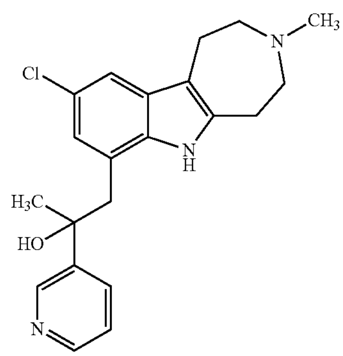 [SMILES: CN1CCc2[nH]c3c(CC(C)(O)c4cccnc4)cc(Cl)cc3c2CC1] |
| A136 | 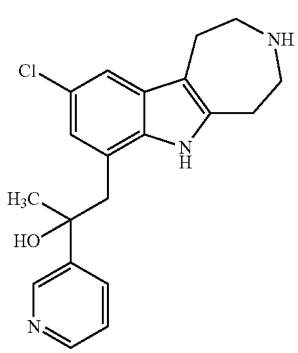 [SMILES: CC(O)(Cc1cc(Cl)cc2c3c([nH]c12)CCNCC3)c1cccnc1] |
| A137 | 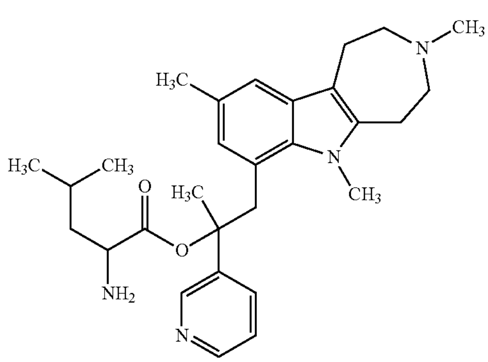 [SMILES: Cc1cc(CC(C)(OC(=O)C(N)CC(C)C)c2cccnc2)c2c(c1)c1c(n2C)CCN(C)CC1] |
| A138 | |
| A139 | |
| A140 | |
| A141 | |

TABLE 1-continued
Representative Compounds of the Invention
| Compound No. | Structure |
|---|---|
| A142 | 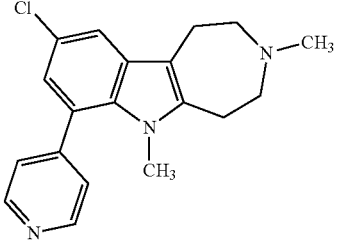 [SMILES: CN1CCc2c(n(C)c3c(-c4ccncc4)cc(Cl)cc23)CC1] |
| A143 | 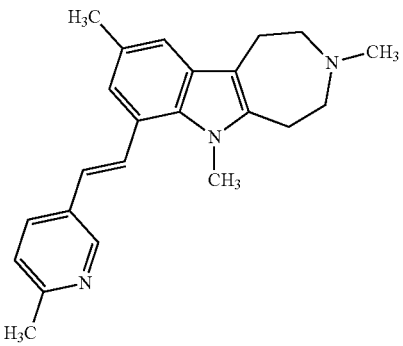 [SMILES: Cc1cc(/C=C/c2ccc(C)nc2)c2c(c1)c1c(n2C)CCN(C)CC1] |
| A144 | 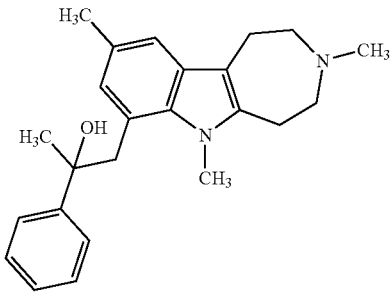 [SMILES: Cc1cc(CC(C)(O)c2ccccc2)c2c(c1)c1c(n2C)CCN(C)CC1] |
| A145 | 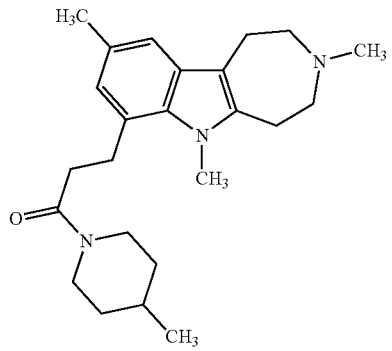 [SMILES: Cc1cc(CCC(=O)N2CCC(C)CC2)c2c(c1)c1c(n2C)CCN(C)CC1] |
| A146 | 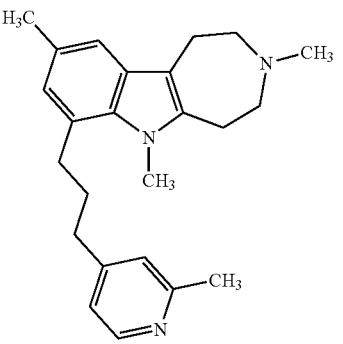 |
| A147 | 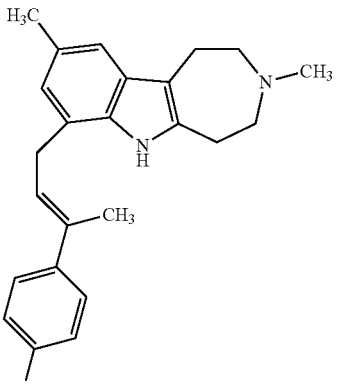 |
| A148 | 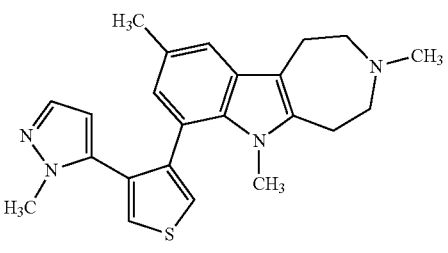 [SMILES: Cc1cc(-c2cscc2-c2ccnn2C)c2c(c1)c1c(n2C)CCN(C)CC1] |
| A149 | 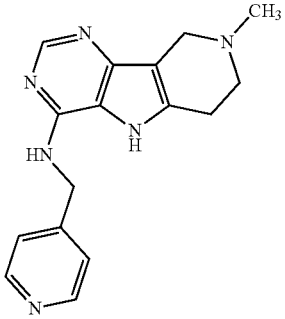 [SMILES: CN1CCc2[nH]c3c(NCc4ccncc4)ncnc3c2C1] |

TABLE 1-continued
Representative Compounds of the Invention
| Compound No. | Structure |
|---|---|
| A150 | 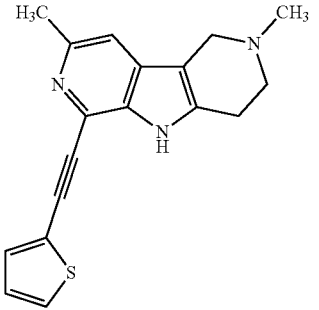 |
| A151 | 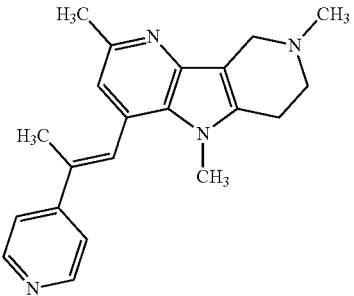 [SMILES: C/C(=C\c1cc(C)nc2c3c(n(C)c12)CCN(C)C3)c1ccncc1] |
| A152 | 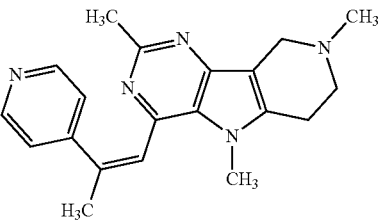 [SMILES: C/C(=C/c1nc(C)nc2c3c(n(C)c12)CCN(C)C3)c1ccncc1] |
| A153 | 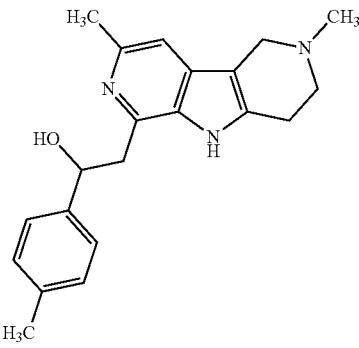 [SMILES: Cc1ccc(C(O)Cc2nc(C)cc3c4c([nH]c23)CCN(C)C4)cc1] |
| A154 | 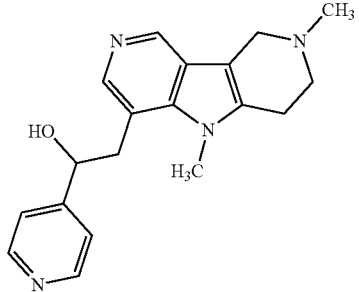 [SMILES: CN1CCc2c(c3cncc(CC(O)c4ccncc4)c3n2C)C1] |
| A155 | 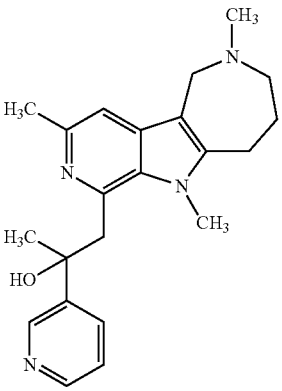 [SMILES: Cc1cc2c3c(n(C)c2c(CC(C)(O)c2cccnc2)n1)CCCN(C)C3] |
| A156 | 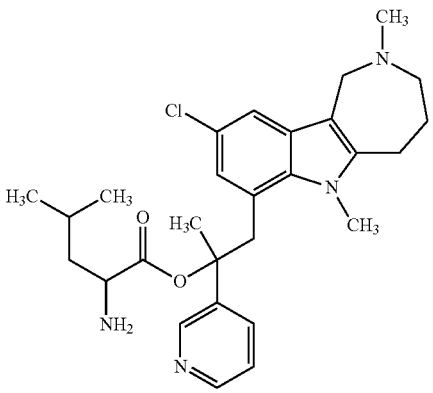 [SMILES: CC(C)CC(N)C(=O)OC(C)(Cc1cc(Cl)cc2c3c(n(C)c12)CCCN(C)C3)c1cccnc1] |
| A157 | 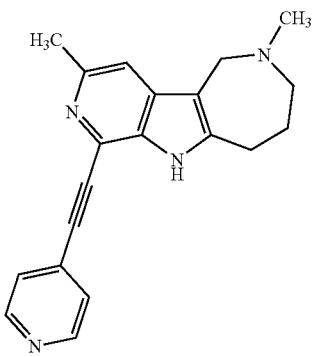 [SMILES: Cc1cc2c3c([nH]c2c(C#Cc2ccncc2)n1)CCCN(C)C3] |
| A158 | 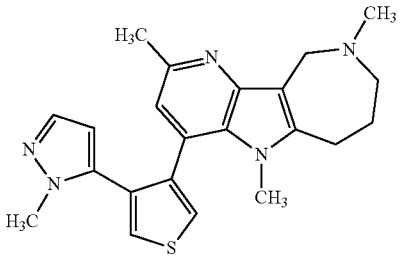 [SMILES: Cc1cc(-c2cscc2-c2ccnn2C)c2c(n1)c1c(n2C)CCCN(C)C1] |

TABLE 1-continued

Representative Compounds of the Invention

| Compound No. | Structure |
|---|---|
| A159 | 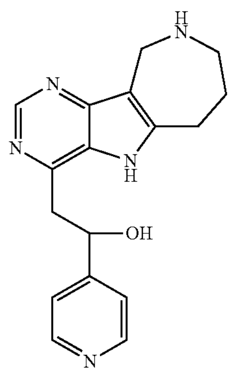 [SMILES: OC(Cc1ncnc2c3c([nH]c12)CCCNC3)c1ccncc1] |
| A160 | 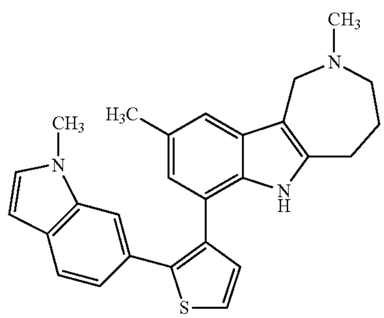 [SMILES: Cc1cc(-c2ccsc2-c2ccc3ccn(C)c3c2)c2[nH]c3c(c2c1)CN(C)CCC3] |

TABLE 2

Representative Compounds of the Invention

| Compound No. | Structure |
|---|---|
| B1 | |
| B2 | |
| B3 | 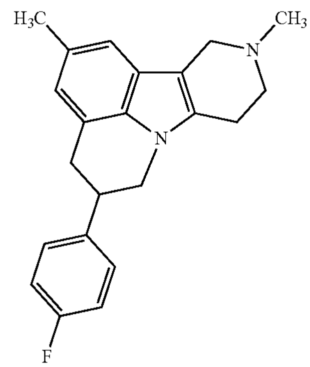 [SMILES: Cc1cc2c3c(c1)c1c(n3CC(c3ccc(F)cc3)C2)CCN(C)C1] |
| B4 | 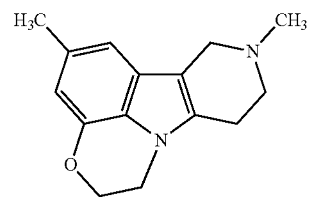 |
| B5 | 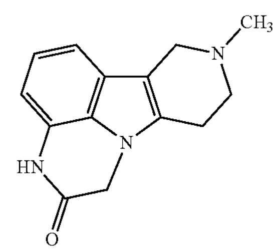 [SMILES: CN1CCc2c(c3cccc4c3n2CC(=O)N4)C1] |
| B6 | 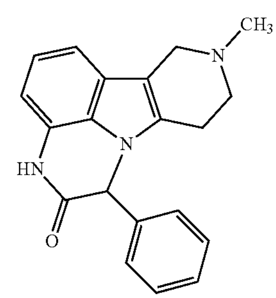 [SMILES: CN1CCc2c(c3cccc4c3n2C(c2ccccc2)C(=O)N4)C1] |
| B7 | 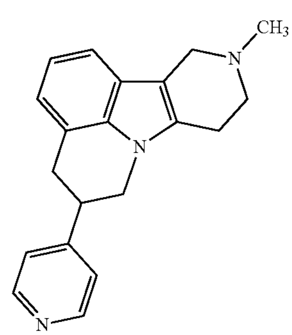 [SMILES: CN1CCc2c(c3cccc4c3n2CC(c2ccncc2)C4)C1] |

TABLE 2-continued

Representative Compounds of the Invention

| Compound No. | Structure |
|---|---|
| B8 | 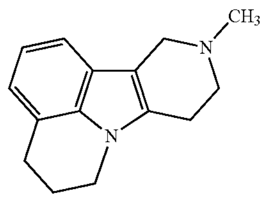 [SMILES: CN1CCc2c(c3cccc4c3n2CCC4)C1] |
| B9 | 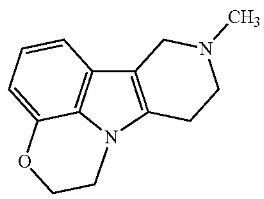 [SMILES: CN1CCc2c(c3cccc4c3n2CCO4)C1] |
| B10 | 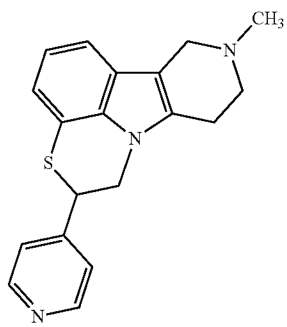 [SMILES: CN1CCc2c(c3cccc4c3n2CC(c2ccncc2)S4)C1] |
| B11 | 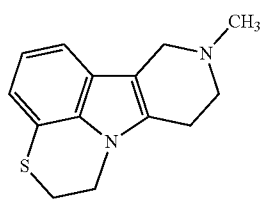 |
| B12 | 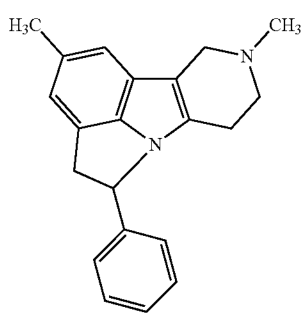 |
| B13 | |
| B14 | |
| B15 | |
| B16 | |

TABLE 2-continued

Representative Compounds of the Invention

| Compound No. | Structure |
|---|---|
| B17 | (structure) |
| B18 | (structure) |
| B19 | (structure) |
| B20 | (structure) |
| B21 | (structure) |
| B22 | (structure) |
| B23 | (structure) |
| B24 | (structure) |

TABLE 2-continued

Representative Compounds of the Invention

| Compound No. | Structure |
|---|---|
| B25 | (structure) |
| B26 | (structure) |
| B27 | (structure) |
| B28 | (structure) |
| B29 | (structure) |
| B30 | (structure) |
| B31 | (structure) |
| B32 | (structure) |

TABLE 2-continued

Representative Compounds of the Invention

| Compound No. | Structure |
|---|---|
| B33 | (structure) |
| B34 | (structure) |
| B35 | (structure) |
| B36 | (structure) |
| B37 | (structure) |
| B38 | (structure) |
| B39 | (structure) |
| B40 | (structure) |

TABLE 2-continued

Representative Compounds of the Invention

| Compound No. | Structure |
|---|---|
| B41 | 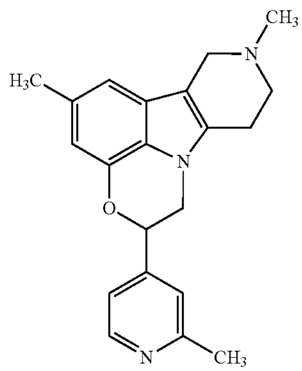 |
| B42 | 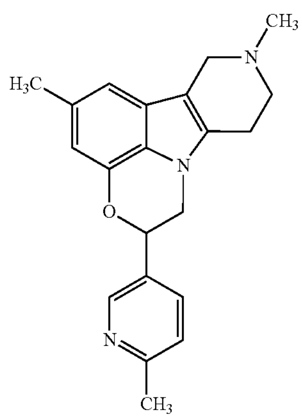 |
| B43 | 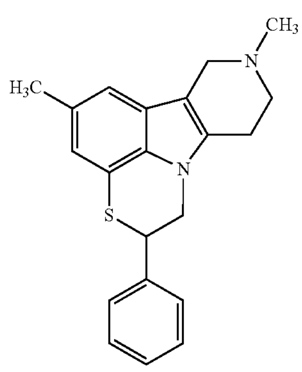 |
| B44 | 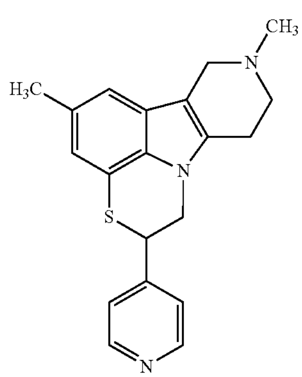 |
| B45 | |
| B46 | |
| B47 | |
| B48 | |

TABLE 2-continued
Representative Compounds of the Invention
| Compound No. | Structure |
|---|---|
| B49 | 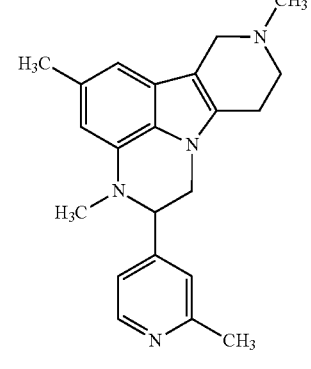 |
| B50 | 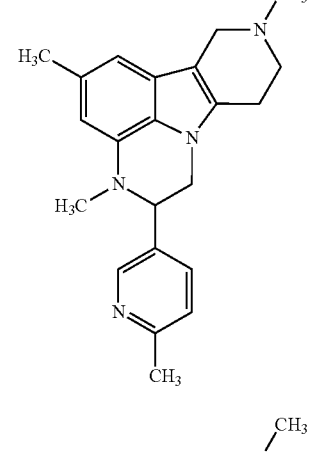 |
| B51 | 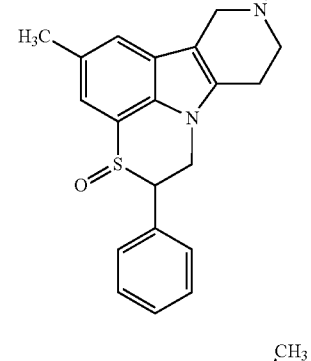 |
| B52 | 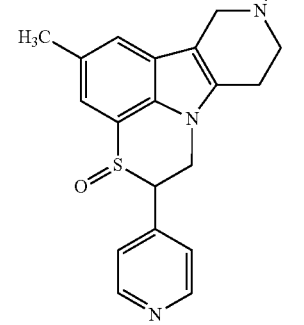 |
| B53 | 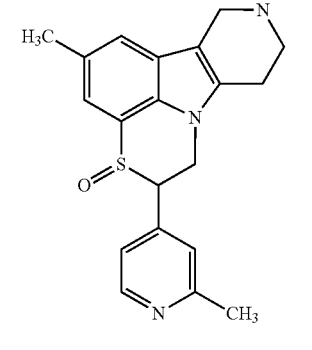 |
| B54 | 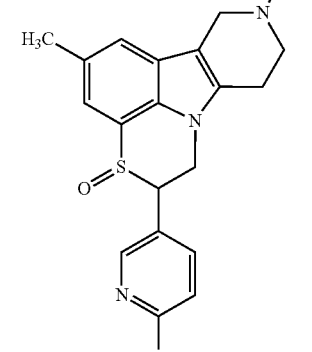 |
| B55 | 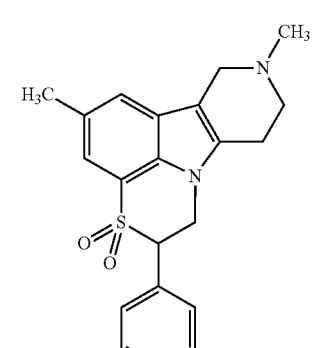 |
| B56 | 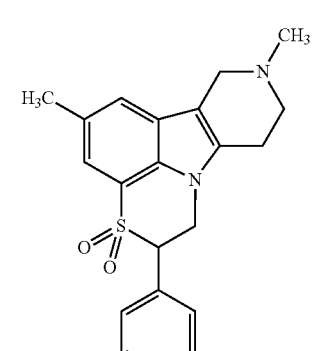 |

TABLE 2-continued

Representative Compounds of the Invention

| Compound No. | Structure |
|---|---|
| B57 | (structure) |
| B58 | (structure) |
| B59 | (structure) |
| B60 | (structure) |
| B61 | (structure) |
| B62 | (structure) |
| B63 | (structure) |

TABLE 2-continued

Representative Compounds of the Invention

| Compound No. | Structure |
|---|---|
| B64 | (structure) |
| B65 | (structure) |
| B66 | (structure) |
| B67 | (structure) |
| B68 | (structure) |
| B69 | (structure) |
| B70 | (structure) |
| B71 | (structure) |

TABLE 2-continued

Representative Compounds of the Invention

| Compound No. | Structure |
|---|---|
| B72 | (structure) |
| B73 | (structure) |
| B74 | (structure) |
| B75 | (structure) |
| B76 | (structure) |
| B77 | (structure) |
| B78 | (structure) |
| B79 | (structure) |

TABLE 2-continued

Representative Compounds of the Invention

| Compound No. | Structure |
|---|---|
| B80 | (structure) |
| B81 | (structure) |
| B82 | (structure) |
| B83 | (structure) |
| B84 | (structure) |
| B85 | (structure) |
| B86 | (structure) |
| B87 | (structure) |

TABLE 2-continued
Representative Compounds of the Invention
| Compound No. | Structure |
|---|---|
| B88 | 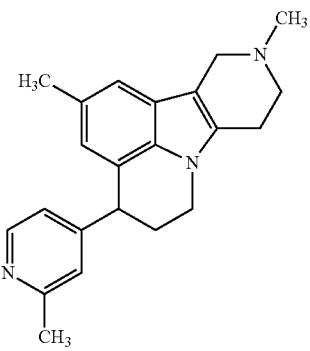 [SMILES: Cc1cc2c3c(c1)c1c(n3CCC2c2ccnc(C)c2)CCN(C)C1] |
| B89 | 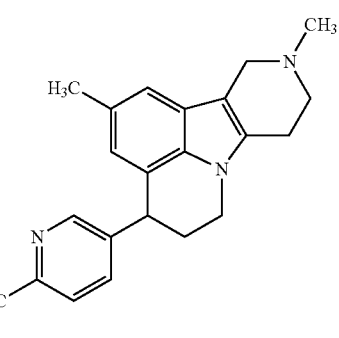 |
| B90 | 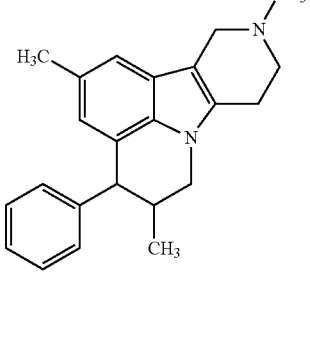 |
| B91 | 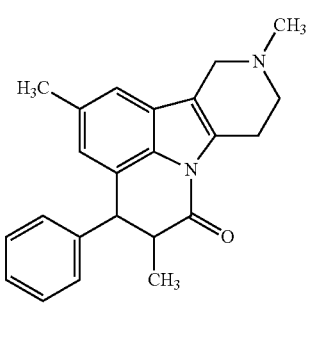 [SMILES: Cc1cc2c3c(c1)c1c(n3C(=O)C(C)C2c2ccccc2)CCN(C)C1] |
| B92 | 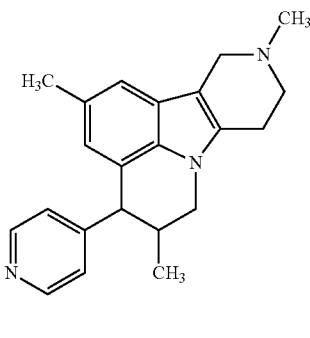 [SMILES: Cc1cc2c3c(c1)c1c(n3CC(C)C2c2ccncc2)CCN(C)C1] |
| B93 | 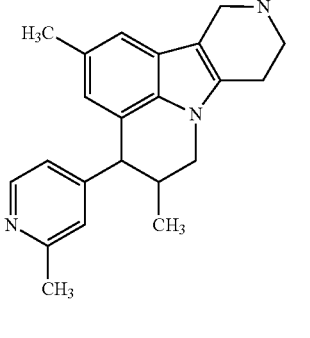 |
| B94 | 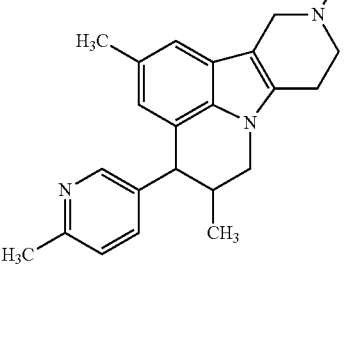 |
| B95 | 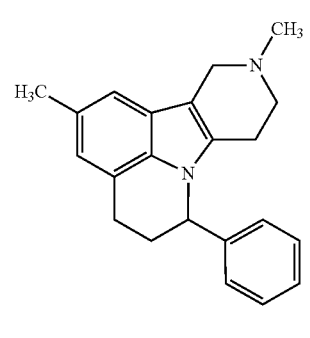 [SMILES: Cc1cc2c3c(c1)c1c(n3C(c3ccccc3)CC2)CCN(C)C1] |

TABLE 2-continued

Representative Compounds of the Invention

| Compound No. | Structure |
|---|---|
| B96 | (structure) |
| B97 | (structure) |
| B98 | (structure) |
| B99 | (structure) |
| B100 | (structure) |
| B101 | (structure) |
| B102 | (structure) |
| B103 | (structure) |
| B104 | (structure) |

TABLE 2-continued

Representative Compounds of the Invention

| Compound No. | Structure |
|---|---|
| B105 | (structure) |
| B106 | (structure) |
| B107 | (structure) |
| B108 | (structure) |
| B109 | (structure) |
| B110 | (structure) |
| B111 | (structure) |
| B112 | (structure) |

TABLE 2-continued
Representative Compounds of the Invention
| Compound No. | Structure |
|---|---|
| B113 | 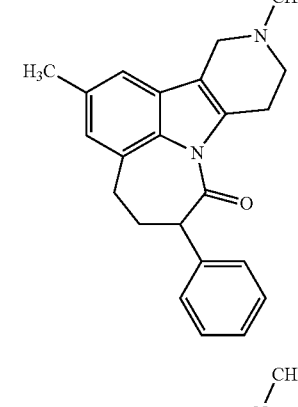 |
| B114 | 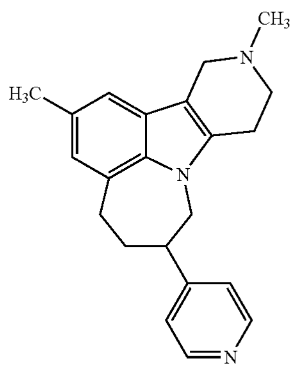 [SMILES: Cc1cc2c3c(c1)c1c(n3CC(c3ccncc3)CC2)CCN(C)C1] |
| B115 | 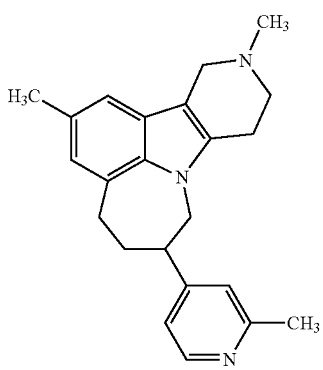 |
| B116 | 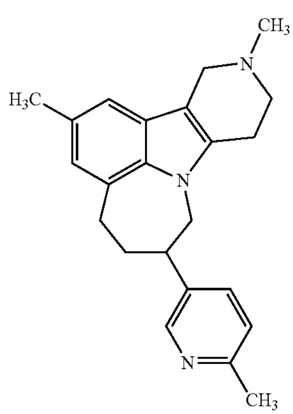 [SMILES: Cc1cc2c3c(c1)c1c(n3CC(c3ccc(C)nc3)CC2)CCN(C)C1] |
| B117 | 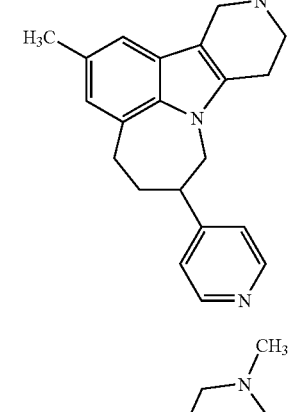 |
| B118 | |
| B119 | |
| B120 | |

TABLE 2-continued
Representative Compounds of the Invention
| Compound No. | Structure |
|---|---|
| B121 | 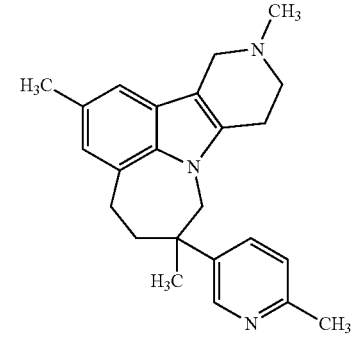 |
| B122 | 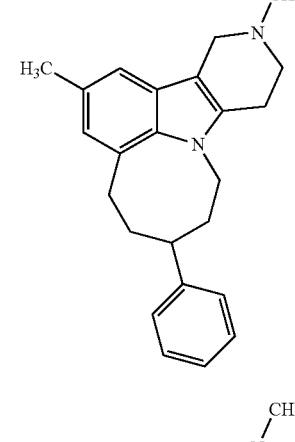 |
| B123 | 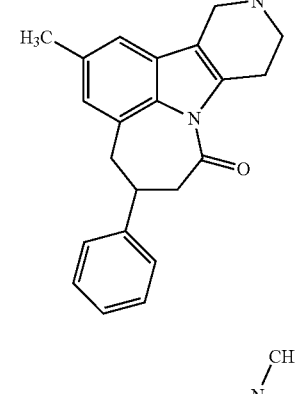 |
| B124 | 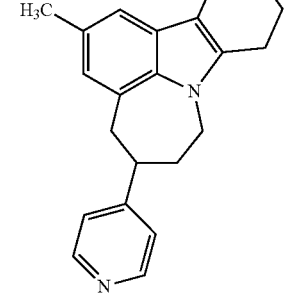 |
| B125 | 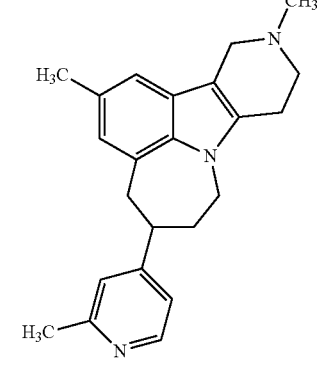 |
| B126 | 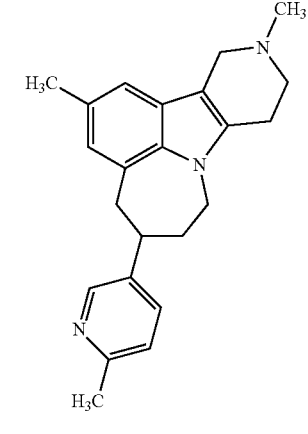 [SMILES: Cc1cc2c3c(c1)c1c(n3CCC(c3ccc(C)nc3)C2)CCN(C)C1] |
| B127 | 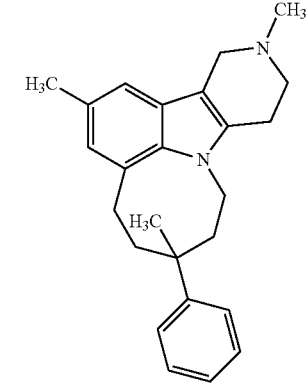 |

TABLE 2-continued

Representative Compounds of the Invention

| Compound No. | Structure |
|---|---|
| B128 | 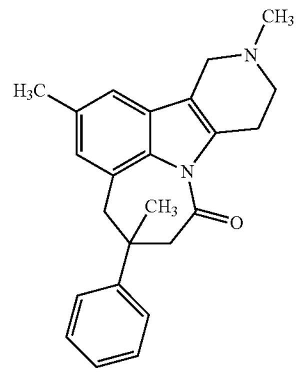 |
| B129 | 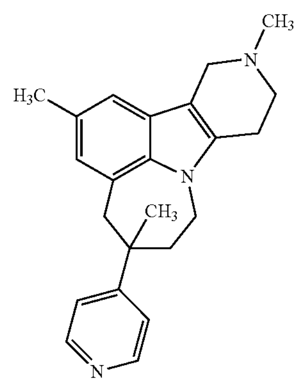 |
| B130 | 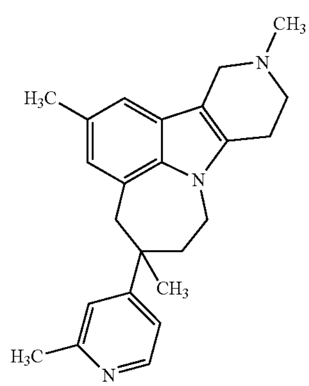 [SMILES: Cc1cc2c3c(c1)c1c(n3CCC(C)(c3ccnc(C)c3)C2)CCN(C)C1] |
| B131 | 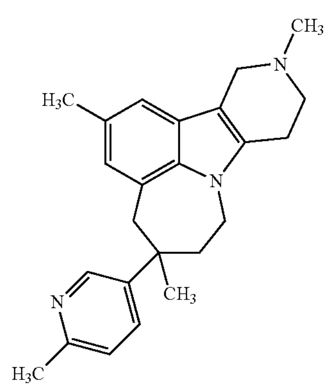 [SMILES: Cc1cc2c3c(c1)c1c(n3CCC(C)(c3ccc(C)nc3)C2)CCN(C)C1] |
| B132 | |
| B133 | |
| B134 | |
| B135 | |

TABLE 2-continued

Representative Compounds of the Invention

| Compound No. | Structure |
|---|---|
| B136 | 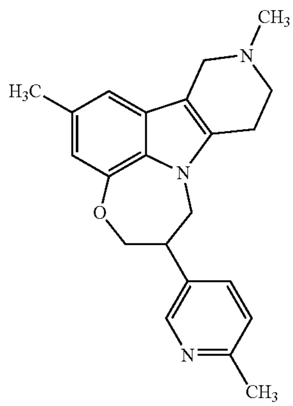 [SMILES: Cc1cc2c3c(c1)c1c(n3CC(c3ccc(C)nc3)CO2)CCN(C)C1] |
| B137 | 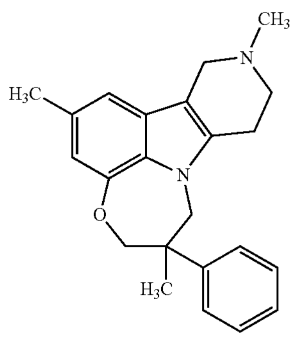 [SMILES: Cc1cc2c3c(c1)c1c(n3CC(C)(c3ccccc3)CO2)CCN(C)C1] |
| B138 | 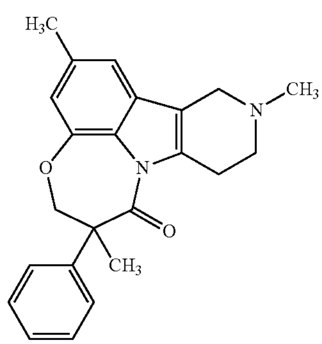 [SMILES: Cc1cc2c3c(c1)c1c(n3C(=O)C(C)(c3ccccc3)CO2)CCN(C)C1] |
| B139 | 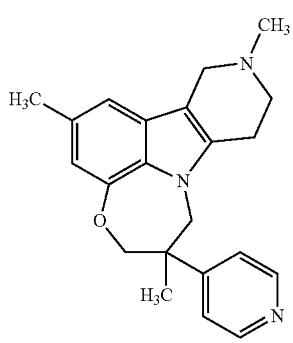 [SMILES: Cc1cc2c3c(c1)c1c(n3CC(C)(c3ccncc3)CO2)CCN(C)C1] |
| B140 | 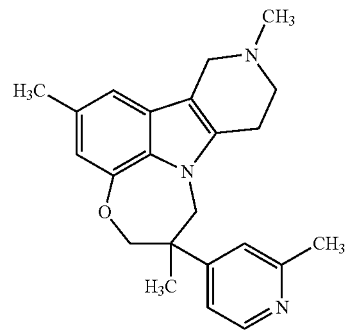 |
| B141 | 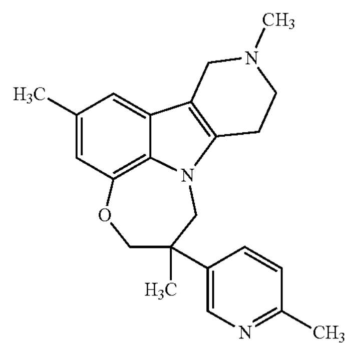 |
| B142 | 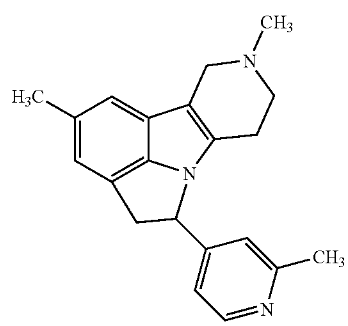 |
| B143 | 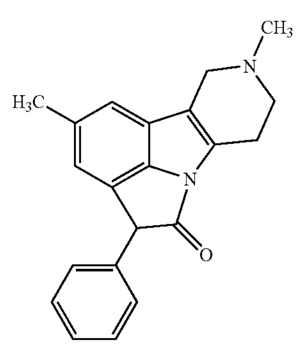 [SMILES: Cc1cc2c3c(c1)c1c(n3C(=O)C2c2ccccc2)CCN(C)C1] |

TABLE 2-continued
Representative Compounds of the Invention
| Compound No. | Structure |
|---|---|
| B144 | 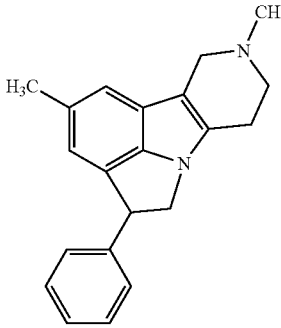 |
| B145 | 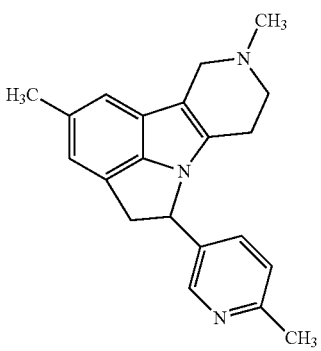 |
| B146 | 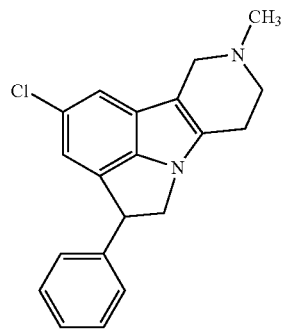 [SMILES: CN1CCc2c(c3cc(Cl)cc4c3n2CC4c2ccccc2)C1] |
| B147 | 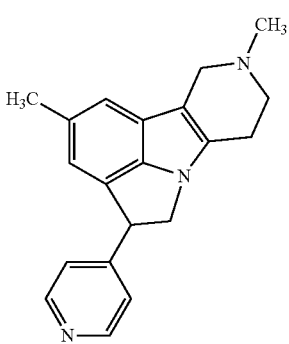 [SMILES: Cc1cc2c3c(c1)c1c(n3CC2c2ccncc2)CCN(C)C1] |
| B148 | 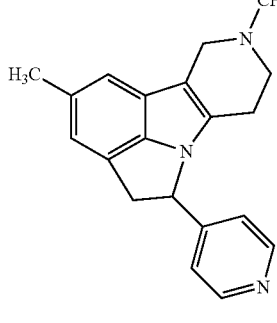 |
| B149 | 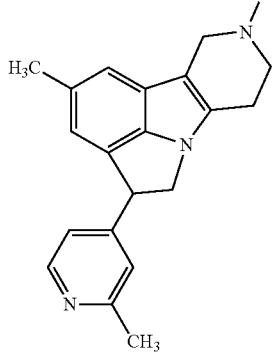 |
| B150 | 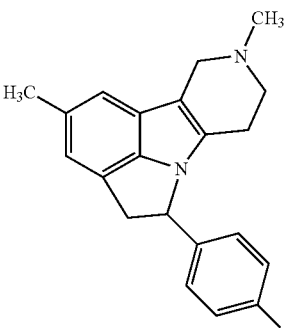 |
| B151 | 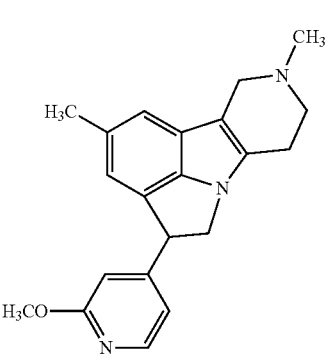 [SMILES: COc1cc(C2Cn3c4c(c5cc(C)cc2c53)CN(C)CC4)ccn1] |

TABLE 2-continued
Representative Compounds of the Invention
| Compound No. | Structure |
|---|---|
| B152 | 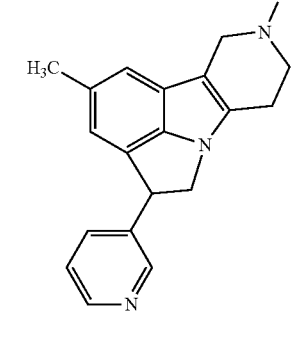 |
| B153 | 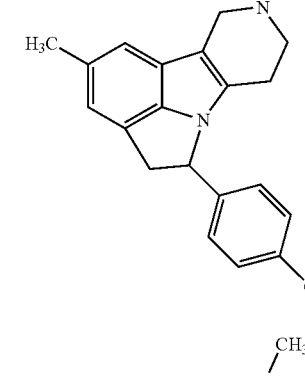 |
| B154 | 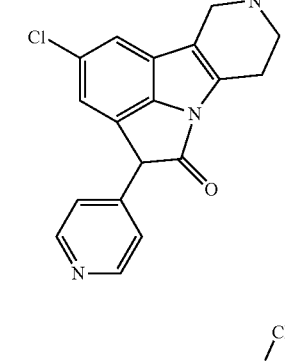 |
| B155 | 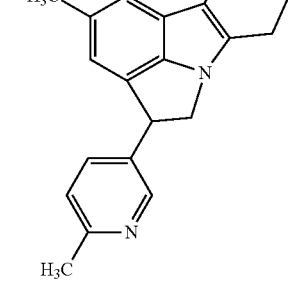 |
| B156 | 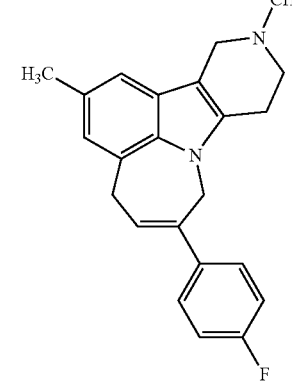 |
| B157 | 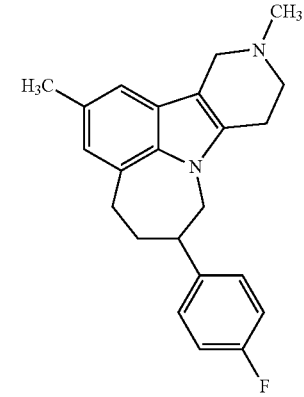 [SMILES: Cc1cc2c3c(c1)c1c(n3CC(c3ccc(F)cc3)CC2)CCN(C)C1] |
| B158 | 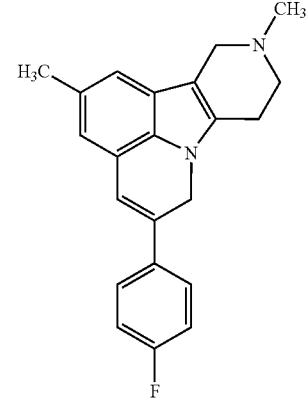 |

TABLE 2-continued
Representative Compounds of the Invention
| Compound No. | Structure |
|---|---|
| B159 | 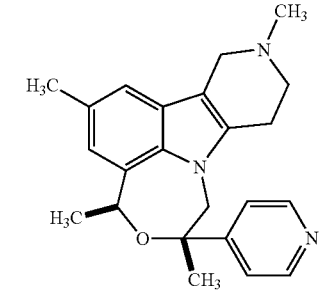 |
| B160 | 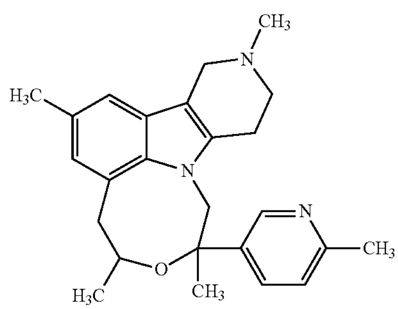 |
| B161 | 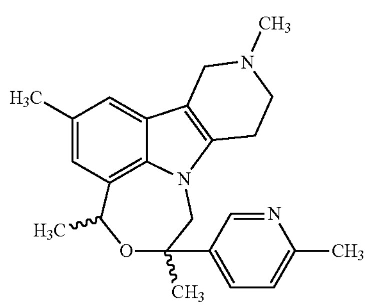 |
| B162 | 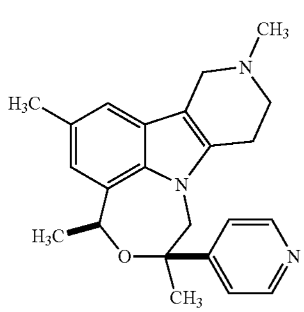 [SMILES: Cc1cc2c3c(c1)c1c(n3C[C@@](C)(c3ccncc3)O[C@H]2C)CCN(C)C1] |
TABLE 2-continued
Representative Compounds of the Invention
| Compound No. | Structure |
|---|---|
| B163 | 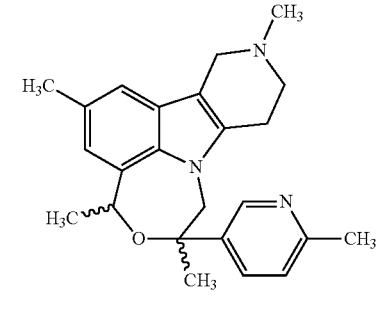 |
| B164 | 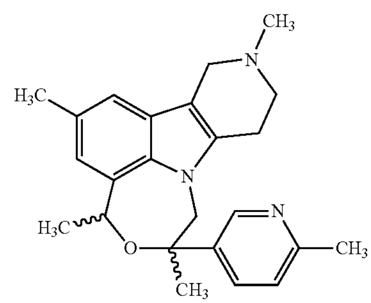 |
| B165 | 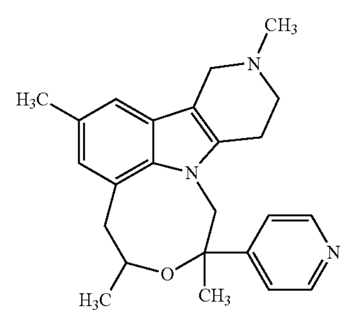 [SMILES: Cc1cc2c3c(c1)c1c(n3CC(C)(c3ccncc3)OC(C)C2)CCN(C)C1] |
| B166 | 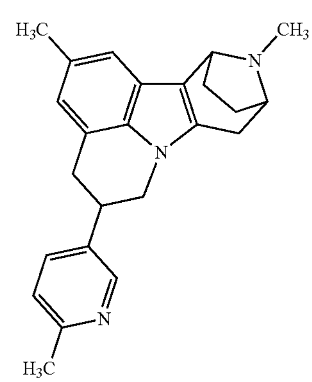 [SMILES: Cc1cc2c3c(c1)c1c(n3CC(c3ccc(C)nc3)C2)CC2CCC1N2C] |

TABLE 2-continued
Representative Compounds of the Invention
| Compound No. | Structure |
|---|---|
| B167 | 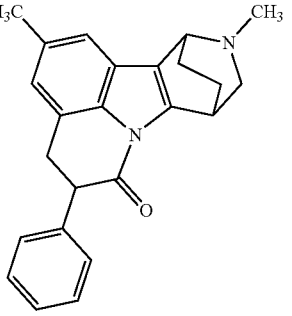 |
| B168 | 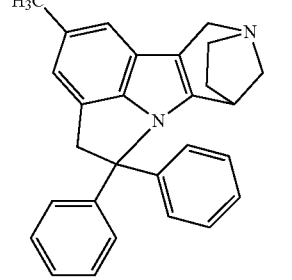 |
| B169 | 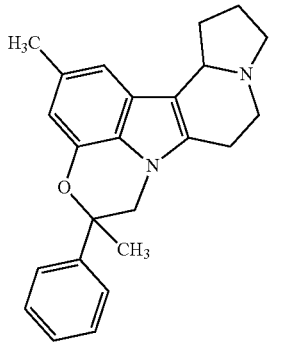 [SMILES: Cc1cc2c3c(c1)c1c(n3CC(C)(c3ccccc3)O2)CCN2CCCC12] |
| B170 | 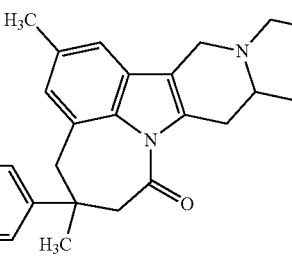 |
| B171 | 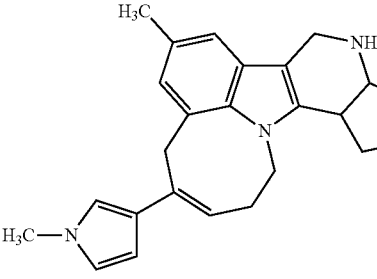 |
| B172 | 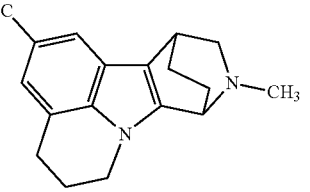 |
| B173 | 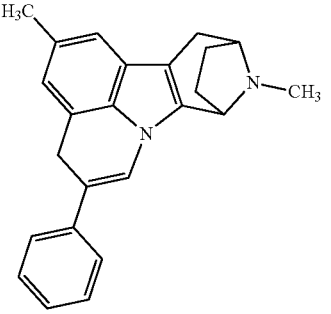 [SMILES: Cc1cc2c3c(c1)c1c(n3C=C(c3ccccc3)C2)C2CCC(C1)N2C] |
| B174 | 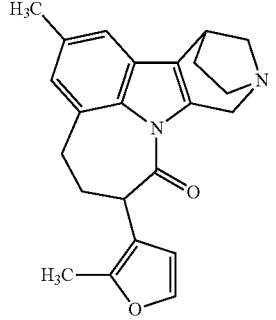 [SMILES: Cc1cc2c3c(c1)c1c(n3C(=O)C(c3ccoc3C)CC2)CN2CCC1C2] |
| B175 | 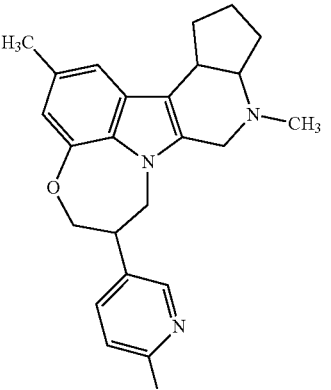 |

TABLE 2-continued

Representative Compounds of the Invention

| Compound No. | Structure |
|---|---|
| B176 | *(structure)* |
| B177 | *(structure)* |
| B178 | *(structure)* |
| B179 | *(structure)* |
| B180 | *(structure)* |
| B181 | *(structure)* |
| B182 | *(structure)* |
| B183 | *(structure)* |

TABLE 2-continued

Representative Compounds of the Invention

| Compound No. | Structure |
|---|---|
| B184 | (structure) |
| B185 | (structure) |
| B186 | (structure) |
| B187 | (structure) |
| B188 | (structure) |
| B189 | (structure) |
| B190 | (structure) |

TABLE 2-continued

Representative Compounds of the Invention

| Compound No. | Structure |
|---|---|
| B191 | (structure) |
| B192 | (structure) |
| B193 | (structure) |
| B194 | (structure) |
| B195 | (structure) |
| B196 | (structure) |
| B197 | (structure) |

TABLE 2-continued
Representative Compounds of the Invention
| Compound No. | Structure |
|---|---|
| B198 | 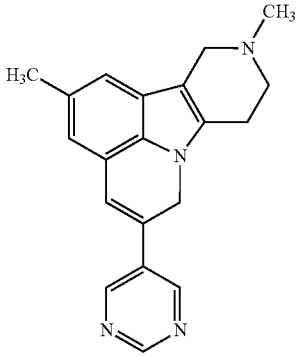 |
| B199 | 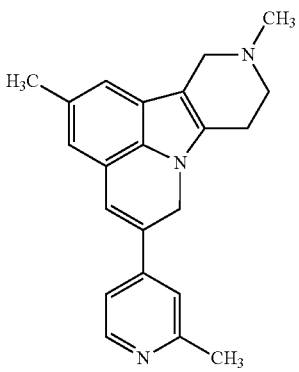 |
| B200 | 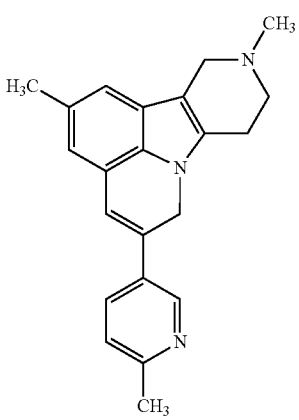 |
| B201 | 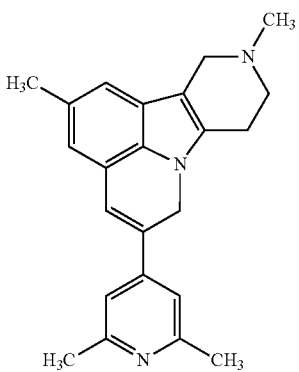 |
| B202 | 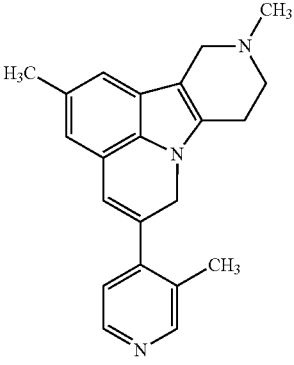 |
| B203 | 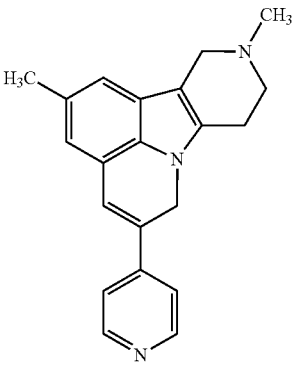 |
| B204 | 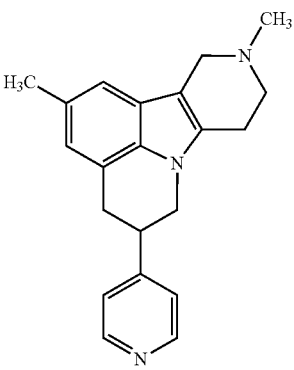 |
| B205 | 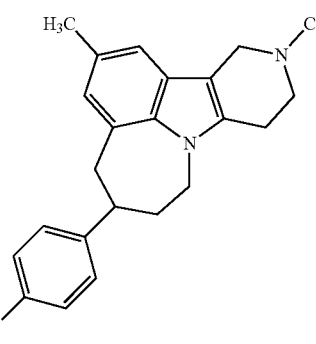 |

TABLE 2-continued
Representative Compounds of the Invention
| Compound No. | Structure |
|---|---|
| B206 | 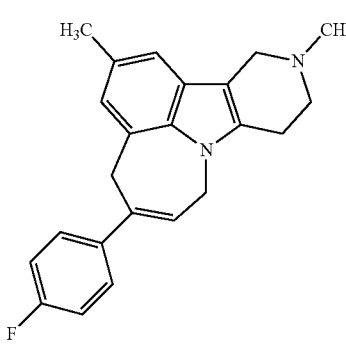 |
| B207 | 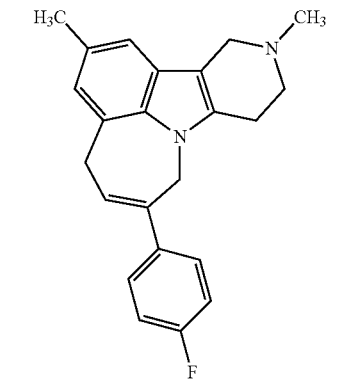 |
| B208 | 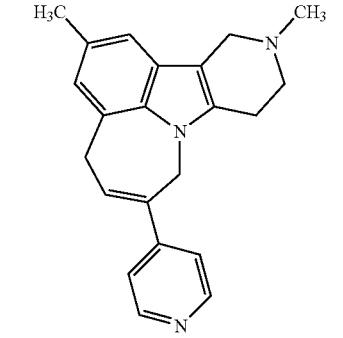 |
| B209 | 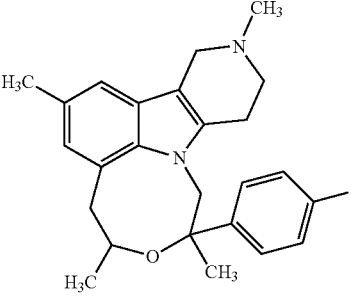 |
| B210 | 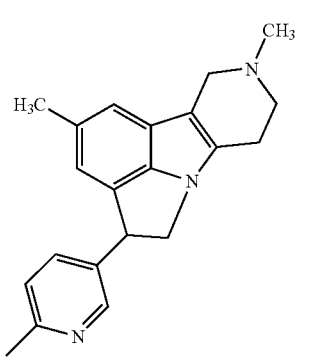 [SMILES: Cc1cc2c3c(c1)c1c(n3CC2c2ccc(C)nc2)CCN(C)C1] |
| B211 | 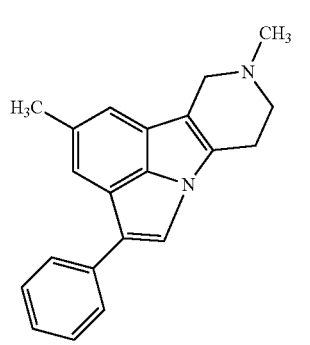 [SMILES: Cc1cc2c(-c3ccccc3)cn3c4c(c(c1)c23)CN(C)CC4] |
| B212 | 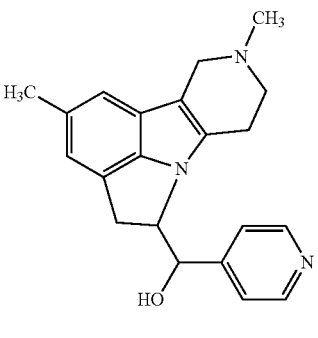 [SMILES: Cc1cc2c3c(c1)c1c(n3C(C(O)c3ccncc3)C2)CCN(C)C1] |
| B213 | 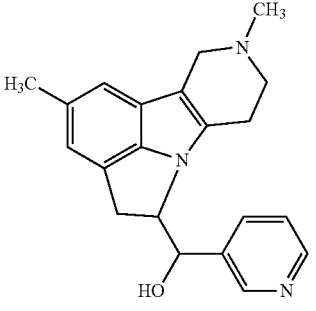 [SMILES: Cc1cc2c3c(c1)c1c(n3C(C(O)c3cccnc3)C2)CCN(C)C1] |

TABLE 2-continued

Representative Compounds of the Invention

| Compound No. | Structure |
|---|---|
| B214 | (structure) |
| B215 | (structure) |
| B216 | (structure) |
| B217 | (structure) |
| B218 | (structure) |
| B219 | (structure) |
| B220 | (structure) |
| B221 | (structure) |
| B222 | (structure) |

TABLE 2-continued
Representative Compounds of the Invention
| Compound No. | Structure |
|---|---|
| B223 | 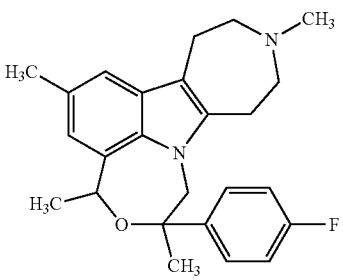 [SMILES: Cc1cc2c3c(c1)c1c(n3CC(C)(c3ccc(F)cc3)OC2C)CCN(C)CC1] |
| B224 | 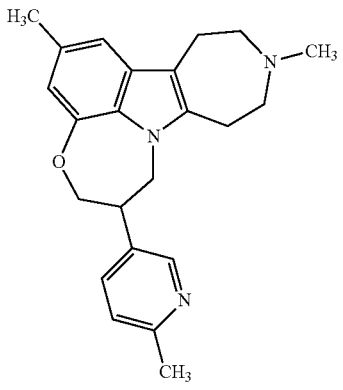 |
| B225 | 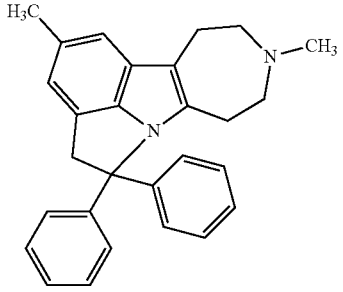 [SMILES: Cc1cc2c3c(c1)c1c(n3C(c3ccccc3)(c3ccccc3)C2)CCN(C)CC1] |
| B226 | 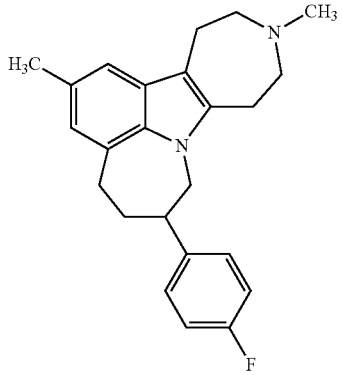 |
| B227 | 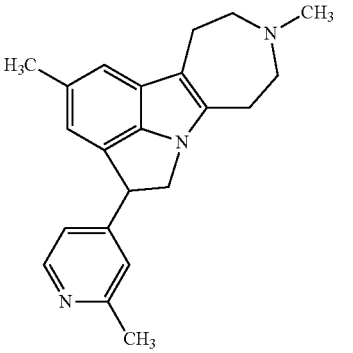 |
| B228 | 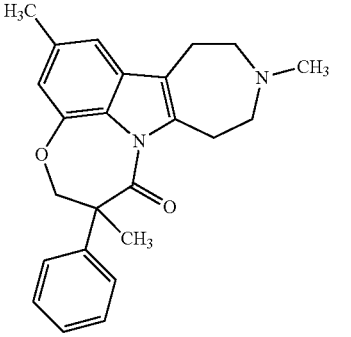 |
| B229 | 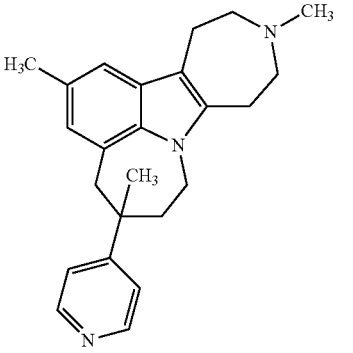 |
| B230 | 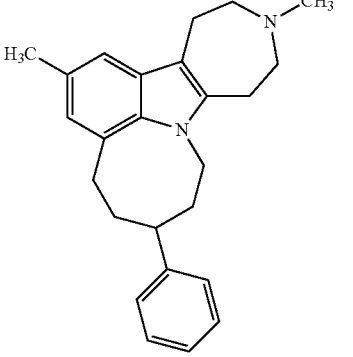 |

TABLE 2-continued
Representative Compounds of the Invention
| Compound No. | Structure |
|---|---|
| B231 | 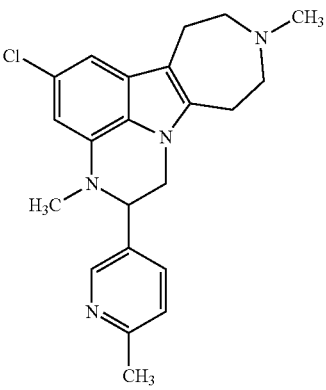 [SMILES: Cc1ccc(C2Cn3c4c(c5cc(Cl)cc(c53)N2C)CCN(C)CC4)cn1] |
| B232 | 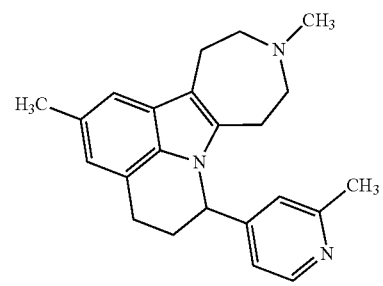 |
| B233 | 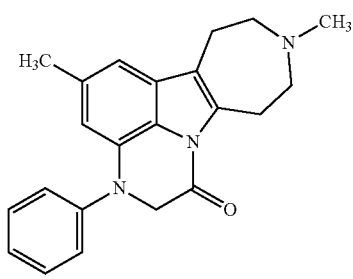 [SMILES: Cc1cc2c3c(c1)c1c(n3C(=O)CN2c2ccccc2)CCN(C)CC1] |
| B234 | 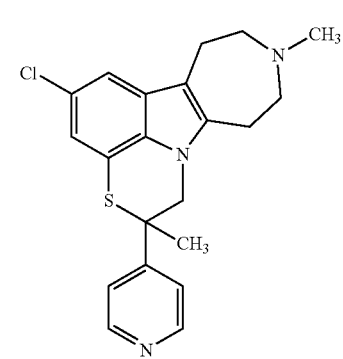 [SMILES: CN1CCc2c(n3c4c(cc(Cl)cc24)SC(C)(c2ccncc2)C3)CC1] |
| B235 | 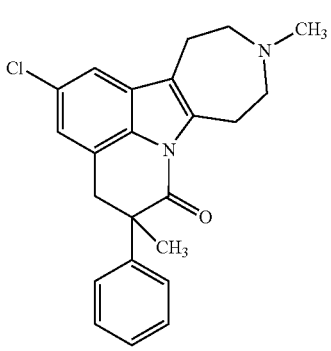 [SMILES: CN1CCc2c(n3c4c(cc(Cl)cc24)CC(C)(c2ccccc2)C3=O)CC1] |
| B236 | 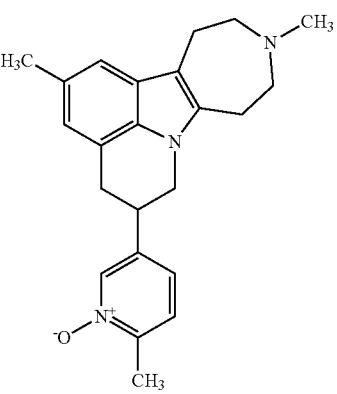 |
| B237 | 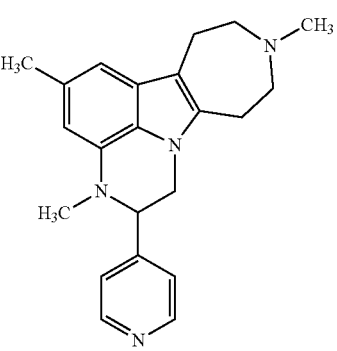 |
| B238 | 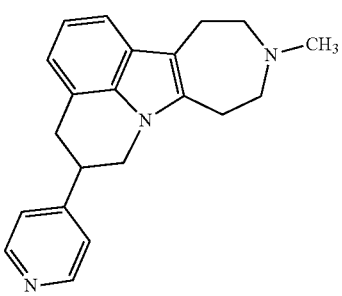 [SMILES: CN1CCc2c(n3c4c(cccc24)CC(c2ccncc2)C3)CC1] |

TABLE 2-continued
Representative Compounds of the Invention
| Compound No. | Structure |
|---|---|
| B239 | 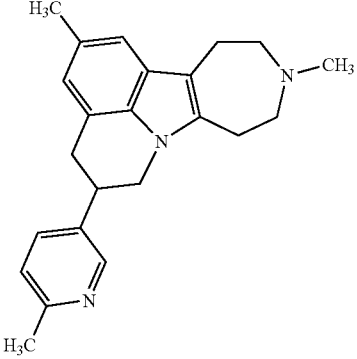 [SMILES: Cc1cc2c3c(c1)c1c(n3CC(c3ccc(C)nc3)C2)CCN(C)CC1] |
| B240 | 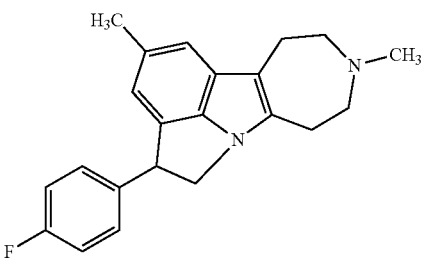 [SMILES: Cc1cc2c3c(c1)c1c(n3CC2c2ccc(F)cc2)CCN(C)CC1] |
| B241 | 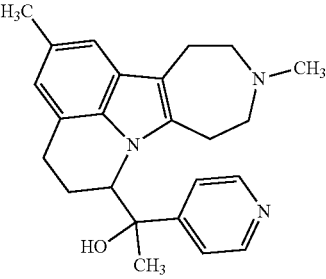 |
| B242 | 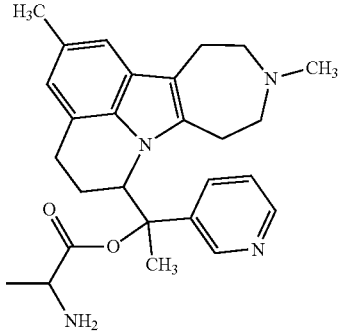 [SMILES: Cc1cc2c3c(c1)c1c(n3C(C(C)(OC(=O)C(C)N)c3cccnc3)CC2)CCN(C)CC1] |
TABLE 3
Representative Compounds of the Invention
| Compound No. | Structure |
|---|---|
| C1 | 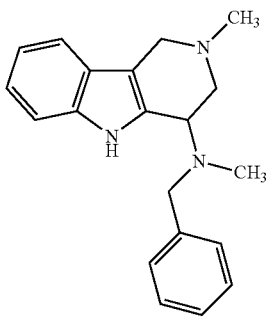 [SMILES: CN1Cc2c([nH]c3ccccc23)C(N(C)Cc2ccccc2)C1] |
| C2 | 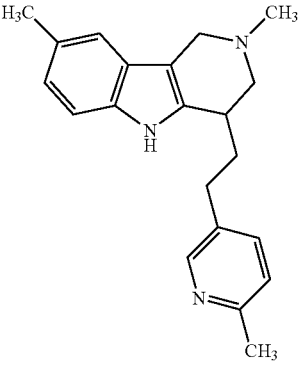 |
| C3 | 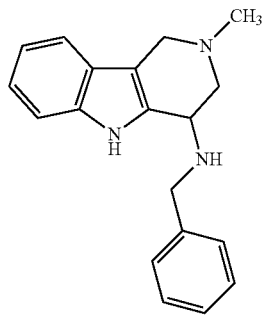 [SMILES: CN1Cc2c([nH]c3ccccc23)C(NCc2ccccc2)C1] |
| C4 | 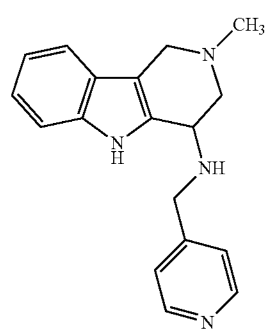 [SMILES: CN1Cc2c([nH]c3ccccc23)C(NCc2ccncc2)C1] |

TABLE 3-continued

Representative Compounds of the Invention

| Compound No. | Structure |
|---|---|
| C5 | (8-methyl-2-methyl-tetrahydro-β-carboline with 4-(pyridin-3-yl)ethynyl substituent, NH indole) |
| C6 | (8-methyl-2-methyl-tetrahydro-β-carboline with 4-((6-methylpyridin-3-yl)ethynyl) substituent, NH indole) |
| C7 | (8-methyl-2-methyl-5-methyl-tetrahydro-β-carboline with 4-(4-fluorophenyl) substituent) |
| C8 | (8-methyl-2-methyl-tetrahydro-β-carboline with 4-(thiophen-2-yl)ethynyl substituent, NH indole) |
| C9 | (8-methyl-2-methyl-5-methyl-tetrahydro-β-carboline with 4-(pyridin-4-yl) substituent) |
| C10 | (8-methyl-2-methyl-5-methyl-tetrahydro-β-carboline with 4-ethynyl substituent) |
| C11 | (8-methyl-2-methyl-5-methyl-tetrahydro-β-carboline with 4-(2-(pyridin-4-yl)prop-1-en-1-yl) substituent) |
| C12 | (8-methyl-2-methyl-5-methyl-tetrahydro-β-carboline with 4-((6-methylpyridin-3-yl)ethynyl) substituent) |

TABLE 3-continued

Representative Compounds of the Invention

| Compound No. | Structure |
|---|---|
| C13 | (structure) |
| C14 | (structure) |
| C15 | (structure) |
| C16 | (structure) |
| C17 | (structure) |
| C18 | (structure) |
| C19 | (structure) |
| C20 | (structure) |

TABLE 3-continued

Representative Compounds of the Invention

| Compound No. | Structure |
|---|---|
| C21 | (structure) |
| C22 | (structure) |
| C23 | (structure) |
| C24 | (structure) |
| C25 | (structure) |
| C26 | (structure) |
| C27 | (structure) |
| C28 | (structure) |
| C29 | (structure) |

TABLE 3-continued

Representative Compounds of the Invention

| Compound No. | Structure |
|---|---|
| C30 | (structure) |
| C31 | (structure) |
| C32 | (structure) |
| C33 | (structure) |
| C34 | (structure) |
| C35 | (structure) |
| C36 | (structure) |
| C37 | (structure) |
| C38 | (structure) |

TABLE 3-continued

Representative Compounds of the Invention

| Compound No. | Structure |
|---|---|
| C39 | (structure) |
| C40 | (structure) |
| C41 | (structure) |
| C42 | (structure) |
| C43 | (structure) |
| C44 | (structure) |
| C45 | (structure) |
| C46 | (structure) |
| C47 | (structure) |

TABLE 3-continued
Representative Compounds of the Invention
| Compound No. | Structure |
|---|---|
| C48 | 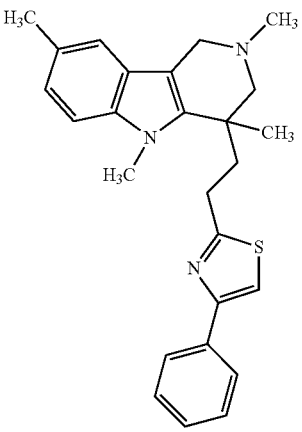 |
| C49 | 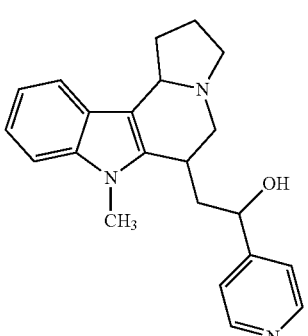 |
| C50 | 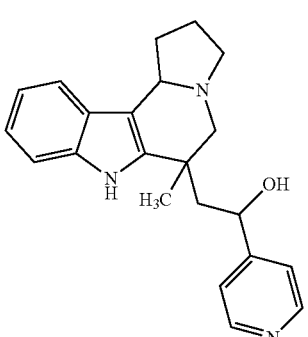 |
| C51 | 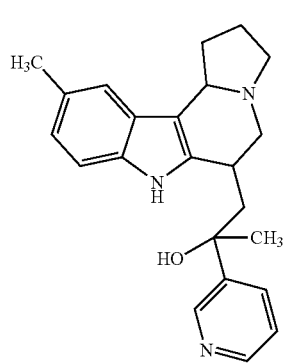 [SMILES: Cc1ccc2[nH]c3c(c2c1)C1CCCN1CC3CC(C)(O)c1cccnc1] |
| C52 | 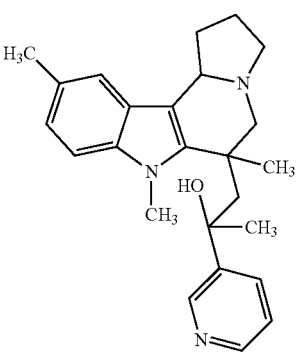 [SMILES: Cc1ccc2c(c1)c1c(n2C)C(C)(CC(C)(O)c2cccnc2)CN2CCCC12] |
| C53 | 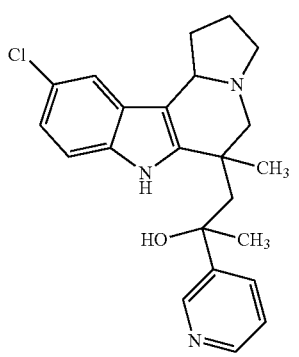 [SMILES: CC(O)(CC1(C)CN2CCCC2c2c1[nH]c1ccc(Cl)cc21)c1cccnc1] |
| C54 | 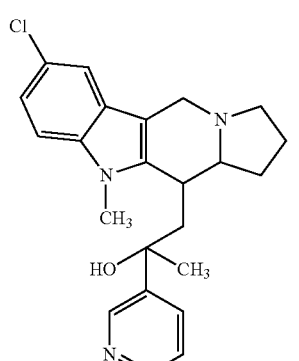 |
| C55 | 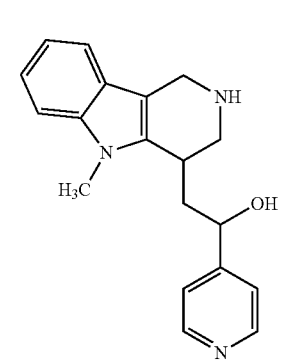 [SMILES: Cn1c2c(c3ccccc31)CNCC2CC(O)c1ccncc1] |

TABLE 3-continued
Representative Compounds of the Invention
| Compound No. | Structure |
|---|---|
| C56 | 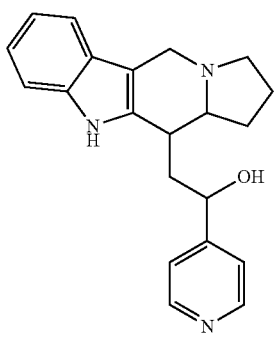 [SMILES: OC(CC1c2[nH]c3ccccc3c2CN2CCCC12)c1ccncc1] |
| C57 | 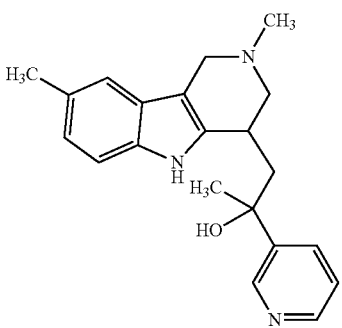 [SMILES: Cc1ccc2[nH]c3c(c2c1)CN(C)CC3CC(C)(O)c1cccnc1] |
| C58 | 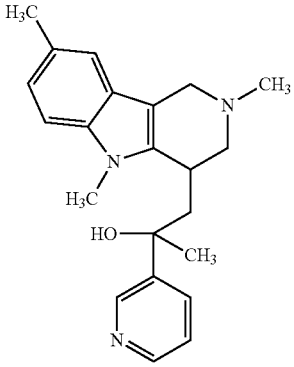 [SMILES: Cc1ccc2c(c1)c1c(n2C)C(CC(C)(O)c2cccnc2)CN(C)C1] |
| C59 | 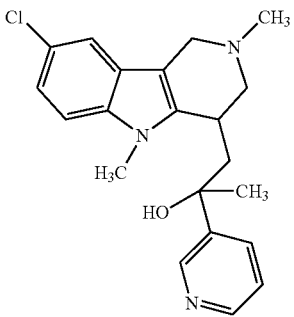 [SMILES: CN1Cc2c(n(C)c3ccc(Cl)cc23)C(CC(C)(O)c2cccnc2)C1] |
| C60 | 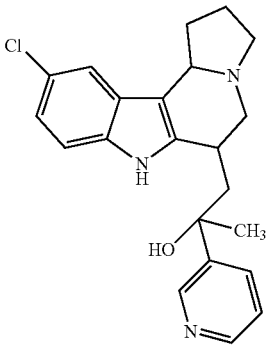 [SMILES: CC(O)(CC1CN2CCCC2c2c1[nH]c1ccc(Cl)cc21)c1cccnc1] |
| C61 | 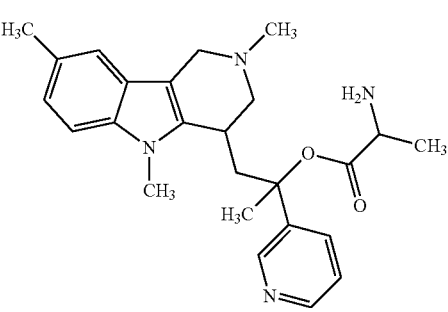 [SMILES: Cc1ccc2c(c1)c1c(n2C)C(CC(C)(OC(=O)C(C)N)c2cccnc2)CN(C)C1] |
| C62 | 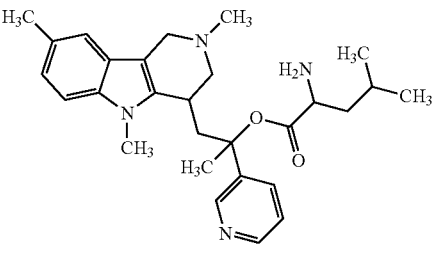 [SMILES: Cc1ccc2c(c1)c1c(n2C)C(CC(C)(OC(=O)C(N)CC(C)C)c2cccnc2)CN(C)C1] |
| C63 | 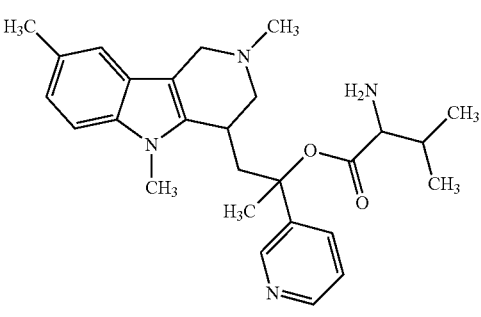 [SMILES: Cc1ccc2c(c1)c1c(n2C)C(CC(C)(OC(=O)C(N)C(C)C)c2cccnc2)CN(C)C1] |

TABLE 3-continued

Representative Compounds of the Invention

| Compound No. | Structure |
|---|---|
| C64 | (structure) |
| C65 | (structure) |
| C66 | (structure) |
| C67 | (structure) |
| C68 | (structure) |
| C69 | (structure) |
| C70 | (structure) |
| C71 | (structure) |
| C72 | (structure) |

TABLE 3-continued
Representative Compounds of the Invention
| Compound No. | Structure |
|---|---|
| C73 | 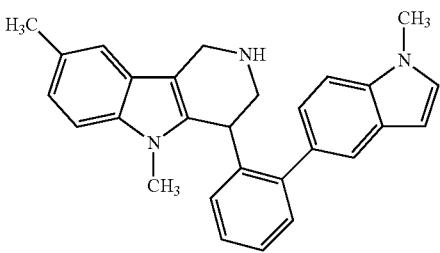 [SMILES: Cc1ccc2c(c1)c1c(n2C)C(c2ccccc2-c2ccc3c(ccn3C)c2)CNC1] |
| C74 | 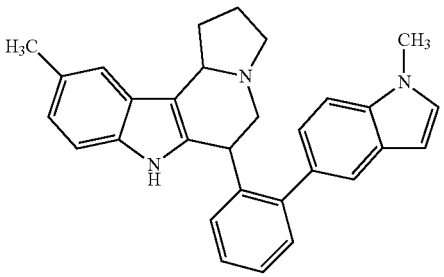 [SMILES: Cc1ccc2[nH]c3c(c2c1)C1CCCN1CC3c1ccccc1-c1ccc2c(ccn2C)c1] |
| C75 | 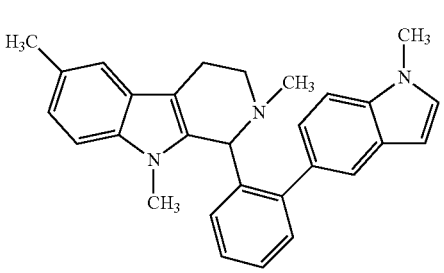 [SMILES: Cc1ccc2c(c1)c1c(n2C)C(c2ccccc2-c2ccc3c(ccn3C)c2)N(C)CC1] |
| C76 | 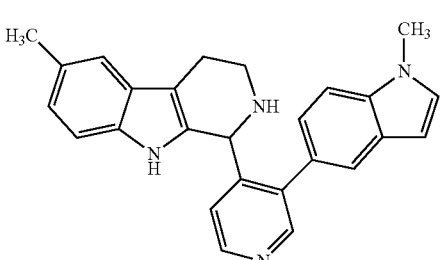 |
| C77 | 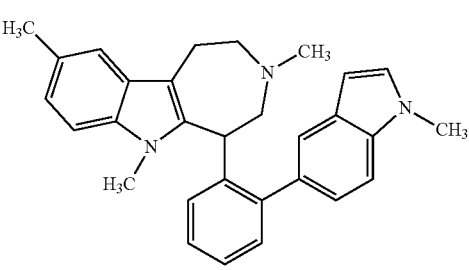 |
| C78 | 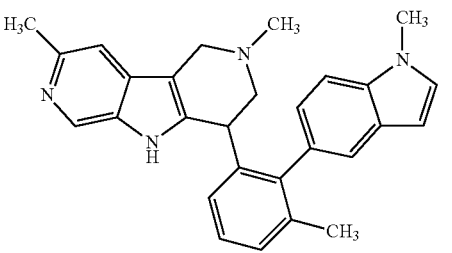 [SMILES: Cc1cc2c3c([nH]c2cn1)C(c1cccc(C)c1-c1ccc2c(ccn2C)c1)CN(C)C3] |
| C79 | 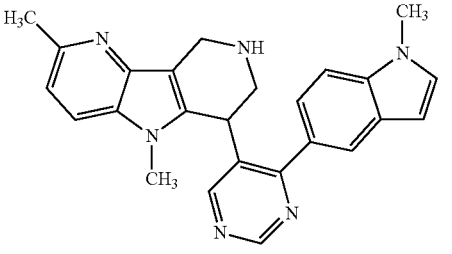 [SMILES: Cc1ccc2c(n1)c1c(n2C)C(c2cncnc2-c2ccc3c(ccn3C)c2)CNC1] |
| C80 | 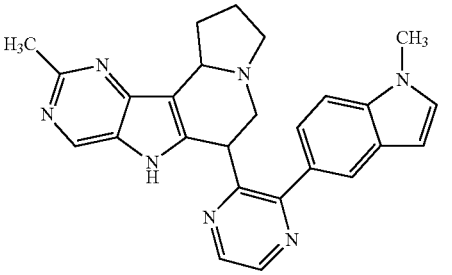 [SMILES: Cc1ncc2[nH]c3c(c2n1)C1CCCN1CC3c1nccnc1-c1ccc2c(ccn2C)c1] |
| C81 | 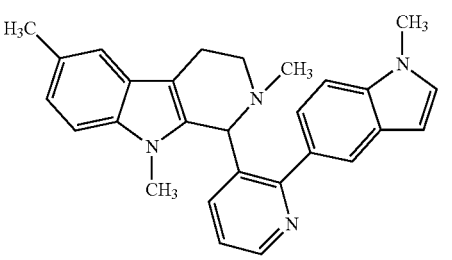 [SMILES: Cc1ccc2c(c1)c1c(n2C)C(c2cccnc2-c2ccc3c(ccn3C)c2)N(C)CC1] |
| C82 | 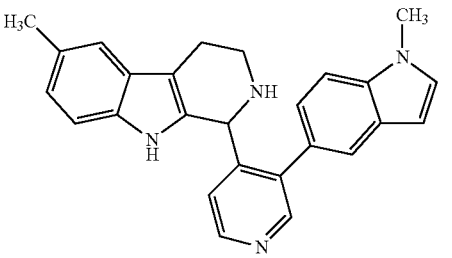 [SMILES: Cc1ccc2[nH]c3c(c2c1)CCNC3c1ccncc1-c1ccc2c(ccn2C)c1] |

TABLE 3-continued

Representative Compounds of the Invention

| Compound No. | Structure |
|---|---|
| C83 | 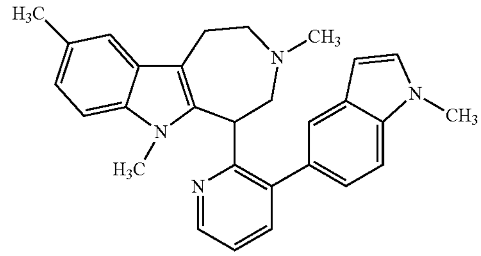 |
| C84 | 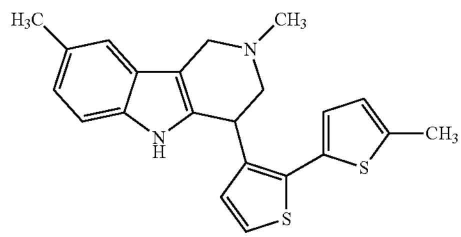 |
| C85 | 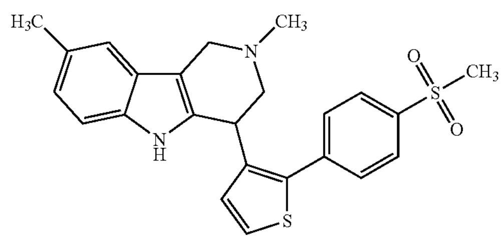 |
| C86 | 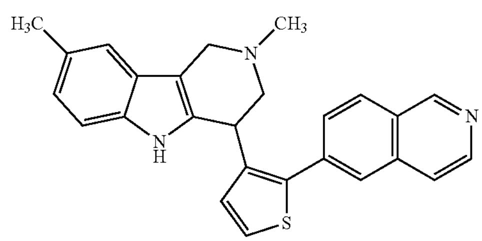 [SMILES: Cc1ccc2[nH]c3c(c2c1)CN(C)CC3c1ccsc1-c1ccc2cnccc2c1] |
| C87 | 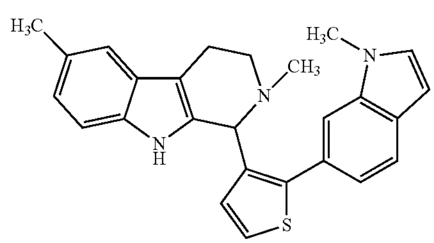 [SMILES: Cc1ccc2[nH]c3c(c2c1)CCN(C)C3c1ccsc1-c1ccc2ccn(C)c2c1] |
| C88 | 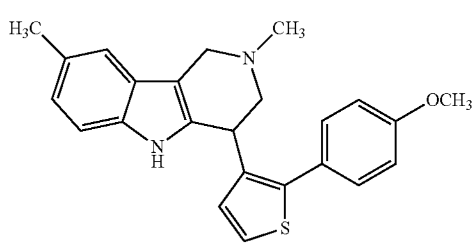 [SMILES: COc1ccc(-c2sccc2C2CN(C)Cc3c2[nH]c2ccc(C)cc32)cc1] |
| C89 | 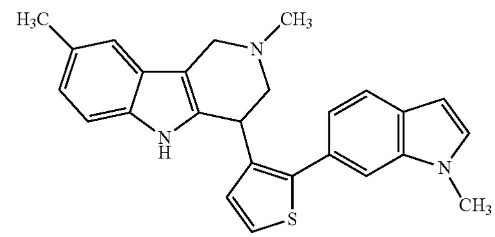 [SMILES: Cc1ccc2[nH]c3c(c2c1)CN(C)CC3c1ccsc1-c1ccc2ccn(C)c2c1] |
| C90 | 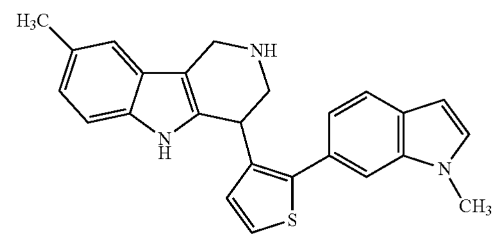 [SMILES: Cc1ccc2[nH]c3c(c2c1)CNCC3c1ccsc1-c1ccc2ccn(C)c2c1] |
| C91 | 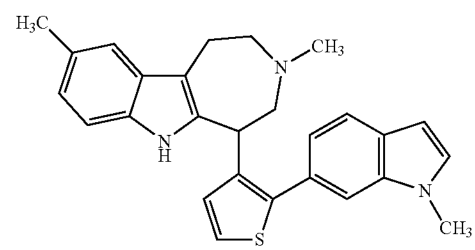 [SMILES: Cc1ccc2[nH]c3c(c2c1)CCN(C)CC3c1ccsc1-c1ccc2ccn(C)c2c1] |
| C92 | 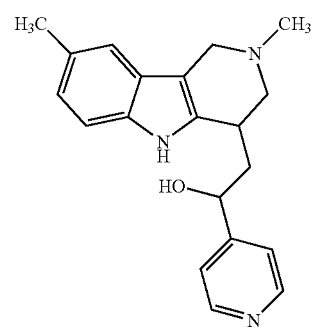 |
| C93 | 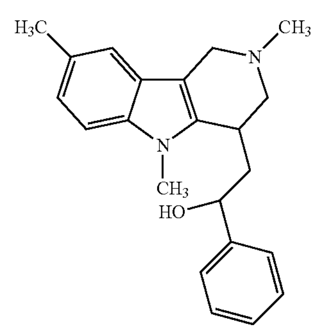 |

TABLE 3-continued

Representative Compounds of the Invention

| Compound No. | Structure |
|---|---|
| C94 | (structure) |
| C95 | (structure) |
| C96 | (structure) |
| C97 | (structure) |
| C98 | (structure) |
| C99 | (structure) |
| C100 | (structure) |
| C101 | (structure) |

TABLE 3-continued
Representative Compounds of the Invention
| Compound No. | Structure |
|---|---|
| C102 | 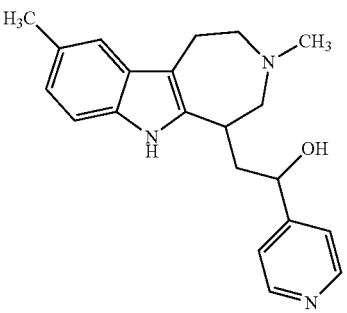 [SMILES: Cc1ccc2[nH]c3c(c2c1)CCN(C)CC3CC(O)c1ccncc1] |
| C103 | 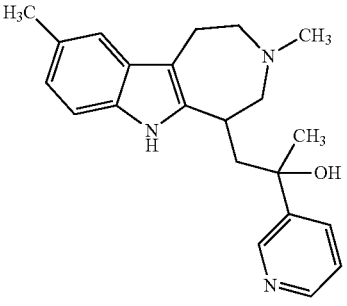 [SMILES: Cc1ccc2[nH]c3c(c2c1)CCN(C)CC3CC(C)(O)c1cccnc1] |
| C104 | 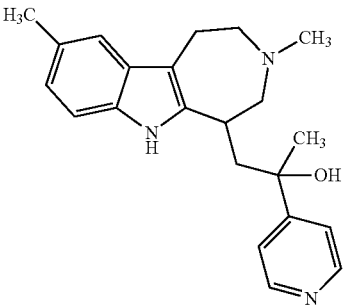 [SMILES: Cc1ccc2[nH]c3c(c2c1)CCN(C)CC3CC(C)(O)c1ccncc1] |
| C105 | 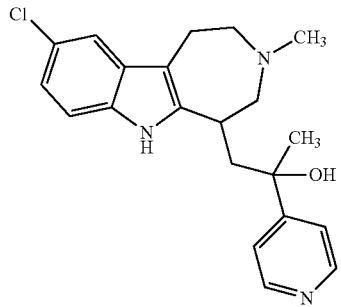 [SMILES: CN1CCc2c([nH]c3ccc(Cl)cc23)C(CC(C)(O)c2ccncc2)C1] |
| C106 | 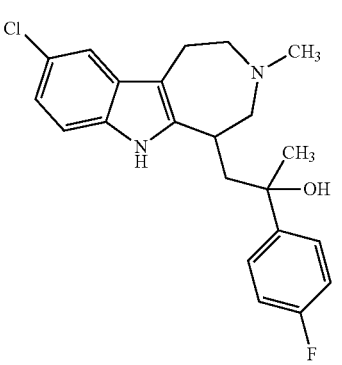 [SMILES: CN1CCc2c([nH]c3ccc(Cl)cc23)C(CC(C)(O)c2ccc(F)cc2)C1] |
| C107 | 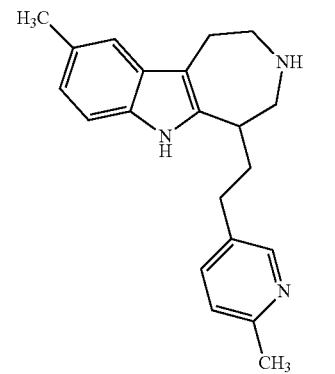 [SMILES: Cc1ccc2[nH]c3c(c2c1)CCNCC3CCc1ccc(C)nc1] |
| C108 | 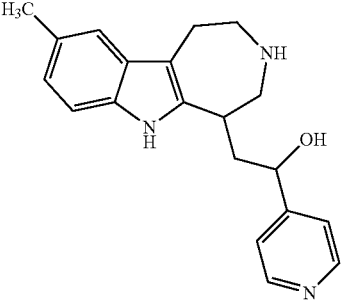 [SMILES: Cc1ccc2[nH]c3c(c2c1)CCNCC3CC(O)c1ccncc1] |
| C109 | 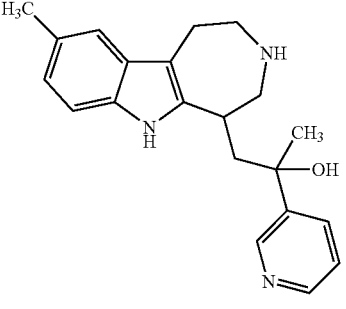 [SMILES: Cc1ccc2[nH]c3c(c2c1)CCNCC3CC(C)(O)c1cccnc1] |

TABLE 3-continued

Representative Compounds of the Invention

| Compound No. | Structure |
|---|---|
| C110 | (9-methyl-2,3,4,5-tetrahydro-1H-azepino[4,5-b]indole with CH2-C(CH3)(OH)-pyridin-4-yl substituent) |
| C111 | (9-chloro-2,3,4,5-tetrahydro-1H-azepino[4,5-b]indole with CH2-C(CH3)(OH)-pyridin-4-yl substituent) |
| C112 | (9-chloro-2,3,4,5-tetrahydro-1H-azepino[4,5-b]indole with CH2-C(CH3)(OH)-(4-fluorophenyl) substituent) |
| C113 | (9-methyl-N-methyl-5-methyl-2,3,4,5-tetrahydro-1H-azepino[4,5-b]indole with CH2CH2-(6-methylpyridin-3-yl) substituent) |
| C114 | (9-methyl-N-methyl-5-methyl-2,3,4,5-tetrahydro-1H-azepino[4,5-b]indole with CH2-CH(OH)-pyridin-4-yl substituent) |
| C115 | (9-methyl-N-methyl-5-methyl-2,3,4,5-tetrahydro-1H-azepino[4,5-b]indole with CH2-C(CH3)(OH)-pyridin-3-yl substituent) |
| C116 | (9-methyl-5-methyl-2,3,4,5-tetrahydro-1H-azepino[4,5-b]indole with CH2CH2-(6-methylpyridin-3-yl) substituent) |
| C117 | (9-methyl-5-methyl-2,3,4,5-tetrahydro-1H-azepino[4,5-b]indole with CH2-CH(OH)-pyridin-4-yl substituent) |

TABLE 3-continued
Representative Compounds of the Invention
| Compound No. | Structure |
|---|---|
| C118 | 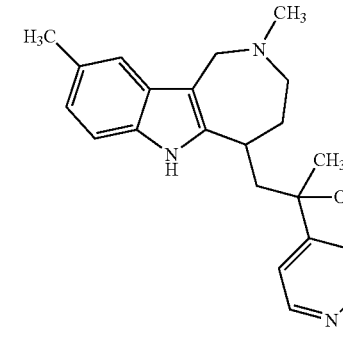 |
| C119 | 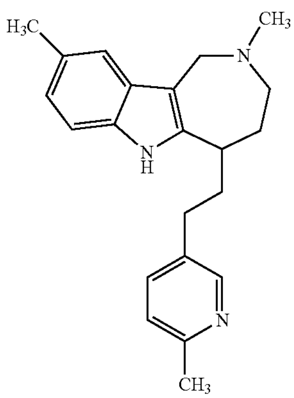 [SMILES: Cc1ccc2[nH]c3c(c2c1)CN(C)CCC3CCc1ccc(C)nc1] |
| C120 | 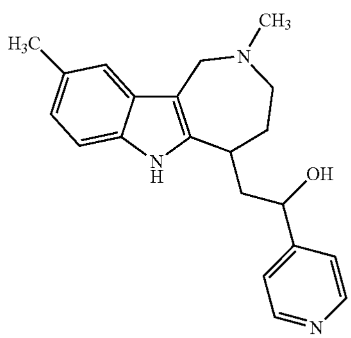 [SMILES: Cc1ccc2[nH]c3c(c2c1)CN(C)CCC3CC(O)c1ccncc1] |
| C121 | 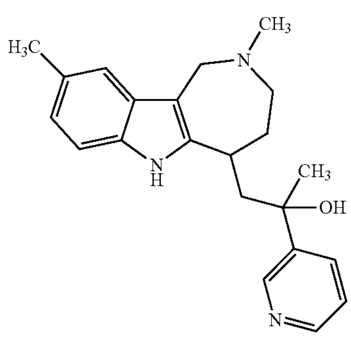 [SMILES: Cc1ccc2[nH]c3c(c2c1)CN(C)CCC3CC(C)(O)c1cccnc1] |
| C122 | 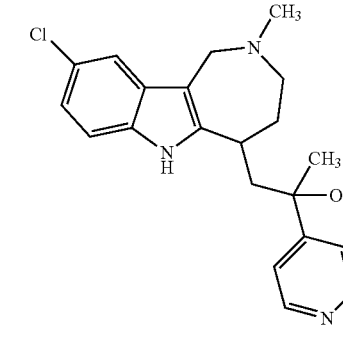 |
| C123 | |
| C124 | |
| C125 | |

TABLE 3-continued
Representative Compounds of the Invention
| Compound No. | Structure |
|---|---|
| C126 | 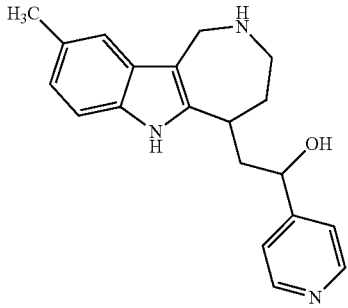 [SMILES: Cc1ccc2[nH]c3c(c2c1)CNCCC3CC(O)c1ccncc1] |
| C127 | 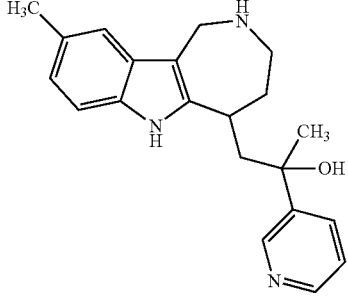 [SMILES: Cc1ccc2[nH]c3c(c2c1)CNCCC3CC(C)(O)c1cccnc1] |
| C128 | 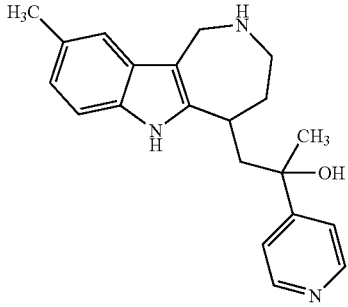 [SMILES: Cc1ccc2[nH]c3c(c2c1)CNCCC3CC(C)(O)c1ccncc1] |
| C129 | 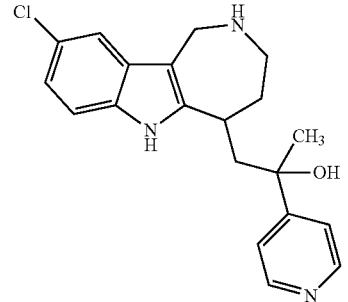 [SMILES: CC(O)(CC1CCNCc2c1[nH]c1ccc(Cl)cc21)c1ccncc1] |
| C130 | 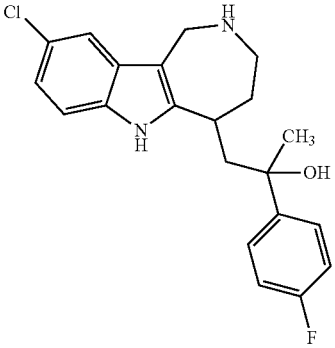 [SMILES: CC(O)(CC1CCNCc2c1[nH]c1ccc(Cl)cc21)c1ccc(F)cc1] |
| C131 | 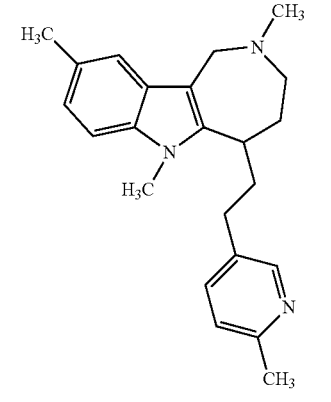 [SMILES: Cc1ccc2c(c1)c1c(n2C)C(CCc2ccc(C)nc2)CCN(C)C1] |
| C132 | 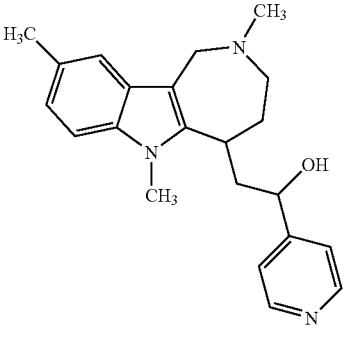 [SMILES: Cc1ccc2c(c1)c1c(n2C)C(CC(O)c2ccncc2)CCN(C)C1] |
| C133 | 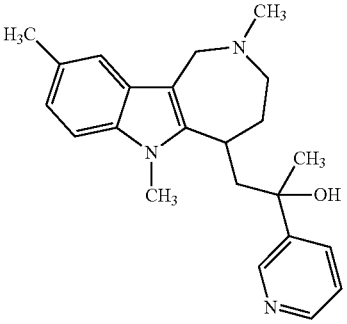 [SMILES: Cc1ccc2c(c1)c1c(n2C)C(CC(C)(O)c2cccnc2)CCN(C)C1] |

TABLE 3-continued

Representative Compounds of the Invention

| Compound No. | Structure |
|---|---|
| C134 | 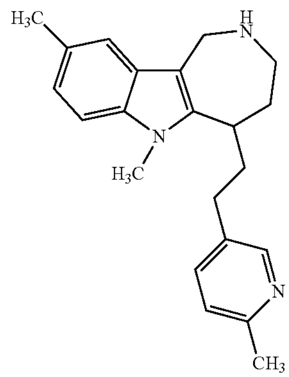 [SMILES: Cc1ccc2c(c1)c1c(n2C)C(CCc2ccc(C)nc2)CCNC1] |
| C135 | 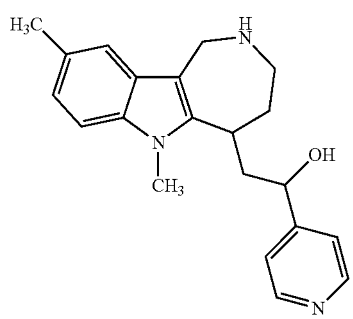 [SMILES: Cc1ccc2c(c1)c1c(n2C)C(CC(O)c2ccncc2)CCNC1] |
| C136 | 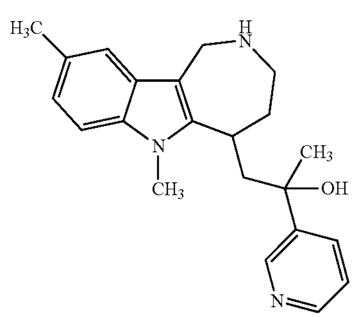 [SMILES: Cc1ccc2c(c1)c1c(n2C)C(CC(C)(O)c2cccnc2)CCNC1] |

TABLE 4

Representative Compounds of the Invention

| Compound No. | Structure |
|---|---|
| D1 | 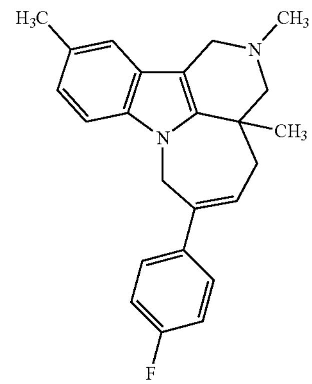 |
| D2 | 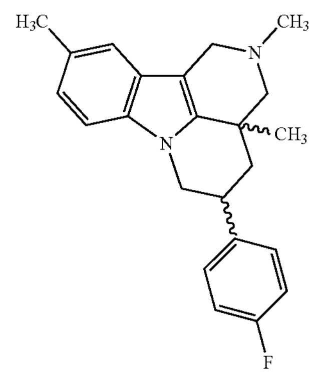 [SMILES: Cc1ccc2c(c1)c1c3n2CC(c2ccc(F)cc2)CC3(C)CN(C)C1] |
| D3 | 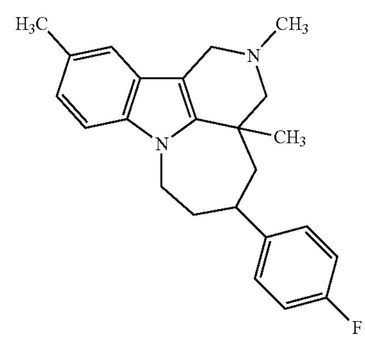 [SMILES: Cc1ccc2c(c1)c1c3n2CCC(c2ccc(F)cc2)CC3(C)CN(C)C1] |
| D4 | 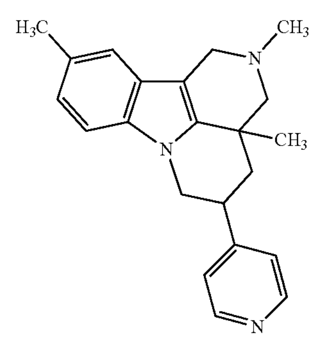 [SMILES: Cc1ccc2c(c1)c1c3n2CC(c2ccncc2)CC3(C)CN(C)C1] |

TABLE 4-continued
Representative Compounds of the Invention
| Compound No. | Structure |
|---|---|
| D5 | 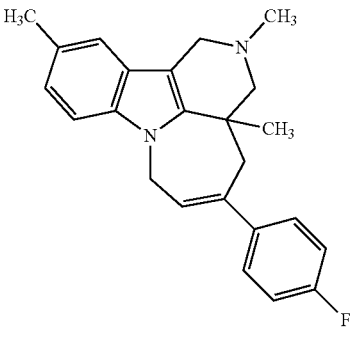 [SMILES: Cc1ccc2c(c1)c1c3n2CC=C(c2ccc(F)cc2)CC3(C)CN(C)C1] |
| D6 | 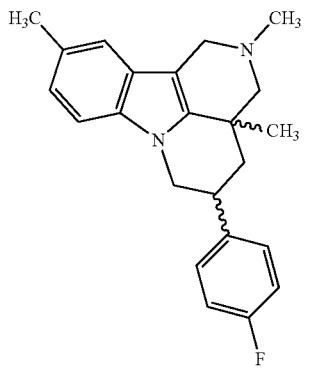 [SMILES: Cc1ccc2c(c1)c1c3n2CC(c2ccc(F)cc2)CC3(C)CN(C)C1] |
| D7 | 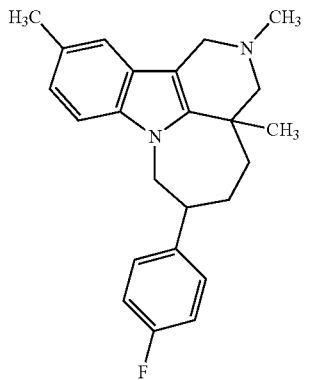 |
| D8 | 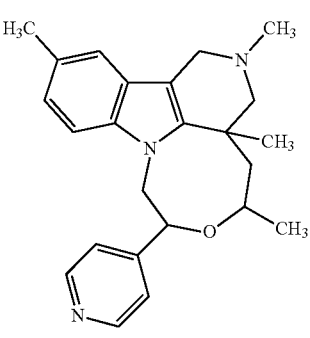 |
| D9 | 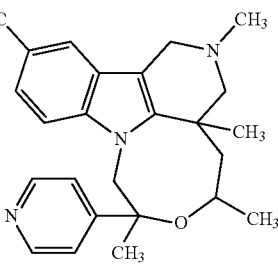 |
| D10 | 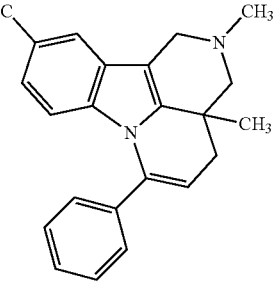 |
| D11 | 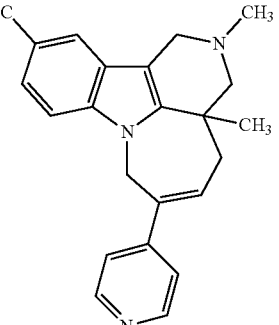 |
| D12 | 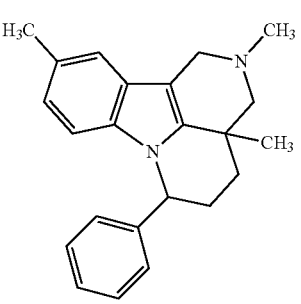 |
| D13 | 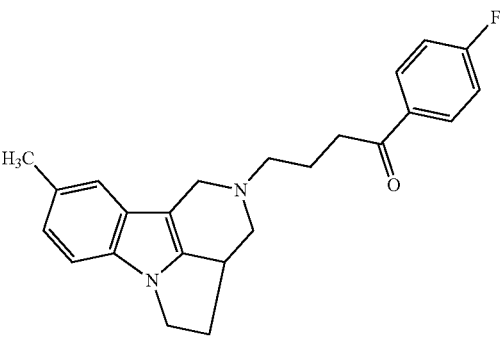 [SMILES: Cc1ccc2c(c1)c1c3n2CCC3CN(CCCC(=O)c2ccc(F)cc2)C1] |

TABLE 4-continued
Representative Compounds of the Invention
| Compound No. | Structure |
|---|---|
| D14 | 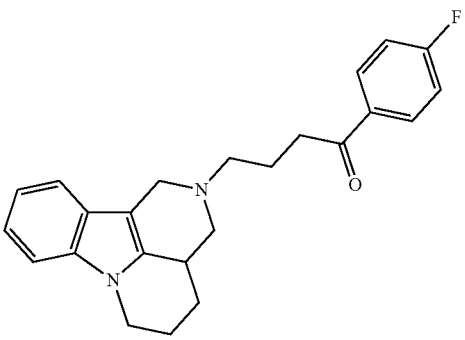 [SMILES: O=C(CCCN1Cc2c3n(c4ccccc24)CCCC3C1)c1ccc(F)cc1] |
| D15 | 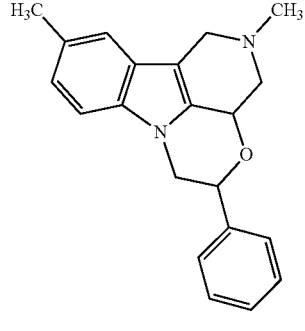 [SMILES: Cc1ccc2c(c1)c1c3n2CC(c2ccccc2)OC3CN(C)C1] |
| D16 | 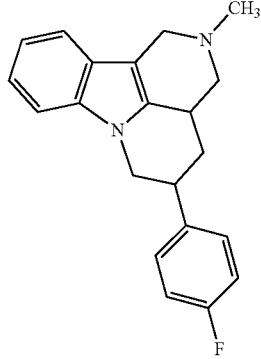 [SMILES: CN1Cc2c3n(c4ccccc24)CC(c2ccc(F)cc2)CC3C1] |
| D17 | 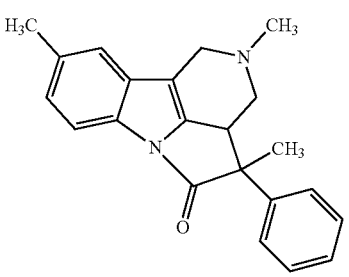 [SMILES: Cc1ccc2c(c1)c1c3n2C(=O)C(C)(c2ccccc2)C3CN(C)C1] |
| D18 | 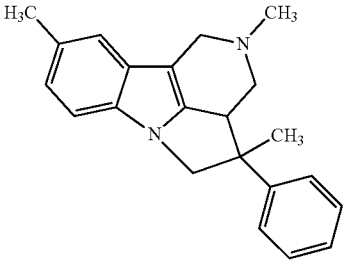 [SMILES: Cc1ccc2c(c1)c1c3n2CC(C)(c2ccccc2)C3CN(C)C1] |
| D19 | 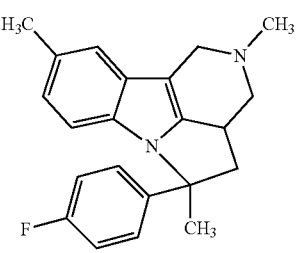 [SMILES: Cc1ccc2c(c1)c1c3n2C(C)(c2ccc(F)cc2)CC3CN(C)C1] |
| D20 | 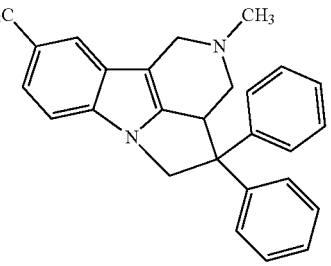 |
| D21 | 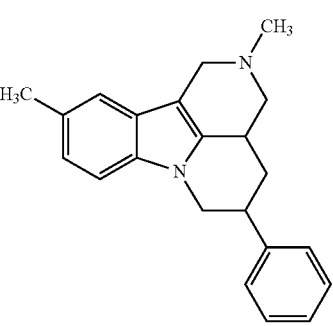 [SMILES: Cc1ccc2c(c1)c1c3n2CC(c2ccccc2)CC3CN(C)C1] |
| D22 | 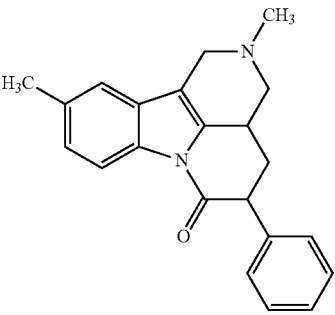 [SMILES: Cc1ccc2c(c1)c1c3n2C(=O)C(c2ccccc2)CC3CN(C)C1] |

TABLE 4-continued

Representative Compounds of the Invention

| Compound No. | Structure |
|---|---|
| D23 | |
| D24 | |
| D25 | |
| D26 | |
| D27 | 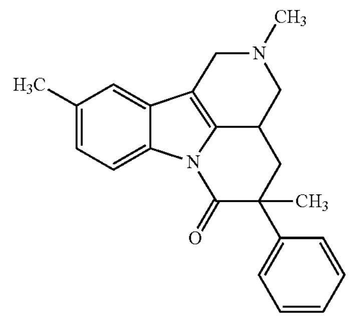 [SMILES: Cc1ccc2c(c1)c1c3n2C(=O)C(C)(c2ccccc2)CC3CN(C)C1] |
| D28 | 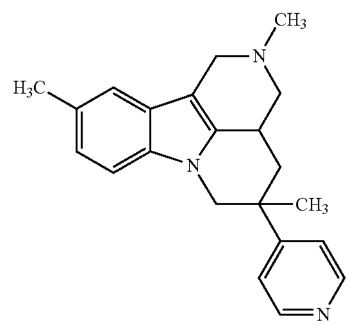 [SMILES: Cc1ccc2c(c1)c1c3n2CC(C)(c2ccncc2)CC3CN(C)C1] |
| D29 | 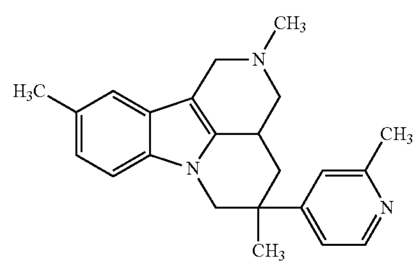 |
| D30 | 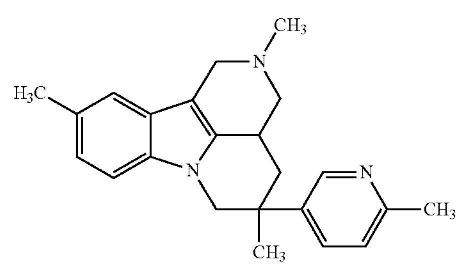 |
| D31 | 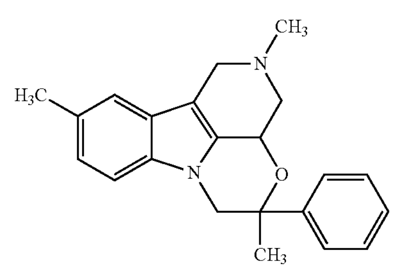 [SMILES: Cc1ccc2c(c1)c1c3n2CC(C)(c2ccccc2)OC3CN(C)C1] |

TABLE 4-continued

Representative Compounds of the Invention

| Compound No. | Structure |
|---|---|
| D32 | (structure) |
| D33 | (structure) |
| D34 | (structure) |
| D35 | (structure) |
| D36 | (structure) |
| D37 | (structure) |
| D38 | (structure) |
| D39 | (structure) |
| D40 | (structure) |
| D41 | (structure) |

TABLE 4-continued
Representative Compounds of the Invention
| Compound No. | Structure |
|---|---|
| D42 | 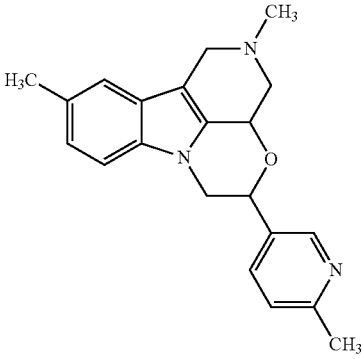 |
| D43 | 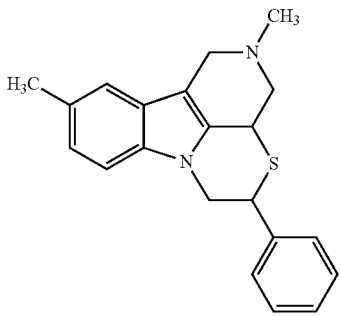 [SMILES: Cc1ccc2c(c1)c1c3n2CC(c2ccccc2)SC3CN(C)C1] |
| D44 | 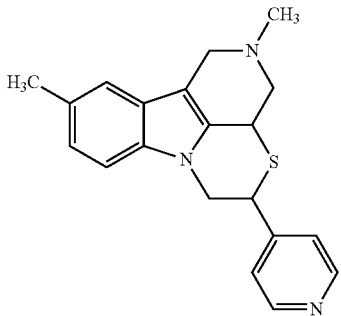 [SMILES: Cc1ccc2c(c1)c1c3n2CC(c2ccncc2)SC3CN(C)C1] |
| D45 | 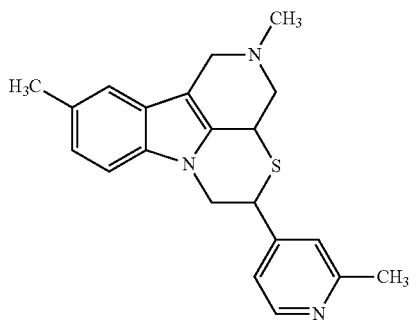 |
| D46 | 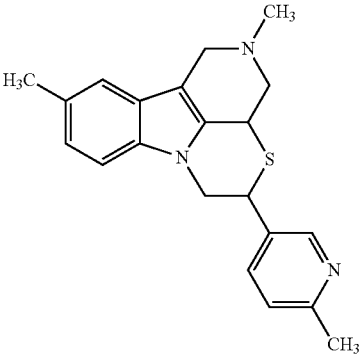 |
| D47 | 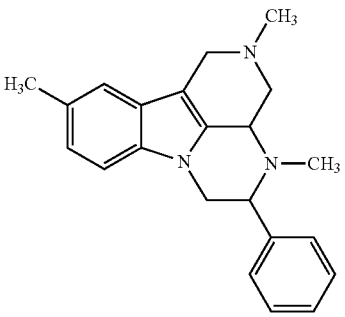 [SMILES: Cc1ccc2c(c1)c1c3n2CC(c2ccccc2)N(C)C3CN(C)C1] |
| D48 | 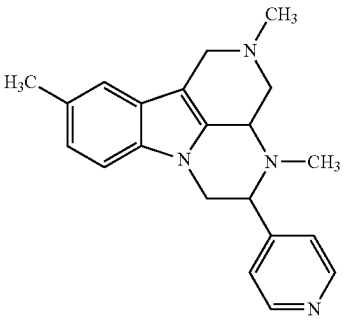 [SMILES: Cc1ccc2c(c1)c1c3n2CC(c2ccncc2)N(C)C3CN(C)C1] |
| D49 | 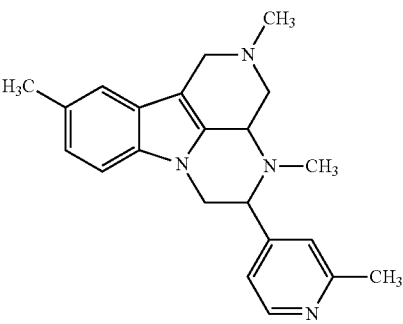 |

TABLE 4-continued

Representative Compounds of the Invention

| Compound No. | Structure |
|---|---|
| D50 | (structure) |
| D51 | (structure) |
| D52 | (structure) |
| D53 | (structure) |
| D54 | (structure) |
| D55 | (structure) |
| D56 | (structure) |
| D57 | (structure) |

TABLE 4-continued

Representative Compounds of the Invention

| Compound No. | Structure |
|---|---|
| D58 | (structure) |
| D59 | (structure) |
| D60 | (structure) |
| D61 | (structure) |
| D62 | (structure) |
| D63 | (structure) |
| D64 | (structure) |
| D65 | (structure) |

TABLE 4-continued

Representative Compounds of the Invention

| Compound No. | Structure |
|---|---|
| D66 | 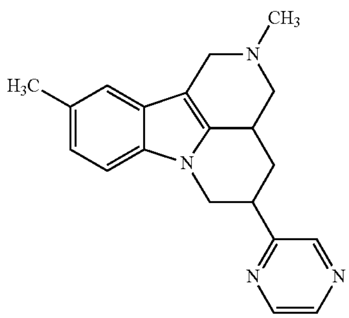 [SMILES: Cc1ccc2c(c1)c1c3n2CC(c2cnccn2)CC3CN(C)C1] |
| D67 | 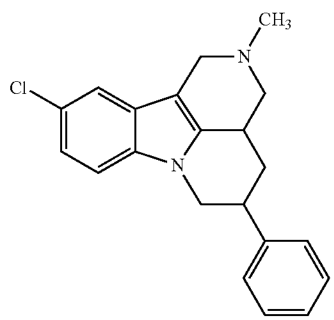 [SMILES: CN1Cc2c3n(c4ccc(Cl)cc24)CC(c2ccccc2)CC3C1] |
| D68 | 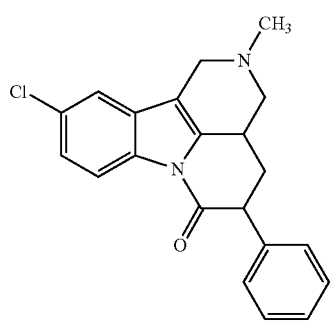 [SMILES: CN1Cc2c3n(c4ccc(Cl)cc24)C(=O)C(c2ccccc2)CC3C1] |
| D69 | 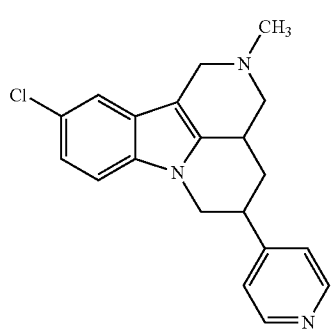 [SMILES: CN1Cc2c3n(c4ccc(Cl)cc24)CC(c2ccncc2)CC3C1] |
| D70 | |
| D71 | |
| D72 | |
| D73 | |

TABLE 4-continued

Representative Compounds of the Invention

| Compound No. | Structure |
|---|---|
| D74 | (structure) |
| D75 | (structure) |
| D76 | (structure) |
| D77 | (structure) |
| D78 | (structure) |
| D79 | (structure) |
| D80 | (structure) |
| D81 | (structure) |
| D82 | (structure) |
| D83 | (structure) |

TABLE 4-continued

Representative Compounds of the Invention

| Compound No. | Structure |
|---|---|
| D84 | 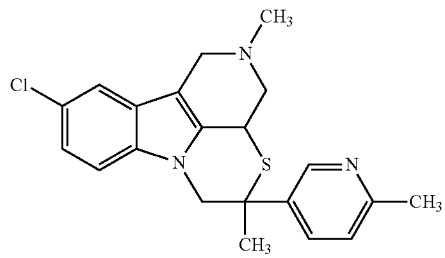 [SMILES: Cc1ccc(C2(C)Cn3c4c(c5cc(Cl)ccc53)CN(C)CC4S2)cn1] |
| D85 | 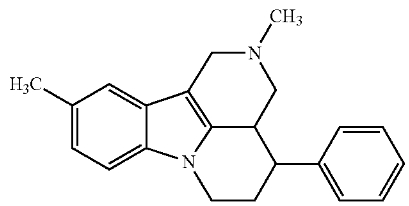 [SMILES: Cc1ccc2c(c1)c1c3n2CCC(c2ccccc2)C3CN(C)C1] |
| D86 | 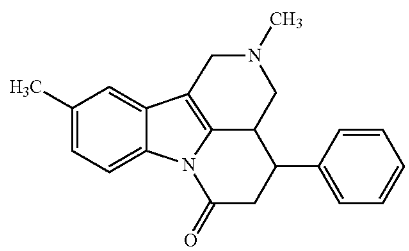 [SMILES: Cc1ccc2c(c1)c1c3n2C(=O)CC(c2ccccc2)C3CN(C)C1] |
| D87 | 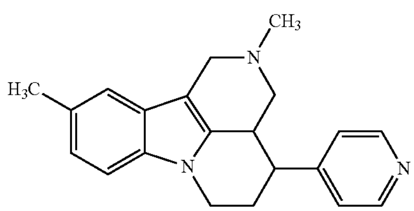 [SMILES: Cc1ccc2c(c1)c1c3n2CCC(c2ccncc2)C3CN(C)C1] |
| D88 | 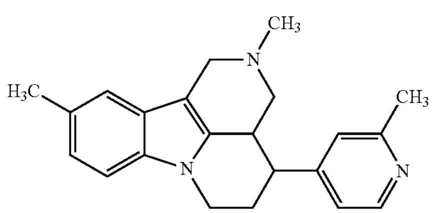 |
| D89 | 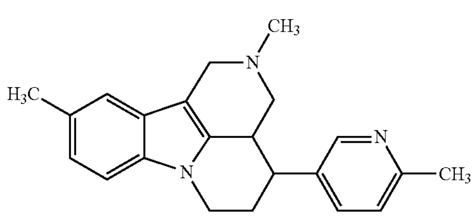 |
| D90 | |
| D91 | |
| D92 | |
| D93 | |
| D94 | |

TABLE 4-continued

Representative Compounds of the Invention

| Compound No. | Structure |
|---|---|
| D95 | [structure] |
| D96 | [structure] |
| D97 | [structure] |
| D98 | [structure] |
| D99 | [structure] |
| D100 | [structure] |
| D101 | [structure] |
| D102 | [structure] |
| D103 | [structure] |

TABLE 4-continued

Representative Compounds of the Invention

| Compound No. | Structure |
|---|---|
| D104 | 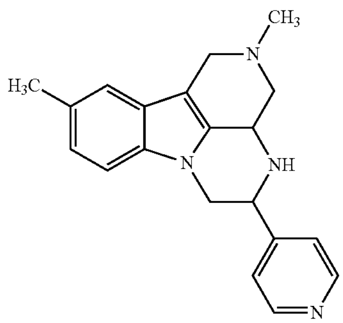 [SMILES: Cc1ccc2c(c1)c1c3n2CC(c2ccncc2)NC3CN(C)C1] |
| D105 | 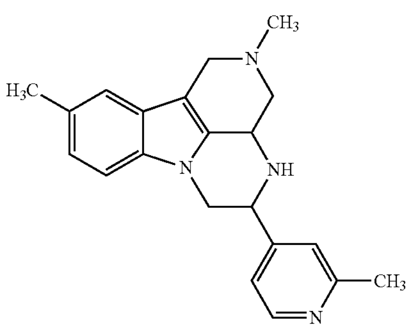 |
| D106 | 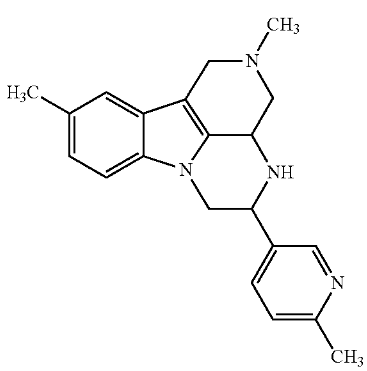 |
| D107 | 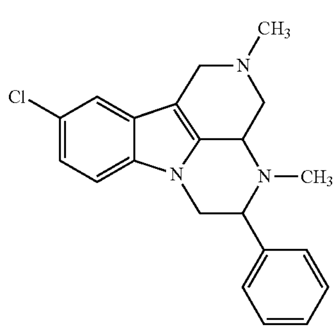 [SMILES: CN1Cc2c3n(c4ccc(Cl)cc24)CC(c2ccccc2)N(C)C3C1] |
| D108 | 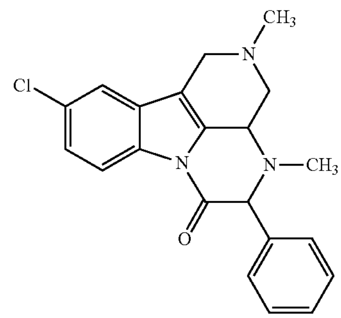 [SMILES: CN1Cc2c3n(c4ccc(Cl)cc24)C(=O)C(c2ccccc2)N(C)C3C1] |
| D109 | 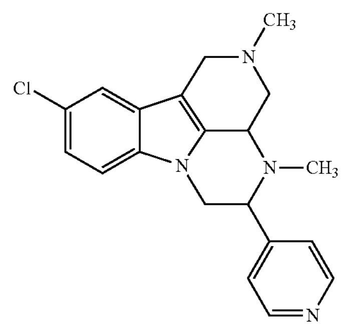 [SMILES: CN1Cc2c3n(c4ccc(Cl)cc24)CC(c2ccncc2)N(C)C3C1] |
| D110 | 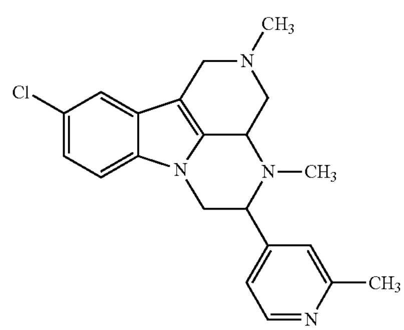 [SMILES: Cc1cc(C2Cn3c4c(c5cc(Cl)ccc53)CN(C)CC4N2C)ccn1] |
| D111 | 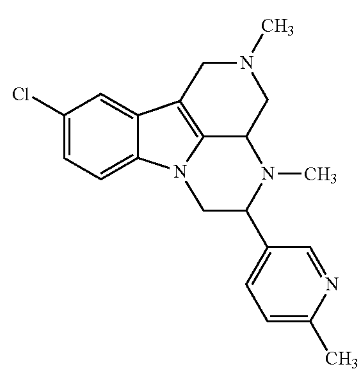 [SMILES: Cc1ccc(C2Cn3c4c(c5cc(Cl)ccc53)CN(C)CC4N2C)cn1] |

TABLE 4-continued
Representative Compounds of the Invention
| Compound No. | Structure |
|---|---|
| D112 | 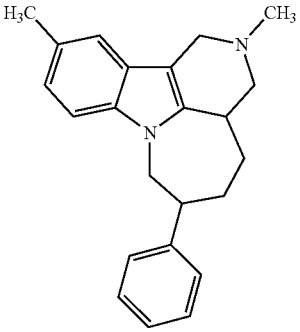 |
| D113 | 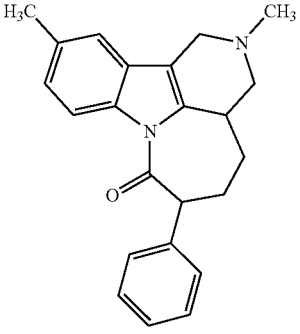 |
| D114 | 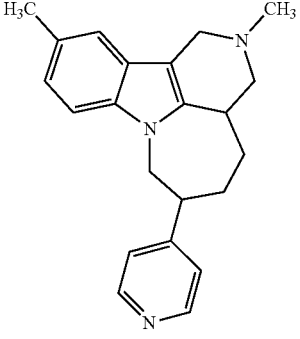 |
| D115 | 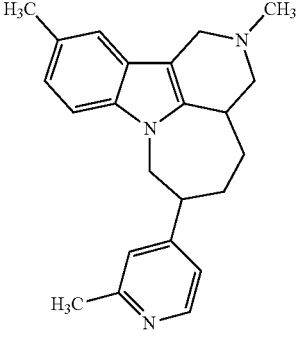 |
| D116 | 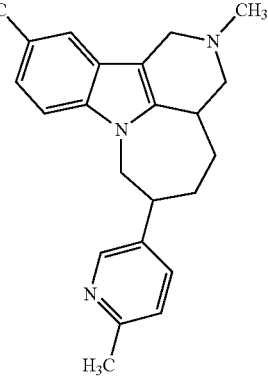 |
| D117 | 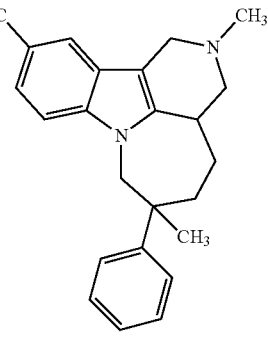 |
| D118 | 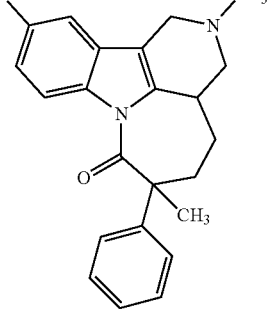 |
| D119 | 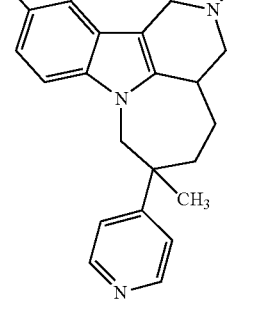 |

TABLE 4-continued
Representative Compounds of the Invention
| Compound No. | Structure |
|---|---|
| D120 | 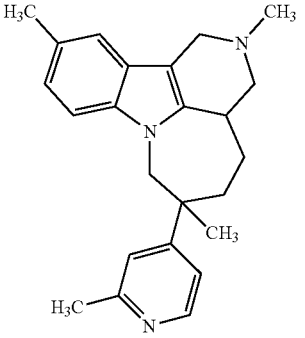 |
| D121 | 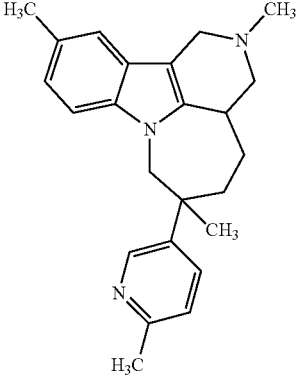 |
| D122 | 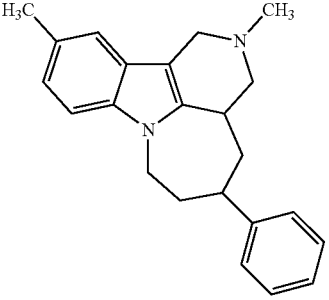 [SMILES: Cc1ccc2c(c1)c1c3n2CCC(c2ccccc2)CC3CN(C)C1] |
| D123 | 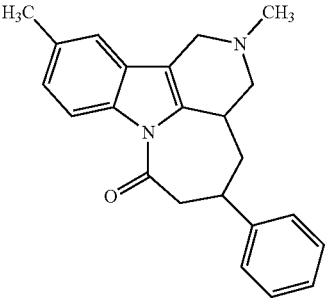 [SMILES: Cc1ccc2c(c1)c1c3n2C(=O)CC(c2ccccc2)CC3CN(C)C1] |
| D124 | 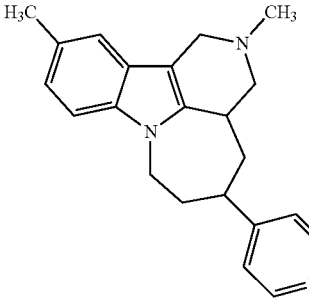 |
| D125 | 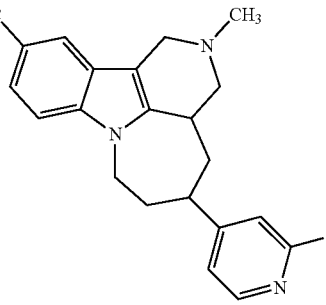 |
| D126 | 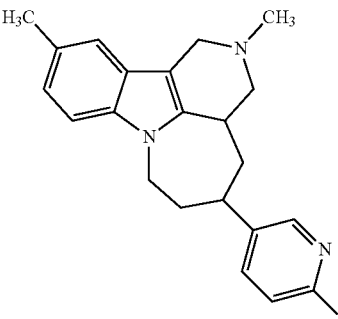 |
| D127 | 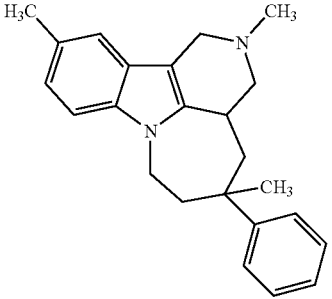 [SMILES: Cc1ccc2c(c1)c1c3n2CCC(C)(c2ccccc2)CC3CN(C)C1] |

TABLE 4-continued
Representative Compounds of the Invention
| Compound No. | Structure |
|---|---|
| D128 | 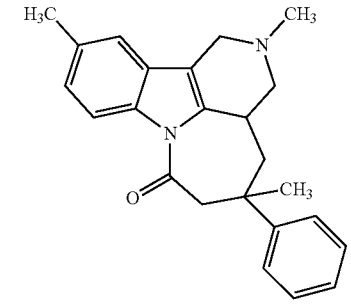 [SMILES: Cc1ccc2c(c1)c1c3n2C(=O)CC(C)(c2ccccc2)CC3CN(C)C1] |
| D129 | 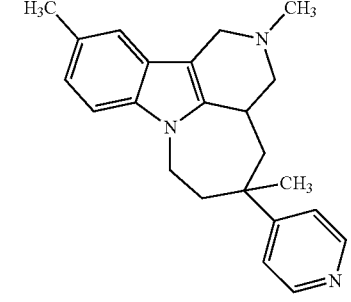 [SMILES: Cc1ccc2c(c1)c1c3n2CCC(C)(c2ccncc2)CC3CN(C)C1] |
| D130 | 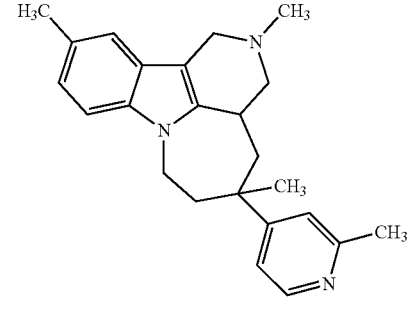 |
| D131 | 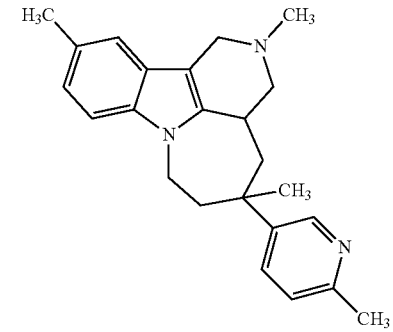 |
| D132 | 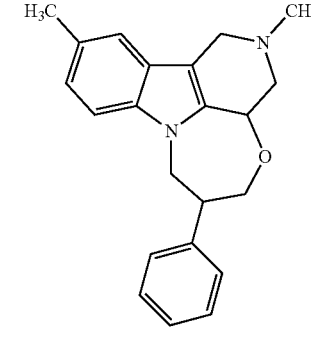 |
| D133 | 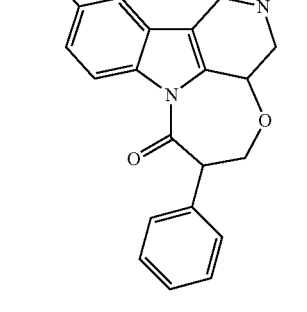 |
| D134 | 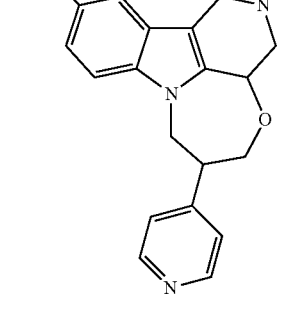 |
| D135 | 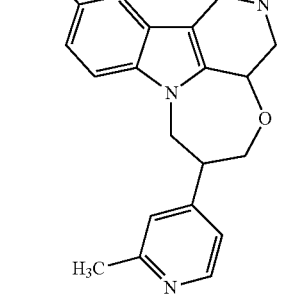 |

TABLE 4-continued
Representative Compounds of the Invention
| Compound No. | Structure |
|---|---|
| D136 | 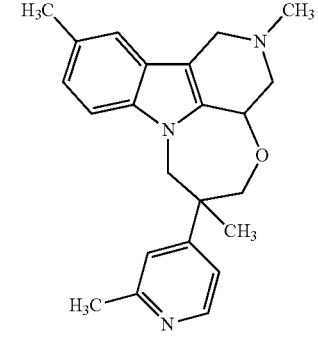 |
| D137 | 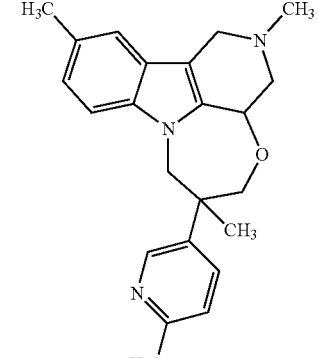 |
| D138 | 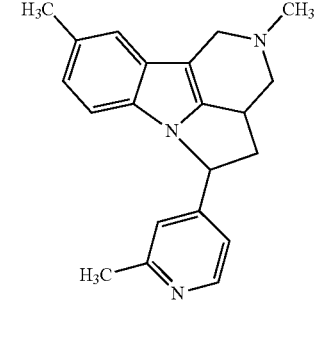 |
| D139 | 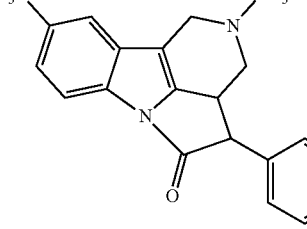 |
| D140 | 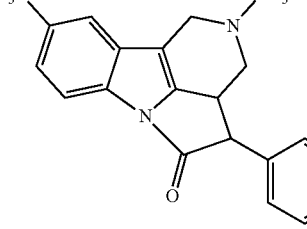 |
| D141 | 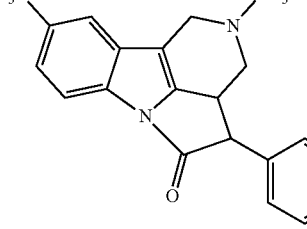 |
| D142 | 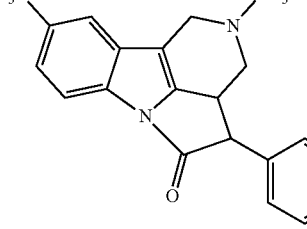 |
| D143 | 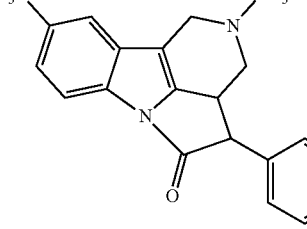 |

TABLE 4-continued

Representative Compounds of the Invention

| Compound No. | Structure |
|---|---|
| D144 | 8-methyl, 1-phenyl substituted tetracyclic indole core |
| D145 | 8-methyl, 1-(6-methylpyridin-3-yl) substituted tetracyclic indole |
| D146 | 8-chloro, 1-phenyl substituted tetracyclic indole |
| D147 | 8-methyl, 1-(pyridin-4-yl) substituted tetracyclic indole |
| D148 | 8-methyl, 1-(pyridin-3-yl) substituted tetracyclic indole |
| D149 | 8-methyl, 1-(2-methylpyridin-4-yl) substituted tetracyclic indole |
| D150 | 8-methyl, 1-(4-fluorophenyl) substituted tetracyclic indole |
| D151 | 8-methyl, 1-(2-methoxypyridin-4-yl) substituted tetracyclic indole |
| D152 | 8-methyl, 1-(pyridin-3-yl) substituted tetracyclic indole |
| D153 | 8-methyl, 1-(4-chlorophenyl) substituted tetracyclic indole |

TABLE 4-continued
Representative Compounds of the Invention
| Compound No. | Structure |
|---|---|
| D154 | 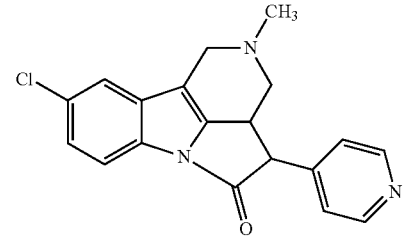 [SMILES: CN1Cc2c3n(c4ccc(Cl)cc24)C(=O)C(c2ccncc2)C3C1] |
| D155 | 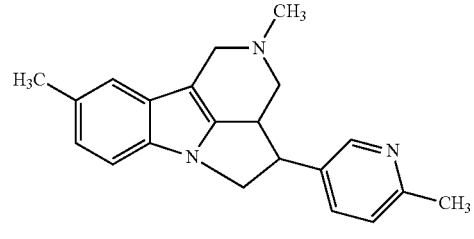 |
| D156 | 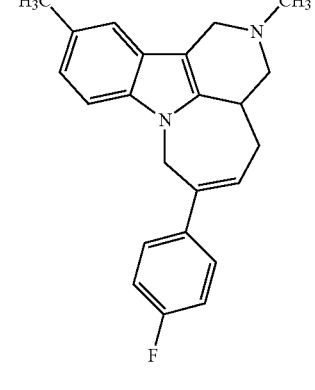 |
| D157 | 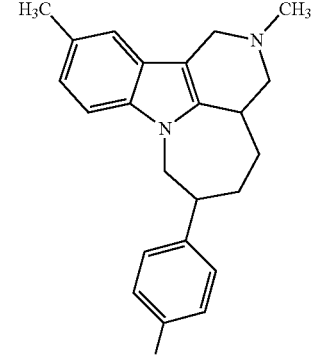 |
| D158 | 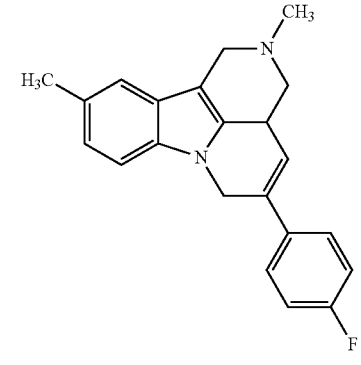 [SMILES: Cc1ccc2c(c1)c1c3n2CC(c2ccc(F)cc2)=CC3CN(C)C1] |
| D159 | 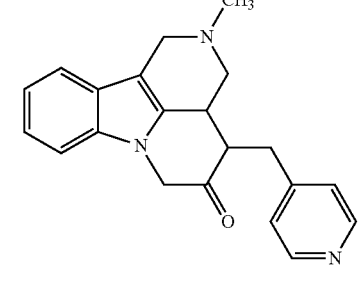 |
| D160 | 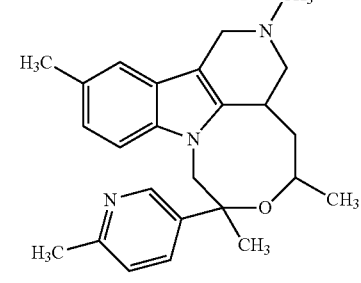 |
| D161 | 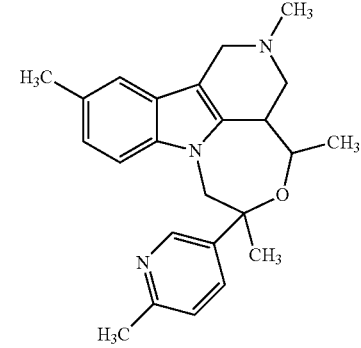 |

TABLE 4-continued

Representative Compounds of the Invention

| Compound No. | Structure |
|---|---|
| D162 | (structure) |
| D163 | (structure) |
| D164 | (structure) |
| D165 | (structure) |
| D166 | (structure) |
| D167 | (structure) |
| D168 | (structure) |
| D169 | (structure) |
| D170 | (structure) |
| D171 | (structure) |

TABLE 4-continued

Representative Compounds of the Invention

| Compound No. | Structure |
|---|---|
| D172 | 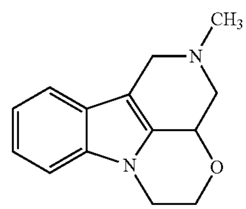 [SMILES: CN1Cc2c3n(c4ccccc24)CCOC3C1] |
| D173 | 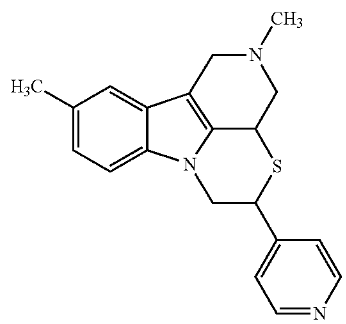 [SMILES: Cc1ccc2c(c1)c1c3n2CC(c2ccncc2)SC3CN(C)C1] |
| D174 | 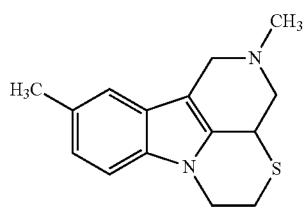 [SMILES: Cc1ccc2c(c1)c1c3n2CCSC3CN(C)C1] |
| D175 | 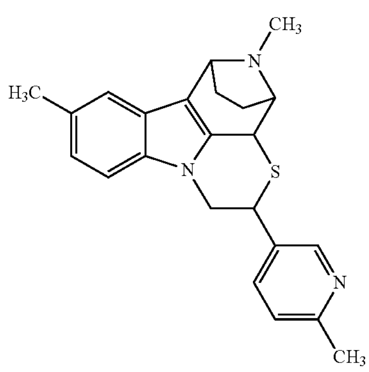 |
| D176 | 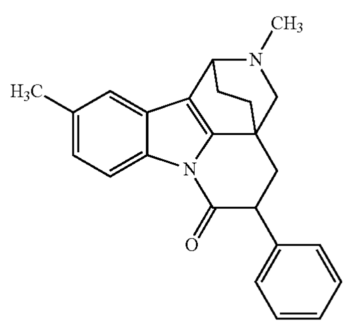 [SMILES: Cc1ccc2c(c1)c1c3n2C(=O)C(c2ccccc2)CC32CCC1N(C)C2] |
| D177 | |
| D178 | |
| D179 | |
| D180 | |
| D181 | |

TABLE 4-continued
Representative Compounds of the Invention
| Compound No. | Structure |
|---|---|
| D182 | 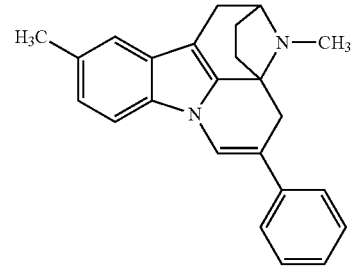 [SMILES: Cc1ccc2c(c1)c1c3n2C=C(c2ccccc2)CC32CCC(C1)N2C] |
| D183 | 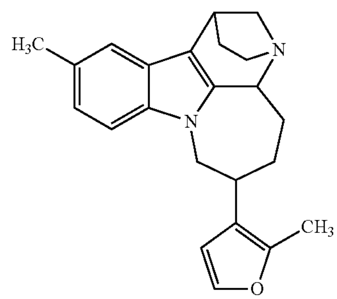 |
| D184 | 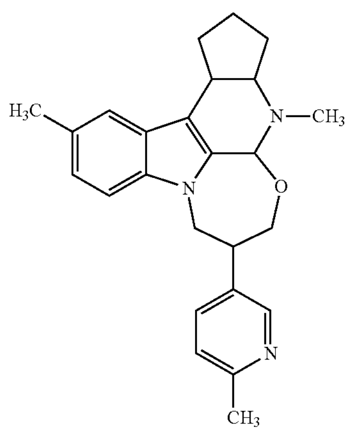 |
| D185 | 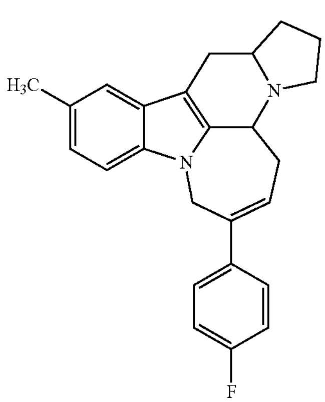 [SMILES: Cc1ccc2c(c1)c1c3n2CC(c2ccc(F)cc2)=CCC3N2CCCC2C1] |
| D186 | 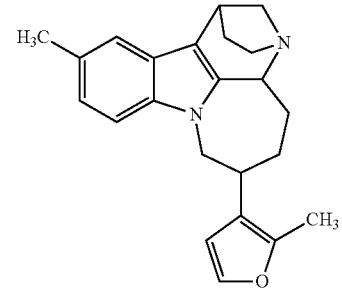 |
| D187 | |
| D188 | |
| D189 | |

TABLE 4-continued

Representative Compounds of the Invention

| Compound No. | Structure |
|---|---|
| D190 | (structure) |
| D191 | (structure) |
| D192 | (structure) |
| D193 | (structure) |
| D194 | (structure) |
| D195 | (structure) |
| D196 | (structure) |
| D197 | (structure) |

TABLE 4-continued

Representative Compounds of the Invention

| Compound No. | Structure |
|---|---|
| D198 | (structure) |
| D199 | (structure) |
| D200 | (structure) |
| D201 | (structure) |
| D202 | (structure) |
| D203 | (structure) |
| D204 | (structure) |
| D205 | (structure) |

TABLE 4-continued

Representative Compounds of the Invention

| Compound No. | Structure |
|---|---|
| D206 | (structure) |
| D207 | (structure) |
| D208 | (structure) |
| D209 | (structure) |
| D210 | (structure) |
| D211 | (structure) |
| D212 | (structure) |
| D213 | (structure) |

TABLE 4-continued

Representative Compounds of the Invention

| Compound No. | Structure |
|---|---|
| D214 | 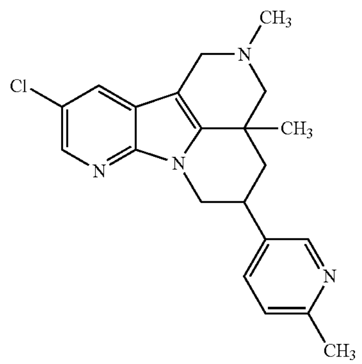 [SMILES: Cc1ccc(C2Cn3c4c(c5cc(Cl)cnc53)CN(C)CC4(C)C2)cn1] |
| D215 | 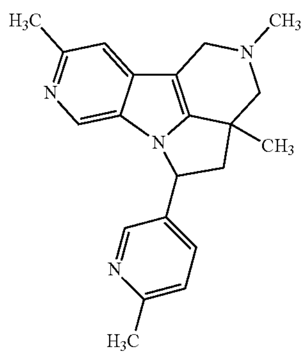 |
| D216 | 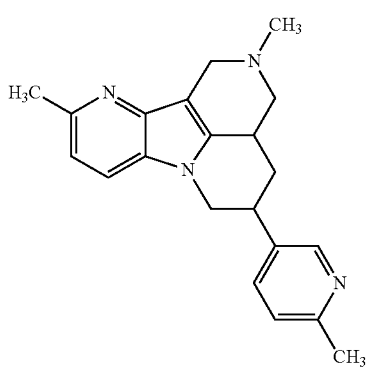 |
| D217 | 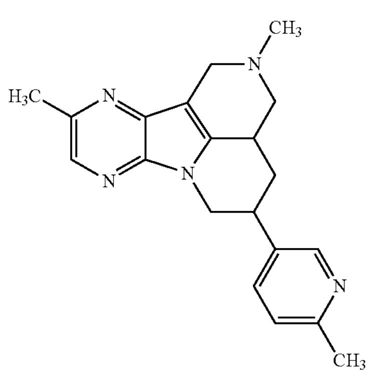 |
| D218 | |
| D219 | |
| D220 | |
| D221 | |

TABLE 4-continued
Representative Compounds of the Invention
| Compound No. | Structure |
|---|---|
| D222 | 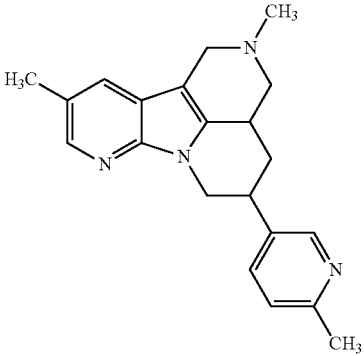 |
| D223 | 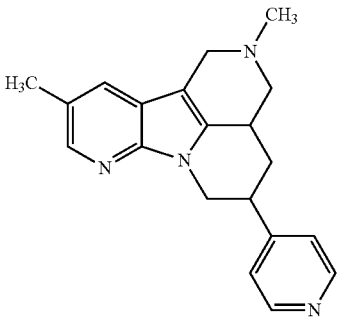 |
| D224 | 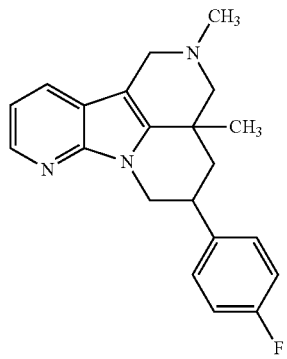 [SMILES: CN1Cc2c3n(c4ncccc24)CC(c2ccc(F)cc2)CC3(C)C1] |
| D225 | 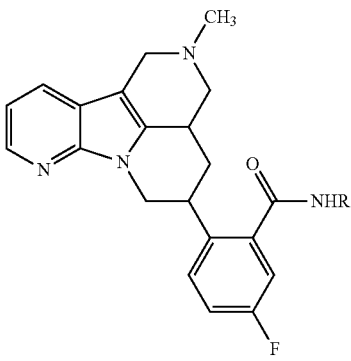 |
| D226 | 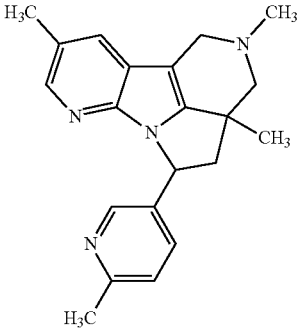 |
| D227 | 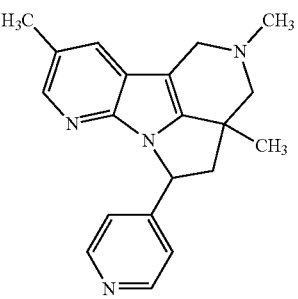 |
| D228 | 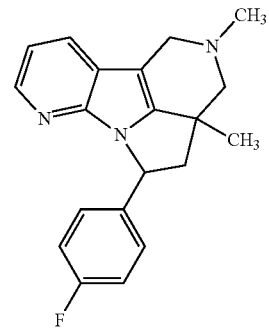 [SMILES: CN1Cc2c3n(c4ncccc24)C(c2ccc(F)cc2)CC3(C)C1] |
| D229 | 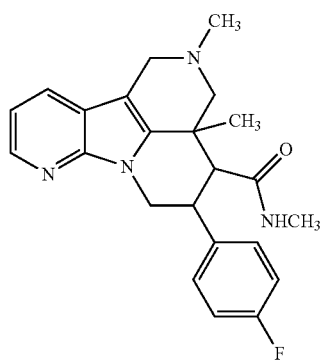 [SMILES: CNC(=O)C1C(c2ccc(F)cc2)Cn2c3c(c4cccnc42)CN(C)CC31C] |

TABLE 4-continued

Representative Compounds of the Invention

| Compound No. | Structure |
|---|---|
| D230 | (structure) |
| D231 | (structure) |
| D232 | (structure) |
| D233 | (structure) |
| D234 | (structure) |
| D235 | (structure) |
| D236 | (structure) |
| D237 | (structure) |
| D238 | (structure) |

TABLE 4-continued

Representative Compounds of the Invention

| Compound No. | Structure |
|---|---|
| D239 | (structure) |
| D240 | (structure) |
| D241 | (structure) |
| D242 | (structure) |
| D243 | (structure) |
| D244 | (structure) |
| D245 | (structure) |
| D246 | (structure) |
| D247 | (structure) |

TABLE 4-continued

Representative Compounds of the Invention

| Compound No. | Structure |
|---|---|
| D248 | (structure) |
| D249 | (structure) |
| D250 | (structure) |
| D251 | (structure) |
| D252 | (structure) |
| D253 | (structure) |
| D254 | (structure) |
| D255 | (structure) |

TABLE 4-continued

Representative Compounds of the Invention

| Compound No. | Structure |
|---|---|
| D256 | (structure) |
| D257 | (structure) |
| D258 | (structure) |
| D259 | (structure) |
| D260 | (structure) |
| D261 | (structure) |
| D262 | (structure) |
| D263 | (structure) |

TABLE 4-continued

Representative Compounds of the Invention

| Compound No. | Structure |
|---|---|
| D264 | 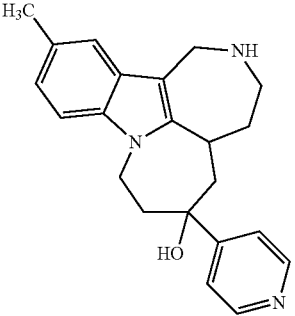 [SMILES: Cc1ccc2c(c1)c1c3n2CCC(O)(c2ccncc2)CC3CCNC1] |
| D265 | 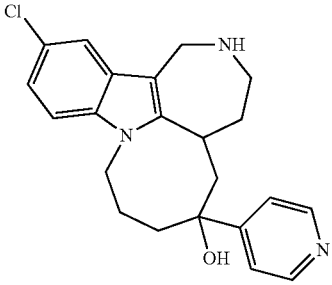 [SMILES: OC1(c2ccncc2)CCCn2c3c(c4cc(Cl)ccc42)CNCCC3C1] |
| D266 | 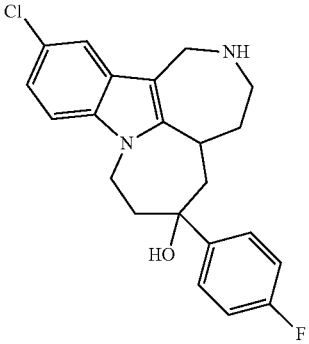 [SMILES: OC1(c2ccc(F)cc2)CCn2c3c(c4cc(Cl)ccc42)CNCCC3C1] |

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Protocol for Chiral Preparative HPLC Separation of Racemic compounds

For chiral separations, samples were dissolved in Methanol and Ethanol according to the solubility of sample and filtered through 0.22 µ PTFE filters. The columns used were CHIRALPAK-AD; 20*250 mm, 10 µ and CHIRALCEL-ODH; 20*250 mm, 5 µ. A flow rate of 12 mL/min-17 mL/min was used according to the resolution. Alkanes such as n-Pentane, Hexane and Heptane (40%-95%) and alcohols such as Ethanol, Isopropyl alcohol and t-Butanol (5%-60%) were used as mobile phase. In some cases alcohol combinations i.e. (Ethanol+Methanol), (Ethanol+IPA), (IPA+Methanol), (t-Butanol+Methanol), (t-Butanol+Ethanol) were used instead of a single alcohol. Diethyl amine (up to 0.3%) was used as modifier in the mobile phase.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal(N); aqueous (aq.); methanol (MeOH); dichloromethane (DCM); ethyl acetate (EtOAc); Retention factor (Rf); room temperature (RT).

General methods of preparing compounds according to the invention are depicted in exemplified methods below. Other compounds of the invention may be prepared by similar methods. Synthetic methods to provide similar intermediates have also been described in, for example, PCT Publication Nos. WO2009-055828, WO2009-094668, WO2009-120717, WO2009-120720, WO2009-038161, WO2009-038162 and WO2009-038164. Synthetic methods to provide azepino[4,5-b]indole intermediates have been described in PCT Publication No. WO-2009-051503. Synthetic methods to provide bicyclo pyrido[3,4-b]indoles have been described in PCT Publication No. WO2009-038163. The synthesis of Compound Nos. A1 to A160 has been described specifically in PCT Publication No. WO2011-103433. The synthesis of Compound Nos. B1 to B242 has been described specifically in PCT Publication No. WO2011-103460. The synthesis of Compound Nos. C1 to C136 has been described specifically in PCT Publication No. WO2011-103487. The synthesis of Compound Nos. D1 to D266 has been described specifically in PCT Publication No. WO2011-103485. The experimental details of each of these Applications are incorporated herein by reference. Exemplified routes to synthesizing particular compounds of the invention are shown in the General Methods below.

General Method A1.

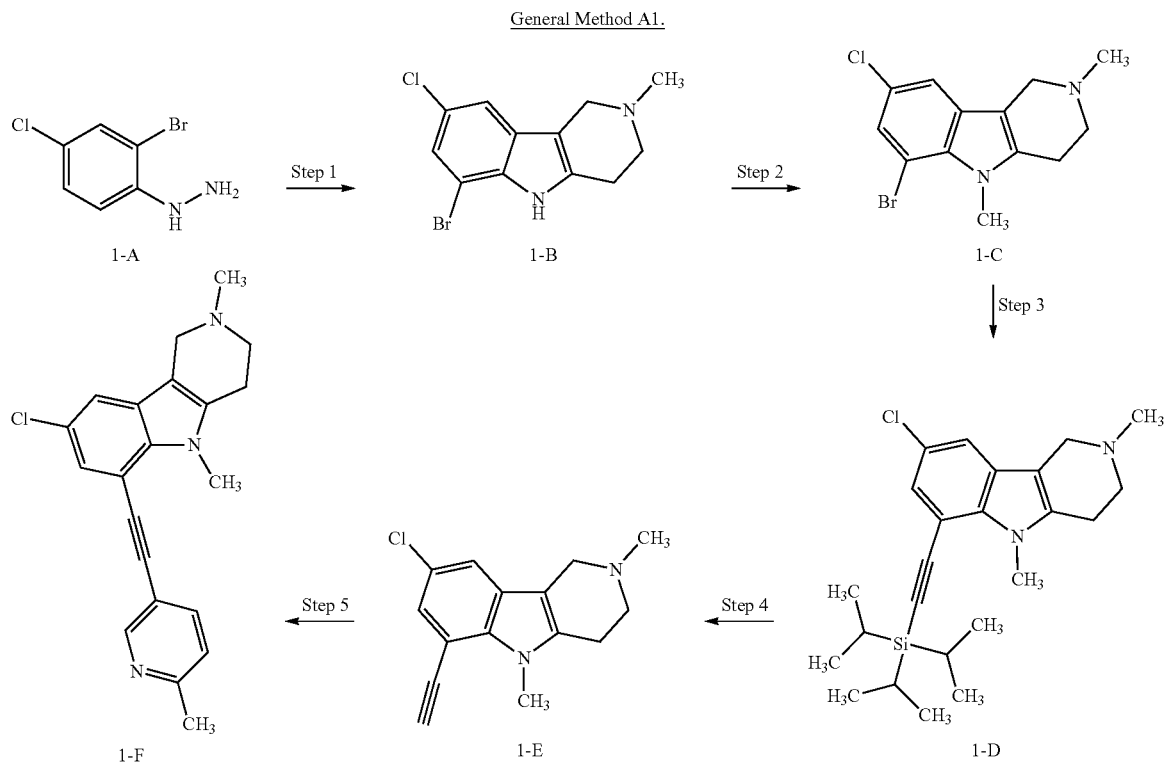

Step 1: Preparation of compound 1-B

A solution of 4-chloro-2-bromophenyl hydrazine hydrochloride (15 g, 58 mmol) and 1-methylpiperidin-4-one (6.57 g, 58 mmol) in 7% $H_2SO_4$ in dioxane (150 mL) is stirred at 80° C. for 5 h. The progress of reaction is monitored by TLC. The reaction mixture is concentrated under reduced pressure to dryness. The residue is basified with aq. NaOH solution and extracted with EtOAc. The organic layer is dried over anhydrous sodium sulfate and concentrated under reduced pressure to afford crude product, which is purified by column chromatography (7% MeOH-DCM) to yield compound 1-B (7.6 g).

Step 2: Preparation of compound 1-C

A stirred solution of 6-bromo-8-chloro-2,3,4,5-tetrahydro-2-methyl-1H-pyrido[4,3-b]indole (1-B) (200 mg, 0.667 mmol) in DMF (2 mL) is cooled to −78° C., followed by addition of sodium hydride (20 mg, 0.800 mmol) and methyl iodide (2M in DMF, 0.3 mL, 0.60 mmol). The reaction mixture is stirred at −78° C. for 5 min. Ice-water is added into the reaction mixture and the mixture is then extracted with EtOAc (2×10 mL). The combined organic layer is dried over anhydrous sodium sulfate and concentrated under reduced pressure to afford crude material, which is purified by column chromatography using silica (100:200 mesh) and 0-4% MeOH:DCM to yield compound 1-C (38 mg).

Step 3: Preparation of compound 1-D

A mixture of 6-bromo-8-chloro-2,3,4,5-tetrahydro-2,5-dimethyl-1H-pyrido[4,3-b]indole (1-C) (210 mg, 0.670 mmol), copper(I)iodide (1.3 mg, 0.007 mmol), dichlorobis(triphenylphosphine) palladium(II) (24 mg, 0.034 mmol) is evacuated and back filled with nitrogen. Triethylamine (2.5 mL) is added, followed by dropwise addition of ethynyltriisopropylsilane (146 mg, 0.804 mmol). The reaction mixture is stirred at 85° C. overnight. Water is added into the reaction mixture and the mixture is then extracted with EtOAc. The organic layer is dried over anhydrous sodium sulfate and concentrated under reduced pressure to afford crude material, which is purified by column chromatography using silica (100:200 mesh) and 0-4% MeOH:DCM to yield compound 1-D (218 mg).

Step 4: Preparation of compound 1-E

To an ice cooled stirred solution of 8-chloro-2,3,4,5-tetrahydro-6-(2-(triisopropylsilyl)ethynyl)-2,5-dimethyl-1H-pyrido[4,3-b]indole (1-D) (212 mg, 0.512 mmol) in dry THF (10 mL) is added tetrabutylammoniumfluoride (1M solution in THF, 1.638 mL, 1.638 mmol). The reaction mixture is allowed to warm to RT and stirring continued for 15 min. Water is added into the reaction mixture and the mixture is extracted with EtOAc (2×25 mL). The organic layer is dried over anhydrous sodium sulfate and concentrated under reduced pressure to afford compound 1-E (166 mg).

Step 5: Preparation of compound 1-F

A mixture of 8-chloro-6-ethynyl-2,3,4,5-tetrahydro-2,5-dimethyl-1H-pyrido[4,3-b]indole (1-E) (166 mg, 0.642 mmol), 5-bromo-2-methylpyridine (132 mg, 0.770 mmol), dichlorobis(triphenyl phosphine)palladium (II) (23 mg, 0.032 mmol) and copper (I) iodide (1.1 mg, 0.006 mmol) is evacuated and back filled with nitrogen. Triethylamine (2 mL) is added dropwise under nitrogen atmosphere. The reaction mixture is stirred at 85° C. overnight. Triethylamine is evaporated under reduced pressure. The residue is dissolved in water (10 mL) and extracted with EtOAc (2×25 mL). The organic layer is washed with water (2×10 mL), dried over anhydrous sodium sulfate and concentrated under reduced pressure to afford crude material, which is purified by column chromatography using neutral alumina and 0-8% MeOH-EtOAc, followed by reverse phase HPLC to yield compound 1-F as the free base (16.23 mg).

General Method A2.

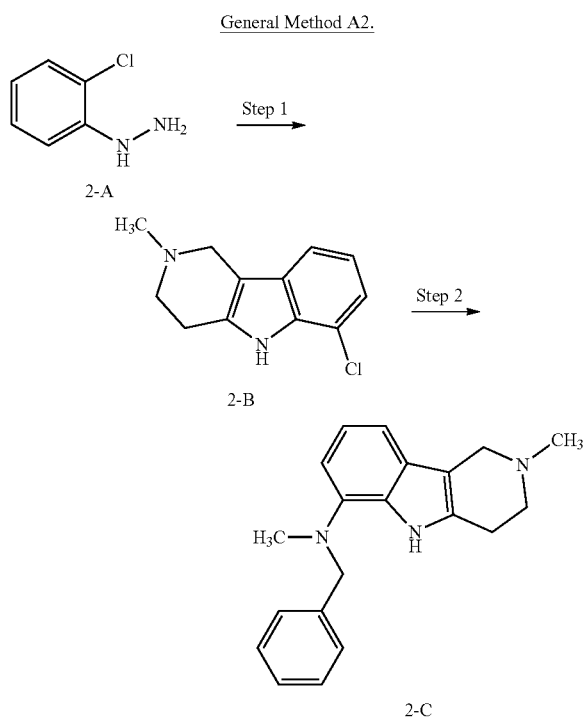

Step 1: Preparation of compound 2-B

To a suspension of 2-chlorophenyl hydrazine hydrochloride (2-A) (19.7 g, 0.110 mol) in dioxane (190 mL) is dropwise added conc. H$_2$SO$_4$ (8 mL, 0.150 mol). After stirring for 10 min, N-methyl-4-piperidone (17.53 g, 0.154 mol) is added into the reaction mixture and stirring continued at RT for 20 min. The reaction mixture is then stirred at 80° C. for 4 h. The progress of reaction is monitored by TLC. The solvent is removed under reduced pressure and the pH of the residue adjusted to pH 8-9 by addition of saturated sodium bicarbonate solution. The aqueous layer is extracted with EtOAc (3×300 mL). The combined organic layer is washed with water, followed by brine, dried over anhydrous sodium sulfate and concentrated under reduced pressure to afford crude material, which is purified by re-crystallization (Ether/Hexane) to yield compound 2-B as a brown solid (7.5 g).

Step 2: Preparation of compound 2-C

To a degassed mixture of 6-chloro-2-methyl-2,3,4,5-tetrahydro-1H-pyrido[4,3-b]indole (2-B) (100 mg, 0.5 mmol), sodium tert-butoxide (576 mg, 6.0 mmol), palladium acetate (22.4 mg, 0.1 mmol) and 2,4 di-tert-butylphosphino-2',4',6'-triisopropyl biphenyl (63.0 mg, 0.15 mmol) is added dry toluene (2 mL). After stirring for 5 min, benzylmethylamine (0.09 mL, 0.7 mmol) is added to the reaction mixture, which is stirred at 100° C. for 16 h. The reaction mixture is filtered and the residue washed with EtOAc. The filtrate is concentrated under reduced pressure to afford crude material, which is purified by reverse phase HPLC to yield benzyl-methyl-(2-methyl-2,3,4,5-tetrahydro-1H-pyrido[4,3-b]indol-6-yl)-amine (2-C) (50 mg).

General Method A3.

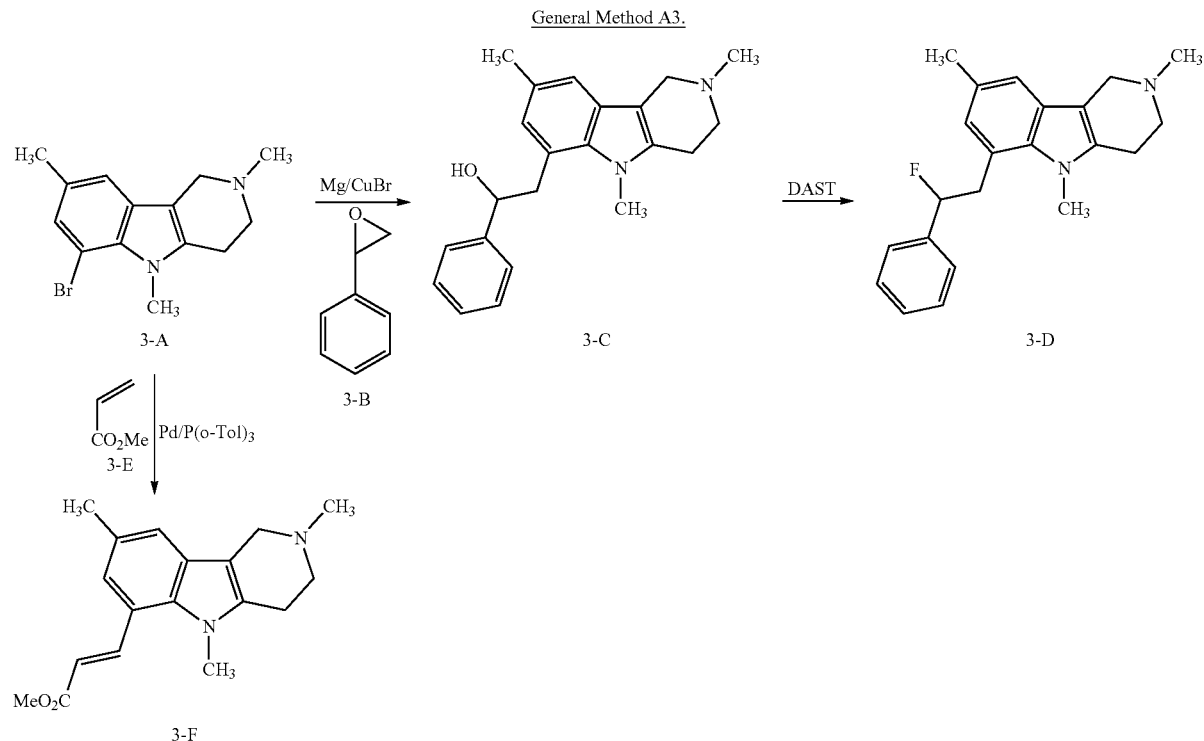

Alcohol compounds of type 3-C can be prepared from the bromo precursor 3-A by treatment with epoxide 3-B under standard Grignard or Grignard-cuprate coupling conditions known to those skilled in the art. Fluorination of 3-C with agents such as Diethylaminosulfur-trifluoride (DAST) provides the fluoro derivative 3-D. Alternatively, treatment of 3-A with alkene 3-E under Heck coupling conditions affords the styryl product of the type 3-F. Alternative coupling conditions including Stille and Suzuki, and the like, using corresponding reagents, will be familiar to those skilled in the art.

General Method B1.

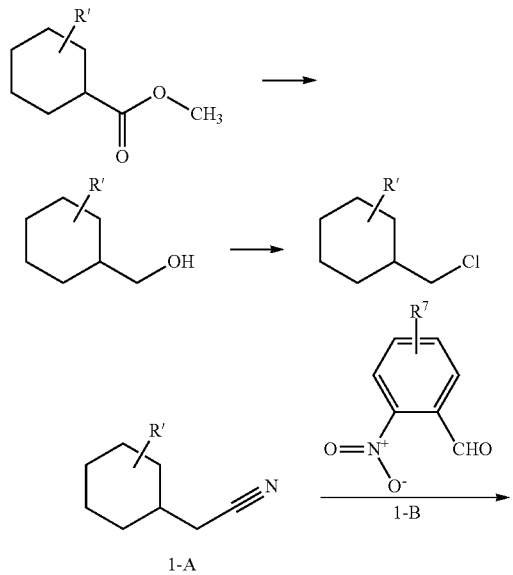

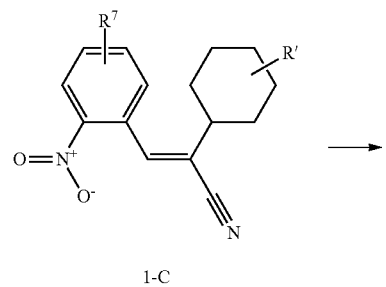

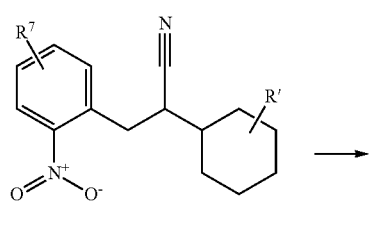

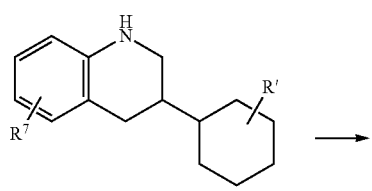

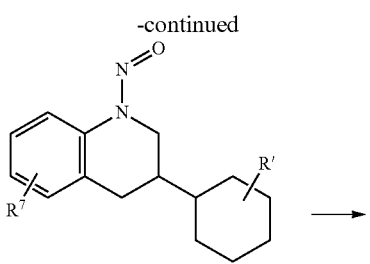

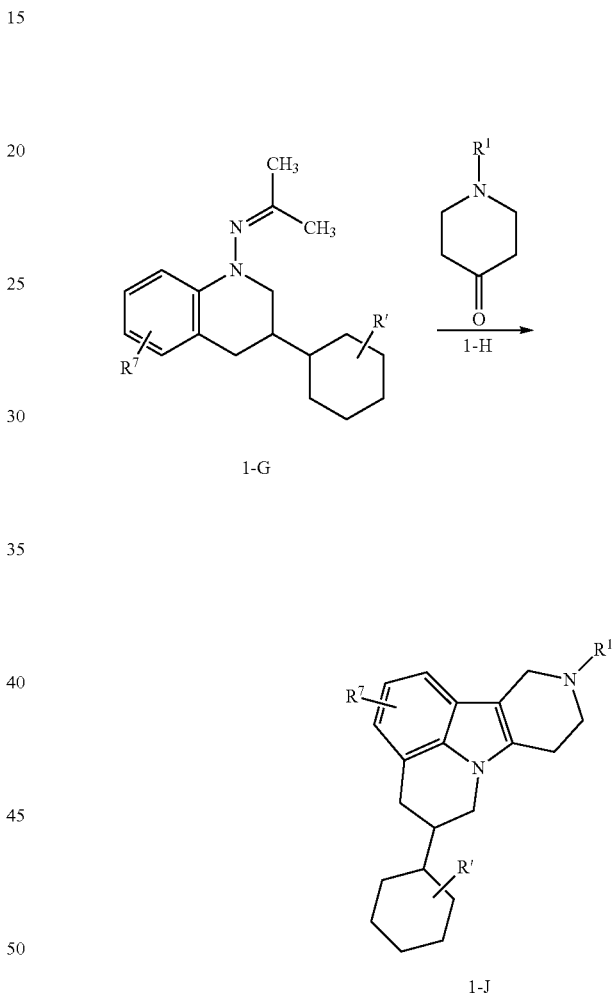

Nitrile compound 1-A, if not commercially available, can be synthesized from precursors such as the halo, hydroxyl and/or ester compounds, using standard functional group conversion means known to those skilled in the art. Compound 1-A is subjected to a condensation reaction with aldehyde 1-B to produce alkene 1-C which is reduced to alkane intermediate 1-D. Hydrogenation of 1-D results in cycfization to the tetrahydroquinoline 1-E which, when subjected to nitrosation conditions, yields nitroso compound 1-F. Reduction of 1-F with zinc dust in the presence of acetone yields ylide 1-G which when heated with acid in the presence of piperidone 1-H, provides the desired final tetracycfic product 1-J.

General Method B2.

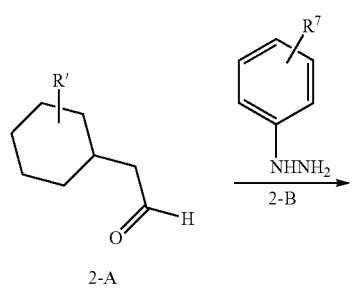
2-A

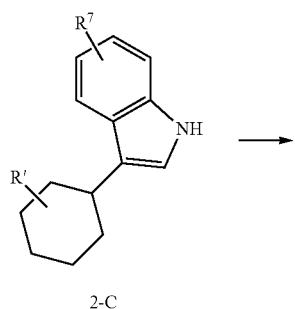
2-C

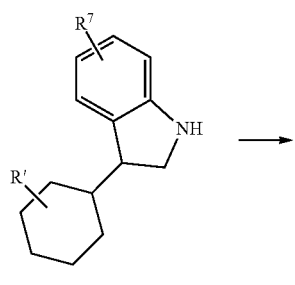
2-D

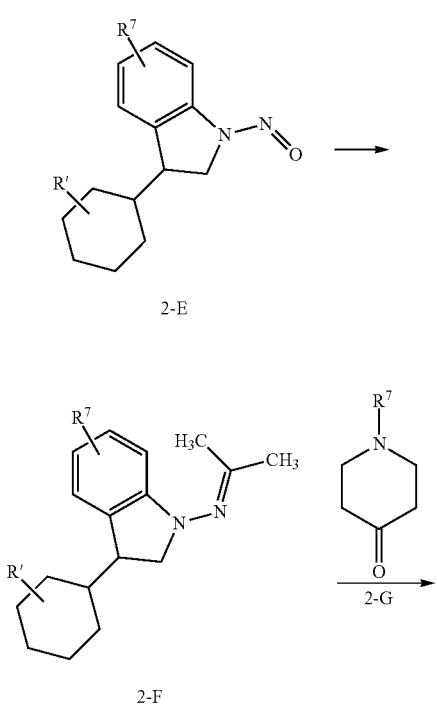
2-E

2-F

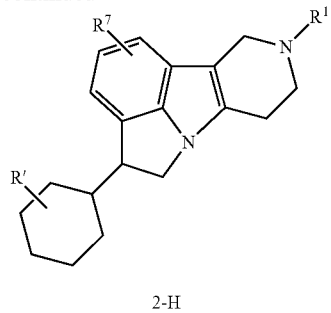
2-H

Aldehyde 2-A is subjected to Fischer-Indole synthesis conditions with hydrazine 2-B to give indole 2-C. Mild reduction of 2-C results in indoline 2-D. In an analogous fashion to the conversion of tetrahydroquinoline 1-E to tetracyclic compound 1-J, indoline 2-D is subjected to nitrosating conditions to give nitroso intermediate 2-E which, when subjected to zinc dust in the presence of acetone, afford ylide 2-F, and thence provides tetracyclic final product 2-H following treatment with piperidone 2-G and acid.

General Method B3.

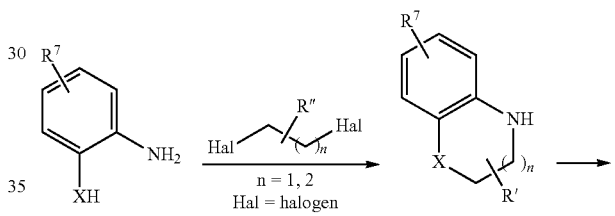

X = O: 3-A
X = S: 3-F
X = NR″: 3-K

X = O: 3-B
X = S: 3-G
X = NR″: 3-L

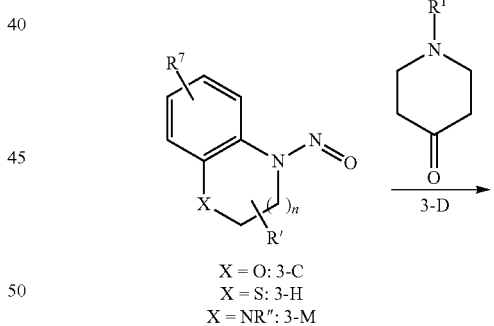

X = O: 3-C
X = S: 3-H
X = NR″: 3-M

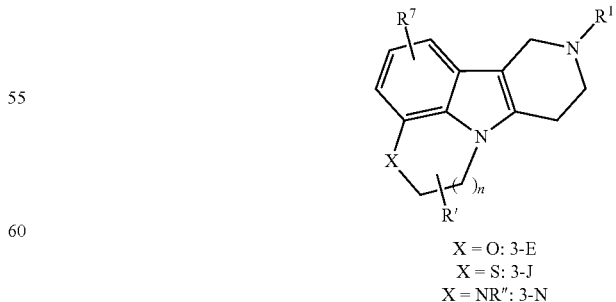

X = O: 3-E
X = S: 3-J
X = NR″: 3-N

Cyclization of o-hydroxy-aniline 3-A with an appropriately substituted dihaloalkane, such as 1,2-dibromoethane, yields benzoxazine 3-B. Nitrosation yields nitroso intermediate 3-C which, when heated with piperidone 3-D in acid produces the desired tetracyclic product 3-F. Alternatively, under similar conditions, the o-amino-thiophenol 3-F (or 2,2'-disulfanediyldianiline derivative) yields the intermediate benzothiazine 3-G and thence the thio analog 3-J. Alternatively, under similar conditions, the o-amino-aniline 3-K (R''=H, alkyl) yields the intermediate tetrahydroquinoxaline 3-L and thence the amino analog 3-N.

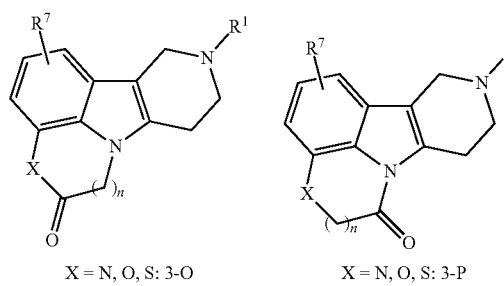

X = N, O, S: 3-O        X = N, O, S: 3-P

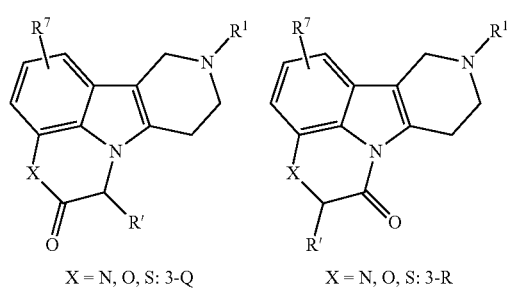

X = N, O, S: 3-Q        X = N, O, S: 3-R

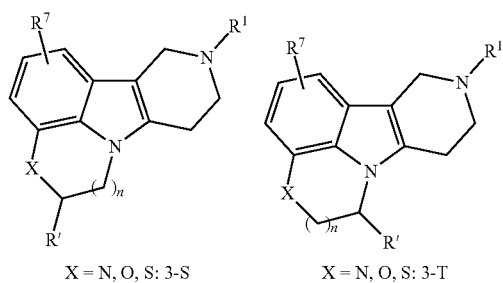

X = N, O, S: 3-S        X = N, O, S: 3-T

Use of alternative haloacetates, such as ethyl-2-bromoacetate in place of the dihaloalkanes, results in the acyl analog of the types 3-O and 3-P. Use of α-substituted ethyl-2-bromoacetate reagents yields substituted analogs of the type 3-Q and 3-R. Compounds 3-S and 3-T can be prepared through reduction of the compounds 3-Q and 3-R, or intermediates thereto, respectively.

An alternative route commences by nucleophilic substitution of the orthohalonitrobenzene compound 3-U with an appropriately substituted nucleophilic alkyl halide 3-V followed by reduction of the nitro group to the amine 3-W. Conversion to the aryl hydrazine 3-X followed by Fischer-Indole reaction with piperidone 3-D as before gives the desired R'-substituted product 3-Y.

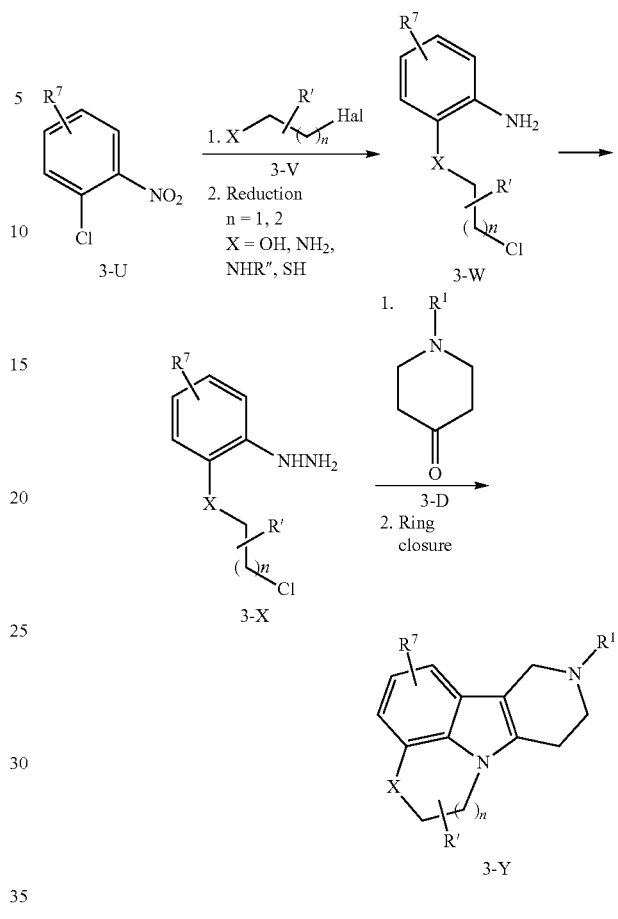

General Method B4.

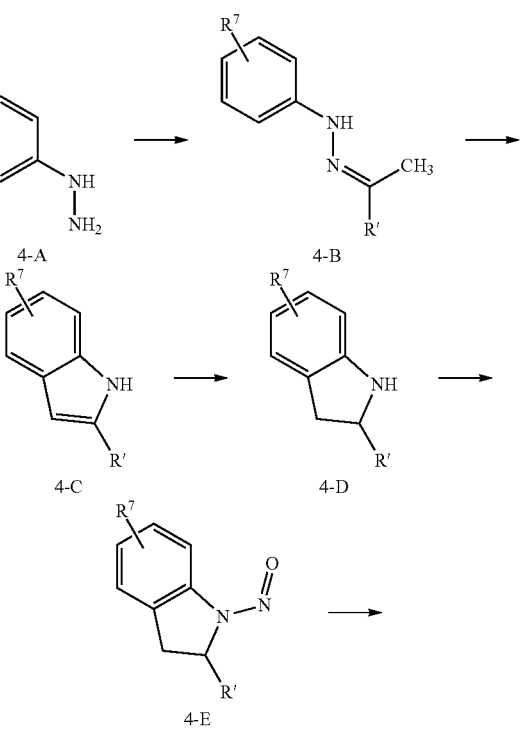

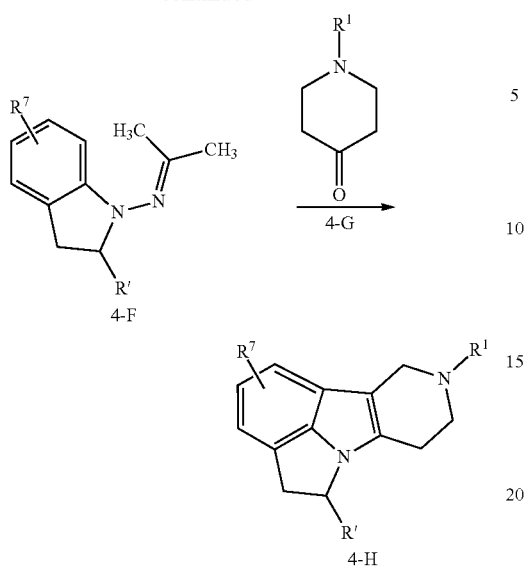

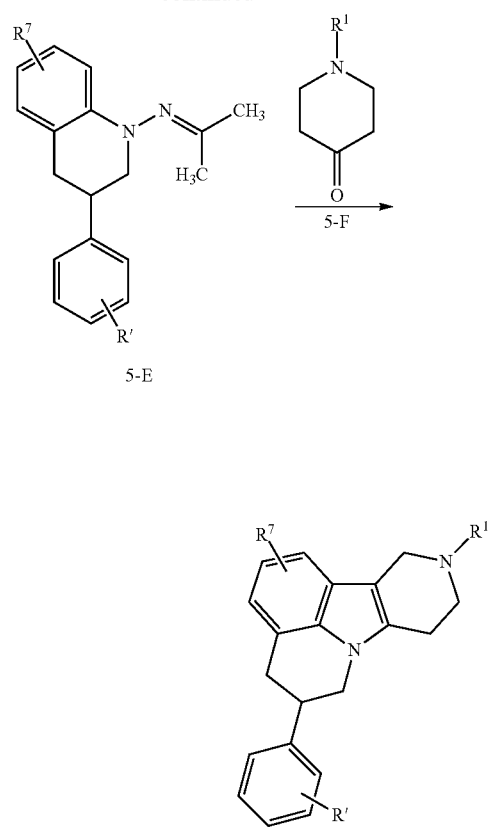

Conversion of phenyl hydrazine 4-A to the intermediate ylide 4-B followed by cyclization yields the indole 4-C. Reduction of the indole 4-C to the indoline 4-D followed by nitrosation yields nitroso derivative 4-E which, after conversion to the successive ylide 4-F, yields the final tetracyclic product 4-H upon treatment with piperidone 4-G.

General Method B5.

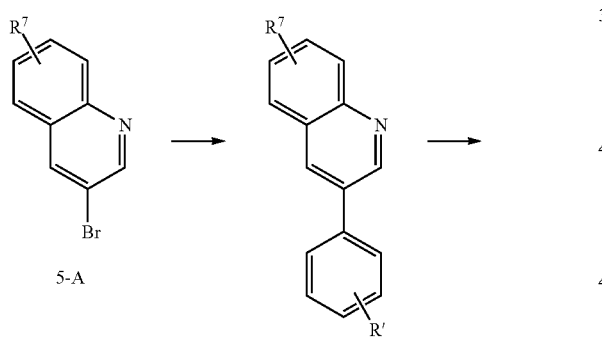

Suzuki-coupling of bromoquinoline 5-A with an appropriately substituted boronic acid yields the aryl-coupled product 5-B. Reduction of 5-B to the tetrahydroquinoline 5-C followed by nitrosation gives the nitroso intermediate 5-D. Conversion of nitroso compound 5-D to the ylide 5-E, followed by heating with piperidone 5-F yields the final desired tetracycle 5-G.

General Method B6.

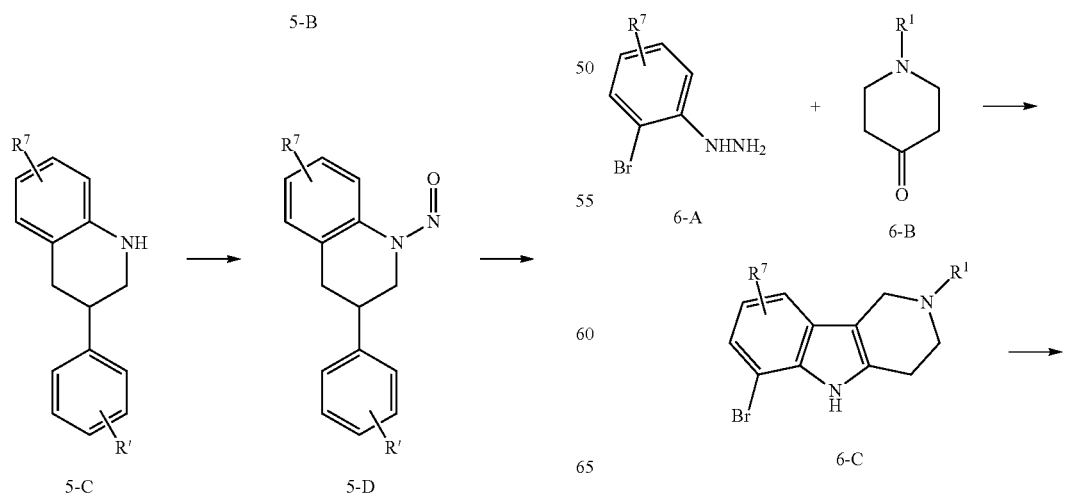

-continued

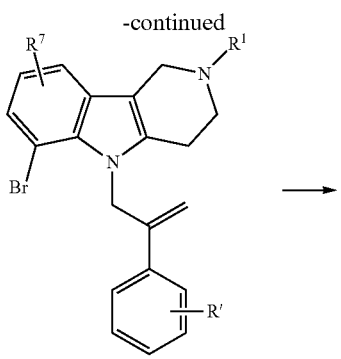

6-D

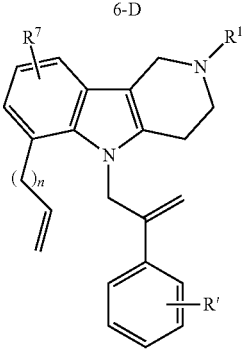

6-E

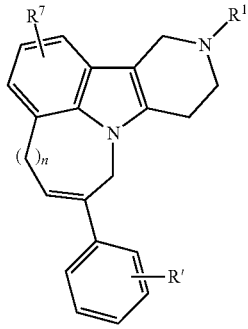

6-F

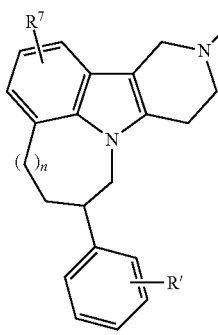

6-G
n = 0, 1

Appropriately substituted aryl hydrazine 6-A is treated with piperidone 6-B to produce the carboline tricycle 6-C. Base-mediated N-alkylation of 6-C with an appropriately substituted propene derivative results in the substituted allyl adduct 6-D. Allylation (n=1) at the bromo-substituted center of 6-D under Stille coupling conditions provides the allylated product 6-E. Finally, conversion to the cyclized tetracyclic azepino product 6-F is achieved under ring-closing metathesis (RCM) conditions involving catalysts known in the art, such as Grubbs "First Generation Catalyst", "Second Generation Catalyst", "Hoveyda-Grubbs Catalyst", and the like. Reduction of 6-F under for example, hydrogenation conditions yields the saturated derivative 6-G. Alternatively, where n=0, vinylation of 6-D provides the vinylated version of 6-E, from which RCM results in the 6-membered analog of 6-F, with successive reduction producing saturated product 6-G.

General Method B7.

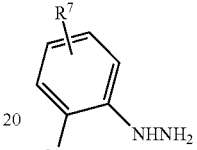 + 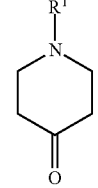

7-A          7-B

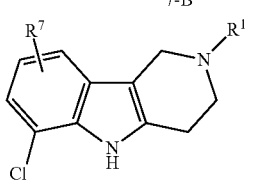

7-C

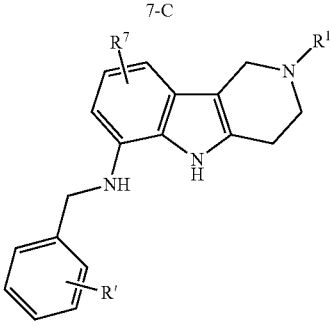

7-D

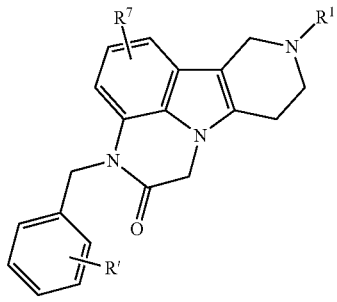

7-E

Treatment of appropriately substituted aryl hydrazine 7-A with piperidone 7-B results in the tricyclic carboline product 7-C. Palladium mediated amination of 7-C at the chloro-center, under Buchwald-Hartwig conditions, provides the aniline product 7-D. Reaction of 7-D with 2-chloroacetyl-chloride results in the tetracyclic piperazinone-type product 7-E.

General Method B8.

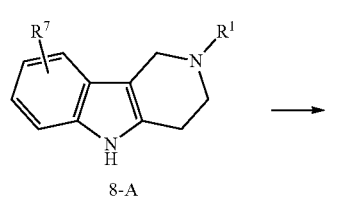
8-A

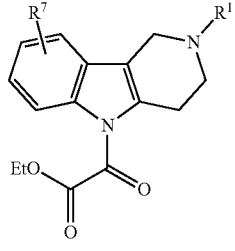
8-B

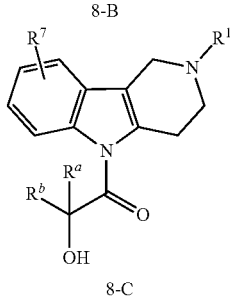
8-C

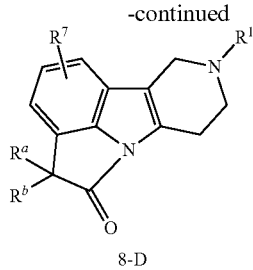
8-D

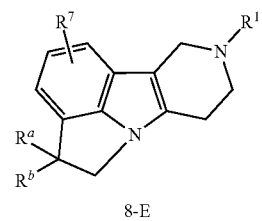
8-E $R^a$ and/or $R^b$ = alkyl, aryl

Treatment of appropriately substituted carboline 8-A with methylmagnesium chloride, followed by diethyl oxalate gave the ester intermediate 8-B which, following successive addition of the Grignard reagent $R^aMgCl$ and/or $R^bMgCl$ (or alternatively 2 equivalents of $R^aMgCl$) provides the tertiary alcohol product 8-C. Acid-mediated cyclization of 8-C affords the tetracyclic amide 8-D, from which reduction of the amide group under standard reductive conditions yields the amine final product 8-E.

General Method B9.

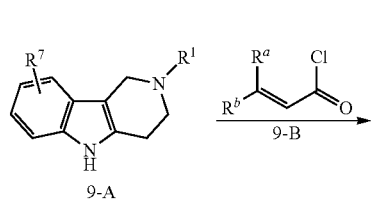
9-A    9-C

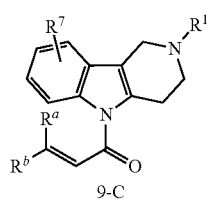

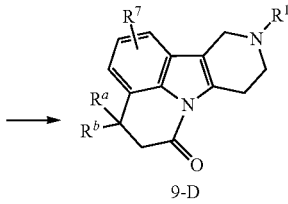
9-D

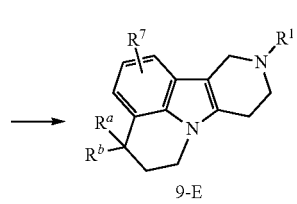
9-E

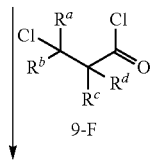
9-F

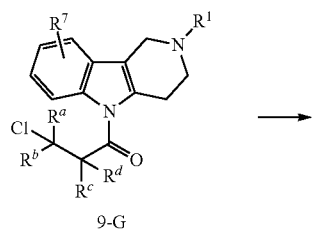
9-G

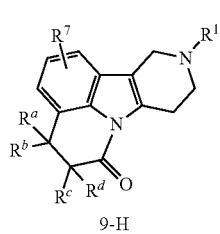
9-H

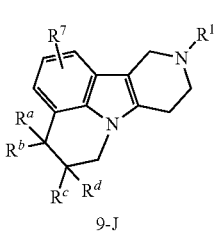
9-J $R^a$ and/or $R^b$ = H, alkyl, aryl

Treatment of appropriately substituted carboline 9-A with an α,□-unsaturated carbonyl compound such as acid chloride 9-B provides the amide 9-C. Lewis-acid-mediated cyclization of 9-C results in the tetracycfic product 9-D, whereupon reduction of which yields the final amine 9-E. Alternatively, treatment of 9-A with appropriately substituted acid chloride such as 9-F yields the amide 9-G, followed by cyclization to amide 9-H and reduction to the amine 9-J.

group under basic conditions produces the secondary amine 10-C. Further conversion, following conditions analogous to those described in General Method 4, yields the desired tetracyclic product 10-G.

General Methods for the preparation of intermediate compounds to provide bicyclic analogs described herein are presented below in General Methods 11-13. Such bicyclic intermediates can be subjected to the conditions described in the Methods presented above.

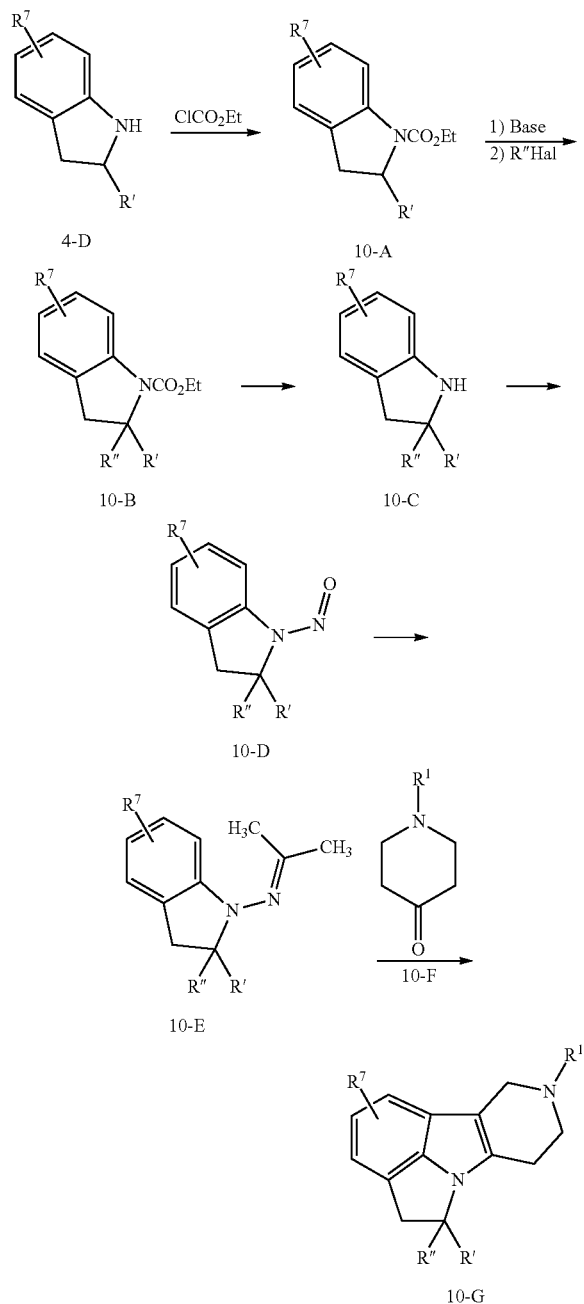

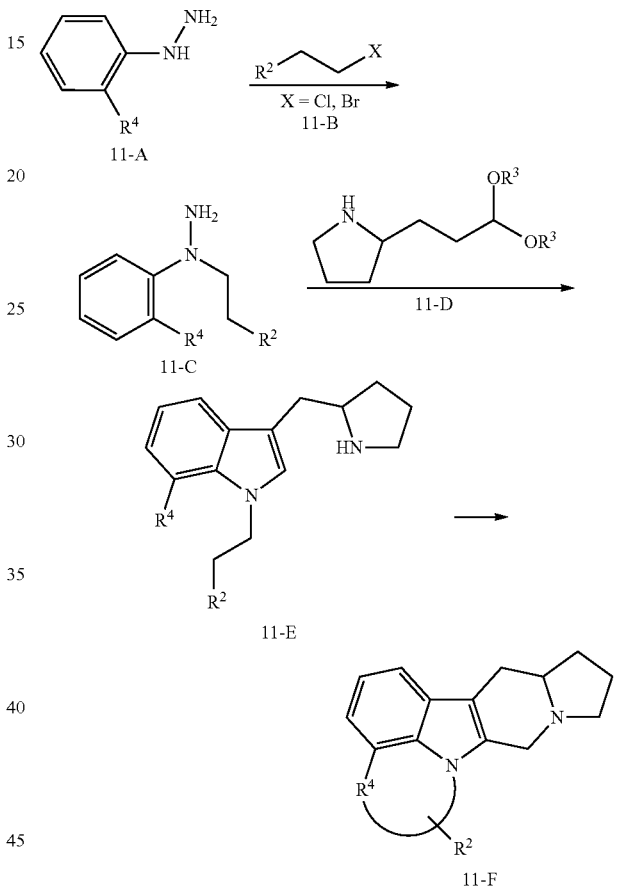

An appropriately substituted arylhydrazine 11-A is treated with alkyl halide 11-B to provide the N-alkylated product 11-C. Ring-closure of 11-C with acetal 11-D gives the 3-substituted indole 11-E which, upon heating with formaldehyde affords the tetracyclic product 11-F. The portion comprising $R^2$ and $R^4$ can be converted to a ring during this route, using the Methods described above.

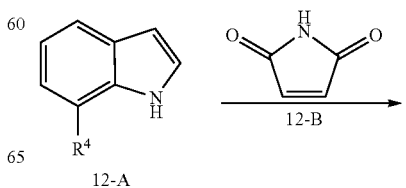

The appropriately substituted indoline such as that from General Method 4,4-D, is converted to the N-carboxyethyl derivative 10-A. Base-mediated alkylation of 10-A leads to the alkylated product 10-B. Removal of the carboxymethyl

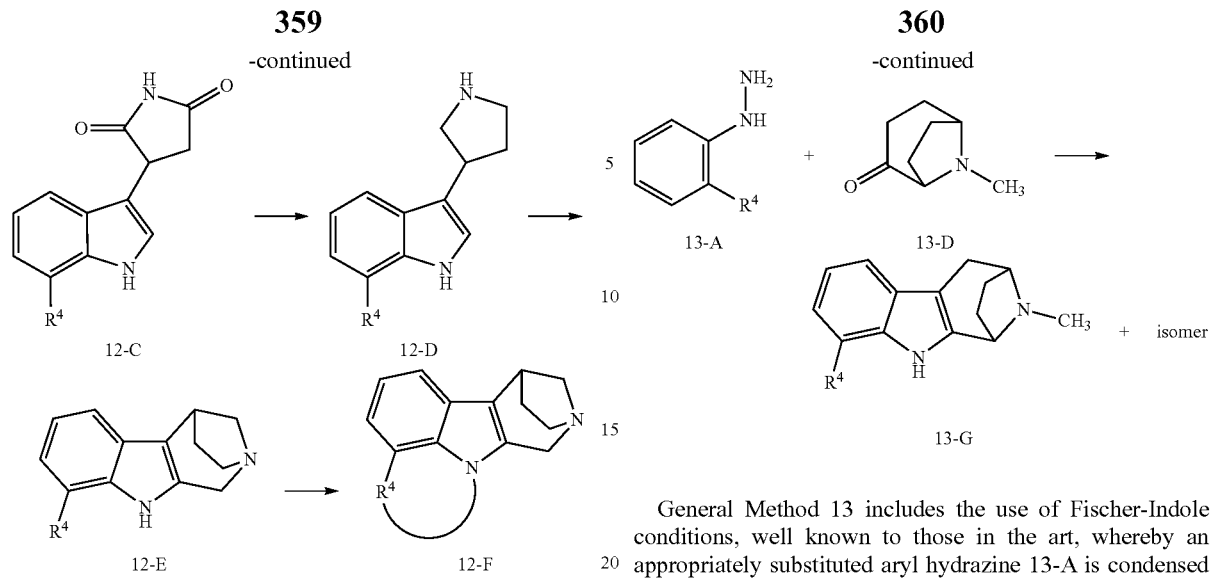

Suitably substituted indole 12-A is reacted with maleimide 12-B to give 3-substituted derivative 12-C, followed by reduction with an appropriate reducing agent to generate substituted 3-(3-pyrrolidinyl)indole 12-D. This 3-(3-pyrrolidinyl)indole 12-D can then be reacted with formaldehyde, under standard Pictet Spingler reaction conditions (U.S. Pat. No. 2,642,438) to give the bicyclo-β-carboline 12-E. This β-carboline can then be functionalized to give cyclic product 12-F in an analogous manner to those steps provided for in the other General Methods described above.

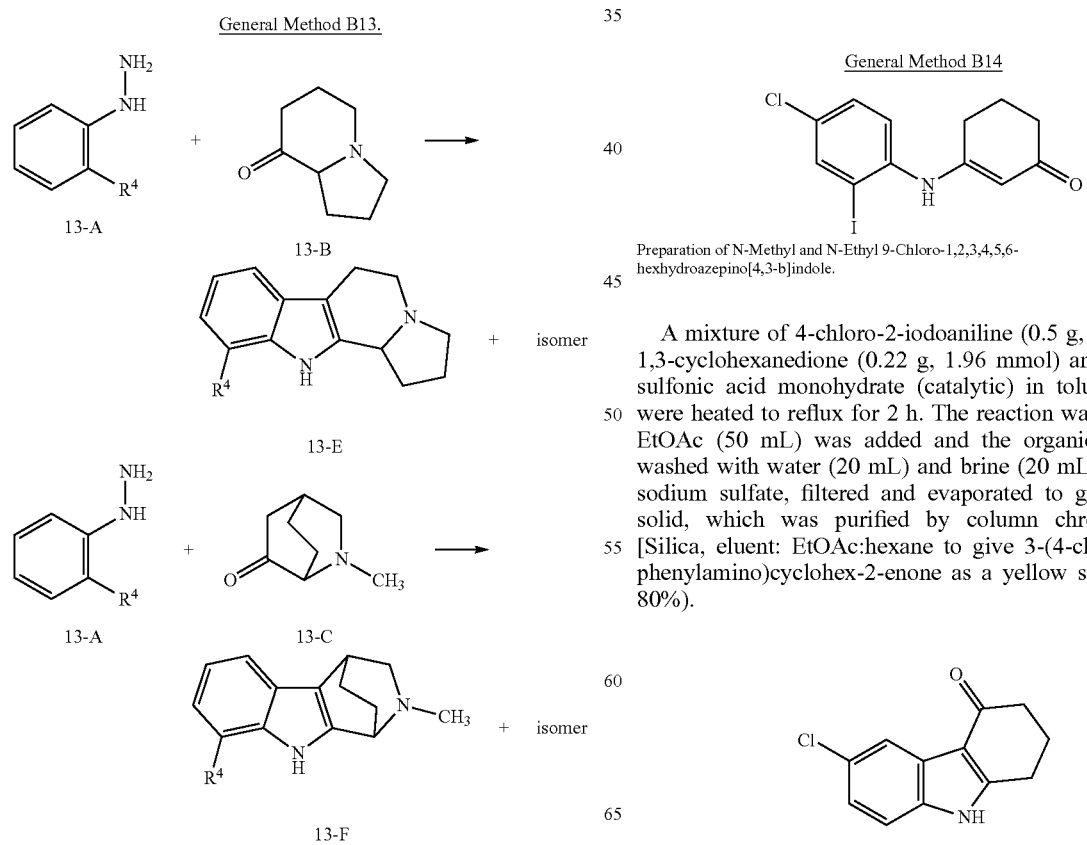

General Method 13 includes the use of Fischer-Indole conditions, well known to those in the art, whereby an appropriately substituted aryl hydrazine 13-A is condensed with various ketones, as exemplified by 13-B-13-D, to form aryl hydrazones, which are heated in dilute acid to complete the cyclization and provide the carboline products 13-E-13-G, respectively. If necessary any isomers can be separated at this stage, or after later steps. The carbolines can then be substituted at the NH position and/or at $R^4$ using the conditions described in the General Methods above. The synthesis of the bicyclic ketone intermediates has been described by Bastable et al. [J. Chem. Soc. Perkin I (1981), 1346-1351]; King et al. [J. Med. Chem. (1993), 36:683-689]; and Mewshaw et al. [J. Med. Chem. (1993), 36:343-352], the experimental details therein are hereby incorporated by reference.

General Method B14

Preparation of N-Methyl and N-Ethyl 9-Chloro-1,2,3,4,5,6-hexhydroazepino[4,3-b]indole.

A mixture of 4-chloro-2-iodoaniline (0.5 g, 1.97 mmol), 1,3-cyclohexanedione (0.22 g, 1.96 mmol) and p-toluenesulfonic acid monohydrate (catalytic) in toluene (6 mL) were heated to reflux for 2 h. The reaction was cooled and EtOAc (50 mL) was added and the organic phase was washed with water (20 mL) and brine (20 mL), dried over sodium sulfate, filtered and evaporated to give a brown solid, which was purified by column chromatography [Silica, eluent: EtOAc:hexane to give 3-(4-chloro-2-iodophenylamino)cyclohex-2-enone as a yellow solid (0.55 g, 80%).

A mixture of 3-(4-chloro-2-iodo-phenylamino)-cyclohex-2-enone (0.5 g, 1.44 mmol), cuprous iodide (27.4 mg, 0.14 mmol), L-proline (33.12 mg, 0.29 mmol) and potassium hydroxide (0.32 g, 5.70 mmol) in DMSO (6 mL) were heated to 90° C. for 24 h. The reaction was cooled and poured into water. The aqueous phase was extracted with EtOAc (3×50 mL). The combined organic phase was washed with brine (25 mL), dried over magnesium sulfate, filtered and the solvent removed under reduced pressure to give a dark brown solid. This was recrystallized using acetonitrile water to give a brown solid (0.17 g, 54%). mp 281-282° C.

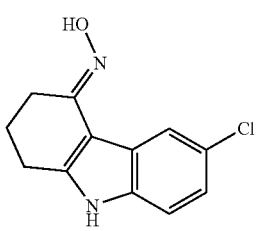 [SMILES: O/N=C1\CCCc2[nH]c3ccc(Cl)cc3c21]

A solution of 6-chloro-2,3-dihydro-1H-carbazol-4(9H)-one (500 mg, 2.27 mmol), hydroxylamine hydrochloride (238 mg, 3.41 mmol) and NaOAc (280 mg, 3.41 mmol) in EtOH:water (4.5:2 mL) was heated to reflux (125° C.) for 5 h. The reaction mixture was concentrated to dryness. Water was added to the residue and the solid filtered, dried under vacuum to yield the title compound.

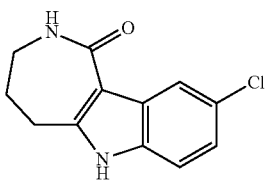 [SMILES: O=C1NCCCc2[nH]c3ccc(Cl)cc3c21]

6-Chloro-2,3-dihydro-1H-carbazol-4(9H)-one oxime (4.39 g, 18.71 mMol) and polyphosphoric acid (119 g) was heated together at 120° C. for 20 min. After cooling to RT, ice-water mixture was added to hydrolyze the mixture and stirred for 2 h. The mixture was filtered and washed with $NH_4OH$ (40 ml) followed by water. The resultant solid was dissolved in MeOH and filtered. The methanolic solution was concentrated to yield 4.7 g of crude as a brown solid. The crude product was purified by flash column chromatography over silica-gel (230-400 mesh) using EtOAc/Hexane followed by MeOH/EtOAc, the product eluting at 2-10% MeOH/EA. Yield: 2.1 g (47.8%).

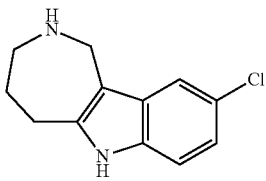 [SMILES: Clc1ccc2[nH]c3c(c2c1)CNCCC3]

To an ice-cooled stirred suspension of Lithiumaluminum hydride (486 mg, 12.8 mmol) in dry THF (29 mL) was added dropwise a solution of 9-chloro-2,3,4,5-tetrahydroazepino[4,3-b]indol-1(6H)-one (380 mg, 1.62 mmol) in dry THF (20 mL), and the reaction mixture heated to reflux for 15 h (89° C.). The reaction mixture was cooled to RT, quenched with water (3 mL), and 15% NaOH solution (6 mL) and water (9 mL), and then diluted with THF. The reaction mixture was filtered through Celite and the filtrate concentrated under reduced pressure to yield the title compound.

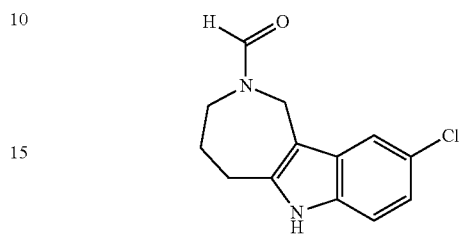

A solution of 9-chloro-1,2,3,4,5,6-hexahydroazepino[4,3-b]indole (360 mg, 1.6 mmol) in THF (1 mL) was added dropwise to ethyl formate (1 mL). The reaction mixture was stirred at RT for 30 min, followed by heating to reflux for 14 h. The solvent was removed under reduced pressure to yield the title compound.

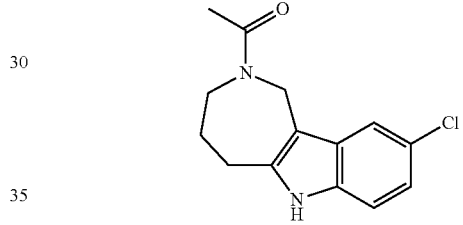

A solution of 9-chloro-1,2,3,4,5,6-hexahydroazepino[4,3-b]indole (360 mg, 1.6 mmol) was stirred in acetic anhydride for 12 h. The solvent was removed under reduced pressure to yield the title compound.

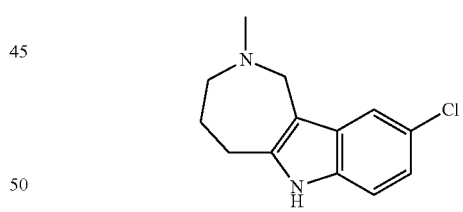

A solution of 9-chloro-1,2,3,4,5,6-hexahydroazepino[4,3-b]indole (12.3 g, 55.9 mmol) in ethylformate (369 mL) was stirred at 55° C. for 2 h. The progress of reaction was monitored by TLC. The reaction mixture was concentrated under reduced pressure and the crude product (13.5 g) was used for the next step without purification. To a stirred suspension of lithiumaluminum hydride (4.13 g, 108.8 mmol) in dry THF (405 mL) was added portionwise 9-chloro-3,4,5,6-tetrahydroazepino[4,3-b]indole-2(1H)-carbaldehyde (13.5 g) and the mixture heated to reflux for 2 h. The progress of reaction was monitored by TLC. The reaction was quenched with saturated aqueous sodium sulfate solution at 0° C., and the mixture filtered. The filtrate was dried over anhydrous sodium sulfate and evaporated to dryness. The residue was washed with diethyl ether to yield the title compound (9.7 g). ¹H NMR (DMSO) δ (ppm): 11.02 (s, 1H, D₂O exchangeable), 7.45 (s, 1H), 7.25-7.22 (d, 1H), 6.98-6.95 (d, 1H), 3.72 (s, 2H), 2.90-2.80 (m, 4H), 2.30 (s, 3H), 1.82-1.77 (m, 2H).

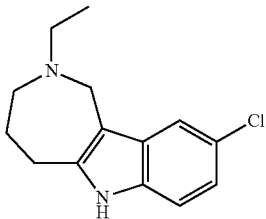 [SMILES: CCN1CCCc2[nH]c3ccc(Cl)cc3c2C1]

To an ice-cooled stirred suspension of lithiumaluminum hydride (390 mg, 10.09 mmol) in 1,4-dioxane (15 mL) was added portionwise 1-(9-chloro-4,5-dihydroazepino[4,3-b]indol-2(1H,3H,6H)-yl)ethanone (300 mg, 1.14 mmol), and the reaction mixture heated to reflux for 6 h. The reaction mixture was quenched with water (1 mL), 15% aq. NaOH solution (3 mL) and water (3 mL), and extracted with warm EtOAc (3×50 mL). The combined organic extract was concentrated and the residue purified by silica gel (230-400 mesh) flash column chromatography (100% EtOAc) to yield the title compound (115 mg).

General Method B15

Preparation of 2,9-dimethyl-1,2,3,4,5,6-hexahydroazepino[4,3-b]indole

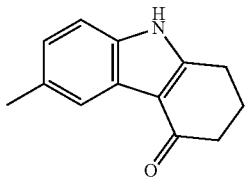

To a solution of p-tolylhydrazine hydrochloride (7.5 g, 47.2 mmol) in 1,4-dioxane:conc. H₂SO₄ (225:16.5 mL) was added cyclohexane-1,3-dione (4.42 g, 39.4 mmol), and the mixture heated to reflux for 16 h (85-90° C.). The reaction mixture was cooled to RT, basified with 15% aqueous KOH (pH 10) and extracted with EtOAc. The organic layer was washed twice with brine, dried over anhydrous sodium sulfate and concentrated under reduced pressure to yield the title compound (7.7 g, crude).

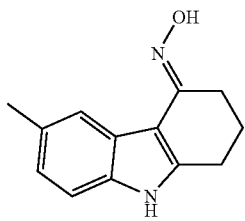 [SMILES: Cc1ccc2[nH]c3c(c2c1)/C(=N/O)CCC3]

A solution of 2,3-dihydro-6-methyl-1H-carbazol-4(9H)-one (5.8 g, 19.1 mmol), hydroxylamine hydrochloride (3.0 g, 43.6 mmol) and NaOAc (3.58 g, 43.6 mmol) in EtOH:water (58:25.3 mL) was heated to reflux (125° C.) for 5 h. The reaction mixture was concentrated to dryness. Water was added to the residue and the solid filtered, dried under vacuum to yield title compound.

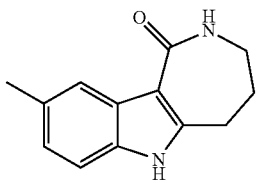 [SMILES: Cc1ccc2[nH]c3c(c2c1)C(=O)NCCC3]

To a preheated (105° C.) solution of polyphosphoric acid (225 g) was added powdered 6-methyl-2,3-dihydro-1H-carbazol-4(9H)-one oxime (10 g) under nitrogen and heating continued for 15 min. The reaction mixture was cooled and to it was added crushed ice water. The crystallized solid obtained was collected by filtration. The solid was washed with water and then by dilute ammonium hydroxide, then dried under vacuum to obtain the desired product (8 g, crude product).

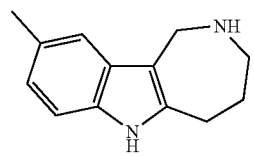

Lithiumaluminum hydride (3 g, 78.95 mmol) was placed in 1,4-dioxane (100 mL) under inert atmosphere and 9-methyl-2,3,4,5-tetrahydroazepino[4,3-b]indol-1(6H)-one (3 g, 14.018 mmol) was added, and the mixture heated to reflux for 15 h. The reaction was monitored by TLC. The reaction was quenched with saturated aqueous sodium sulfate at 0° C., and the reaction mixture filtered. The filtrate was dried over anhydrous sodium sulfate and evaporated to dryness to afford solid, which was washed with water followed by EtOAc, and dried to afford 1.25 g of the title compound.

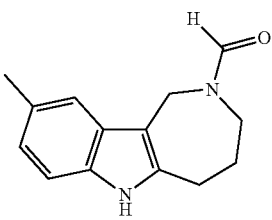 [SMILES: Cc1ccc2[nH]c3c(c2c1)CN(C=O)CCC3]

9-Methyl-1,2,3,4,5,6-hexahydroazepino[4,3-b]indole (0.25 g, 1.25 mmol) was taken in ethylformate (18 mL, 227 mmol) and stirred at 55° C. for 3 h. The reaction was monitored by TLC. The reaction mixture was evaporated under reduced pressure and used for the next step without purification (0.2 g).

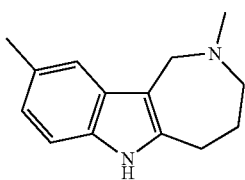 [SMILES: Cc1ccc2[nH]c3c(c2c1)CN(C)CCC3]

To a stirred suspension of lithiumaluminum hydride (2 g, 52.63 mmol) in dry THF (150 mL) was added portionwise 9-methyl-3,4,5,6-tetrahydroazepino[4,3-b]indole-2(1H)-carbaldehyde (5.9 g, 25.87 mmol) and the reaction mixture stirred at 55° C. for 2 h. The progress of reaction was monitored by TLC. The reaction mixture was quenched with saturated sodium aqueous sulfate solution at 0° C. and then filtered. The filtrate was dried over anhydrous sodium sulfate and evaporated to dryness to afford the title compound (5.2 g). $^1$H NMR (DMSO) δ (ppm): 7.12-7.05 (m, 2H), 6.80-6.6.76 (d, 1H), 3.65 (s, 2H), 2.90-2.80 (m, 4H), 2.34 (s, 3H), 2.26 (s, 3H), 1.80-1.72 (m, 2H).

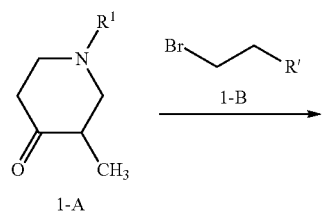

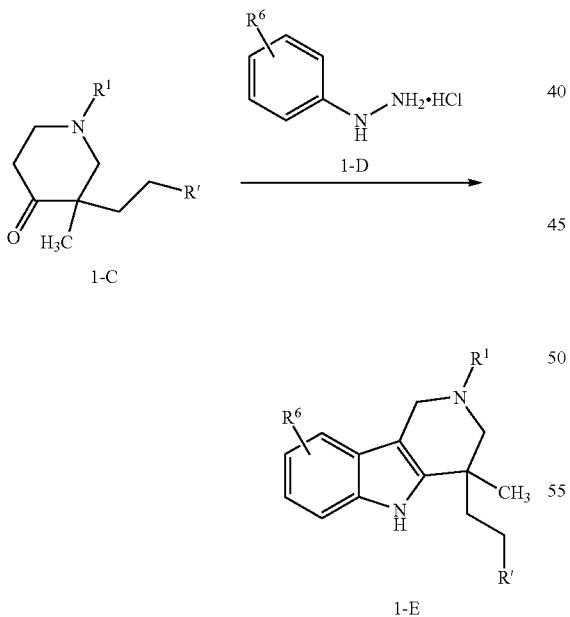

Treatment of appropriately substituted dimethylpiperidine 1-A with bases such as sodium hydride followed by addition of electrophile 1-B provides the alkylated product 1-C which, after heating with appropriately substituted hydrazine 1-D in the presence of acid provides the cyclized carboline product 1-E.

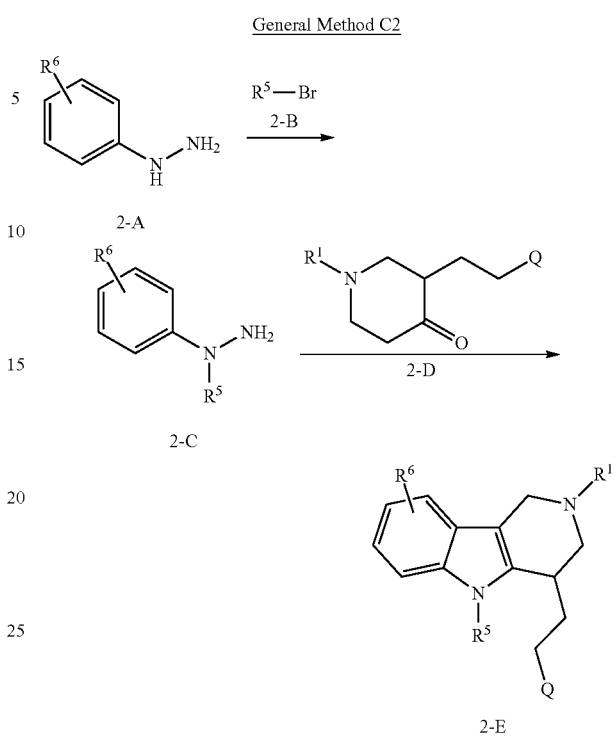

Treatment of appropriately substituted hydrazine 2-A with base and electrophile 2-B yields alkylated hydrazine product 2-C which, after heating with acid and appropriately substituted piperidone 2-D provides the cyclized carboline product 2-E.

Substituted piperidones of the type exemplified as compound 2-D in General Method 2 can be prepared through a number of means known to those skilled in the art. Common utilized conditions comprise a base-mediated treatment of compound 3-A with an electrophile such as R—X to produce the α-substituted product 3-B, which would be utilized as described in General Methods 1 and 2 to prepare compounds of the type 3-C. R can also be aromatic, wherein conditions can comprise palladium-mediated coupling reagents. Alternative electrophiles could include, for example, aldehydes, esters, carbonates, anhydrides, and the like.

Compounds of formulae (A1)-(A4), (A1a-A1r), (A3a)-(A3h), and variations thereof, are exemplified in Table 1 as compounds A1-A160. Compounds of formulae (B1)-(B4), (B1a)-(B1bm), (B3a-B3d), and variations thereof, are exemplified in Table 2 as compounds B1-B242. Compounds of formulae (C1)-(C4), (C1a)-(C1r), (C3a)-(C3h), and variations thereof, are exemplified in Table 3 as compounds C1-C136. Compounds of formulae (D1)-(D4), (D1a)-(D1bm), (D3a)-(D3d), and variations thereof, are exemplified in Table 4 as compounds D1-D266.

In one aspect, a selective adrenergic receptor $\alpha_{2B}$ antagonist as provided herein exhibits the ability to cross blood-brain barrier. In another aspect, a selective adrenergic receptor $\alpha_{2B}$ antagonist as provided herein is not able to cross blood-brain barrier. In one aspect, a selective adrenergic receptor $\alpha_{2B}$ antagonist as provided herein exerts its therapeutic effect in the brain only. In one aspect, a selective adrenergic receptor $\alpha_{2B}$ antagonist as provided herein exerts its therapeutic effect in the periphery only. In one aspect, a selective adrenergic receptor $\alpha_{2B}$ antagonist as provided herein exerts its therapeutic effect both in the brain and peripherally.

Preferably, the selective adrenergic receptor $\alpha_{2B}$ antagonists are orally bioavailable. However, the compounds may also be formulated for parenteral (e.g., intravenous) administration. In some settings, parenteral administration of a selective adrenergic receptor $\alpha_{2B}$ antagonist may be desired. For example, intra-renal delivery may offer treatment options for acute and chronic renal failure and acute decompensated congestive heart failure.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., reducing the blood pressure of an individual, promoting renal blood flow and/or decreasing or inhibiting sodium reabsorption.

Methods as provided herein may comprise administering to an individual a pharmacological composition that contains an effective amount of a compound and a pharmaceutically acceptable carrier. The effective amount of the compound may in one aspect be a dose of between about 0.01 and about 100.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Compositions comprising a compound provided herein are also described. In one variation, the composition comprises a compound and a pharmaceutically acceptable carrier or excipient. In another variation, a composition of substantially pure compound is provided.

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for any one or more of the following uses: treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention also provides compositions (including pharmacological compositions) as described herein for the use in treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption and other methods described herein.

The following Examples are provided to illustrate but not to limit the invention.

All references disclosed herein are incorporated herein by reference in their entireties.

EXAMPLES

Example B1

Determination of the Ability of Compounds of the Invention to Bind an Adrenergic Receptor Adrenergic $\alpha_{2A}$ To evaluate in radioligand binding assays the activity of compounds, human recombinant adrenergic $\alpha_{2A}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds were incubated with 1 nM [$^3$H]MK-912 for 60 min at 25° C. MK912 is (2S-trans)-1,3,4,5',6,6', 7,12b-octahydro-1',3'-dimethyl-spiro[2H-benzofuro[2,3-a] quinolizine-2,4'(1'H)-pyrimidin]-2'(3'H)-one hydrochloride. Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Compounds were tested in this biochemical assay and percent inhibition of specific binding was determined. Biochemical assay results are presented as the percent inhibition of specific binding in Tables B1A-B1D.

Adrenergic $\alpha_{2B}$

To evaluate in radioligand binding assays the activity of compounds, human recombinant adrenergic $\alpha_{2B}$ receptor expressed in Chinese hamster ovary (CHO) K1 cells (Uhlen, S. et al, Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds were incubated with 2.5 nM [$^3$H]Rauwolscine for 60 min at 25° C. Non-specific binding was estimated in the presence of 10 µM Prazosin. Receptor proteins were filtered and washed, the filters were then counted to determine [$^3$H]Rauwolscine specifically bound. Compounds were screened at 1 µM or lower, using 1% DMSO as vehicle. Compounds were tested in this biochemical assay and percent inhibition of specific binding was determined. Biochemical assay results are presented as the percent inhibition of specific binding in Tables B1A-B1D.

Adrenergic $\alpha_{1B}$

To evaluate in radioligand binding assays the activity of compounds, rat adrenergic $\alpha_{1B}$ receptor obtained from Wistar Rat liver (Garcia-S'ainz, J. et al, Biochem. Biophys. Res. Commun. 186:760, 1992; Michel, A. et al, Br. J. Pharmacol. 98:883, 1989) in a modified Tris-HCl buffer (50 mM Tris-HCl buffer, pH 7.4, 0.5 mM EDTA) was used. Compounds were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H] Prazosin specifically bound. Compounds were screened at 1 µM or lower, using 1% DMSO as vehicle. Compounds were tested in this biochemical assay and percent inhibition of specific binding was determined. Biochemical assay results are presented as the percent inhibition of specific binding in Tables B1A-B1D.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. et al, Br. J. Pharmacol. 115(6):981, 1995) in a 50 mM Tris-HCl buffer, pH 7.4, was used. Compounds were incubated with 0.6 nM [3H]Prazosin for 60 min at 25° C. Non-specific binding was estimated in the presence of 10 µM phentolamine. Receptor proteins were filtered and washed, the filters were then counted to determine [3H]Prazosin specifically bound. Compounds were screened at 1 µM or lower, using 1% DMSO as vehicle. Biochemical assay results are presented as the percent inhibition of specific binding in Tables B1A-B1D.

TABLE B1A

Percentage inhibition of ligand binding to aminergic G protein-coupled receptors by compounds of the invention:

| Compound No. | Adrenergic (0.1 µM) | | | | Adrenergic (0.03 µM) |
|---|---|---|---|---|---|
| | $\alpha_{1B}$ | $\alpha_{2A}$ | $\alpha_{2B}$ | $\alpha_{1D}$ | $\alpha_{2B}$ |
| A7 | 2 | 10 | −9 | 4 | — |
| A8 | −3 | 20 | −1 | 3 | — |
| A9 | −9 | 0 | −7 | −1 | — |
| A10 | 11 | 23 | 8 | 26 | — |
| A11 | −1 | 4 | 14 | −1 | — |
| A12 | 2 | −4 | 6 | 38 | — |
| A13 | −9 | −12 | 5 | 8 | — |
| A14 | 0 | 12 | −3 | −9 | — |
| A15 | 0 | 20 | 21 | 5 | — |
| A16 | 1 | 31 | 17 | −2 | — |
| A17 | 9 | 14 | 21 | −5 | — |
| A18 | 30 | 6 | 38 | 34 | — |
| A43 | −1 | 7 | — | — | 26 |
| A44 | −3 | −5 | — | — | 31 |

TABLE B1B

Percentage inhibition of ligand binding to aminergic G protein-coupled receptors by compounds of the invention:

| Compound No. | Adrenergic (1 μM) | | | Adrenergic (0.1 μM) | | | |
|---|---|---|---|---|---|---|---|
| | $\alpha_{1D}$ | $\alpha_{2A}$ | $\alpha_{2B}$ | $\alpha_{1B}$ | $\alpha_{2A}$ | $\alpha_{2B}$ | $\alpha_{1D}$ |
| B1 | 28 | 15 | 47 | — | — | — | — |
| B2 | 24 | 89 | 74 | — | — | — | — |
| B3 | 38 | 89 | 68 | — | — | — | — |
| B12 | — | — | — | 28 | 75 | 72 | 28 |
| B160 | — | — | — | 2 | −1 | −8 | 15 |
| B161 | — | — | — | 2 | 13 | 7 | 1 |
| B162 | — | — | — | −6 | 14 | 27 | −2 |
| B163 | — | — | — | 6 | 5 | 4 | 15 |
| B164 | — | — | — | 12 | 6 | 16 | 2 |
| B165 | — | — | — | 0 | 40 | 43 | 0 |
| B210 | — | — | — | — | — | 14 | — |
| B211 | — | — | — | — | — | 82 | — |

TABLE B1C

Percentage inhibition of ligand binding to aminergic G protein-coupled receptors by compounds of the invention:

| Compound No. | Adrenergic (0.1 μM) | | | |
|---|---|---|---|---|
| | $\alpha_{1B}$ | $\alpha_{2A}$ | $\alpha_{2B}$ | $\alpha_{1D}$ |
| C47 | 34 | 15 | 32 | 10 |
| C48 | 20 | 2 | −12 | 13 |

TABLE B1D

Percentage inhibition of ligand binding to aminergic G protein-coupled receptors by compounds of the invention:

| Compound No. | Adrenergic (0.1 μM) | | | |
|---|---|---|---|---|
| | $\alpha_{1B}$ | $\alpha_{2A}$ | $\alpha_{2B}$ | $\alpha_{1D}$ |
| D10 | −3 | −1 | −6 | −6 |
| D11 | 16 | 8 | 30 | −5 |
| D12 | 10 | 5 | −7 | −3 |

Example B2

Functional Activity on Recombinant Adrenergic $\alpha_{1B}$, Adrenergic $\alpha_{2A}$, Adrenergic $\alpha_{2B}$ and Adrenergic $\alpha_{1D}$ Receptors Using Aequorin and GTPγS Functional Assays To study the functional activity of compounds of the invention on the human recombinant adrenergic $\alpha_{2B}$, adrenergic $\alpha_{2A}$, adrenergic $\alpha_{1B}$ or adrenergic $\alpha_{1D}$ with Aequorin functional assays and on the human recombinant adrenergic $\alpha_{2B}$ receptor with GTPγS assay, CHO—K1 cell lines expressing adrenergic $\alpha_{2B}$, adrenergic $\alpha_{2A}$, adrenergic $\alpha_{1B}$ or adrenergic $\alpha_{1D}$ recombinant receptor, mitochondrial apoaequorin and Gα16 are used for the Aequorin assay. CHO—K1 cell line expressing the recombinant $\alpha_{2B}$ receptor is amplified to prepare membranes used for the GTPγS assay.

The following reference agonists are used as both the reference ligand in agonist mode and as the agonist that needs to be inhibited in antagonist mode.

| Assay | $\alpha_{1B}$ (aeq) | $\alpha_{1D}$ (aeq) | $\alpha_{2A}$ (aeq) | $\alpha_{2B}$ (aeq) | $\alpha_{2B}$ (GTPgS) |
|---|---|---|---|---|---|
| Agonist ligand | Cirazoline | Cirazoline | UK 14304 | Oxymetazoline | Guanfacine |

Aequorin Assay Procedure: Aequorin adrenergic $\alpha_{1B}$ (FAST-008A), adrenergic $\alpha_{2A}$ (FAST-006A) or adrenergic $\alpha_{2B}$ (FAST-007A) cells are grown 18 h prior to the test in media without antibiotics. They are then detached by gentle flushing with PBS-EDTA (5 mM EDTA), recovered by centrifugation and re-suspended in "assay buffer" (DMEM/HAM's F12 with HEPES+0.1% BSA protease free). Cells are incubated at RT for at least 4 h with Coelenterazine h (Molecular Probes). Dose response curves with reference compounds are performed before testing the compounds of the invention. The $\alpha_{1B}$ reference agonist and antagonist are cirazoline and qinazofine, respectively. The $\alpha_{2A}$ reference agonist and antagonist are UK14,304 and rauwolscine, respectively. The $\alpha_{2B}$ reference agonist and antagonist are oxymetazoline and rauwolscine, respectively.

For agonist testing, 50 μL of cell suspension are injected on 50 μL of test compound or reference agonist plated in a 96-well plate. The resulting emission of light is recorded using the Hamamatsu Functional Drug Screening System 6000 (FDSS 6000). For antagonist testing, following an incubation of 15 min. after the first injection, 100 μL of reference agonist at a concentration corresponding to its $EC_{80}$ is injected on the 100 μL of the mixture of cell suspension and test compound. The resulting emission of light is recorded using the same luminometer as for agonist testing. To standardize the emission of recorded light (determination of the "100% signal") across plates and across different experiments, some of the wells contained 100 μM digitonin or a saturating concentration of ATP (20 μM). Plates also contained the reference agonist at a concentration equivalent to the $EC_{80}$ obtained during the test validation.

Agonist activity of test compound is expressed as a percentage of the activity of the reference agonist at its $EC_{100}$ concentration. Antagonist activity of test compound is expressed as a percentage of the inhibition of reference agonist activity at its $EC_{80}$ concentration.

Compounds are tested for agonist & antagonist activity at the human adrenergic $\alpha_{1B}$ (FAST-008A), adrenergic $\alpha_{2A}$ (FAST-006A) or adrenergic $\alpha_{2B}$ (FAST-007A) at the following nanomolar concentrations, in duplicate: Agonist (nM): 0.3, 1, 3, 10, 30, 100, 300, 1000, 3000, 10000; Antagonist (nM): 0.15, 0.5, 1.5, 5, 15, 50, 150, 500, 1500, 5000.

GTPγS Assay Procedure: The procedure is carried out with the following: assay buffer [20 mM HEPES pH 7.4; 100 mM NaCl, 10 μg/mL saponin, 1 mM $MgCl_2$]; membranes [Recombinant CHO—K1-adrenergic $\alpha_{2B}$ membrane extracts thawed on ice and diluted in assay buffer to give 10 μg/well and kept on ice]; GDP [diluted in assay buffer to give 3 μM final concentration]; beads [PVT-WGA (Amersham, RPNQ0001), diluted in assay buffer at 0.5 mg/well]; GTPγ$^{35}$S [(PerkinElmer NEG030X), diluted in assay buffer to give 0.1 nM final concentration]; ligand [Guanfacine (Tocris, 1030) as reference agonist and Rauwolscine (Tocris, 891) as reference antagonist, diluted in assay buffer]. Membranes are mixed with GDP (volume:volume) and incubated for at least 15 min. on ice. In parallel, GTPγ[$^{35}$S] is mixed with the beads (volume:volume) just before starting the reaction.

For agonist testing, the following reagents are successively added in the wells of an Optiplate (Perkin Elmer): 50

µL of test or reference ligand, 20 µL of the membranes:GDP mix, 10 µL of assay buffer and 20 µL of the GTPγ[$^{35}$S]:beads mix. For antagonist testing, the following reagents are successively added in the wells of an Optiplate (Perkin Elmer): 50 µL of test or reference ligand, 20 µL of the membranes:GDP mix, and then after an incubation of 15 min. at RT, 10 µL of reference ligand at historical EC$_{80}$ concentration and 20 µL of the GTPγ[$^{35}$S]:beads mix.

The plates are covered with a top seal, mixed on an orbital shaker for 2 min, and then incubated for 1 h at RT. Then the plates are centrifuged for 10 min. at 2000 rpm, incubated at RT 4 h and counted for 1 min/well with a Perkin Elmer TopCount reader.

Compounds are tested for antagonist activity at the human adrenergic α$_{2B}$ receptor (FAST-007G) at the following nanomolar concentrations, in duplicate: Agonist and antagonist (nM): 0.3, 1, 3, 10, 30, 100, 300, 1000, 3000, 10000.

Inverse Agonist Activity

SPA 35S-GTPgS and Radioligand Binding experiments are conducted with Euroscreen membrane preparations. Compound is tested for inverse agonist activity at the human Adrenergic α$_{2A}$ receptor using GTPg35S binding functional assay (FAST-006G) in dose-response and in duplicates.

Example B3

Cell Culture and Cell Viability Assay

SH-SY5Y cells cultured in DMEM/F12 media supplemented with 10% FBS were seeded in 96-well microplates at 150,000 cells/cm$^2$. After 24 h, cells were depleted from FBS and kept in culture for 24 h before the experiment. A stock solution was prepared by dissolving the calcium ionophore 4-Br-A23187 (Calbiochem Cat.N° 100107) in DMSO at 25 mM. Cells were then treated with 4-Br-A23187 (2 µM), hydrogen peroxide (300 µM) or the mitochondrial toxin rotenone (25 µM) in the presence of vehicle or Compound of the Invention for 24 h. Cell death was determined by measurements of LDH release according to the Cytotoxicity Detection KitPlus (Roche, Mannheim, Germany). Cell viability was determined by measuring the capacity of cells to metabolize MTS tetrazolium (MTS) according to the Cytotoxicity Detection KitPlus (Roche, Mannheim, Germany) and MTS reduction was assessed by the CellTiter 96® AQueous One Solution Cell Proliferation assay (Promega Corporation, Madison, Wis., USA). Compounds were screened at 10 nM, using DMSO as vehicle. Assay results for the experiments with Br-A23187 are presented as the MTS reduction capacity (cell viability) of untreated cells (control), 4-Br-A23187-treated cells (vehicle), and co-incubation of Br-A23187 with Compounds of the Invention treated cells and using p-trifluoromethoxyphenylhydrazone (FCCP) at 10 µM for 30 min as a control. This assay assesses the ability of the test compounds to protect against cell death mediated by mitochondrial dysfunction. In the assay, the calcium ionophore 4-Br-A23187 was used to challenge the cells, causing calcium levels to rise in mitochondria, which leads to depolarization and cell death. Test compounds were assessed for their ability to prevent cell death in response to challenge with 4-Br-A23187.

TABLE B3

Relative Cytoprotection efficiency of compounds of the invention

| Compound No. | Relative Cytoprotective capacity | SE | p value |
|---|---|---|---|
| Control | 100 | 1.47E−06 | — |
| Vehicle | 0 | 0 | — |
| A1 | −1.10264 | 48.94656 | ns |
| A2 | −4.4068 | 30.13848 | ns |
| A3 | 35.08263 | 11.90545 | ns |
| A5 | 28.81883 | 6.21819 | 0.0435 |
| A6 | 27.59688 | 3.322046 | 0.0142 |
| A9 | 15.84906 | 12.76087 | ns |
| A11 | 37.63225 | 18.00517 | ns |
| A12 | 35.74884 | 18.90774 | ns |
| A13 | 19.74211 | 12.6988 | ns |
| A17 | 10.7958 | 19.56162 | ns |
| A18 | 26.00401 | 19.9292 | ns |
| C43 | 9.618124 | 27.03942 | ns |
| C44 | −0.63416 | 27.95942 | ns |
| C45 | 4.347974 | 27.88415 | ns |
| C46 | −0.04527 | 28.24442 | ns |
| C48 | 52.14072 | 23.16085 | ns |
| D2 | 38.36419 | 24.02967 | ns |
| D5 | 72.11077 | 1.524916 | 4.00E−04 |
| D7 | 72.05842 | 8.628121 | 0.014 |
| D8 | 73.11748 | 10.89231 | 0.0215 |
| D9 | 81.05257 | 2.423629 | 9.00E−04 |
| D11 | 30.32596 | 2.105927 | 0.0048 |
| D12 | 32.51647 | 14.49203 | ns |

Example B4

Cell Culture and Cell Viability Assay

Cell Culture. SH-SY5Y cells stably transfected with a doxycycline-inducible wild-type α-synuclein (α-syn) gene along with control SH-SY5Y cells over-expressing the β-galactosidase (β-gal) gene (a gift from L. Stefanis, Division of Basic Neurosciences, Biomedical Research Foundation of the Academy of Athens, Athens, Greece) are cultured as described by Vekrellis et al. (Vekrellis K, Xilouri M, Emmanouilidou E, Stefanis L. (2009). Inducible over-expression of a-syn in human neuronal cells leads to caspase-dependent non-apoptotic death. J. Neurochem. 109, 1348-1362). In accordance with this method, cells are cultured and maintained in RPMI 1640, 10% fetal bovine serum supplemented with 250 µg/mL G418 and 50 µg/mL Hygromycin B. Expression of α-syn is switched off in stock cultures with doxycycline (2 µg/mL). For experimental procedures, cells are plated at (4–8×10$^4$ cells/cm$^2$) and differentiated in absence of doxycycline and in the presence of 20 µM all-trans retinoic acid (RA) (Sigma, St Louis, Mo., USA).

Viability Assay: Cells are cultured in 96-well plates. After 24 h, cells are treated with RA and Compounds of Invention at 0.1 and 10 nM in the absence of doxycyline. Culture medium with RA and drugs is fully replaced after 7 days. Cell viability is measured by the release of lactate dehydrogenase (LDH) from necrotic cells into the culture medium and by measuring the capacity of cells to metabolize MTS tetrazolium (MTS) after 14 days in culture. LDH leakage is assessed according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA).

Immunoblotting of α-synuclein and α-synuclein Aggregates: Cells stably expressing α-synuclein are cultured in 6-well plates at a density of 4×10$^4$ cells/cm$^2$ cells per well.

Cells are differentiated and treated with Compound of the Invention at 10 nM in absence of dox after 24 h of plating. Drug treatments are repeated after 7 days in freshly prepared medium containing RA. After 14 days, cells are washed twice with cold PBS and lysed in lysys buffer containing 1% Triton X-100, 20 mM HEPES, 150 mM NaCl, 10% glycerol, 1 mM EGTA, 1.5 mM $MgCl_2$, 1 mM PMSF pH 7.4, and 1× protease inhibitor mixture (Roche, Mannheim, Germany). Lysates are homogenized and subjected to four successive freeze-thaw cycles to disrupt membranes. Triton soluble fractions and triton insoluble pellets are obtained by ultra-centrifugation at 100,000×g for 30 min at 4° C. The concentration of protein in each fraction is determined by BCA assay (Thermo Scientific). Samples from total, soluble and triton insoluble fractions, are boiled in 1× sample buffer (20 mM Tris, 1% glycerol, 180 mM β-mercaptoethanol, 0.003% bromophenol blue, and 2% SDS, pH 6.8), loaded on 12% SDS-PAGE gels, and transferred to polyvinylidene difluoride (PVDF) membranes (0.2 μM-pore immobilon Biorad). Membranes are blocked in 1×TBS-Tween (20 mM Tris, pH 7.4, 150 mM NaCl, and 0.2% Tween 20) containing 5% milk for 1 h and incubated overnight at 4° C. with the following primary antibodies in blocking solution at the indicated dilutions: monoclonal anti-α-synuclein α-syn-1 (1:1000; BD Transduction Laboratories). (Perrin, R. J., Payton, J. E., Barnett, D. H., Wraight, C. L., Woods, W. S., Ye, L., and George, J. M. (2003). Epitope mapping and specificity of the anti-α-synuclein monoclonal antibody Syn-1 in mouse brain and cultured cell lines. Neurosci. Lett. 349, 133-135), and monoclonal vimentin (1:1000; BD PharMingen). Primary antibodies are detected with secondary anti-mouse antibodies conjugated to HRP (1:5000).

Isolation of RNA and RT-quantitative PCR (RT-qPCR): SH-SY5Y cells stably over-expressing α-syn are treated with Compound of the Invention (10 nM). Total RNA from these cells as well as control cells not treated with Compound is extracted using the E.Z.N.A RNA extraction Kit (OMEGAbiotek, Norcross, Ga.). 1 μg of RNA is reverse transcribed to cDNA using the M-Mulv reverse transcriptase enzyme (Promega Corporation, Madison, Wis., USA). RT-qPCR of cDNA templates is carried out using TAQMAN probes for human α-synuclein (Hs00240906_M1) and TAQ-MAN masterMix (Applied Biosystems) and a Mx3005P real-time PCR system (Agilent Technologies Inc., Santa Clara, Calif.). Levels of alpha-tubulin mRNA are used to normalize the amounts of total RNA between samples. Fold changes are calculated as described by (Pfaffl, M. W. (2001). A new mathematical model for relative quantification in real-time RT-PCR. Nucleic Acids Res 29, e45).

Example B5

Insulin Secretion Ability—In Vitro

Islet Isolation and In-Vitro Insulin Release from Rat Islets: Rat isolated pancreatic islets are prepared from rat pancreas by collagenase digestion. After digestion, islets are hand-picked and incubated in a humidified atmosphere with RPMI 1640 tissue culture medium supplemented with 10% (vol/vol) fetal bovine serum and penicillin/streptomycin [Carter J D, Dula S B, Corbin K L, Wu R, Nunemaker C S. (2009) "A practical guide to rodent islet isolation and assesment." Biol. Proced. Online 11(1): 3-31]. In-vitro insulin secretion is measured in static incubations. Prior to experiments, islets are preincubated for 1 hour at 37° C. in a Krebs-Ringer bicarbonate buffer composed of 120 mM NaCl, 25 mM $NaHCO_3$, 5 mM KCl, 1 mM $MgCl_2$, 2.5 mM $CaCl_2$, 2.8 mM glucose and 0.5% bovine serum albumin. The medium is gassed with 100% $CO_2$ for 15 minutes to obtain constant pH. Next, groups of 15 islets are incubated in 1 mL for 60 minutes at 37° C. in Krebs-Ringer buffered solution supplemented with glucose (2.8 mM as low glucose or 20 mM as high glucose), test compound, clonidine, yohimbine or norepinephrine as indicated. Immediately after incubation, an aliquot of the medium is removed for analysis of insulin content by ELISA (Mercodia). This assay demonstrates the effect of the test compound on insulin release, in competition with either norepinephrine or clonidine.

Example B6

Insulin Secretion Ability—In Vitro

To demonstrate the insulin secretion ability and/or glucose lowering effect of a test compound of the invention, several animal models are used, including clonidine (an $\alpha_{2A}$ agonist) induced, norepinephrine (a natural ligand of $\alpha_{2A}$) induced, glucose induced, and spontaneous (no agonist) rat (nomal Wistar rats or spontaneously hypertensive rats with obesity (SHR.OB)) models of hyperglycemia and norepinephrine induced and spontaneous (no agonist) obese mouse (ob/ob) models of hyperglycemia. These models and their pathophysiology are reported in e.g., Kuhn C. M. et al., *Pharmacol. Biochem. Behav.* 26:491-495 (1987); Velliquette R. A. and Ernsberger P, *J. Pharmacol. Exp. Ther.* 306:646-657 (2003); Rosengren A. H., et al., *Science,* 327:217-220 (2010); Chen B., et al., *Exp. Biol. Med.,* 236:309-414 (2011); and Saperstein R., et al., *Metabolism,* 39:445-451 (1990). To rule out the possible hypoglycemic effects, normoglycemic rats are used. Male or female 16 week old spontaneously hypertensive obese rats (SHR.OB), 10 week old male Wistar rats and 10 week old male ob/ob mice are utilized in these studies. Free access to standard lab chow and reverse osmosis (RO) water is supplied to all rats. All aspects of this work, including housing and feeding, experimentation and disposal of animals are performed in general accordance with the Guide for the Care and Use of Laboratory Animals (National Academy Press, Washington, D.C., 1996).

Effect of Test Compound on Blood Glucose Levels in Clonidine Induced Rat Models of Hyperglycemia:

In separate studies, six hour fasted SHR.OB or Wistar rats are randomized according to their baseline blood glucose levels and divided into several groups with an "n" of 4 for group depending on the experimental design. All the experimental agents are dissolved in sterile saline or appropriate solvents and administered sub-cutaneously (SC), oral (PO) or intra-peritoneal (IP) as indicated. The vehicle group received saline alone via SC route. Test compound at doses of 0 (vehicle), 6 mg/kg and 18 mg/kg in SHR.OB rats; and 0 (vehicle), 5 mg/kg and 15 mg/kg to Wistar rats are administered via SC route at −30 minutes. Hyperglycemia is induced in both SHR.OB and Wistar rats with clonidine at a dose of 0.05 mg/kg via PO route at 0 min. At all the study points, blood glucose levels are measured by one touch glucose meter (Lifescan, Milpitas, Calif.). The tip of the tail is snipped by sharp scissors and gently squeezed for a drop of blood. The glucose strip is inserted in the slot of the hand-held glucose meter and a drop of blood is added to the strip. Within 20 seconds, the device determined the blood glucose levels. Blood glucose levels are recorded at −30, 0, 15, 30, 60 and 120 minutes.

Effect of Test Compound on Blood Glucose and Serum Insulin Levels in Norepinephrine Induced Rat Models of Hyperglycemia:

All experimental conditions and experimental procedures are identical to that of clonidine induced rat models of hyperglycemia in SHR.OB and Wistar rats except norepinephrine is given in the place of clonidine at a dose of 1 mg/kg via IP route; and test compound is tested at a single dose, 15 or 18 mg/kg via SC route. In further studies, both blood glucose and serum insulin levels are measured in the same study at 10 or 30 mg/kg SC doses of test compound.

Effect of Test Compound on Blood Glucose and Serum Insulin Levels in Norepinephrine Induced ob/ob Mouse Model Hyperglycemia:

Studies with ob/ob mice, all experimental procedures are identical to that of norepinephrine induced rat models of hyperglycemia and test compound is tested via SC route at a dose of 30 mg/kg. Number of mice used per group per time point are 3.

Effect of Test Compound on Blood Glucose and Serum Insulin Levels in Ob/Ob Mouse Model Spontaneous Hyperglycemia with No Norephinephrine:

All experimental procedures are identical to that of studies conducted in ob/ob mice where norepinephrine is not given at 0 minutes; and test compound at a dose of 30 mg/kg via SC route is dosed at −30 minutes. Number of mice used per group and each time point are 3. Effect of test compound on blood glucose and serum insulin levels in glucose induced (oral glucose tolerance test—OGTT) rat SHR.OB model of hyperglycemia:

All experimental procedures are identical to that of norepinephrine induced hyperglycemia in SHR.OB rats except glucose is given in the place of norepinephrine at 0 minutes at a dose of 6 g/kg via oral route as reported by Chen et al, *Exp. Biol. Med.*, 236:309-414 (2011). Number of rats used per group are 8.

This assay demonstrates the effect of the test compound on insulin secretion ability in norepinephrine or clonidine induced hyperglycemia ob/ob mice.

Effect of Test Compound on Blood Glucose Levels in Normoglycemic Rats:

In addition to the studies with rat models of hyperglycemia, the effect of test compound at high dose (18 mg/kg, SC) on blood glucose levels is also tested in normoglycemic SHR.OB rats, which is an animal model of metabolic syndrome. This is to rule out possible hypoglycemic effects in normoglycemic rats. The experimental protocol in this study is identical to that of the other studies except that the rats are normoglycemic and are not administered clonidine or norepinephrine at 0 minutes.

Example B7

Blood Pressure Lowering Ability—In Vivo

To demonstrate the blood pressure lowering effect of an test compound, male spontaneously hypertensive rats (SHR) are used. SHR rats are anaesthetized with sodium pentobarbital (50 mg/kg IP). The left carotid artery cannulated with a polyethylene catheter (38 cm in length; PE60, Portex, Ltd.) connected with a polyurethane tubing (12 cm in length; PU-40, Cat. # BB520-40, Scientific Commodities, Inc.), which is tunneled under the skin and exited through the nape of the neck. The arterial cannula is connected to a pressure transducer through a swivel system, allowing free roaming during continuous recording of mean arterial pressure and heart rate. The animals are housed individually with food and water freely available during recovery. On the following day, the arterial cannula is connected via a Statham (P 23×L) pressure transducer to a NEC/San-Ei amplifier and data acquisition and analysis system (Power Lab 8/SP) for direct mean arterial pressure and heart rate measurements. To determine the effect of test compound on systolic blood pressure, oral or i.v. bolus or i.v. escalating doses of compound administration in every 30 minutes is performed and systolic blood pressure is monitored at various time points, baseline data is collected during 0 to 120 minutes time points; test compound is dosed at 120 minutes; and compound effect is monitored from 120 minutes to 255 minutes.

This assay demonstrates the effect of the test compound on lowering blood pressure while potentially also lowering blood glucose levels when test compound is administered orally (10 mg/kg) or i.v., bolus (1 mg/kg) or i.v., escalating doses (1, 3, 10 and 30 mg/kg/iv for every 30 minutes).

Example B8

Synergistic Studies with Other Secretagogue Drugs

Similar to the methods mentioned in the earlier section (Insulin Secreation Ability—in vitro), male Sprague Dawley rats are anesthetized with a mixture of ketamine and xilazine (1:1) and their abdominal walls are cut open. Ten milliliter Hank's buffer saline containing collagenase (2 mg/ml) is injected into the common bile duct of the rat. The pancreas swollen with the digestion solution is quickly excised and immersed into a plastic culture bottle with solution for 12 minutes-14 minutes incubation at 37° C. The digested suspension obtained is washed with Hank's buffer complement with 0.2% bovine serum albumin. Islets are obtained from a rat by gradient centrifugation (Histopaque-1077). After, islets are cultured for 24 hours in RPMI medium and collected for tests. Different scretagogue drugs like sulfonylureas (nateglinide, a meglitinide class) or sulfonylureas (glibenclamide, a second generation sulfonylureas or glimepiride, a third generation sulfonylurea) are tested with Test compound and found synergism (Figure. 8, Figure. 23 and Figure. 24).

Test Compound Blocks pERK1/2: For Western blotting, whole-cell extracts, cells are washed with ice-cold PBS and lysate with lysis buffer and collected by scraping. The protein concentration is determined using a BCA Protein Assay Reagent Kit. Cell lysates containing 30 μg proteins are electrophoresed on 10% SDS-PAGE and then transferred onto a PVDF membrane. The membranes are rinsed with TEST, followed by incubation with p-ERK (mouse, 1/1000, SCBT) or ERK (rabbit, 1/1000, SCBT) for 2 or 1 hour, respectively, at room temperature. After being washed with TEST, the membranes are incubated with the anti-mouse or anti-rabbit, respectively, HRP antibody (1:5000; Rockland) for 1 hour. Immunoreactive bands are visualized by ECL Western blotting detection (PIERCE). As shown in the Figure. 25 (Westernblot), Test compound blocked pERK1/2 norepinephrine mediated effects in rat pancreatic islets.

Example B9

Human Clinical Studies

The compound is studied in a clinical trial of adult-onset type 2 diabetic patients whose blood glucose levels remain suboptimally controlled despite use of metformin. The study compares the active compound against a matched placebo with the primary objective of comparing mean hemoglobin A1c changes from baseline to the end of the study between the active compound and placebo.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of regulating blood glucose levels in an individual in need thereof comprising administering to the individual an effective amount of a compound of formula (A1), (A2), (A3), (A4), (B1), (B2), (B3), (B4), (C1), (C2), (C3), (C4), (D1), (D2), (D3), or (D4); or a salt, solvate or N-oxide thereof:

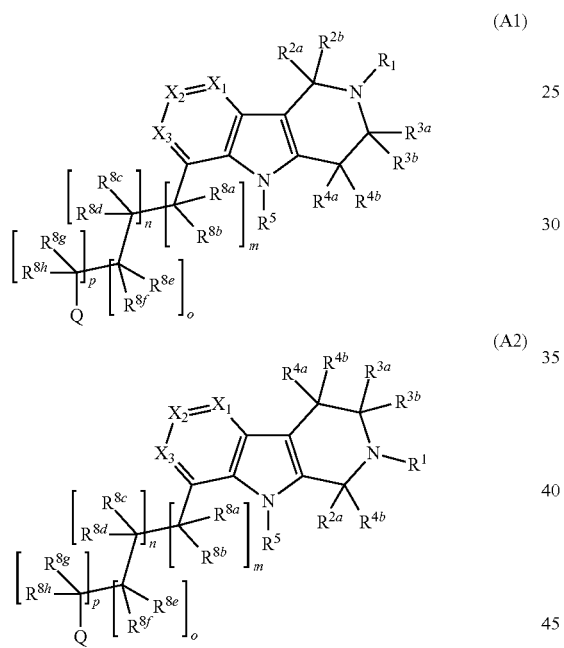

wherein for formula (A1) or (A2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

$R^5$ is H or unsubstituted $C_1$-$C_8$ alkyl;

each $X^1$, $X^2$ and $X^3$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$═CR$^{10a}$R$^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

or

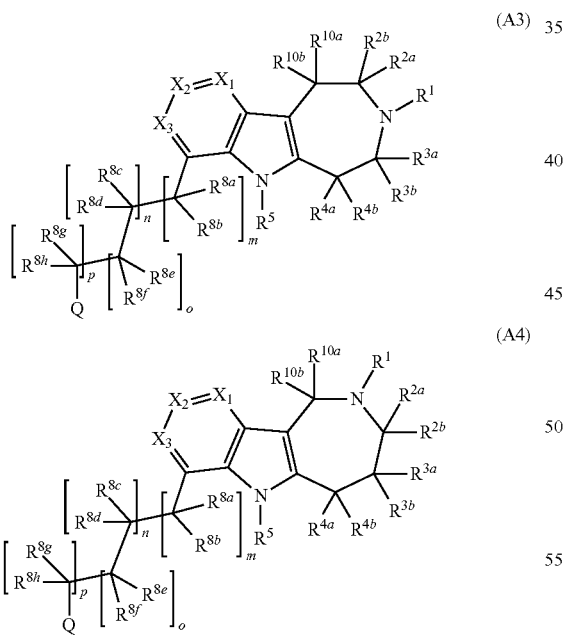

wherein for formula (A3) or (A4):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

$R^5$ is H or unsubstituted $C_1$-$C_8$ alkyl;

each m, n, o and p is independently 0 or 1;

each $X^1$, $X^2$ and $X^3$ is independently N, CH or CR$^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —$CR^9$=$CR^{10a}R^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety; or

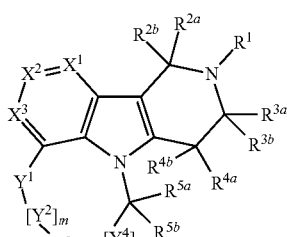

(B1)

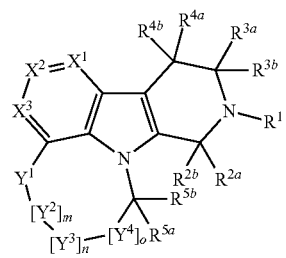

(B2)

wherein for formula (B1) or (B2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each m, n, or o is independently 0 or 1;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m, n and o are each 0, then $R^{5a}$ and $R^{7a}$ are taken together to form a bond, or when m is 1, and n and o are each 0, then $R^{5a}$ and $R^{7c}$ are taken together to form a bond, or when m and n are each 1, and o is 0, then $R^{5a}$ and $R^{7e}$ are taken together to form a bond, or when m, n and o are each 1, then $R^{5a}$ and $R^{7g}$ are taken together to form a bond;

each m, n and o is independently 0 or 1;

each $X^1$, $X^2$ and $X^3$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

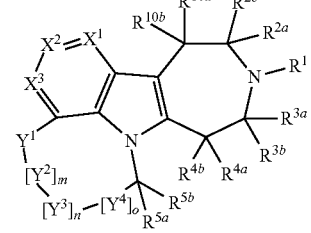

(B3)

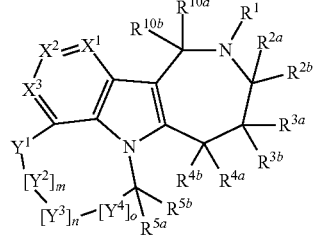

(B4)

wherein for formula (B3) or (B4):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each m, n and o is independently 0 or 1;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m, n and o are each 0, then $R^{5a}$ and $R^{7a}$ are taken together to form a bond, or when m is 1, and n and o are each 0, then $R^{5a}$ and $R^{7c}$ are taken together to form a bond, or when m and n are each 1, and o is 0, then $R^{5a}$ and $R^{7e}$ are taken together to form a bond, or when m, n and o are each 1, then $R^{5a}$ and $R^{7g}$ are taken together to form a bond;

each m, n and o is independently 0 or 1;

each $X^1$, $X^2$ and $X^3$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

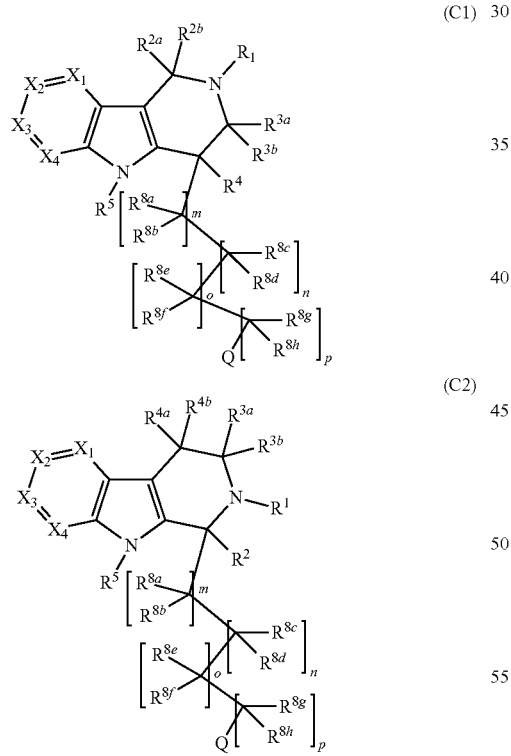

(C1)

(C2)

wherein for formula (C1) or (C2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—$CH_2CH_2CH_2$—) moiety or a butylene (—$CH_2CH_2CH_2CH_2$—) moiety, or $R^1$ and $R^{2a}$, where present, are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$, where present, are taken together to form an ethylene (—$CH_2CH_2$—) moiety or a propylene (—$CH_2CH_2CH_2$—) moiety or $R^1$ and $R^{4a}$, where present, are taken together to form an ethylene (—$CH_2CH_2$—) moiety or a propylene (—$CH_2CH_2CH_2$—) moiety;

each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—$CH_2CH_2CH_2$—) moiety or a butylene (—$CH_2CH_2CH_2CH_2$—) moiety, or $R^{2a}$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^2$ and $R^4$ are taken together to form a methylene (—$CH_2$—) moiety or an ethylene (—$CH_2CH_2$—) moiety or $R^{2a}$ and $R^4$ are taken together to form a methylene (—$CH_2$—) moiety or an ethylene (—$CH_2CH_2$—) moiety, or $R^2$ and a vicinal $R^{8(a-h)}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety or $R^{3a}$ and $R^{4a}$ are taken together to form a propylene (—$CH_2CH_2CH_2$—) moiety or a butylene (—$CH_2CH_2CH_2CH_2$—) moiety;

each $R^4$ or $R^{4a}$, where present, is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—CH$_2$CH$_2$CH$_2$—) moiety, or R$^{4a}$ and R$^1$ are taken together to form an ethylene (—CH$_2$CH$_2$—) moiety or a propylene (—CH$_2$CH$_2$CH$_2$—) moiety, or R$^4$ and R$^{2a}$ are taken together to form a methylene (—CH$_2$—) moiety or an ethylene (—CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^4$ and R$^{3a}$ are taken together to form a propylene (—CH$_2$CH$_2$CH$_2$—) moiety or a butylene (—CH$_2$CH$_2$CH$_2$CH$_2$—) moiety, or R$^{4a}$ and R$^{1a}$ are taken together to form a propylene (—CH$_2$CH$_2$CH$_2$—) moiety or a butylene (—CH$_2$CH$_2$CH$_2$CH$_2$—) moiety, or R$^4$ and a vicinal R$^{8(a-h)}$ are taken together to form a bond;

R$^5$ is H or unsubstituted C$_1$-C$_8$ alkyl;

each X$^1$, X$^2$, X$^3$ and X$^4$ is independently N, CH or CR$^6$;

each m, n, o and p is independently 0 or 1;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$, R$^{8f}$, R$^{8g}$ and R$^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal R$^{8(a-h)}$ to form a substituted or unsubstituted methylene moiety or a moiety of the formula —OCH$_2$CH$_2$O—, or is taken together with a geminal R$^{8(a-b)}$ and the carbon to which they are attached to form a carbonyl moiety or a cycloalkyl moiety, or is taken together with a vicinal R$^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal R$^{8(a-h)}$ to form a bond provided when an R$^{8(a-h)}$ is taken together with a vicinal R$^{8(a-h)}$ to form a bond, the geminal R$^{8(a-h)}$ is other than hydroxyl and thiol and thiol, or is taken together with vicinal R$^2$, where present, to form a bond, or is taken together with vicinal R$^4$, where present, to form a bond; and Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety;

or

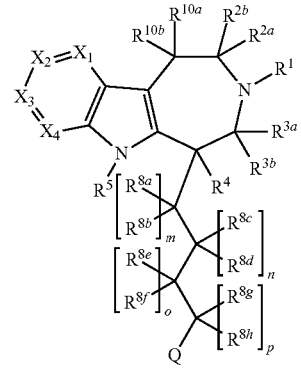

(C3)

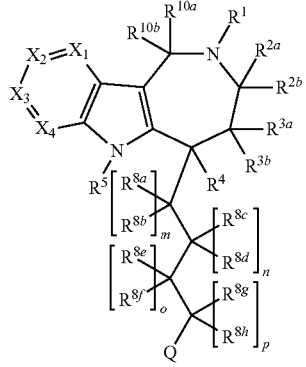

(C4)

wherein for formula (C3) or (C4):

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$, R$^{2b}$, R$^{3a}$, R$^{3b}$, R$^{10a}$ and R$^{10b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and a vicinal $R^{8a}$, where present, are taken together to form a bond;

$R^5$ is H or unsubstituted $C_1$-$C_8$ alkyl;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol, or is taken together with vicinal $R^4$ to form a bond; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$═CR$^{10a}$R$^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

or

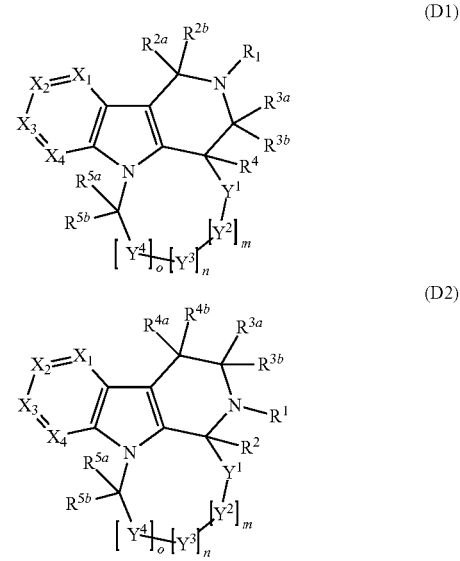

wherein for formula (D1) or (D2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—CH$_2$CH$_2$CH$_2$—) moiety or a butylene (—CH$_2$CH$_2$CH$_2$CH$_2$—) moiety, or $R^1$ and $R^{2a}$, where present, are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^4$, where present, are taken together to form an ethylene (—CH$_2$CH$_2$—) moiety or a propylene (—CH$_2$CH$_2$CH$_2$—) moiety or $R^1$ and $R^{4a}$, where present, are taken together to form an ethylene (—CH$_2$CH$_2$—) moiety or a propylene (—CH$_2$CH$_2$CH$_2$—) moiety;

each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—$CH_2CH_2CH_2$—) moiety or a butylene (—$CH_2CH_2CH_2CH_2$—) moiety, or $R^{2a}$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^2$ and $R^4$ are taken together to form a methylene (—$CH_2$—) moiety or an ethylene (—$CH_2CH_2$—) moiety or $R^{2a}$ and $R^4$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety or $R^{3a}$ and $R^{4a}$ are taken together to form a propylene (—$CH_2CH_2CH_2$—) moiety or a butylene (—$CH_2CH_2CH_2CH_2$—) moiety;

each $R^4$ or $R^{4a}$, where present, is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^{4a}$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^{4a}$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each m, n and o is independently 0 or 1; each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or
when m is 1, and n-o are each 0, then $R^{5a}$ and $R^{7c}$ are taken together to form a bond, or
when m-n are each 1, and o is 0, then $R^{5a}$ and $R^{7e}$ are taken together to form a bond, or
when m-o are each 1, then $R^{5a}$ and $R^{7g}$ are taken together to form a bond;

each m, n and o is independently 0 or 1;
each $X^1$, $X^2$, $X^3$ and $X^4$ is independently N, CH or $CR^6$;
$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;
$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;
$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;
$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^2$ are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

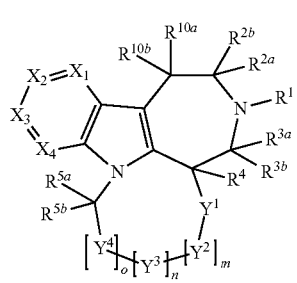

(D3)

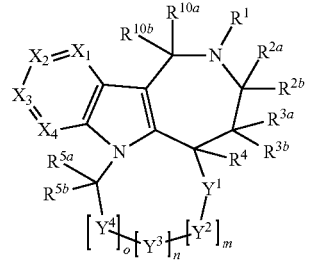

(D4)

wherein for formula (D3) or (D4):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each m, n and o is independently 0 or 1;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

2. The method of claim 1, wherein the method reduces blood glucose level in the individual.

3. The method of claim 2, wherein the method reduces blood glucose level in the individual for a period of more than 0.5 hours following administration.

4. The method of claim 1, wherein the method stabilizes the blood glucose level in the individual.

5. The method of claim 1, wherein the compound binds to and is an antagonist of the adrenergic receptor $\alpha_{2A}$, and wherein the compound either (a) also binds to and is an antagonist of the adrenergic receptor $\alpha_{2B}$ or (b) the compound is not an antagonist of the adrenergic receptor $\alpha_{2B}$ and the compound is administered in conjunction with a diuretic, an angiotensin-converting enzyme (ACE) inhibitor, an angiotensin-2 receptor antagonist, a beta blocker, a calcium channel blocker, or any combination thereof.

6. The method of claim 5, wherein the compound binds to and is an antagonist of the adrenergic receptor $\alpha_{2B}$.

7. The method of claim 5, wherein the compound binds to and is an antagonist of the adrenergic receptor $\alpha_{1B}$.

8. The method of claim 7, wherein the compound is not an antagonist of the adrenergic receptor $\alpha_{2B}$ and the compound is administered in conjunction with a diuretic, an angiotensin-converting enzyme (ACE) inhibitor, an angiotensin-2 receptor antagonist, a beta blocker, a calcium channel blocker, or any combination thereof.

9. A kit comprising (i) a compound of formula (A1), (A2), (A3), (A4), (B1), (B2), (B3), (B4), (C1), (C2), (C3), (C4), (D1), (D2), (D3), or (D4); or a salt, solvate or N-oxide thereof, or a pharmaceutically acceptable salt thereof, and (ii) instructions for use for regulating blood glucose levels in an individual in need thereof;

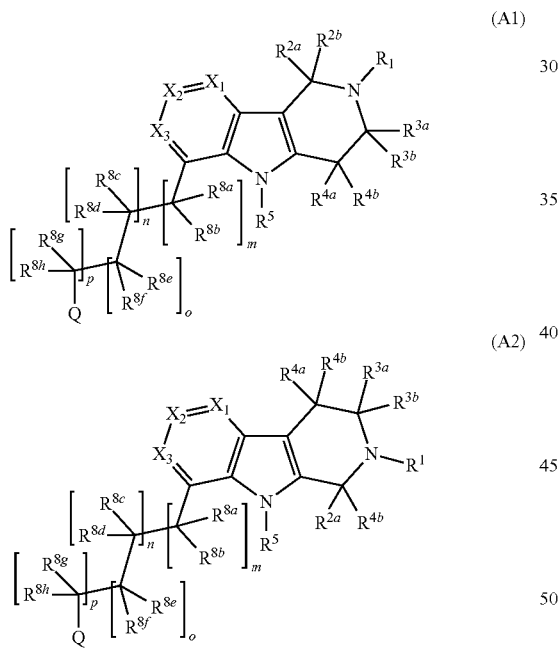

wherein for formula (A1) or (A2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

$R^5$ is H or unsubstituted $C_1$-$C_8$ alkyl;

each $X^1$, $X^2$ and $X^3$ is independently N, CH or CR$^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ $R^{8d}$ $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal R$^{8(a-h)}$ to form a substituted or unsubstituted methylene moiety or a moiety of the formula —OCH$_2$CH$_2$O—, or is taken together with a geminal R$^{8(a-h)}$ and the carbon to which they are attached to form a carbonyl moiety or a cycloalkyl moiety, or is taken together with a vicinal R$^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal R$^{8(a-h)}$ to form a bond provided when an R$^{8(a-h)}$ is taken together with a vicinal R$^{8(a-h)}$ to form a bond, the geminal R$^{8(a-h)}$ is other than hydroxyl and thiol and thiol; and Q is substituted or unsubstituted aryl, substituted or unsubstituted heteroaryl, substituted or unsubstituted C$_3$-C$_8$ cycloalkyl, substituted or unsubstituted C$_3$-C$_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety;

or

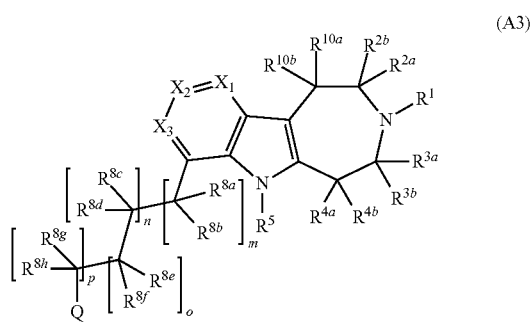

(A3)

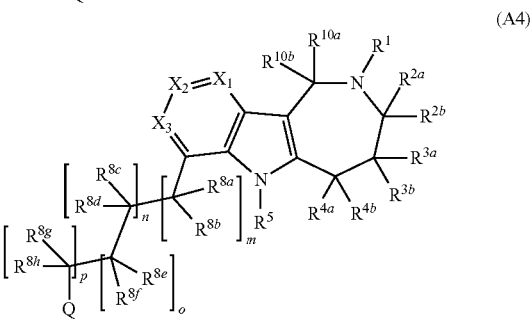

(A4)

wherein for formula (A3) or (A4):

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$, R$^{2b}$, R$^{3a}$, R$^{3b}$, R$^{4a}$, R$^{4b}$, R$^{10a}$ and R$^{10b}$, is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R$^2$, R$^3$, R$^4$ or R$^{10}$ to form a carbonyl moiety or a cycloalkyl moiety;

R$^5$ is H or unsubstituted C$_1$-C$_8$ alkyl;

each m, n, o and p is independently 0 or 1;

each X$^1$, X$^2$ and X$^3$ is independently N, CH or CR$^6$;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$, R$^{8f}$, R$^{8g}$ and R$^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal R$^{8(a-h)}$ to form a substituted or unsubstituted methylene moiety or a moiety of the formula —OCH$_2$CH$_2$O—, or is taken together with a geminal R$^{8(a-h)}$ and the carbon to which they are attached to form a carbonyl moiety or a cycloalkyl moiety, or is taken together with a vicinal R$^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety,
or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol; and
Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula $-CR^9=CR^{10a}R^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;
or

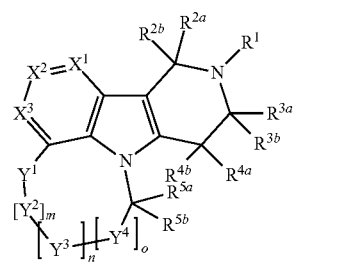

(B1)

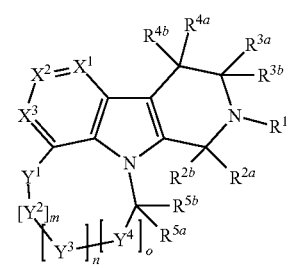

(B2)

wherein for formula (B1) or (B2):
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;
each $R^{2a}$ and $R^{2b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;
each $R^{3a}$ and $R^{3b}$ is independently H, substituted or unsubstituted $C_1$-$C_8$ alkyl, halo, cyano, hydroxyl, alkoxy, nitro, substituted or unsubstituted amino, hydroxyl, alkoxy, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;
each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;
each m, n, or o is independently 0 or 1;
each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or
when m, n and o are each 0, then $R^{5a}$ and $R^{7a}$ are taken together to form a bond, or
when m is 1, and n and o are each 0, then $R^{5a}$ and $R^{7c}$ are taken together to form a bond, or
when m and n are each 1, and o is 0, then $R^{5a}$ and $R^{7e}$ are taken together to form a bond, or
when m, n and o are each 1, then $R^{5a}$ and $R^{7e}$ are taken together to form a bond;

each m, n and o is independently 0 or 1;

each $X^1$, $X^2$ and $X^3$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_i$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

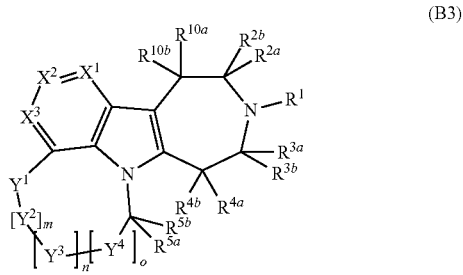

(B3)

-continued

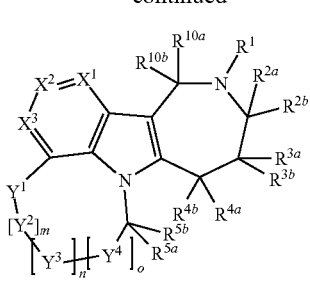
(B4)

wherein for formula (B3) or (B4):
R¹ is H, hydroxyl, substituted or unsubstituted C₁-C₈ alkyl, substituted or unsubstituted C₂-C₈ alkenyl, substituted or unsubstituted C₂-C₈ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C₁-C₈ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;
each $R^{2a}$, $R^{2b}$, $R^{3a}$, $R^{3b}$, $R^{4a}$, $R^{4b}R^{10a}$ and $R^{10b}$ is independently H, hydroxyl, nitro, cyano, halo, substituted or unsubstituted C₁-C₈ alkyl, substituted or unsubstituted C₂-C₈ alkenyl, substituted or unsubstituted C₂-C₈ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C₁-C₈perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R², R³, R⁴ or R¹⁰ to form a carbonyl moiety or a cycloalkyl moiety;
each m, n and o is independently 0 or 1;
each $R^{5a}$ and $R^{5b}$ is independently H, hydroxyl, halo, nitro, cyano, substituted or unsubstituted C₁-C₈ alkyl, substituted or unsubstituted C₁-C₈ alkoxy, C₁-C₈ perhaloalkyl, C₁-C₈ perhaloalkoxy, substituted or unsubstituted C₂-C₈ alkenyl, substituted or unsubstituted C₂-C₈ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or
when m, n and o are each 0, then $R^{5a}$ and $R^{7a}$ are taken together to form a bond, or
when m is 1, and n and o are each 0, then $R^{5a}$ and $R^{7c}$ are taken together to form a bond, or
when m and n are each 1, and o is 0, then $R^{5a}$ and $R^{7e}$ are taken together to form a bond, or when m, n and o are each 1, then $R^{5a}$ and $R^{7g}$ are taken together to form a bond;
each m, n and o is independently 0 or 1;
each $X^1$, $X^2$ and $X^3$ is independently N, CH or $CR^6$;
$Y^1$ is $CR^{7a}R^{7b}$, $NR^8$, O, S, S(O) or SO₂, provided that when $Y^1$ is $NR^8$, O, S, S(O) or SO₂, then $Y^2$, where present, is $CR^{7c}R^{7d}$;
$Y^2$, where present, is $CR^{7c}R^{7d}$, $NR^8$, O, S, S(O) or SO₂, provided that when $Y^2$ is $NR^8$, O, S, S(O) or SO₂, then $Y^1$ is $CR^{7a}R^{7b}$ and $Y^3$, where present, is $CR^{7e}R^{7f}$;
$Y^3$, where present, is $CR^{7e}R^{7f}$, $NR^8$, O, S, S(O) or SO₂, provided that when $Y^3$ is $NR^8$, O, S, S(O) or SO₂, then $Y^2$ is $CR^{7c}R^{7d}$ and $Y^4$, where present, is $CR^{7g}R^{7h}$;
$Y^4$, where present, is $CR^{7g}R^{7h}$, $NR^8$, O, S, S(O) or SO₂, provided that when $Y^4$ is $NR^8$, O, S, S(O) or SO₂, then $Y^3$ is $CR^{7e}R^{7f}$;
each R⁶ is independently hydroxyl, nitro, cyano, halo, C₁-C₈ perhaloalkyl, substituted or unsubstituted C₁-C₈ alkyl, substituted or unsubstituted C₂-C₈ alkenyl, substituted or unsubstituted C₂-C₈ alkynyl, substituted or unsubstituted aryl, substituted or unsubstituted heteroaryl, C₁-C₈ perhaloalkoxy, substituted or unsubstituted C₁-C₈ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
each $R^{7a}$ and $R^{7b}$ is independently H, hydroxyl, halo, nitro, cyano, substituted or unsubstituted C₁-C₈ alkyl, substituted or unsubstituted C₁-C₈ alkoxy, C₁-C₈ perhaloalkyl, C₁-C₈ perhaloalkoxy, substituted or unsubstituted C₂-C₈ alkenyl, substituted or unsubstituted C₂-C₈ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond;
each $R^{7c}$ and $R^{7d}$, where present, is independently H, hydroxyl, halo, nitro, cyano, substituted or unsubstituted C₁-C₈ alkyl, substituted or unsubstituted C₁-C₈ alkoxy, C₁-C₈ perhaloalkyl, C₁-C₈ perhaloalkoxy, substituted or unsubstituted C₂-C₈ alkenyl, substituted or unsubstituted C₂-C₈ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;
each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

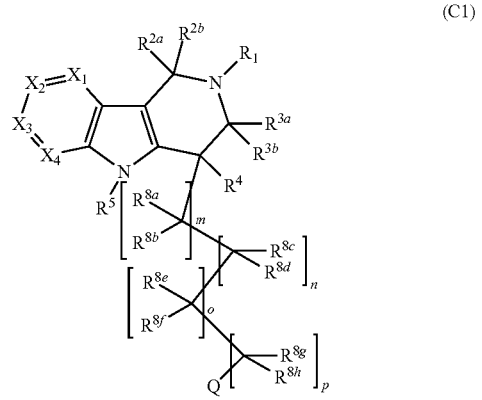

(C1)

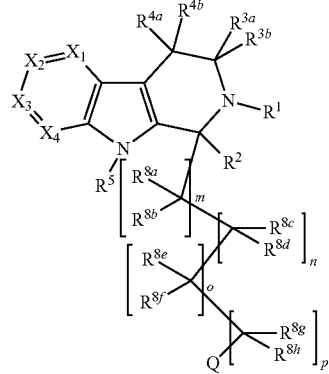

(C2)

wherein for formula (C1) or (C2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—$CH_2CH_2CH_2$—) moiety or a butylene (—$CH_2CH_2CH_2CH_2$—) moiety, or $R^1$ and $R^{2a}$, where present, are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$, where present, are taken together to form an ethylene (—$CH_2CH_2$—) moiety or a propylene (—$CH_2CH_2CH_2$—) moiety or $R^1$ and $R^{4a}$, where present, are taken together to form an ethylene (—$CH_2CH_2$—) moiety or a propylene (—$CH_2CH_2CH_2$—) moiety;

each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—$CH_2CH_2CH_2$—) moiety or a butylene (—$CH_2CH_2CH_2CH_2$—) moiety, or $R^{2a}$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^2$ and $R^4$ are taken together to form a methylene (—$CH_2$—) moiety or an ethylene (—$CH_2CH_2$—) moiety or $R^{2a}$ and $R^4$ are taken together to form a methylene (—$CH_2$—) moiety or an ethylene (—$CH_2CH_2$—) moiety, or $R^2$ and a vicinal $R^{8(a-h)}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety or $R^{3a}$ and $R^{4a}$ are taken together to form a propylene (—$CH_2CH_2CH_2$—) moiety or a butylene (—$CH_2CH_2CH_2CH_2$—) moiety;

each $R^4$ or $R^{4a}$, where present, is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^{4a}$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^{4a}$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety, or $R^4$ and a vicinal $R^{8(a-h)}$ are taken together to form a bond;

$R^5$ is H or unsubstituted $C_1$-$C_8$ alkyl;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —$S(O)_2$-alkyl, —$S(O)_2$-aryl, —$S(O)_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol, or is taken together with vicinal $R^2$, where present, to form a bond, or is taken together with vicinal $R^4$, where present, to form a bond; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —$CR^9$=$CR^{10a}R^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

or

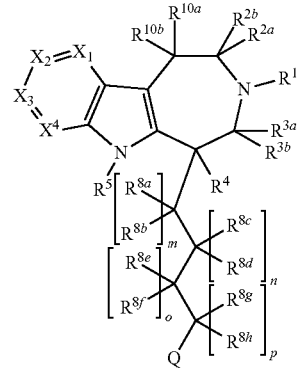

(C3)

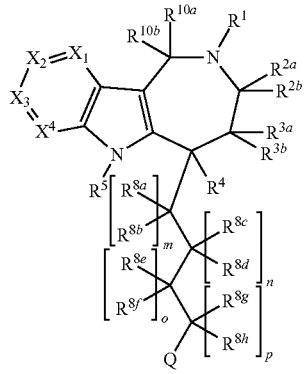

(C4)

wherein for formula (C3) or (C4):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

$R^{2a}$, $R^{2b}$, $R^{3a}$, $R^{3b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and a vicinal $R^{8a}$, where present, are taken together to form a bond;

$R^5$ is H or unsubstituted $C_1$-$C_8$ alkyl;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted orunsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol and thiol, or is taken together with vicinal $R^4$ to form a bond; and Q is substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl, substituted or unsubstituted heterocyclyl, substituted or unsubstituted amino, alkoxy, aminoacyl, acyloxy, carboxyl, carbonylalkoxy, cyano, alkynyl, aminocarbonylalkoxy, acylamino, or is a group of the formula —CR$^9$=CR$^{10a}$R$^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

or

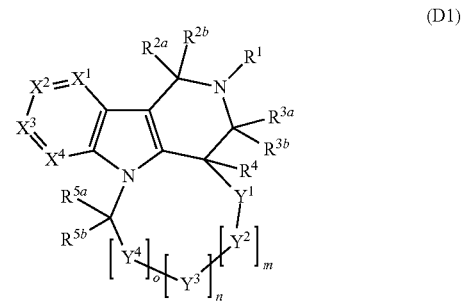

(D1)

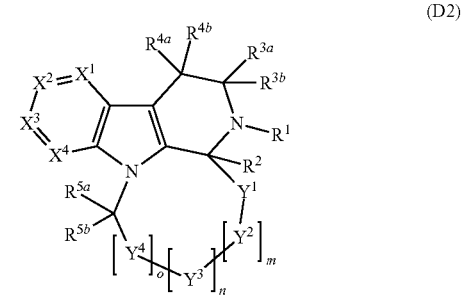

(D2)

wherein for formula (D1) or (D2):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$, where present, are taken together to form a propylene (—CH$_2$CH$_2$CH$_2$—) moiety or a butylene (—CH$_2$CH$_2$CH$_2$CH$_2$—) moiety, or $R^1$ and $R^{2a}$, where present, are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^4$, where present, are taken together to form an ethylene (—CH$_2$CH$_2$—) moiety or a propylene (—CH$_2$CH$_2$CH$_2$—) moiety or $R^1$ and $R^{4a}$, where present, are taken together to form an ethylene (—CH$_2$CH$_2$—) moiety or a propylene (—CH$_2$CH$_2$CH$_2$—) moiety;

each $R^2$, $R^{2a}$ and $R^{2b}$, where present, is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^2$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^2$ and $R^{3a}$ are taken together to form an ethylene (—CH$_2$CH$_2$—) moiety or a propylene (—CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^2$ and $R^4$ are taken together to form a methylene (—CH$_2$—) moiety or an ethylene (—CH$_2$CH$_2$—) moiety or $R^{2a}$ and $R^4$ are taken together to form a methylene (—CH$_2$—) moiety or an ethylene (—CH$_2$CH$_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^2$ are taken together to form an ethylene (—CH$_2$CH$_2$—) moiety or a propylene (—CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^4$ are taken together to form a propylene (—CH$_2$CH$_2$CH$_2$—) moiety or a butylene (—CH$_2$CH$_2$CH$_2$CH$_2$—) moiety or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^4$ or $R^{4a}$, where present, is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—CH$_2$CH$_2$—) moiety or a propylene (—CH$_2$CH$_2$CH$_2$—) moiety, or $R^{4a}$ and $R^1$ are taken together to form an ethylene (—CH$_2$CH$_2$—) moiety or a propylene (—CH$_2$CH$_2$CH$_2$—) moiety, or $R^4$ and $R^{2a}$ are taken together to form a methylene (—CH$_2$—) moiety or an ethylene (—CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^4$ and $R^{3a}$ are taken together to form a propylene (—CH$_2$CH$_2$CH$_2$—) moiety or a butylene (—CH$_2$CH$_2$CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety, or $R^4$ and $R^{7a}$ are taken together to form a bond;

each m, n and o is independently 0 or 1; each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$, $X^3$ and $X^4$ is independently N, CH or $CR^6$;

$Y^1$ is $CR^{7a}R^{7b}$, $NR^8$, O, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^2$ are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_i$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_i$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

or

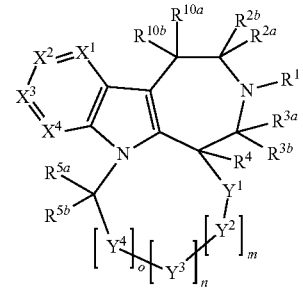

(D3)

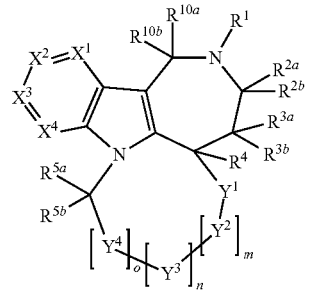

(D4)

wherein for formula (D3) or (D4):

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$perhaloalkoxy, alkoxy, aryloxy, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$, $R^{3a}$, $R^{3b}$, $R^{10a}$ and $R^{10b}$, is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$ or $R^{10}$ to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each m, n and o is independently 0 or 1;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{5a}$ and $R^{5b}$ are taken together with the carbon to which they are attached to form a carbonyl moiety, or when m-o are each 0, then $R^{5a}$ and $R^{7a}$ are taken together to form a bond, or when m is 1, and n-o are each 0, then $R^{5a}$ and $R^{7c}$ are taken together to form a bond, or when m-n are each 1, and o is 0, then $R^{5a}$ and $R^{7e}$ are taken together to form a bond, or when m-o are each 1, then $R^{5a}$ and $R^{7g}$ are taken together to form a bond;

each m, n and o is independently 0 or 1;

each $X^1$, $X^2$, $X^3$ and $X^4$ is independently N, CH or $CR^6$;

$Y^1$ is $CR^{7a}R^{7b}$, $NR^8$, O, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7c}$ and $R^{7d}$ are taken together with the carbon to which they are attached to form a carbonyl moiety, or $R^{7c}$ and $R^{7a}$, where present, are taken together to form a bond, or $R^{7c}$ and $R^{7e}$ are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy aminosulfonyl, sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$perhaloalkoxy, alkoxy, aryloxy, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl or carbonylalkylenealkoxy.

\* \* \* \* \*